(12) United States Patent
Blankenship et al.

(10) Patent No.: US 9,782,478 B1
(45) Date of Patent: Oct. 10, 2017

(54) PROSTATE-SPECIFIC MEMBRANE ANTIGEN BINDING PROTEINS AND RELATED COMPOSITIONS AND METHODS

(71) Applicant: APTEVO RESEARCH AND DEVELOPMENT LLC, Seattle, WA (US)

(72) Inventors: John W. Blankenship, Seattle, WA (US); Elaine Todd Sewell, Seattle, WA (US); Philip Tan, Edmonds, WA (US)

(73) Assignee: Aptevo Research and Development LLC, Seattle, WA (US)

( * ) Notice: Subject to any disclaimer, the term of this patent is extended or adjusted under 35 U.S.C. 154(b) by 0 days.

(21) Appl. No.: 15/585,921

(22) Filed: May 3, 2017

Related U.S. Application Data

(63) Continuation of application No. 14/113,353, filed as application No. PCT/US2012/034575 on Apr. 20, 2012, now abandoned.

(60) Provisional application No. 61/478,449, filed on Apr. 22, 2011.

(51) Int. Cl.
*A61K 39/00* (2006.01)
*A61K 39/395* (2006.01)

(52) U.S. Cl.
CPC .. *A61K 39/39558* (2013.01); *A61K 2039/505* (2013.01)

(58) Field of Classification Search
CPC ............... A61K 39/39558; A61K 2039/505
See application file for complete search history.

(56) References Cited

U.S. PATENT DOCUMENTS

| | | | |
|---|---|---|---|
| 5,834,597 A | 11/1998 | Tso et al. | |
| 5,929,212 A | 7/1999 | Jolliffe et al. | |
| 5,932,448 A | 8/1999 | Tso et al. | |
| 6,150,508 A | 11/2000 | Murphy et al. | |
| 6,551,592 B2 | 4/2003 | Thierfelder et al. | |
| 6,828,422 B1 | 12/2004 | Achim et al. | |
| 6,962,981 B1 | 11/2005 | Murphy et al. | |
| 7,201,900 B2 | 4/2007 | Murphy et al. | |
| 7,381,803 B1 | 6/2008 | Weiner et al. | |
| 7,476,513 B2 | 1/2009 | Murphy et al. | |
| 7,507,796 B2 | 3/2009 | Little et al. | |
| 7,713,524 B2 | 5/2010 | Bourel et al. | |
| 7,776,311 B1 | 8/2010 | McBride et al. | |
| 7,811,564 B2 | 10/2010 | Cuello et al. | |
| 7,820,166 B2 | 10/2010 | Lanzavecchia | |
| 7,833,528 B2 | 11/2010 | Griffiths et al. | |
| 7,875,278 B2 | 1/2011 | Cardarelli et al. | |
| 8,003,774 B2 | 8/2011 | Stavenhagen et al. | |
| 8,066,989 B2 | 11/2011 | Lindhofer et al. | |
| 8,101,722 B2 | 1/2012 | Kufer et al. | |
| 8,114,965 B2 | 2/2012 | Maddon et al. | |
| 8,158,573 B2 | 4/2012 | McBride et al. | |
| 8,188,239 B2 | 5/2012 | Hansen et al. | |
| 8,236,308 B2 | 8/2012 | Kischel et al. | |
| 8,470,330 B2 | 6/2013 | Maddon et al. | |
| 8,518,403 B2 | 8/2013 | Hoffmann et al. | |
| 8,629,247 B2 | 1/2014 | Moffett et al. | |
| 8,632,777 B2 | 1/2014 | Elsasser et al. | |
| 8,663,638 B2 | 3/2014 | Lindhofer et al. | |
| 8,709,421 B2 | 4/2014 | Heiss et al. | |
| 8,734,791 B2 | 5/2014 | Lazar et al. | |
| 8,759,496 B2 | 6/2014 | Govindan et al. | |
| 2003/0118592 A1 | 6/2003 | Ledbetter et al. | |
| 2003/0133939 A1 | 7/2003 | Ledbetter et al. | |
| 2004/0024188 A1 | 2/2004 | Murphy et al. | |
| 2004/0120958 A1 | 6/2004 | Bander et al. | |
| 2005/0136049 A1 | 6/2005 | Ledbetter et al. | |
| 2006/0088539 A1 | 4/2006 | Bander | |
| 2006/0286030 A1 | 12/2006 | Boumsell et al. | |
| 2007/0059306 A1 | 3/2007 | Grosmaire et al. | |
| 2007/0128671 A1 | 6/2007 | Murphy et al. | |
| 2007/0160617 A1 | 7/2007 | Ma et al. | |
| 2008/0176247 A1 | 7/2008 | Chou et al. | |
| 2008/0213256 A1 | 9/2008 | Kufer et al. | |
| 2008/0260738 A1 | 10/2008 | Moore et al. | |
| 2009/0175867 A1 | 7/2009 | Thompson et al. | |
| 2009/0258005 A1 | 10/2009 | Gill et al. | |
| 2009/0274649 A1 | 11/2009 | Qu et al. | |
| 2009/0298195 A1 | 12/2009 | Ruker et al. | |
| 2011/0081345 A1 | 4/2011 | Moore et al. | |

(Continued)

FOREIGN PATENT DOCUMENTS

CN 1421459 A 6/2003
EP 1210374 B1 10/2006

(Continued)

OTHER PUBLICATIONS

Alberola-Ila et al., "Stimulation through the TCR/CD3 complex up-regulates the CD2 surface expression on human T Lymphocytes," J. Immunol. 146(4):1085-1092 (1991).
Altschuler et al., "Generation of Recombinant Antibodies and Means for Increasing Their Affinity," Biocemistry (Moscow) 75:1584-1605 (2010) originally published in Uspekhi Biologicheskoi Khimii, 50:203-258 (2010).
Bander et al., "Targeting Metastatic Prostate Cancer with Radiolabeled Monoclonal Antibody J591 to the Extracellular Domain of Prostate Specific Membrane Antigen," J. Urology 170:1717-1721 (2003).
Brown et al., "A novel monoclonal antibody 107-1A4 with high prostate specificity: generation, chracterization of antigen expression, and targeting of human prostate cancer xenografts," Prostate Canc. Prostatic Dis. 1:208-215 (1998).

(Continued)

*Primary Examiner* — Stephen Rawlings
(74) *Attorney, Agent, or Firm* — Cooley LLP

(57) ABSTRACT

The present invention relates to mono-specific and multi-specific polypeptide therapeutics that specifically target cells expressing prostate-specific membrane antigen (PSMA) and are useful for the treatment of prostate cancer (e.g., castrate-resistant prostate cancer), tumor-related angiogenesis or benign prostatic hyperplasia (BPH). In one embodiment, the multi-specific polypeptide therapeutics bind both PSMA-expressing cells and the T-cell receptor complex on T cells to induce target-dependent T-cell cytotoxicity, activation and proliferation.

19 Claims, 9 Drawing Sheets

(56) References Cited

U.S. PATENT DOCUMENTS

| | | |
|---|---|---|
| 2011/0189209 A1 | 8/2011 | Neville, Jr. et al. |
| 2011/0250216 A1 | 10/2011 | Ma et al. |
| 2011/0262439 A1 | 10/2011 | Kufer et al. |
| 2011/0275787 A1 | 11/2011 | Kufer et al. |
| 2011/0293619 A1 | 12/2011 | Kufer et al. |
| 2012/0171115 A1 | 7/2012 | Hudson et al. |
| 2012/0195900 A1 | 8/2012 | Ghayur et al. |
| 2012/0244162 A1 | 9/2012 | Kufer et al. |
| 2012/0301400 A1 | 11/2012 | Williams et al. |
| 2012/0321626 A1 | 12/2012 | Zhou |
| 2013/0078249 A1 | 3/2013 | Ast et al. |
| 2013/0095106 A1 | 4/2013 | Lindhofer |
| 2013/0129723 A1 | 5/2013 | Blankenship et al. |
| 2013/0129729 A1 | 5/2013 | Kischel et al. |
| 2013/0129730 A1 | 5/2013 | Kufer et al. |
| 2013/0165389 A1 | 6/2013 | Schellenberger et al. |
| 2013/0196377 A1 | 8/2013 | Lee et al. |
| 2013/0224205 A1 | 8/2013 | Hofmeister et al. |
| 2013/0253172 A1 | 9/2013 | Gurney et al. |
| 2013/0309234 A1 | 11/2013 | Lindhofer |
| 2013/0323204 A1 | 12/2013 | Rossi et al. |
| 2014/0050660 A1 | 2/2014 | Chang et al. |
| 2014/0056895 A1 | 2/2014 | Baurin et al. |
| 2014/0056897 A1 | 2/2014 | Buelow et al. |
| 2014/0081002 A1 | 3/2014 | Lee et al. |
| 2014/0099254 A1 | 4/2014 | Chang et al. |
| 2014/0099318 A1 | 4/2014 | Huang et al. |
| 2014/0112914 A1 | 4/2014 | Nezu et al. |
| 2014/0127210 A1 | 5/2014 | Kim et al. |
| 2014/0147382 A1 | 5/2014 | Goldenberg et al. |
| 2014/0154252 A1 | 6/2014 | Thompson et al. |
| 2014/0161800 A1 | 6/2014 | Blankenship et al. |
| 2014/0178388 A1 | 6/2014 | Chou et al. |
| 2015/0274844 A1 | 10/2015 | Blankenship et al. |

FOREIGN PATENT DOCUMENTS

| | | |
|---|---|---|
| EP | 1726650 A1 | 11/2006 |
| EP | 1629011 B1 | 1/2010 |
| EP | 1691833 B1 | 3/2010 |
| EP | 1587837 B1 | 6/2012 |
| EP | 2326350 B1 | 9/2013 |
| EP | 1912677 B1 | 10/2013 |
| JP | 11-506310 A | 6/1999 |
| JP | 2002-518041 A | 6/2005 |
| WO | WO 97/35616 A1 | 10/1997 |
| WO | WO 99/47554 A1 | 9/1999 |
| WO | WO 01/09192 A1 | 2/2001 |
| WO | WO 02/098897 A2 | 12/2002 |
| WO | WO 03/034903 A2 | 5/2003 |
| WO | WO 2013/092001 A1 | 6/2003 |
| WO | WO 03/064606 A2 | 8/2003 |
| WO | WO 2004/106380 A2 | 12/2004 |
| WO | WO 2005/014618 A2 | 2/2005 |
| WO | WO 2005/040220 A1 | 5/2005 |
| WO | WO 2005/070456 A2 | 8/2005 |
| WO | WO 2005/100404 A1 | 10/2005 |
| WO | WO 2005/123129 A2 | 12/2005 |
| WO | WO 2006/089230 A2 | 8/2006 |
| WO | WO 2006/089231 A2 | 8/2006 |
| WO | WO 2007/113172 A2 | 10/2007 |
| WO | WO 2007/146968 A2 | 12/2007 |
| WO | WO 2009/127046 A1 | 10/2009 |
| WO | WO 2009/130575 A2 | 10/2009 |
| WO | WO 2010/037836 A2 | 4/2010 |
| WO | WO 2010/040105 A2 | 4/2010 |
| WO | WO 2010/042904 A2 | 4/2010 |
| WO | WO 2010/118522 A1 | 10/2010 |
| WO | WO 2011/000054 A1 | 1/2011 |
| WO | WO 2012/125850 A1 | 9/2012 |
| WO | WO 2012/145714 A2 | 10/2012 |
| WO | WO 2012/156429 A1 | 11/2012 |
| WO | WO 2013/026839 A1 | 2/2013 |
| WO | WO 2013/104804 A2 | 7/2013 |
| WO | WO 2013/121175 A1 | 8/2013 |
| WO | WO 2013/128027 A1 | 9/2013 |
| WO | WO 2013/128194 A1 | 9/2013 |
| WO | WO 2013/132268 A1 | 9/2013 |
| WO | WO 2013/158856 A2 | 10/2013 |
| WO | WO 2013/172961 A1 | 11/2013 |
| WO | WO 2013/173820 A2 | 11/2013 |
| WO | WO 2014/012085 A2 | 1/2014 |
| WO | WO 2014/056783 A1 | 4/2014 |
| WO | WO 2014/079000 A1 | 5/2014 |
| WO | WO 2014/100490 A1 | 6/2014 |
| WO | WO 2014/108483 A1 | 7/2014 |
| WO | WO 2014/110601 A1 | 7/2014 |

OTHER PUBLICATIONS

Buhler et al., "A bispecific diabody directed against prostate-specific membrane antigen and CD3 induces T-cell mediated lysis of prostate cancer cells," Canc. Immunol. Immunother. 57(1):43-52 (2008).

Caldus et al., "Humanization of the anti-CD18 antibody 6.7: an unexpected effect of a framework residue in binding to antigen," Mol. Immunol. 38:941-952 (2003).

Carter, "Bispecific human IgG by design," J. Immunol. Methods 248:7-15 (2001).

Casset et al., "A peptide mimetic of an anti-CD4 monoclonal antibody by rational design," Biochem. Biophys. Res. Commun. 307:198-205 (2003).

Chien et al., "Significant structural and functional change of an antigen-binding site by a distant amino acid substitution: Proposal of a structural mechanism," Proc. Natl. Acad. Sci. USA 86:5532-5536 (1989).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol. 169:3076-3084 (2002).

Evazalipour et al., "Camel Heavy Chain Antibodies Against Prostate-Specific Membrane Antigen," Hybridoma 31(6):424-429 (2012).

Examination Report, European Patent Office appl. No. 12773598.3, 4 pages (dated Jun. 29, 2016).

Fortmuller et al., "Effective Targeting of Prostate Cancer by Lymphocytes Redirected by a PSMA x CD3 Bispecific Single-Chain Diabody," Prostate 71:588-596 (2011).

George et al., "Differential Effects of Anti-$\beta_2$-Glycoprotein I Antibodies on Endothelial Cells and on the Manifestations of Experimental Antiphospholipid Syndrome," Circulation 97:900-906 (1998).

Giusti et al., "Somatic diversification of S107 from an antiphosphocholine to an anti-DNA autoantibody is due to a single base change in its heavy chain variable region," Proc. Natl. Acad. Sci. USA 84:2926-2930 (1987).

Güssow and Seemann, "Humanization of Monoclonal Antibodies," Meth. Enzymol. 203:99-121.

Holliger and Hudson, "Engineered antibody fragments and the rise of single domains," Nat. Biotechnol. 23(9):1126-1136(2005).

Holm et al., "Functional mapping and single chain construction of the anti-cytokeratin 8 monoclonal antibody TS1," Mol. Immunol. 44:1075-1084 (2007).

Hu et al., "Minibody: A Novel Engineered Anti-Carcinoembryonic Antigen Antibody Fragment (Single-Chain FVC$_H$3) Which Exhibits Rapoid, High-Level Targeting of Xenografts," Cancer Res. 36:3055-3061 (1996).

Inoue et al., "Efficient production of a functional mouse/human chimeric Fab' against human urokinase-type plasminogen activator by Bacillus brevis," Appl. Microbiol. Biotechnol. 48:487-492 (1997).

International Search Report, PCT Appl. No. PCT/US2012/034575, 6 pages (dated Nov. 2, 2012).

Kim et al., "Anti-CD30 diabody-drug conjugates with potent antitumor activity," Mol. Cancer Ther. 7:2486-2497 (2008).

MacCallum et al., "Antibody-antigen Interactions: Contact Analysis and Binding Site Topography," J. Mol. Biol. 262:732-745 (1996).

(56) References Cited

OTHER PUBLICATIONS

Mariuzza et al., "The Structural Basis of Antigen-Antibody Recognition," Ann. Rev. Biophys. Biophys. Chem. 16:139-159 (1987).
Marvin and Zhu, "Recombinant approaches to IgG-like bispecific antibodies," Acta Pharmacol. Sin. 26:649-658 (2005).
Müller et al., "The first constant domain ($C_H1$ and $C_L$) of an antibody used as heterodimerization domain for bispecific miniantibodies," FEBS Lett. 422:259-264 (1998).
Muyldermans, "Single domain camel antibodies: current status," Rev. Mol. Biotechnol. 74:277-302 (2001).
Omidfar et al., "Production and Characterization of a New Antibody Specific for the Mutant EGF Receptor, EGFRvIII, in Camelus bactrianus," Tumor Biol. 25:179-187 (2004).
Orcutt et al., "A modular IgG-scFv bispecific antibody topology," Prot. Eng. Des. Select. 23(4):221-228 (published online Dec. 17, 2009).
Rudikoff et al., "Single amino acid substitution altering antigen-binding specificity," Proc. Natl. Acad. Sci. USA 79:1979-1983 (1982).
Search Report, SG appl. No. 2013077086, 17 pages (dated Jan. 7, 2015).
Shen et al., "Single Variable Domain-IgG Fusion. A Novel Recombinant Approach to Fc Domain-Containing Bispecific Antibodies," J. Biol. Chem. 281(16):10706-10714 (2006).
Supplementary European Search Report, EP appl. No. 12773598.3, 9 pages (dated Dec. 12, 2014).
Vajdos et al., "Comprehensive Functional Maps of the Antigen-binding Site of an Anti-ErbB2 Antibody Obtained with Shotgun Scanning Mutagenesis," J. Mol. Biol. 320:415-428 (2002).
Wang et al., "Identification of Prostate Specific Membrane Antigen (PSMA) as the Target of Monoclonal Antibody 107-1A4 by Proteinchip; Array, Surface-Enhanced Laser Desorption/Ionization (SELDI) Technology," Int. J. Cancer 92(6):871-876 (2001).
Winkler et al., "Changing the Antigen Binding Specificity by Single Point Mutations of an Anti-p24 (HIV-1) Antibody," J. Immunol. 165:4505-4514 (2000).
Written Opinion of the International Searching Authority, PCT Appl. No. PCT/US2012/034575, 6 pages (dated Nov. 2, 2012).
Written Opinion, SG appl. No. 2013077086, 15 pages (dated Jan. 7, 2015).
Wu et al., "Humanization of a Murine Monoclonal Antibody by Simultaneous Optimization of Framework and CDR Residues," J. Mol. Biol. 294:151-162 (1999).
Zhang et al., "A Human Monoclonal Antimelanoma. Single-Chain Fv Antibody Derived from Tumor-infiltrating Lymphocytes," Cancer Res. 55:3584-3591 (1995).

SEQUENCE LISTING

```
<160> NUMBER OF SEQ ID NOS: 165

<210> SEQ ID NO 1
<211> LENGTH: 357
<212> TYPE: DNA
<213> ORGANISM: Mus musculus

<400> SEQUENCE: 1
gagatccagc tgcaacagtc tggacctgag ctggtgaagc ctggggcttc agtgaagatg     60
tcctgcaagg cttctggata cacattcact gactactaca tgcactgggt gaagcagaac    120
aatggagaga gccttgagtg gattggatat tttaatcctt ataatgatta tactagatac    180
aaccagaatt tcaatggcaa ggccacattg actgtagaca gtcctccag cacagcctac     240 atgcagctca cagcctgac atctgaggac tctgcattct attactgtgc aagatcggat     300
ggttactacg atgctatgga ctactggggt caaggaacct cagtcaccgt ctcctcg       357

<210> SEQ ID NO 2
<211> LENGTH: 111
<212> TYPE: PRT
<213> ORGANISM: Mus musculus

<400> SEQUENCE: 2

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met His Trp Val Lys Gln Asn Asn Gly Glu Ser Leu Glu Trp Ile
        35                  40                  45

Gly Tyr Phe Asn Pro Tyr Asn Asp Tyr Thr Arg Tyr Asn Gln Asn Phe
    50                  55                  60

Asn Gly Lys Ala Thr Leu Thr Val Asp Lys Ser Ser Ser Thr Ala Tyr
```

```
                65                  70                  75                  80
Met Gln Leu Asn Ser Leu Thr Ser Glu Asp Ser Ala Phe Tyr Tyr Cys
                    85                  90                  95

Ala Arg Ser Asp Gly Tyr Tyr Asp Ala Met Asp Tyr Trp Gly Gln
            100                 105                 110

<210> SEQ ID NO 3
<211> LENGTH: 327
<212> TYPE: DNA
<213> ORGANISM: Mus musculus

<400> SEQUENCE: 3
gatgtccaga taacccagtc tccatcttat cttgctgcat ctcctggaga aaccattact    60
attaattgca gggcaagtaa gagcattagc aaatatttag cctggtatca agagaaacct   120
gggaaagcta ataagcttct tatccattct ggatccactt tgcaatctgg aattccatca   180
aggttcagtg gcagtggatc tggtacagat ttcactctca ccatcagtag cctggagcct   240
gaagattttg caatgtatta ctgtcaacag catattgaat cccgtggac gttcggtggt   300 ggcaccaaac tggaaattaa acgggct                                       327

<210> SEQ ID NO 4
<211> LENGTH: 327
<212> TYPE: DNA
<213> ORGANISM: Artificial Sequence
<220> FEATURE:
<223> OTHER INFORMATION: modified (mature) murine 107-1A4 VL domain used
      in construction of chimeric sequences

<400> SEQUENCE: 4
gatgtccaga taacccagtc tccatcttat cttgctgcat ctcctggaga aaccattact    60
attaattgca gggcaagtaa gagcattagc aaatatttag cctggtatca agagaaacct   120
gggaaagcta ataagctact tatccattct ggatccactt tgcaatctgg aataccatca   180
aggttcagtg gcagtggatc tggtacagat ttcactctca ccatcagtag cctggagcct   240
gaagattttg caatgtatta ctgtcaacag catattgaat cccgtggac gttcggtggt   300 ggcaccaaac tggaaattaa acgggcc                                       327

<210> SEQ ID NO 5
<211> LENGTH: 109
<212> TYPE: PRT
<213> ORGANISM: Mus musculus

<400> SEQUENCE: 5

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Ala Asn Lys Leu Leu Ile
            35                  40                  45

His Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Ile Glu Tyr Pro Trp
                85                  90                  95

Thr Phe Gly Gly Gly Thr Lys Leu Glu Ile Lys Arg Ala
                100                 105
```

<210> SEQ ID NO 6
<211> LENGTH: 33
<212> TYPE: DNA
<213> ORGANISM: Mus musculus

<400> SEQUENCE: 6
tctggataca cattcactga ctactacatg cac                          33

<210> SEQ ID NO 7
<211> LENGTH: 30
<212> TYPE: DNA
<213> ORGANISM: Mus musculus

<400> SEQUENCE: 7
tattttaatc cttataatga ttatactaga                              30

<210> SEQ ID NO 8
<211> LENGTH: 42
<212> TYPE: DNA
<213> ORGANISM: Mus musculus

<400> SEQUENCE: 8
tgtgcaagat cggatggtta ctacgatgct atggactact gg                42

<210> SEQ ID NO 9
<211> LENGTH: 11
<212> TYPE: PRT
<213> ORGANISM: Mus musculus

<400> SEQUENCE: 9

Ser Gly Tyr Thr Phe Thr Asp Tyr Tyr Met His
1               5                   10

<210> SEQ ID NO 10
<211> LENGTH: 10
<212> TYPE: PRT
<213> ORGANISM: Mus musculus

<400> SEQUENCE: 10

Tyr Phe Asn Pro Tyr Asn Asp Tyr Thr Arg
1               5                   10

<210> SEQ ID NO 11
<211> LENGTH: 14
<212> TYPE: PRT
<213> ORGANISM: Mus musculus

<400> SEQUENCE: 11

Cys Ala Arg Ser Asp Gly Tyr Tyr Asp Ala Met Asp Tyr Trp
1               5                   10

<210> SEQ ID NO 12
<211> LENGTH: 18
<212> TYPE: DNA
<213> ORGANISM: Mus musculus

<400> SEQUENCE: 12
aagagcatta gcaaatat                                           18

<210> SEQ ID NO 13
<211> LENGTH: 9
<212> TYPE: DNA
<213> ORGANISM: Mus musculus

<400> SEQUENCE: 13 tctggatcc                                                                9

<210> SEQ ID NO 14
<211> LENGTH: 27
<212> TYPE: DNA
<213> ORGANISM: Mus musculus

<400> SEQUENCE: 14
caacagcata ttgaataccc gtggacg                                           27

<210> SEQ ID NO 15
<211> LENGTH: 6
<212> TYPE: PRT
<213> ORGANISM: Mus musculus

<400> SEQUENCE: 15

Lys Ser Ile Ser Lys Tyr
1               5

<210> SEQ ID NO 16
<211> LENGTH: 3
<212> TYPE: PRT
<213> ORGANISM: Mus musculus

<400> SEQUENCE: 16

Ser Gly Ser
1

<210> SEQ ID NO 17
<211> LENGTH: 9
<212> TYPE: PRT
<213> ORGANISM: Mus musculus

<400> SEQUENCE: 17

Gln Gln His Ile Glu Tyr Pro Trp Thr
1               5

<210> SEQ ID NO 18
<211> LENGTH: 735
<212> TYPE: DNA
<213> ORGANISM: Artificial Sequence
<220> FEATURE:
<223> OTHER INFORMATION: murine scFv (VH-VL orientation)

<400> SEQUENCE: 18
gagatccagc tgcaacagtc tggacctgag ctggtgaagc ctggggcttc agtgaagatg       60
tcctgcaagg cttctggata cacattcact gactactaca tgcactgggt gaagcagaac      120
aatggagaga gccttgagtg gattggatat tttaatcctt ataatgatta ctagataca       180 aaccagaatt tcaatggcaa ggccacattg actgtagaca gtcctccag cacagcctac       240 atgcagctca acagcctgac atctgaggac tctgcattct attactgtgc aagatcggat      300
ggttactacg atgctatgga ctactggggt caaggaacct cagtcaccgt ctcctcaggc      360
ggcggcggaa gcggcggtgg cggcagcagc ggcggcggcg gcagcgatgt ccagataacc      420
cagtctccat cttatcttgc tgcatctcct ggagaaacca ttactattaa ttgcagggca      480
agtaagagca ttagcaaata tttagcctgg tatcaagaga acctgggaa agctaataag      540 ctacttatcc attctggatc cactttgcaa tctggaatac catcaaggtt cagtggcagt      600
ggatctggta cagatttcac tctcaccatc agtagcctgg agcctgaaga ttttgcaatg      660

-continued

```
tattactgtc aacagcatat tgaatacccg tggacgttcg gtggtggcac caaactggaa      720
attaaacggg cctcg                                                      735
```

<210> SEQ ID NO 19
<211> LENGTH: 245
<212> TYPE: PRT
<213> ORGANISM: Artificial Sequence
<220> FEATURE:
<223> OTHER INFORMATION: murine scFv (VH-VL orientation)

<400> SEQUENCE: 19

```
Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met His Trp Val Lys Gln Asn Asn Gly Glu Ser Leu Glu Trp Ile
            35                  40                  45

Gly Tyr Phe Asn Pro Tyr Asn Asp Tyr Thr Arg Tyr Asn Gln Asn Phe
        50                  55                  60

Asn Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Phe Tyr Tyr Cys
                85                  90                  95

Ala Arg Ser Asp Gly Tyr Tyr Asp Ala Met Asp Tyr Trp Gly Gln Gly
            100                 105                 110

Thr Ser Val Thr Val Ser Ser Gly Gly Gly Ser Gly Gly Gly Gly
        115                 120                 125

Ser Ser Gly Gly Gly Gly Ser Asp Val Gln Ile Thr Gln Ser Pro Ser
    130                 135                 140

Tyr Leu Ala Ala Ser Pro Gly Glu Thr Ile Thr Ile Asn Cys Arg Ala
145                 150                 155                 160

Ser Lys Ser Ile Ser Lys Tyr Leu Ala Trp Tyr Gln Glu Lys Pro Gly
                165                 170                 175

Lys Ala Asn Lys Leu Leu Ile His Ser Gly Ser Thr Leu Gln Ser Gly
            180                 185                 190

Ile Pro Ser Arg Phe Ser Gly Ser Gly Ser Gly Thr Asp Phe Thr Leu
        195                 200                 205

Thr Ile Ser Ser Leu Glu Pro Glu Asp Phe Ala Met Tyr Tyr Cys Gln
    210                 215                 220

Gln His Ile Glu Tyr Pro Trp Thr Phe Gly Gly Gly Thr Lys Leu Glu
225                 230                 235                 240

Ile Lys Arg Ala Ser
                245
```

<210> SEQ ID NO 20
<211> LENGTH: 732
<212> TYPE: DNA
<213> ORGANISM: Artificial Sequence
<220> FEATURE:
<223> OTHER INFORMATION: murine scFv (VL-VH orientation)

<400> SEQUENCE: 20

```
gatgtccaga taacccagtc tccatcttat cttgctgcat ctcctggaga aaccattact       60
attaattgca gggcaagtaa gagcattagc aaatatttag cctggtatca agagaaacct      120
gggaaagcta ataagctact tatccattct ggatccactt tgcaatctgg aataccatca      180
```

```
aggttcagtg gcagtggatc tggtacagat ttcactctca ccatcagtag cctggagcct      240
gaagattttg caatgtatta ctgtcaacag catattgaat acccgtggac gttcggtggt      300
ggcaccaaac tggaaattaa acgggccggc ggcggcggaa gcggcggtgg cggcagcagc      360
ggcggcggcg gcagcgagat ccagctgcaa cagtctggac ctgagctggt gaagcctggg      420
gcttcagtga agatgtcctg caaggcttct ggatacacat tcactgacta ctacatgcac      480
tgggtgaagc agaacaatgg agagagcctt gagtggattg gatattttaa tccttataat      540
gattatacta gatacaacca gaatttcaat ggcaaggcca cattgactgt agacaagtcc      600
tccagcacag cctacatgca gctcaacagc ctgacatctg aggactctgc attctattac      660
tgtgcaagat cggatggtta ctacgatgct atggactact ggggtcaagg aacctcagtc      720
accgtctcct cg                                                          732
```

<210> SEQ ID NO 21
<211> LENGTH: 244
<212> TYPE: PRT
<213> ORGANISM: Artificial Sequence
<220> FEATURE:
<223> OTHER INFORMATION: murine scFv (VL-VH orientation)

<400> SEQUENCE: 21

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Ala Asn Lys Leu Leu Ile
        35                  40                  45

His Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Ile Glu Tyr Pro Trp
                85                  90                  95

Thr Phe Gly Gly Gly Thr Lys Leu Glu Ile Lys Arg Ala Gly Gly Gly
            100                 105                 110

Gly Ser Gly Gly Gly Gly Ser Gly Gly Gly Gly Ser Glu Ile Gln
        115                 120                 125

Leu Gln Gln Ser Gly Pro Glu Leu Val Lys Pro Gly Ala Ser Val Lys
    130                 135                 140

Met Ser Cys Lys Ala Ser Gly Tyr Thr Phe Thr Asp Tyr Tyr Met His
145                 150                 155                 160

Trp Val Lys Gln Asn Asn Gly Glu Ser Leu Glu Trp Ile Gly Tyr Phe
                165                 170                 175

Asn Pro Tyr Asn Asp Tyr Thr Arg Tyr Asn Gln Asn Phe Asn Gly Lys
            180                 185                 190

Ala Thr Leu Thr Val Asp Lys Ser Ser Thr Ala Tyr Met Gln Leu
        195                 200                 205

Asn Ser Leu Thr Ser Glu Asp Ser Ala Phe Tyr Tyr Cys Ala Arg Ser
    210                 215                 220

Asp Gly Tyr Tyr Asp Ala Met Asp Tyr Trp Gly Gln Gly Thr Ser Val
225                 230                 235                 240

Thr Val Ser Ser
```

<210> SEQ ID NO 22

<211> LENGTH: 324
<212> TYPE: DNA
<213> ORGANISM: Artificial Sequence
<220> FEATURE:
<223> OTHER INFORMATION: humanized VL domain

<400> SEQUENCE: 22

```
gatatccaga tgacccagtc tccatccgcc atgtctgcat ctgtaggaga cagagtcacc      60
atcacttgcc gggcgagtaa gagcattagc aaatatttag cctggtttca gcagaaacca     120
gggaaagttc ctaagctccg catccattct ggatctactt tgcaatcagg ggtcccatct     180
cggttcagtg gcagtggatc tgggacagaa tttactctca ccatcagcag cctgcagcct     240
gaagattttg caacttatta ctgtcaacag catattgaat acccgtggac gttcggccaa     300
gggaccaagg tggaaatcaa acga                                             324
```

<210> SEQ ID NO 23
<211> LENGTH: 108
<212> TYPE: PRT
<213> ORGANISM: Artificial Sequence
<220> FEATURE:
<223> OTHER INFORMATION: humanized VL domain

<400> SEQUENCE: 23

```
Asp Ile Gln Met Thr Gln Ser Pro Ser Ala Met Ser Ala Ser Val Gly
1               5                   10                  15
Asp Arg Val Thr Ile Thr Cys Arg Ala Ser Lys Ser Ile Ser Lys Tyr
            20                  25                  30
Leu Ala Trp Phe Gln Gln Lys Pro Gly Lys Val Pro Lys Leu Arg Ile
        35                  40                  45
His Ser Gly Ser Thr Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln His Ile Glu Tyr Pro Trp
                85                  90                  95
Thr Phe Gly Gln Gly Thr Lys Val Glu Ile Lys Arg
            100                 105
```

<210> SEQ ID NO 24
<211> LENGTH: 357
<212> TYPE: DNA
<213> ORGANISM: Artificial Sequence
<220> FEATURE:
<223> OTHER INFORMATION: humanized VH domain #1

<400> SEQUENCE: 24

```
gaggtccagc tggtacagtc tggggctgag gtgaagaagc tggggctac agtgaagatc        60
tcctgcaagg cttctggata cacattcact gactactaca tgcactgggt gcaacaggcc     120
cctggaaaag gcttgagtg gatgggatat tttaatcctt ataatgatta tactagatac     180
gcagagaagt tccagggcag agtcaccata accgcggaca cgtctacaga cacagcctac     240
atggagctga gcagcctgag atctgaggac acggccgtgt attactgtgc aagatcggat     300
ggttactacg atgctatgga ctactgggt caaggaacca cagtcaccgt ctcctcg         357
```

<210> SEQ ID NO 25
<211> LENGTH: 119
<212> TYPE: PRT
<213> ORGANISM: Artificial Sequence
<220> FEATURE:

<223> OTHER INFORMATION: humanized VH domain #1

<400> SEQUENCE: 25

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Tyr Phe Asn Pro Tyr Asn Asp Tyr Thr Arg Tyr Ala Glu Lys Phe
    50                  55                  60

Gln Gly Arg Val Thr Ile Thr Ala Asp Thr Ser Thr Ala Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Asp Gly Tyr Tyr Asp Ala Met Asp Tyr Trp Gly Gln Gly
                100                 105                 110

Thr Thr Val Thr Val Ser Ser
            115

<210> SEQ ID NO 26
<211> LENGTH: 357
<212> TYPE: DNA
<213> ORGANISM: Artificial Sequence
<220> FEATURE:
<223> OTHER INFORMATION: humanized VH domain #2

<400> SEQUENCE: 26
caggtccagc tggtacagtc tggggctgag gtgaagaagc ctggggcttc agtgaaggtc      60
tcctgcaagg cttctggata cacattcact gactactaca tgcactgggt gcgacaggcc     120
cctggacaag gcttgagtg gatgggatat tttaatcctt ataatgatta ctagatac       180
gcacagaagt tccagggcag agtcaccatg accaggaca cgtctatcag cacagcctac      240
atggagctga gcagcctgag atctgacgac acggccgtgt attactgtgc aagatcggat     300
ggttactacg atgctatgga ctactgggt caaggaacca cagtcaccgt ctcctcg        357

<210> SEQ ID NO 27
<211> LENGTH: 119
<212> TYPE: PRT
<213> ORGANISM: Artificial Sequence
<220> FEATURE:
<223> OTHER INFORMATION: humanized VH domain #2

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Tyr Phe Asn Pro Tyr Asn Asp Tyr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
            85                  90                  95

Ala Arg Ser Asp Gly Tyr Tyr Asp Ala Met Asp Tyr Trp Gly Gln Gly

Thr Thr Val Thr Val Ser Ser
    115

<210> SEQ ID NO 28
<211> LENGTH: 726
<212> TYPE: DNA
<213> ORGANISM: Artificial Sequence
<220> FEATURE:
<223> OTHER INFORMATION: humanized scFv A (VL-VH#1 orientation)

<400> SEQUENCE: 28

| gatatccaga tgacccagtc tccatccgcc atgtctgcat ctgtaggaga cagagtcacc | 60 |
| atcacttgcc gggcgagtaa gagcattagc aaatatttag cctggtttca gcagaaacca | 120 |
| gggaaagttc ctaagctccg catccattct ggatctactt tgcaatcagg ggtcccatct | 180 |
| cggttcagtg gcagtggatc tgggacagaa tttactctca ccatcagcag cctgcagcct | 240 |
| gaagattttg caacttatta ctgtcaacag catattgaat acccgtggac gttcggccaa | 300 |
| gggaccaagg tggaaatcaa acgaggtggc ggagggtctg gggtggcgg atccggaggt | 360 |
| ggtggctctg aggtccagct ggtacagtct ggggctgagg tgaagaagcc tggggctaca | 420 |
| gtgaagatct cctgcaaggc ttctggatac acattcactg actactacat gcactgggtg | 480 |
| caacaggccc ctggaaaagg gcttgagtgg atgggatatt ttaatcctta taatgattat | 540 |
| actagatacg cagagaagtt ccagggcaga gtcaccataa ccgcggacac gtctacagac | 600 |
| acagcctaca tggagctgag cagcctgaga tctgaggaca cggccgtgta ttactgtgca | 660 |
| agatcggatg gttactacga tgctatggac tactggggtc aaggaaccac agtcaccgtc | 720 |
| tcctcg | 726 |

<210> SEQ ID NO 29
<211> LENGTH: 726
<212> TYPE: DNA
<213> ORGANISM: Artificial Sequence
<220> FEATURE:
<223> OTHER INFORMATION: humanized scFv B (VL-VH#2 orientation)

<400> SEQUENCE: 29

| gatatccaga tgacccagtc tccatccgcc atgtctgcat ctgtaggaga cagagtcacc | 60 |
| atcacttgcc gggcgagtaa gagcattagc aaatatttag cctggtttca gcagaaacca | 120 |
| gggaaagttc ctaagctccg catccattct ggatctactt tgcaatcagg ggtcccatct | 180 |
| cggttcagtg gcagtggatc tgggacagaa tttactctca ccatcagcag cctgcagcct | 240 |
| gaagattttg caacttatta ctgtcaacag catattgaat acccgtggac gttcggccaa | 300 |
| gggaccaagg tggaaatcaa acgaggtggc ggagggtctg gggtggcgg atccggaggt | 360 |
| ggtggctctc aggtccagct ggtacagtct ggggctgagg tgaagaagcc tggggcttca | 420 |
| gtgaaggtct cctgcaaggc ttctggatac acattcactg actactacat gcactgggtg | 480 |
| cgacaggccc ctggacaagg gcttgagtgg atgggatatt ttaatcctta taatgattat | 540 |
| actagatacg cacagaagtt ccagggcaga gtcaccatga ccagggacac gtctatcagc | 600 |
| acagcctaca tggagctgag cagcctgaga tctgacgaca cggccgtgta ttactgtgca | 660 |
| agatcggatg gttactacga tgctatggac tactggggtc aaggaaccac agtcaccgtc | 720 |
| tcctcg | 726 |

<210> SEQ ID NO 30

<211> LENGTH: 242
<212> TYPE: PRT
<213> ORGANISM: Artificial Sequence
<220> FEATURE:
<223> OTHER INFORMATION: humanized scFv A (VL-VH#1 orientation)

<400> SEQUENCE: 30

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Glu Val Gln Leu Val
        115                 120                 125

Gln Ser Gly Ala Glu Val Lys Lys Pro Gly Ala Thr Val Lys Ile Ser
    130                 135                 140

Cys Lys Ala Ser Gly Tyr Thr Phe Thr Asp Tyr Tyr Met His Trp Val
145                 150                 155                 160

Gln Gln Ala Pro Gly Lys Gly Leu Glu Trp Met Gly Tyr Phe Asn Pro
                165                 170                 175

Tyr Asn Asp Tyr Thr Arg Tyr Ala Glu Lys Phe Gln Gly Arg Val Thr
            180                 185                 190

Ile Thr Ala Asp Thr Ser Thr Asp Thr Ala Tyr Met Glu Leu Ser Ser
        195                 200                 205

Leu Arg Ser Glu Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser

<210> SEQ ID NO 31
<211> LENGTH: 242
<212> TYPE: PRT
<213> ORGANISM: Artificial Sequence
<220> FEATURE:
<223> OTHER INFORMATION: humanized scFv B (VL-VH#2 orientation)

<400> SEQUENCE: 31

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
            115                 120                 125

Gln Ser Gly Ala Glu Val Lys Lys Pro Gly Ala Ser Val Lys Val Ser
130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
                180                 185                 190

Met Thr Arg Asp Thr Ser Ile Ser Thr Ala Tyr Met Glu Leu Ser Ser
            195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser

<210> SEQ ID NO 32
<211> LENGTH: 732
<212> TYPE: DNA
<213> ORGANISM: Artificial Sequence
<220> FEATURE:
<223> OTHER INFORMATION: humanized scFv A (VH#1-VL orientation)

<400> SEQUENCE: 32
gaggtccagc tggtacagtc tggggctgag gtgaagaagc ctggggctac agtgaagatc      60
tcctgcaagg cttctggata cacattcact gactactaca tgcactgggt gcaacaggcc     120
cctggaaaag gcttgagtg gatgggatat tttaatcctt ataatgatta tactagatac      180
gcagagaagt tccagggcag agtcaccata accgcggaca cgtctacaga cacagcctac     240
atggagctga gcagcctgag atctgaggac acggccgtgt attactgtgc aagatcggat     300
ggttactacg atgctatgga ctactggggt caaggaacca cagtcaccgt ctcctcaggt     360
ggcggagggt ctgggggtgg cggatccgga ggtggtggct ctgatatcca gatgacccag     420
tctccatccg ccatgtctgc atctgtagga gacagagtca ccatcacttg ccgggcgagt     480
aagagcatta gcaaatattt agcctggttt cagcagaaac cagggaaagt tcctaagctc     540
cgcatccatt ctggatctac tttgcaatca ggggtcccat ctcggttcag tgcagtgga    600 tctgggacag aatttactct caccatcagc agcctgcagc tgaagatttt gcaacttat     660 tactgtcaac agcatattga ataccgtgg acgttcggcc aagggaccaa ggtggaaatc     720
aaacgagcct cg                                                         732

<210> SEQ ID NO 33
<211> LENGTH: 732
<212> TYPE: DNA
<213> ORGANISM: Artificial Sequence
<220> FEATURE:
<223> OTHER INFORMATION: humanized scFv B (VH#2-VL orientation)

<400> SEQUENCE: 33

```
caggtccagc tggtacagtc tggggctgag gtgaagaagc ctggggcttc agtgaaggtc    60
tcctgcaagg cttctggata cacattcact gactactaca tgcactgggt gcgacaggcc   120
cctggacaag ggcttgagtg gatgggatat tttaatcctt ataatgatta ctagatac    180
gcacagaagt tccagggcag agtcaccatg accagggaca cgtctatcag cacagcctac   240
atggagctga gcagcctgag atctgacgac acggccgtgt attactgtgc aagatcggat   300
ggttactacg atgctatgga ctactggggt caaggaacca cagtcaccgt ctcctcaggt   360
ggcggagggt ctgggggtgg cggatccgga ggtggtggct ctgatatcca gatgacccag   420
tctccatccg ccatgtctgc atctgtagga gacagagtca ccatcacttg ccgggcgagt   480
aagagcatta gcaaatattt agcctggttt cagcagaaac agggaaagt tcctaagctc    540
cgcatccatt ctggatctac tttgcaatca ggggtcccat ctcggttcag tggcagtgga   600
tctgggacag aatttactct caccatcagc agcctgcagc ctgaagattt tgcaacttat   660
tactgtcaac agcatattga atacccgtgg acgttcggcc aagggaccaa ggtggaaatc   720
aaacgcgcct cg                                                      732

<210> SEQ ID NO 34
<211> LENGTH: 244
<212> TYPE: PRT
<213> ORGANISM: Artificial Sequence
<220> FEATURE:
<223> OTHER INFORMATION: humanized scFv A (VH#1-VL orientation)

<400> SEQUENCE: 34

Glu Val Gln Leu Val Gln Ser Gly Ala Glu Val Lys Lys Pro Gly Ala
  1               5                  10                  15

Thr Val Lys Ile Ser Cys Lys Ala Ser Gly Tyr Thr Phe Thr Asp Tyr
                 20                  25                  30

Tyr Met His Trp Val Gln Gln Ala Pro Gly Lys Gly Leu Glu Trp Met
             35                  40                  45

Gly Tyr Phe Asn Pro Tyr Asn Asp Tyr Thr Arg Tyr Ala Glu Lys Phe
         50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Asp Gly Tyr Tyr Asp Ala Met Asp Tyr Trp Gly Gln Gly
            100                 105                 110

Thr Thr Val Thr Val Ser Ser Gly Gly Gly Gly Ser Gly Gly Gly Gly
            115                 120                 125

Ser Gly Gly Gly Gly Ser Asp Ile Gln Met Thr Gln Ser Pro Ser Ala
            130                 135                 140

Met Ser Ala Ser Val Gly Asp Arg Val Thr Ile Thr Cys Arg Ala Ser
145                 150                 155                 160

Lys Ser Ile Ser Lys Tyr Leu Ala Trp Phe Gln Gln Lys Pro Gly Lys
                165                 170                 175

Val Pro Lys Leu Arg Ile His Ser Gly Ser Thr Leu Gln Ser Gly Val
            180                 185                 190

Pro Ser Arg Phe Ser Gly Ser Gly Ser Gly Thr Glu Phe Thr Leu Thr
            195                 200                 205

Ile Ser Ser Leu Gln Pro Glu Asp Phe Ala Thr Tyr Tyr Cys Gln Gln
            210                 215                 220

His Ile Glu Tyr Pro Trp Thr Phe Gly Gln Gly Thr Lys Val Glu Ile
```

Lys Arg Ala Ser

<210> SEQ ID NO 35
<211> LENGTH: 244
<212> TYPE: PRT
<213> ORGANISM: Artificial Sequence
<220> FEATURE:
<223> OTHER INFORMATION: humanized scFv B (VH#2-VL orientation)

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Tyr Phe Asn Pro Tyr Asn Asp Tyr Thr Arg Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ser Asp Gly Tyr Tyr Asp Ala Met Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ala
    130                 135                 140

Met Ser Ala Ser Val Gly Asp Arg Val Thr Ile Thr Cys Arg Ala Ser
145                 150                 155                 160

Lys Ser Ile Ser Lys Tyr Leu Ala Trp Phe Gln Gln Lys Pro Gly Lys
                165                 170                 175

Val Pro Lys Leu Arg Ile His Ser Gly Ser Thr Leu Gln Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

His Ile Glu Tyr Pro Trp Thr Phe Gly Gln Gly Thr Lys Val Glu Ile
225                 230                 235                 240

Lys Arg Ala Ser

<210> SEQ ID NO 36
<211> LENGTH: 1494
<212> TYPE: DNA
<213> ORGANISM: Artificial Sequence
<220> FEATURE:
<223> OTHER INFORMATION: TSC085 chimeric SMIP (murine VL-VH scFv -
      human Fc)

<400> SEQUENCE: 36
atggaagcac cagcgcagct tctcttcctc ctgctactct ggctcccaga taccaccggt      60
gatgtccaga taacccagtc tccatcttat cttgctgcat ctcctggaga aaccattact     120
attaattgca gggcaagtaa gagcattagc aaatatttag cctggtatca agagaaacct     180
gggaaagcta ataagctact tatccattct ggatccactt tgcaatctgg aataccatca     240

-continued

```
aggttcagtg gcagtggatc tggtacagat ttcactctca ccatcagtag cctggagcct    300
gaagattttg caatgtatta ctgtcaacag catattgaat acccgtggac gttcggtggt    360
ggcaccaaac tggaaattaa acgggccggc ggcggcggaa gcggcggtgg cggcagcagc    420
ggcggcggcg gcagcgagat ccagctgcaa cagtctggac ctgagctggt gaagcctggg    480
gcttcagtga agatgtcctg caaggcttct ggatacacat tcactgacta ctacatgcac    540
tgggtgaagc agaacaatgg agagagcctt gagtggattg gatattttaa tccttataat    600
gattatacta gatacaacca gaatttcaat ggcaaggcca cattgactgt agacaagtcc    660
tccagcacag cctacatgca gctcaacagc ctgacatctg aggactctgc attctattac    720
tgtgcaagat cggatggtta ctacgatgct atggactact ggggtcaagg aacctcagtc    780
accgtctcct cgagtgagcc caaatcttct gacaaaactc acacatgccc accgtgccca    840
gcacctgaag ccgcgggtgc accgtcagtc ttcctcttcc ccccaaaacc caaggacacc    900
ctcatgatct cccggacccc tgaggtcaca tgcgtggtgg tggacgtgag ccacgaagac    960
cctgaggtca agttcaactg gtacgtggac ggcgtggagg tgcataatgc caagacaaag   1020
ccgcgggagg agcagtacaa cagcacgtac cgtgtggtca gcgtcctcac cgtcctgcac   1080
caggactggc tgaatggcaa ggcgtacgcg tgcgcggtct ccaacaaagc cctcccagcc   1140
cccatcgaga aaaccatctc caaagccaaa gggcagcccc gagaaccaca ggtgtacacc   1200
ctgcccccat cccgggatga gctgaccaag aaccaggtca gcctgacctg cctggtcaaa   1260
ggcttctatc caagcgacat cgccgtggag tgggagagca atgggcagcc ggagaacaac   1320
tacaagacca cgcctcccgt gctggactcc gacggctcct tcttcctcta cagcaagctc   1380
accgtggaca agagcaggtg gcagcagggg aacgtcttct catgctccgt gatgcatgag   1440
gctctgcaca accactacac gcagaagagc ctctccctgt ctccgggtaa atga         1494
```

<210> SEQ ID NO 37
<211> LENGTH: 1497
<212> TYPE: DNA
<213> ORGANISM: Artificial Sequence
<220> FEATURE:
<223> OTHER INFORMATION: TSC092 chimeric SMIP (murine VH-VL scFv -
      human Fc)

<400> SEQUENCE: 37

```
atggaagcac cagcgcagct tctcttcctc ctgctactct ggctcccaga taccaccggt     60
gagatccagc tgcaacagtc tggacctgag ctggtgaagc ctggggcttc agtgaagatg    120
tcctgcaagg cttctggata cacattcact gactactaca tgcactgggt gaagcagaac    180 aatgagaga gccttgagtg gattggatat tttaatcctt ataatgatta ctactagatac    240 aaccagaatt tcaatggcaa ggccacattg actgtagaca agtcctccag cacagcctac    300
atgcagctca acagcctgac atctgaggac tctgcattct attactgtgc aagatcggat    360
ggttactacg atgctatgga ctactggggt caaggaacct cagtcaccgt ctcctcaggc    420
ggcggcggaa gcggcggtgg cggcagcagc ggcggcggcg gcagcgatgt ccagataacc    480
cagtctccat cttatcttgc tgcatctcct ggagaaacca ttactattaa ttgcagggca    540
agtaagagca ttagcaaata tttagcctgg tatcaagaga aacctgggaa agctaataag    600
ctacttatcc attctggatc cactttgcaa tctggaatac catcaaggtt cagtggcagt    660
ggatctggta cagatttcac tctcaccatc agtagcctgg agcctgaaga ttttgcaatg    720
tattactgtc aacagcatat tgaatacccg tggacgttcg gtggtggcac caaactggaa    780
```

-continued

```
attaaacggg cctcgagtga gcccaaatct tctgacaaaa ctcacacatg cccaccgtgc      840
ccagcacctg aagccgcggg tgcaccgtca gtcttcctct ccccccaaa acccaaggac      900
accctcatga tctcccggac ccctgaggtc acatgcgtgg tggtggacgt gagccacgaa      960
gaccctgagg tcaagttcaa ctggtacgtg acggcgtgg aggtgcataa tgccaagaca     1020
aagccgcggg aggagcagta caacagcacg taccgtgtgg tcagcgtcct caccgtcctg     1080
caccaggact ggctgaatgg caaggcgtac gcgtgcgcgg tctccaacaa agccctccca     1140
gcccccatcg agaaaaccat ctccaaagcc aaagggcagc ccgagaacc acaggtgtac     1200
accctgcccc catcccggga tgagctgacc aagaaccagg tcagcctgac ctgcctggtc     1260
aaaggcttct atcccagcga catcgccgtg gagtgggaga gcaatgggca gccggagaac     1320
aactacaaga ccacgcctcc cgtgctggac tccgacggct ccttcttcct ctacagcaag     1380
ctcaccgtgg acaagagcag gtggcagcag gggaacgtct tctcatgctc cgtgatgcat     1440
gaggctctgc acaaccacta cacgcagaag agcctctccc tgtctccggg taaatga     1497
```

<210> SEQ ID NO 38
<211> LENGTH: 477
<212> TYPE: PRT
<213> ORGANISM: Artificial Sequence
<220> FEATURE:
<223> OTHER INFORMATION: TSC085 chimeric SMIP (murine VL-VH scFv - human Fc)

<400> SEQUENCE: 38

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Ala Asn Lys Leu Leu Ile
            35                  40                  45

His Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Ile Glu Tyr Pro Trp
                85                  90                  95

Thr Phe Gly Gly Gly Thr Lys Leu Glu Ile Lys Arg Ala Gly Gly Gly
                100                 105                 110

Gly Ser Gly Gly Gly Gly Ser Gly Gly Gly Gly Ser Glu Ile Gln
            115                 120                 125

Leu Gln Gln Ser Gly Pro Glu Leu Val Lys Pro Gly Ala Ser Val Lys
        130                 135                 140

Met Ser Cys Lys Ala Ser Gly Tyr Thr Phe Thr Asp Tyr Tyr Met His
145                 150                 155                 160

Trp Val Lys Gln Asn Asn Gly Glu Ser Leu Glu Trp Ile Gly Tyr Phe
                165                 170                 175

Asn Pro Tyr Asn Asp Tyr Thr Arg Tyr Asn Gln Asn Phe Asn Gly Lys
                180                 185                 190

Ala Thr Leu Thr Val Asp Lys Ser Ser Thr Ala Tyr Met Gln Leu
            195                 200                 205

Asn Ser Leu Thr Ser Glu Asp Ser Ala Phe Tyr Tyr Cys Ala Arg Ser
        210                 215                 220

Asp Gly Tyr Tyr Asp Ala Met Asp Tyr Trp Gly Gln Gly Thr Ser Val
```

```
                225                 230                 235                 240
Thr Val Ser Ser Glu Pro Lys Ser Asp Lys Thr His Thr Cys
                245                 250                 255

Pro Pro Cys Pro Ala Pro Glu Ala Ala Gly Ala Pro Ser Val Phe Leu
                260                 265                 270

Phe Pro Pro Lys Pro Lys Asp Thr Leu Met Ile Ser Arg Thr Pro Glu
                275                 280                 285

Val Thr Cys Val Val Val Asp Val Ser His Glu Asp Pro Glu Val Lys
                290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Ala Tyr Ala Cys Ala
                340                 345                 350

Val Ser Asn Lys Ala Leu Pro Ala Pro Ile Glu Lys Thr Ile Ser Lys
                355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
                420                 425                 430

Ser Phe Phe Leu Tyr Ser Lys Leu Thr Val Asp Lys Ser Arg Trp Gln
                435                 440                 445

Gln Gly Asn Val Phe Ser Cys Ser Val Met His Glu Ala Leu His Asn
                450                 455                 460

His Tyr Thr Gln Lys Ser Leu Ser Leu Ser Pro Gly Lys
465                 470                 475

<210> SEQ ID NO 39
<211> LENGTH: 478
<212> TYPE: PRT
<213> ORGANISM: Artificial Sequence
<220> FEATURE:
<223> OTHER INFORMATION: TSC092 chimeric SMIP (murine VH-VL scFv -
      human Fc)

<400> SEQUENCE: 39

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met His Trp Val Lys Gln Asn Asn Gly Glu Ser Leu Glu Trp Ile
            35                  40                  45

Gly Tyr Phe Asn Pro Tyr Asn Asp Tyr Thr Arg Tyr Asn Gln Asn Phe
        50                  55                  60

Asn Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Phe Tyr Tyr Cys
                85                  90                  95

Ala Arg Ser Asp Gly Tyr Tyr Asp Ala Met Asp Tyr Trp Gly Gln Gly
                100                 105                 110
```

```
Thr Ser Val Thr Val Ser Gly Gly Gly Ser Gly Gly Gly
            115                 120                 125
Ser Ser Gly Gly Gly Ser Asp Val Gln Ile Thr Gln Ser Pro Ser
        130                 135                 140
Tyr Leu Ala Ala Ser Pro Gly Glu Thr Ile Thr Ile Asn Cys Arg Ala
145                 150                 155                 160
Ser Lys Ser Ile Ser Lys Tyr Leu Ala Trp Tyr Gln Glu Lys Pro Gly
                165                 170                 175
Lys Ala Asn Lys Leu Leu Ile His Ser Gly Ser Thr Leu Gln Ser Gly
            180                 185                 190
Ile Pro Ser Arg Phe Ser Gly Ser Gly Ser Gly Thr Asp Phe Thr Leu
        195                 200                 205
Thr Ile Ser Ser Leu Glu Pro Glu Asp Phe Ala Met Tyr Tyr Cys Gln
210                 215                 220
Gln His Ile Glu Tyr Pro Trp Thr Phe Gly Gly Gly Thr Lys Leu Glu
225                 230                 235                 240
Ile Lys Arg Ala Ser Ser Glu Pro Lys Ser Ser Asp Lys Thr His Thr
                245                 250                 255
Cys Pro Pro Cys Pro Ala Pro Glu Ala Ala Gly Ala Pro Ser Val Phe
            260                 265                 270
Leu Phe Pro Pro Lys Pro Lys Asp Thr Leu Met Ile Ser Arg Thr Pro
        275                 280                 285
Glu Val Thr Cys Val Val Val Asp Val Ser His Glu Asp Pro Glu Val
290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
                325                 330                 335
Leu Thr Val Leu His Gln Asp Trp Leu Asn Gly Lys Ala Tyr Ala Cys
            340                 345                 350
Ala Val Ser Asn Lys Ala Leu Pro Ala Pro Ile Glu Lys Thr Ile Ser
        355                 360                 365
Lys Ala Lys Gly Gln Pro Arg Glu Pro Gln Val Tyr Thr Leu Pro Pro
370                 375                 380
Ser Arg Asp Glu Leu Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
            420                 425                 430
Gly Ser Phe Phe Leu Tyr Ser Lys Leu Thr Val Asp Lys Ser Arg Trp
        435                 440                 445
Gln Gln Gly Asn Val Phe Ser Cys Ser Val Met His Glu Ala Leu His
450                 455                 460
Asn His Tyr Thr Gln Lys Ser Leu Ser Leu Ser Pro Gly Lys
465                 470                 475

<210> SEQ ID NO 40
<211> LENGTH: 1488
<212> TYPE: DNA
<213> ORGANISM: Artificial Sequence
<220> FEATURE:
<223> OTHER INFORMATION: TSC188 humanized SMIP (human VL-VH#1 scFv-Fc)

<400> SEQUENCE: 40
```

| | |
|---|---|
| atggaagcac cagcgcagct tctcttcctc ctgctactct ggctcccaga taccaccggt | 60 |
| gatatccaga tgacccagtc tccatccgcc atgtctgcat ctgtaggaga cagagtcacc | 120 |
| atcacttgcc gggcgagtaa gagcattagc aaatatttag cctggtttca gcagaaacca | 180 |
| gggaaagttc ctaagctccg catccattct ggatctactt tgcaatcagg ggtcccatct | 240 |
| cggttcagtg gcagtggatc tgggacagaa tttactctca ccatcagcag cctgcagcct | 300 |
| gaagattttg caacttatta ctgtcaacag catattgaat acccgtggac gttcggccaa | 360 |
| gggaccaagg tggaaatcaa acgaggtggc ggagggtctg ggggtggcgg atccggaggt | 420 |
| ggtggctctg aggtccagct ggtacagtct ggggctgagg tgaagaagcc tggggctaca | 480 |
| gtgaagatct cctgcaaggc ttctggatac acattcactg actactacat gcactgggtg | 540 |
| caacaggccc ctggaaaagg gcttgagtgg atgggatatt ttaatcctta taatgattat | 600 |
| actagatacg cagagaagtt ccagggcaga gtcaccataa ccgcggacac gtctacagac | 660 |
| acagcctaca tggagctgag cagcctgaga tctgaggaca cggccgtgta ttactgtgca | 720 |
| agatcggatg gttactacga tgctatggac tactggggtc aaggaaccac agtcaccgtc | 780 |
| tcctcgagtg agcccaaatc ttctgacaaa actcacacat gcccaccgtg cccagcacct | 840 |
| gaagccgcgg gtgcaccgtc agtcttcctc ttccccccaa aacccaagga caccctcatg | 900 |
| atctcccgga cccctgaggt cacatgcgtg gtggtggacg tgagccacga agaccctgag | 960 |
| gtcaagttca actggtacgt ggacggcgtg gaggtgcata atgccaagac aaagccgcgg | 1020 |
| gaggagcagt acaacagcac gtaccgtgtg gtcagcgtcc tcaccgtcct gcaccaggac | 1080 |
| tggctgaatg gcaaggcgta cgcgtgcgcg gtctccaaca aagccctccc agcccccatc | 1140 |
| gagaaaacca tctccaaagc caaagggcag ccccgagaac cacaggtgta caccctgccc | 1200 |
| ccatcccggg atgagctgac caagaaccag gtcagcctga cctgcctggt caaaggcttc | 1260 |
| tatccaagcg acatcgccgt ggagtgggag agcaatgggc agccggagaa caactacaag | 1320 |
| accacgcctc ccgtgctgga ctccgacggc tccttcttcc tctacagcaa gctcaccgtg | 1380 |
| gacaagagca ggtggcagca ggggaacgtc ttctcatgct ccgtgatgca tgaggctctg | 1440 |
| cacaaccact acacgcagaa gagcctctcc ctgtctccgg gtaaatga | 1488 |

<210> SEQ ID NO 41
<211> LENGTH: 1488
<212> TYPE: DNA
<213> ORGANISM: Artificial Sequence
<220> FEATURE:
<223> OTHER INFORMATION: TSC189 humanized SMIP (human VL-VH#2 scFv-Fc)

<400> SEQUENCE: 41

| | |
|---|---|
| atggaagcac cagcgcagct tctcttcctc ctgctactct ggctcccaga taccaccggt | 60 |
| gatatccaga tgacccagtc tccatccgcc atgtctgcat ctgtaggaga cagagtcacc | 120 |
| atcacttgcc gggcgagtaa gagcattagc aaatatttag cctggtttca gcagaaacca | 180 |
| gggaaagttc ctaagctccg catccattct ggatctactt tgcaatcagg ggtcccatct | 240 |
| cggttcagtg gcagtggatc tgggacagaa tttactctca ccatcagcag cctgcagcct | 300 |
| gaagattttg caacttatta ctgtcaacag catattgaat acccgtggac gttcggccaa | 360 |
| gggaccaagg tggaaatcaa acgaggtggc ggagggtctg ggggtggcgg atccggaggt | 420 |
| ggtggctctc aggtccagct ggtacagtct ggggctgagg tgaagaagcc tggggcttca | 480 |
| gtgaaggtct cctgcaaggc ttctggatac acattcactg actactacat gcactgggtg | 540 |
| cgacaggccc ctggacaagg gcttgagtgg atgggatatt ttaatcctta taatgattat | 600 |

```
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg ttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtaaatga                1488
```

<210> SEQ ID NO 42
<211> LENGTH: 475
<212> TYPE: PRT
<213> ORGANISM: Artificial Sequence
<220> FEATURE:
<223> OTHER INFORMATION: TSC188 humanized SMIP (human VL-VH#1 scFv-Fc)

<400> SEQUENCE: 42

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Glu Val Gln Leu Val
        115                 120                 125

Gln Ser Gly Ala Glu Val Lys Lys Pro Gly Ala Thr Val Lys Ile Ser
    130                 135                 140

Cys Lys Ala Ser Gly Tyr Thr Phe Thr Asp Tyr Tyr Met His Trp Val
145                 150                 155                 160

Gln Gln Ala Pro Gly Lys Gly Leu Glu Trp Met Gly Tyr Phe Asn Pro
                165                 170                 175

Tyr Asn Asp Tyr Thr Arg Tyr Ala Glu Lys Phe Gln Gly Arg Val Thr
            180                 185                 190

Ile Thr Ala Asp Thr Ser Thr Asp Thr Ala Tyr Met Glu Leu Ser Ser
        195                 200                 205
```

-continued

Leu Arg Ser Glu Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 43
<211> LENGTH: 475
<212> TYPE: PRT
<213> ORGANISM: Artificial Sequence
<220> FEATURE:
<223> OTHER INFORMATION: TSC189 humanized SMIP (human VL-VH#2 scFv-Fc)

<400> SEQUENCE: 43

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly
                100                 105                 110

Ser Gly Gly Gly Gly Ser Gly Gly Gly Ser Gln Val Gln Leu Val
            115                 120                 125

Gln Ser Gly Ala Glu Val Lys Lys Pro Gly Ala Ser Val Lys Val Ser
130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
                180                 185                 190

Met Thr Arg Asp Thr Ser Ile Ser Thr Ala Tyr Met Glu Leu Ser Ser
            195                 200                 205

Leu Arg Ser Asp Asp Thr Ala Val Tyr Tyr Cys Ala Arg Ser Asp Gly
        210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475

<210> SEQ ID NO 44
<211> LENGTH: 1794
<212> TYPE: DNA
<213> ORGANISM: Artificial Sequence
<220> FEATURE:

<223> OTHER INFORMATION: chimeric TSC084 Interceptor (murine VL-VH
      107-1A4 scFv-Fc-CH1)

<400> SEQUENCE: 44

| | | |
|---|---|---|
| atggaagcac cagcgcagct tctcttcctc ctgctactct ggctcccaga taccaccggt | 60 |
| gatgtccaga taacccagtc tccatcttat cttgctgcat ctcctggaga aaccattact | 120 |
| attaattgca gggcaagtaa gagcattagc aaatatttag cctggtatca agagaaacct | 180 |
| gggaaagcta ataagctact tatccattct ggatccactt tgcaatctgg aataccatca | 240 |
| aggttcagtg gcagtggatc tggtacagat ttcactctca ccatcagtag cctggagcct | 300 |
| gaagattttg caatgtatta ctgtcaacag catattgaat acccgtggac gttcggtggt | 360 |
| ggcaccaaac tggaaattaa acgggccggc ggcggcggaa gcggcggtgg cggcagcagc | 420 |
| ggcggcggcg gcagcgagat ccagctgcaa cagtctggac ctgagctggt gaagcctggg | 480 |
| gcttcagtga agatgtcctg caaggcttct ggatacacat tcactgacta ctacatgcac | 540 |
| tgggtgaagc agaacaatgg agagagcctt gagtggattg gatattttaa tcctt ataat | 600 |
| gattatacta gatacaacca gaatttcaat ggcaaggcca cattgactgt agacaagtcc | 660 |
| tccagcacag cctacatgca gctcaacagc ctgacatctg aggactctgc attctattac | 720 |
| tgtgcaagat cggatggtta ctacgatgct atggactact ggggtcaagg aacctcagtc | 780 |
| accgtctcct cgagcgagcc caaatcttct gacaaaactc acacatgccc accgtgccca | 840 |
| gcacctgaag ccgcgggtgc accgtcagtc ttcctcttcc ccccaaaacc caaggacacc | 900 |
| ctcatgatct cccggacccc tgaggtcaca tgcgtggtgg tggacgtgag ccacgaagac | 960 |
| cctgaggtca agttcaactg gtacgtggac ggcgtggagg tgcataatgc caagacaaag | 1020 |
| ccgcgggagg agcagtacaa cagcacgtac cgtgtggtca gcgtcctcac cgtcctgcac | 1080 |
| caggactggc tgaatggcaa ggcgtacgcg tgcgcggtct ccaacaaagc cctcccagcc | 1140 |
| cccatcgaga aaaccatctc caaagccaaa gggcagcccc gagaaccaca ggtgtacacc | 1200 |
| ctgcccccat cccgggatga gctgaccaag aaccaggtca gcctgacctg cctggtcaaa | 1260 |
| ggcttctatc caagcgacat cgccgtggag tgggagagca atgggcagcc ggagaacaac | 1320 |
| tacaagacca cgcctcccgt gctggactcc gacggctcct tcttcctcta cagcaagctc | 1380 |
| accgtggaca gagcaggtg gcagcagggg aacgtcttct catgctccgt gatgcatgag | 1440 |
| gctctgcaca accactacac gcagaagagc ctctccctgt ctccgggtaa atctagagcc | 1500 |
| tccaccaagg gcccatcggt cttccccctg gcaccctcct ccaagagcac ctctggggc | 1560 |
| acagcggccc tgggctgcct ggtcaaggac tacttccccg agccggtgac ggtgtcgtgg | 1620 |
| aactcaggcg ccctgaccag cggcgtgcac accttcccgg ctgtcctaca gtcctcagga | 1680 |
| ctctactccc tcagcagcgt ggtgaccgtg ccctccagca gcttgggcac ccagacctac | 1740 |
| atctgcaacg tgaatcacaa gcccagcaac accaaggtgg acaagaaagt ttga | 1794 |

<210> SEQ ID NO 45
<211> LENGTH: 1821
<212> TYPE: DNA
<213> ORGANISM: Artificial Sequence
<220> FEATURE:
<223> OTHER INFORMATION: TSC093 Interceptor (Cris7 scFv-Fc-CkYAE)

<400> SEQUENCE: 45

| | |
|---|---|
| atggaagcac cagcgcagct tctcttcctc ctgctactct ggctcccaga taccaccggt | 60 |
| caggtccagc tggtgcagtc tggggcgga gtggtgcagc ctgggcggtc actgaggctg | 120 |

```
tcctgcaagg cttctggcta cacctttact agatctacga tgcactgggt aaggcaggcc      180
cctggaaagg gtctggaatg gattggatac attaatccta gcagtgctta tactaattac      240
aatcagaaat tcaaggacag gttcacaatc agcgcagaca atccaagag cacagccttc       300 ctgcagatgg acagcctgag gcccgaggac accggcgtct atttctgtgc acggccccaa      360
gtccactatg attacaacgg gtttccttac tggggccaag ggactcccgt cactgtctct      420
agcggtggcg gagggtctgg gggtggcgga tccggaggtg gtggctctgc acaagacatc      480
cagatgaccc agtctccaag cagcctgtct gcaagcgtgg gggacaggt caccatgacc       540 tgcagtgcca gctcaagtgt aagttacatg aactggtacc agcagaagcc cggcaaggcc      600
cccaaaagat ggatttatga ctcatccaaa ctggcttctg gagtccctgc tcgcttcagt      660
ggcagtgggt ctgggaccga ctataccctc acaatcagca gcctgcagcc cgaagatttc      720
gccacttatt actgccagca gtggagtcgt aacccaccca cgttcggagg ggggaccaag      780
ctacaaatta cacgctcgag tgagcccaaa tcttctgaca aaactcacac atgcccaccg      840
tgcccagcac ctgaagccgc gggtgcaccg tcagtcttcc tcttcccccc aaaacccaag      900
gacaccctca tgatctcccg gacccctgag gtcacatgcg tggtggtgga cgtgagccac      960
gaagaccctg aggtcaagtt caactggtac gtggacggcg tggaggtgca taatgccaag      1020
acaaagccgc gggaggagca gtacaacagc acgtaccgtg tggtcagcgt cctcaccgtc      1080
ctgcaccagg actggctgaa tggcaaggcg tacgcgtgcg cggtctccaa caaagccctc      1140
ccagccccca tcgagaaaac catctccaaa gccaaagggc agccccgaga accacaggtg      1200
tacaccctgc ccccatcccg ggatgagctg accaagaacc aggtcagcct gacctgcctg      1260
gtcaaaggct tctatccaag cgacatcgcc gtggagtggg agagcaatgg gcagccggag      1320
aacaactaca agaccacgcc tcccgtgctg gactccgacg gctccttctt cctctacagc      1380
aagctcaccg tggacaagag caggtggcag caggggaacg tcttctcatg ctccgtgatg      1440
catgaggctc tgcacaacca ctacacgcag aagagcctct ccctgtctcc gggtaaatct      1500
agaactgtgg ctgcaccatc tgtcttcatc ttcccgccat ctgatgagca gttgaaatct      1560
ggaactgcct ctgttgtgtg cctgctgaat tacttctatc ccagagaggc caaagtacag      1620
tggaaggtgg ataacgccct ccaatcgggt aactcccagg agagtgccac agagcaggac      1680
agcaaggaca gcacctacag cctcagcagc gagctgacgc tgagcaaagc agactacgag      1740
aaacacaaag tctacgcctg cgaagtcacc catcagggcc tgagctcgcc cgtcacaaag      1800
agcttcaaca ggggagagtg a                                                1821
```

<210> SEQ ID NO 46
<211> LENGTH: 577
<212> TYPE: PRT
<213> ORGANISM: Artificial Sequence
<220> FEATURE:
<223> OTHER INFORMATION: TSC084 Interceptor (murine VL-VH 107-1A4 scFv-Fc-CH1)

<400> SEQUENCE: 46

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Ala Asn Lys Leu Leu Ile
        35                  40                  45

His Ser Gly Ser Thr Leu Gln Ser Gly Ile Pro Ser Arg Phe Ser Gly
```

```
            50                  55                  60
Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Ile Glu Tyr Pro Trp
                     85                  90                  95

Thr Phe Gly Gly Gly Thr Lys Leu Glu Ile Lys Arg Ala Gly Gly Gly
                100                 105                 110

Gly Ser Gly Gly Gly Gly Ser Gly Gly Gly Gly Ser Glu Ile Gln
                115                 120                 125

Leu Gln Gln Ser Gly Pro Glu Leu Val Lys Pro Gly Ala Ser Val Lys
        130                 135                 140

Met Ser Cys Lys Ala Ser Gly Tyr Thr Phe Thr Asp Tyr Tyr Met His
145                 150                 155                 160

Trp Val Lys Gln Asn Asn Gly Glu Ser Leu Glu Trp Ile Gly Tyr Phe
                165                 170                 175

Asn Pro Tyr Asn Asp Tyr Thr Arg Tyr Asn Gln Asn Phe Asn Gly Lys
                180                 185                 190

Ala Thr Leu Thr Val Asp Lys Ser Ser Thr Ala Tyr Met Gln Leu
                195                 200                 205

Asn Ser Leu Thr Ser Glu Asp Ser Ala Phe Tyr Tyr Cys Ala Arg Ser
        210                 215                 220

Asp Gly Tyr Tyr Asp Ala Met Asp Tyr Trp Gly Gln Gly Thr Ser Val
225                 230                 235                 240

Thr Val Ser Ser Glu Pro Lys Ser Ser Asp Lys Thr His Thr Cys
                245                 250                 255

Pro Pro Cys Pro Ala Pro Glu Ala Ala Gly Ala Pro Ser Val Phe Leu
                260                 265                 270

Phe Pro Pro Lys Pro Lys Asp Thr Leu Met Ile Ser Arg Thr Pro Glu
                275                 280                 285

Val Thr Cys Val Val Val Asp Val Ser His Glu Asp Pro Glu Val Lys
                290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Ala Tyr Ala Cys Ala
                340                 345                 350

Val Ser Asn Lys Ala Leu Pro Ala Pro Ile Glu Lys Thr Ile Ser Lys
                355                 360                 365

Ala Lys Gly Gln Pro Arg Glu Pro Gln Val Tyr Thr Leu Pro Pro Ser
                370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
                420                 425                 430

Ser Phe Phe Leu Tyr Ser Lys Leu Thr Val Asp Lys Ser Arg Trp Gln
                435                 440                 445

Gln Gly Asn Val Phe Ser Cys Ser Val Met His Glu Ala Leu His Asn
                450                 455                 460

His Tyr Thr Gln Lys Ser Leu Ser Leu Ser Pro Gly Lys Ser Arg Ala
465                 470                 475                 480
```

-continued

```
Ser Thr Lys Gly Pro Ser Val Phe Pro Leu Ala Pro Ser Ser Lys Ser
            485                 490                 495

Thr Ser Gly Gly Thr Ala Ala Leu Gly Cys Leu Val Lys Asp Tyr Phe
            500                 505                 510

Pro Glu Pro Val Thr Val Ser Trp Asn Ser Gly Ala Leu Thr Ser Gly
            515                 520                 525

Val His Thr Phe Pro Ala Val Leu Gln Ser Ser Gly Leu Tyr Ser Leu
            530                 535                 540

Ser Ser Val Val Thr Val Pro Ser Ser Ser Leu Gly Thr Gln Thr Tyr
545                 550                 555                 560

Ile Cys Asn Val Asn His Lys Pro Ser Asn Thr Lys Val Asp Lys Lys
                565                 570                 575

Val

<210> SEQ ID NO 47
<211> LENGTH: 586
<212> TYPE: PRT
<213> ORGANISM: Artificial Sequence
<220> FEATURE:
<223> OTHER INFORMATION: TSC093 Interceptor (Cris7 scFv-Fc-CkYAE)

<400> SEQUENCE: 47

Gln Val Gln Leu Val Gln Ser Gly Gly Val Val Gln Pro Gly Arg
1               5                   10                  15

Ser Leu Arg Leu Ser Cys Lys Ala Ser Gly Tyr Thr Phe Thr Arg Ser
                20                  25                  30

Thr Met His Trp Val Arg Gln Ala Pro Gly Lys Gly Leu Glu Trp Ile
            35                  40                  45

Gly Tyr Ile Asn Pro Ser Ser Ala Tyr Thr Asn Tyr Asn Gln Lys Phe
        50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Ser Gly Gly
        115                 120                 125

Gly Gly Ser Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190

Ser Gly Val Pro Ala Arg Phe Ser Gly Ser Gly Ser Gly Thr Asp Tyr
        195                 200                 205

Thr Leu Thr Ile Ser Ser Leu Gln Pro Glu Asp Phe Ala Thr Tyr Tyr
    210                 215                 220

Cys Gln Gln Trp Ser Arg Asn Pro Thr Phe Gly Gly Gly Thr Lys
225                 230                 235                 240

Leu Gln Ile Thr Arg Ser Ser Glu Pro Lys Ser Ser Asp Lys Thr His
                245                 250                 255
```

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Ser
465                 470                 475                 480

Arg Thr Val Ala Ala Pro Ser Val Phe Ile Phe Pro Pro Ser Asp Glu
                485                 490                 495

Gln Leu Lys Ser Gly Thr Ala Ser Val Val Cys Leu Leu Asn Tyr Phe
            500                 505                 510

Tyr Pro Arg Glu Ala Lys Val Gln Trp Lys Val Asp Asn Ala Leu Gln
        515                 520                 525

Ser Gly Asn Ser Gln Glu Ser Ala Thr Glu Gln Asp Ser Lys Asp Ser
    530                 535                 540

Thr Tyr Ser Leu Ser Ser Glu Leu Thr Leu Ser Lys Ala Asp Tyr Glu
545                 550                 555                 560

Lys His Lys Val Tyr Ala Cys Glu Val Thr His Gln Gly Leu Ser Ser
                565                 570                 575

Pro Val Thr Lys Ser Phe Asn Arg Gly Glu
            580                 585

<210> SEQ ID NO 48
<211> LENGTH: 2283
<212> TYPE: DNA
<213> ORGANISM: Artificial Sequence
<220> FEATURE:
<223> OTHER INFORMATION: humanized TSC194 Scorpion (huVL-VH#2 107-1A4
      scFv-Fc-Cris7 scFv)

<400> SEQUENCE: 48
atggaagcac cagcgcagct tctcttcctc ctgctactct ggctcccaga taccaccggt    60
gatatccaga tgacccagtc tccatccgcc atgtctgcat ctgtaggaga cagagtcacc   120
atcacttgcc gggcgagtaa gagcattagc aaatatttag cctggtttca gcagaaacca   180

```
gggaaagttc ctaagctccg catccattct ggatctactt tgcaatcagg ggtcccatct      240
cggttcagtg gcagtggatc tgggacagaa tttactctca ccatcagcag cctgcagcct      300
gaagattttg caacttatta ctgtcaacag catattgaat acccgtggac gttcggccaa      360
gggaccaagg tggaaatcaa acgaggtggc ggagggtctg ggggtggcgg atccggaggt      420
ggtggctctc aggtccagct ggtacagtct ggggctgagg tgaagaagcc tggggcttca      480
gtgaaggtct cctgcaaggc ttctggatac acattcactg actactacat gcactgggtg      540
cgacaggccc ctggacaagg gcttgagtgg atgggatatt ttaatcctta taatgattat      600
actagatacg cacagaagtt ccagggcaga gtcaccatga ccaggacac gtctatcagc       660 acagcctaca tggagctgag cagcctgaga tctgacgaca cggccgtgta ttactgtgca      720
agatcggatg gttactacga tgctatggac tactggggtc aaggaaccac agtcaccgtc      780
tcctcgagtg agcccaaatc ttctgacaaa actcacacat gcccaccgtg cccagcacct      840
gaagccgcgg gtgcaccgtc agtcttcctc ttcccccca aacccaagga cacccctcatg       900 atctcccgga cccctgaggt cacatgcgtg gtggtggacg tgagccacga agaccctgag      960
gtcaagttca actggtacgt ggacggcgtg gaggtgcata atgccaagac aaagccgcgg     1020
gaggagcagt acaacagcac gtaccgtgtg gtcagcgtcc tcaccgtcct gcaccaggac     1080
tggctgaatg gcaaggcgta cgcgtgcgcg gtctccaaca agccctccc agcccccatc      1140 gagaaaacca tctccaaagc caaagggcag ccccgagaac cacaggtgta caccctgccc     1200
ccatcccggg atgagctgac caagaaccag gtcagcctga cctgcctggt caaaggcttc     1260
tatccaagcg acatcgccgt ggagtgggag agcaatgggc agccggagaa caactacaag     1320
accacgcctc ccgtgctgga ctccgacggc tccttcttcc tctacagcaa gctcaccgtg     1380
gacaagagca ggtggcagca ggggaacgtc ttctcatgct ccgtgatgca tgaggctctg     1440
cacaaccact acacgcagaa gagcctctcc ctgtctccgg gtcagaggca caacaattct     1500
tccctgaata caggaactca gatggcaggt cattctccga attctcaggt ccagctggtg     1560
cagtctgggg gcggagtggt gcagcctggg cggtcactga ggctgtcctg caaggcttct     1620
ggctacacct ttactagatc tacgatgcac tgggtaaggc aggcccctgg aaagggtctg     1680
gaatggattg gatacattaa tcctagcagt gcttatacta attacaatca gaaattcaag     1740
gacaggttca caatcagcgc agacaaatcc aagagcacag ccttcctgca gatggacagc     1800
ctgaggcccg aggacaccgg cgtctatttc tgtgcacggc cccaagtcca ctatgattac     1860
aacgggtttc cttactgggg ccaagggact cccgtcactg tctctagcgg tggcggaggg     1920
tctgggggtg gcggatccgg aggtggtggc tctgcacaag acatccagat gacccagtct     1980
ccaagcagcc tgtctgcaag cgtggggac agggtcacca tgacctgcag tgccagctca     2040
agtgtaagtt acatgaactg gtaccagcag aagcccggca aggcccccaa agatggatt      2100 tatgactcat ccaaactggc ttctggagtc cctgctcgct tcagtggcag tgggtctggg     2160
accgactata ccctcacaat cagcagcctg agcccgaag atttcgccac ttattactgc      2220
cagcagtgga gtcgtaaccc acccacgttc ggagggggga ccaagctaca aattacacga     2280
taa                                                                   2283
```

<210> SEQ ID NO 49
<211> LENGTH: 740
<212> TYPE: PRT
<213> ORGANISM: Artificial Sequence
<220> FEATURE:

<223> OTHER INFORMATION: humanized TSC194 Scorpion (huVL-VH#2 107-1A4 scFv-Fc-Cris7 scFv)

<400> SEQUENCE: 49

| | | | | | | | | | | | | | | |
|---|---|---|---|---|---|---|---|---|---|---|---|---|---|---|
| Asp | Ile | Gln | Met | Thr | Gln | Ser | Pro | Ser | Ala | Met | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Lys | Ser | Ile | Ser | Lys | Tyr |
| | | | 20 | | | | | 25 | | | | | 30 | | |
| Leu | Ala | Trp | Phe | Gln | Gln | Lys | Pro | Gly | Lys | Val | Pro | Lys | Leu | Arg | Ile |
| | | | 35 | | | | | 40 | | | | | 45 | | |
| His | Ser | Gly | Ser | Thr | Leu | Gln | Ser | Gly | Val | Pro | Ser | Arg | Phe | Ser | Gly |
| | | 50 | | | | | 55 | | | | | 60 | | | |
| Ser | Gly | Ser | Gly | Thr | Glu | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | His | Ile | Glu | Tyr | Pro | Trp |
| | | | | 85 | | | | | 90 | | | | | 95 | |
| Thr | Phe | Gly | Gln | Gly | Thr | Lys | Val | Glu | Ile | Lys | Arg | Gly | Gly | Gly | Gly |
| | | | 100 | | | | | 105 | | | | | 110 | | |
| Ser | Gly | Gly | Gly | Gly | Ser | Gly | Gly | Gly | Ser | Gln | Val | Gln | Leu | Val |
| | | 115 | | | | | 120 | | | | | 125 | | | |
| Gln | Ser | Gly | Ala | Glu | Val | Lys | Lys | Pro | Gly | Ala | Ser | Val | Lys | Val | Ser |
| | 130 | | | | | 135 | | | | | 140 | | | | |
| Cys | Lys | Ala | Ser | Gly | Tyr | Thr | Phe | Thr | Asp | Tyr | Tyr | Met | His | Trp | Val |
| 145 | | | | | 150 | | | | | 155 | | | | | 160 |
| Arg | Gln | Ala | Pro | Gly | Gln | Gly | Leu | Glu | Trp | Met | Gly | Tyr | Phe | Asn | Pro |
| | | | | 165 | | | | | 170 | | | | | 175 | |
| Tyr | Asn | Asp | Tyr | Thr | Arg | Tyr | Ala | Gln | Lys | Phe | Gln | Gly | Arg | Val | Thr |
| | | | 180 | | | | | 185 | | | | | 190 | | |
| Met | Thr | Arg | Asp | Thr | Ser | Ile | Ser | Thr | Ala | Tyr | Met | Glu | Leu | Ser | Ser |
| | | 195 | | | | | 200 | | | | | 205 | | | |
| Leu | Arg | Ser | Asp | Asp | Thr | Ala | Val | Tyr | Tyr | Cys | Ala | Arg | Ser | Asp | Gly |
| | 210 | | | | | 215 | | | | | 220 | | | | |
| Tyr | Tyr | Asp | Ala | Met | Asp | Tyr | Trp | Gly | Gln | Gly | Thr | Thr | Val | Thr | Val |
| 225 | | | | | 230 | | | | | 235 | | | | | 240 |
| Ser | Ser | Ser | Glu | Pro | Lys | Ser | Ser | Asp | Lys | Thr | His | Thr | Cys | Pro | Pro |
| | | | | 245 | | | | | 250 | | | | | 255 | |
| Cys | Pro | Ala | Pro | Glu | Ala | Ala | Gly | Ala | Pro | Ser | Val | Phe | Leu | Phe | Pro |
| | | | 260 | | | | | 265 | | | | | 270 | | |
| Pro | Lys | Pro | Lys | Asp | Thr | Leu | Met | Ile | Ser | Arg | Thr | Pro | Glu | Val | Thr |
| | | 275 | | | | | 280 | | | | | 285 | | | |
| Cys | Val | Val | Val | Asp | Val | Ser | His | Glu | Asp | Pro | Glu | Val | Lys | Phe | Asn |
| | 290 | | | | | 295 | | | | | 300 | | | | |
| Trp | Tyr | Val | Asp | Gly | Val | Glu | Val | His | Asn | Ala | Lys | Thr | Lys | Pro | Arg |
| 305 | | | | | 310 | | | | | 315 | | | | | 320 |
| Glu | Glu | Gln | Tyr | Asn | Ser | Thr | Tyr | Arg | Val | Val | Ser | Val | Leu | Thr | Val |
| | | | | 325 | | | | | 330 | | | | | 335 | |
| Leu | His | Gln | Asp | Trp | Leu | Asn | Gly | Lys | Ala | Tyr | Ala | Cys | Ala | Val | Ser |
| | | | 340 | | | | | 345 | | | | | 350 | | |
| Asn | Lys | Ala | Leu | Pro | Ala | Pro | Ile | Glu | Lys | Thr | Ile | Ser | Lys | Ala | Lys |
| | | 355 | | | | | 360 | | | | | 365 | | | |
| Gly | Gln | Pro | Arg | Glu | Pro | Gln | Val | Tyr | Thr | Leu | Pro | Pro | Ser | Arg | Asp |
| | 370 | | | | | 375 | | | | | 380 | | | | |
| Glu | Leu | Thr | Lys | Asn | Gln | Val | Ser | Leu | Thr | Cys | Leu | Val | Lys | Gly | Phe |
| 385 | | | | | 390 | | | | | 395 | | | | | 400 |

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
        420                 425                 430

Phe Leu Tyr Ser Lys Leu Thr Val Asp Lys Ser Arg Trp Gln Gln Gly
    435                 440                 445

Asn Val Phe Ser Cys Ser Val Met His Glu Ala Leu His Asn His Tyr
450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
            485                 490                 495

Val Gln Leu Val Gln Ser Gly Gly Val Val Gln Pro Gly Arg Ser
        500                 505                 510

Leu Arg Leu Ser Cys Lys Ala Ser Gly Tyr Thr Phe Thr Arg Ser Thr
    515                 520                 525

Met His Trp Val Arg Gln Ala Pro Gly Lys Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560

Asp Arg Phe Thr Ile Ser Ala Asp Lys Ser Lys Ser Thr Ala Phe Leu
            565                 570                 575

Gln Met Asp Ser Leu Arg Pro Glu Asp Thr Gly Val Tyr Phe Cys Ala
            580                 585                 590

Arg Pro Gln Val His Tyr Asp Tyr Asn Gly Phe Pro Tyr Trp Gly Gln
        595                 600                 605

Gly Thr Pro Val Thr Val Ser Ser Gly Gly Gly Ser Gly Gly Gly
    610                 615                 620

Gly Ser Gly Gly Gly Gly Ser Ala Gln Asp Ile Gln Met Thr Gln Ser
625                 630                 635                 640

Pro Ser Ser Leu Ser Ala Ser Val Gly Asp Arg Val Thr Met Thr Cys
            645                 650                 655

Ser Ala Ser Ser Ser Val Ser Tyr Met Asn Trp Tyr Gln Gln Lys Pro
        660                 665                 670

Gly Lys Ala Pro Lys Arg Trp Ile Tyr Asp Ser Ser Lys Leu Ala Ser
    675                 680                 685

Gly Val Pro Ala Arg Phe Ser Gly Ser Gly Ser Gly Thr Asp Tyr Thr
    690                 695                 700

Leu Thr Ile Ser Ser Leu Gln Pro Glu Asp Phe Ala Thr Tyr Tyr Cys
705                 710                 715                 720

Gln Gln Trp Ser Arg Asn Pro Pro Thr Phe Gly Gly Gly Thr Lys Leu
            725                 730                 735

Gln Ile Thr Arg
            740

<210> SEQ ID NO 50
<211> LENGTH: 2283
<212> TYPE: DNA
<213> ORGANISM: Artificial Sequence
<220> FEATURE:
<223> OTHER INFORMATION: humanized TSC199 Scorpion (huVL-VH#1 107-1A4
      scFv-Fc-Cris7 scFv)

<400> SEQUENCE: 50
atggaagcac cagcgcagct tctcttcctc ctgctactct ggctcccaga taccaccggt    60

```
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg ggggtggcgg atccggaggt    420
ggtggctctg aggtccagct ggtacagtct ggggctgagg tgaagaagcc tggggctaca    480
gtgaagatct cctgcaaggc ttctggatac acattcactg actactacat gcactgggtg    540
caacaggccc ctggaaaagg gcttgagtgg atgggatatt taatccttta atgattat      600 actagatacg cagagaagtt ccagggcaga gtcaccataa ccgcggacac gtctacagac    660
acagcctaca tggagctgag cagcctgaga tctgaggaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa acccaaggga cccctcatg    900 atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac acaggtgta caccctgccc    1200 ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtcagaggca aacaattct   1500 tccctgaata caggaactca gatggcaggt cattctccga attctcaggt ccagctggtg   1560
cagtctgggg gcggagtggt gcagcctggg cggtcactga ggctgtcctg caaggcttct   1620
ggctacacct ttactagatc tacgatgcac tgggtaaggc aggcccctgg aaagggtctg   1680
gaatggattg gatacattaa tcctagcagt gcttatacta attacaatca gaaattcaag   1740
gacaggttca caatcagcgc agacaaatcc aagagcacag ccttcctgca gatggacagc   1800
ctgaggcccg aggacaccgg cgtctatttc tgtgcacggc cccaagtcca ctatgattac   1860
aacgggtttc cttactgggg ccaagggact cccgtcactg tctctagcgg tggcggaggg   1920 tctggggtg gcggatccgg aggtggtggc tctgcacaag acatccagat gacccagtct   1980
ccaagcagcc tgtctgcaag cgtggggac agggtcacca tgacctgcag tgccagctca   2040
agtgtaagtt acatgaactg gtaccagcag aagcccggca aggcccccaa agatggatt   2100 tatgactcat ccaaactggc ttctggagtc cctgctcgct tcagtggcag tgggtctggg   2160
accgactata ccctcacaat cagcagcctg cagcccgaag atttcgccac ttattactgc   2220
cagcagtgga gtcgtaaccc acccacgttc ggagggggga ccaagctaca aattacacga   2280
taa                                                                2283
```

<210> SEQ ID NO 51

<211> LENGTH: 740
<212> TYPE: PRT
<213> ORGANISM: Artificial Sequence
<220> FEATURE:
<223> OTHER INFORMATION: humanized TSC199 Scorpion (huVL-VH#1 107-1A4 scFv-Fc-Cris7 scFv)

<400> SEQUENCE: 51

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Glu Val Gln Leu Val
        115                 120                 125

Gln Ser Gly Ala Glu Val Lys Lys Pro Gly Ala Thr Val Lys Ile Ser
    130                 135                 140

Cys Lys Ala Ser Gly Tyr Thr Phe Thr Asp Tyr Tyr Met His Trp Val
145                 150                 155                 160

Gln Gln Ala Pro Gly Lys Gly Leu Glu Trp Met Gly Tyr Phe Asn Pro
                165                 170                 175

Tyr Asn Asp Tyr Thr Arg Tyr Ala Glu Lys Phe Gln Gly Arg Val Thr
            180                 185                 190

Ile Thr Ala Asp Thr Ser Thr Asp Thr Ala Tyr Met Glu Leu Ser Ser
        195                 200                 205

Leu Arg Ser Glu Asp Thr Ala Val Tyr Tyr Cys Ala Arg Ser Asp Gly
    210                 215                 220

Tyr Tyr Asp Ala Met Asp Tyr Trp Gly Gln Gly Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp

```
                370             375             380
Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
                485                 490                 495

Val Gln Leu Val Gln Ser Gly Gly Val Val Gln Pro Gly Arg Ser
            500                 505                 510

Leu Arg Leu Ser Cys Lys Ala Ser Gly Tyr Thr Phe Thr Arg Ser Thr
        515                 520                 525

Met His Trp Val Arg Gln Ala Pro Gly Lys Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560

Asp Arg Phe Thr Ile Ser Ala Asp Lys Ser Lys Ser Thr Ala Phe Leu
                565                 570                 575

Gln Met Asp Ser Leu Arg Pro Glu Asp Thr Gly Val Tyr Phe Cys Ala
            580                 585                 590

Arg Pro Gln Val His Tyr Asp Tyr Asn Gly Phe Pro Tyr Trp Gly Gln
        595                 600                 605

Gly Thr Pro Val Thr Val Ser Ser Gly Gly Gly Ser Gly Gly Gly
    610                 615                 620

Gly Ser Gly Gly Gly Gly Ser Ala Gln Asp Ile Gln Met Thr Gln Ser
625                 630                 635                 640

Pro Ser Ser Leu Ser Ala Ser Val Gly Asp Arg Val Thr Met Thr Cys
                645                 650                 655

Ser Ala Ser Ser Ser Val Ser Tyr Met Asn Trp Tyr Gln Gln Lys Pro
            660                 665                 670

Gly Lys Ala Pro Lys Arg Trp Ile Tyr Asp Ser Ser Lys Leu Ala Ser
        675                 680                 685

Gly Val Pro Ala Arg Phe Ser Gly Ser Gly Ser Gly Thr Asp Tyr Thr
    690                 695                 700

Leu Thr Ile Ser Ser Leu Gln Pro Glu Asp Phe Ala Thr Tyr Tyr Cys
705                 710                 715                 720

Gln Gln Trp Ser Arg Asn Pro Pro Thr Phe Gly Gly Gly Thr Lys Leu
                725                 730                 735

Gln Ile Thr Arg
            740

<210> SEQ ID NO 52
<211> LENGTH: 1800
<212> TYPE: DNA
<213> ORGANISM: Artificial Sequence
<220> FEATURE:
<223> OTHER INFORMATION: TSC125 Interceptor (Cris7 scFv-Fc-CH1)
```

<400> SEQUENCE: 52

```
atggaagcac cagcgcagct tctcttcctc ctgctactct ggctcccaga taccaccggt      60
caggtccagc tggtgcagtc tgggggcgga gtggtgcagc ctgggcggtc actgaggctg     120
tcctgcaagg cttctggcta cacctttact agatctacga tgcactgggt aaggcaggcc     180
cctggaaagg gtctggaatg gattggatac attaatccta gcagtgctta ctactaattac    240
aatcagaaat tcaaggacag gttcacaatc agcgcagaca atccaagag cacagccttc     300
ctgcagatgg acagcctgag gcccgaggac accggcgtct atttctgtgc acggccccaa    360
gtccactatg attacaacgg gtttccttac tggggccaag ggactcccgt cactgtctct    420
agcggtggcg gagggtctgg gggtggcgga tccggaggtg gtggctctgc acaagacatc    480
cagatgaccc agtctccaag cagcctgtct gcaagcgtgg gggacagggt caccatgacc    540
tgcagtgcca gctcaagtgt aagttacatg aactggtacc agcagaagcc cggcaaggcc    600
cccaaaagat ggatttatga ctcatccaaa ctggcttctg gagtccctgc tcgcttcagt    660
ggcagtgggt ctgggaccga ctataccctc acaatcagca gcctgcagcc cgaagatttc    720
gccacttatt actgccagca gtggagtcgt aacccaccca cgttcggagg ggggaccaag    780
ctacaaatta cacgctcgag tgagcccaaa tcttctgaca aaactcacac atgcccaccg    840
tgcccagcac ctgaagccgc gggtgcaccg tcagtcttcc tcttcccccc aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tgcaaggcg tacgcgtgcg cggtctccaa caaagccctc   1140
ccagccccca tcgagaaaac catctccaaa gccaaagggc agccccgaga accacaggtg   1200
tacaccctgc cccatcccg ggatgagctg accaagaacc aggtcagcct gacctgcctg   1260
gtcaaaggct tctatccaag cgacatcgcc gtggagtggg agagcaatgg gcagccggag   1320
aacaactaca agaccacgcc tcccgtgctg gactccgacg gctccttctt cctctacagc   1380
aagctcaccg tggacaagag caggtggcag caggggaacg tcttctcatg ctccgtgatg   1440
catgaggctc tgcacaacca ctacacgcag aagagcctct ccctgtctcc gggtaaatct   1500
agagcctcca ccaagggccc atcggtcttc ccccctggcac cctcctccaa gagcacctct   1560
gggggcacag cggccctggg ctgcctggtc aaggactact ccccgagcc ggtgacggtg   1620
tcgtggaact caggcgccct gaccagcggc gtgcacacct tcccggctgt cctacagtcc   1680
tcaggactct actccctcag cagcgtggtg accgtgccct ccagcagctt gggcacccag   1740
acctacatct gcaacgtgaa tcacaagccc agcaacacca aggtggacaa gaaagtttga   1800
```

<210> SEQ ID NO 53
<211> LENGTH: 1809
<212> TYPE: DNA
<213> ORGANISM: Artificial Sequence
<220> FEATURE:
<223> OTHER INFORMATION: humanized TSC192 Interceptor (huVL-VH#2 107-1A4 scFv-Fc-CkYAE)

<400> SEQUENCE: 53

```
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
```

```
gggaaagttc ctaagctccg catccattct ggatctactt tgcaatcagg ggtcccatct      240
cggttcagtg gcagtggatc tgggacagaa tttactctca ccatcagcag cctgcagcct      300
gaagattttg caacttatta ctgtcaacag catattgaat acccgtggac gttcggccaa      360
gggaccaagg tggaaatcaa acgaggtggc ggagggtctg ggggtggcgg atccggaggt      420
ggtggctctc aggtccagct ggtacagtct ggggctgagg tgaagaagcc tggggcttca      480
gtgaaggtct cctgcaaggc ttctggatac acattcactg actactacat gcactgggtg      540
cgacaggccc ctggacaagg gcttgagtgg atgggatatt ttaatcctta taatgattat      600
actagatacg cacagaagtt ccagggcaga gtcaccatga ccaggacacg tctatcagc      660 acagcctaca tggagctgag cagcctgaga tctgacgaca cggccgtgta ttactgtgca      720
agatcggatg gttactacga tgctatggac tactggggtc aaggaaccac agtcaccgtc      780
tcctcgagtg agcccaaatc ttctgacaaa actcacacat gcccaccgtg cccagcacct      840
gaagccgcgg gtgcaccgtc agtcttcctc ttccccccaa aacccaagga caccctcatg      900
atctcccgga cccctgaggt cacatgcgtg gtggtggacg tgagccacga agaccctgag      960
gtcaagttca actggtacgt ggacggcgtg gaggtgcata atgccaagac aaagccgcgg      1020
gaggagcagt acaacagcac gtaccgtgtg gtcagcgtcc tcaccgtcct gcaccaggac      1080
tggctgaatg gcaaggcgta cgcgtgcgcg gtctccaaca aagccctccc agccccatc      1140 gagaaaacca tctccaaagc caagggcagc cccgagaac acaggtgta caccctgccc      1200 ccatcccggg atgagctgac caagaaccag gtcagcctga cctgcctggt caaaggcttc      1260
tatccaagcg acatcgccgt ggagtgggag agcaatgggc agccggagaa caactacaag      1320
accacgcctc ccgtgctgga ctccgacggc tccttcttcc tctacagcaa gctcaccgtg      1380
gacaagagca ggtggcagca ggggaacgtc ttctcatgct ccgtgatgca tgaggctctg      1440
cacaaccact acacgcagaa gagcctctcc ctgtctccgg gtaaatctag aactgtggct      1500
gcaccatctg tcttcatctt cccgccatct gatgagcagt tgaaatctgg aactgcctct      1560
gttgtgtgcc tgctgaatta cttctatccc agagaggcca agtacagtg gaaggtggat      1620 aacgccctcc aatcgggtaa ctcccaggag agtgccacag agcaggacag caaggacagc      1680
acctacagcc tcagcagcga gctgacgctg agcaaagcag actacgagaa acacaaagtc      1740
tacgcctgcg aagtcaccca tcagggcctg agctcgcccg tcacaaagag cttcaacagg      1800
ggagagtga                                                              1809
```

<210> SEQ ID NO 54
<211> LENGTH: 1809
<212> TYPE: DNA
<213> ORGANISM: Artificial Sequence
<220> FEATURE:
<223> OTHER INFORMATION: humanized TSC193 Interceptor (huVL-VH#1 107-1A4
      scFv-Fc-CkYAE)

<400> SEQUENCE: 54

```
atggaagcac cagcgcagct tctcttcctc ctgctactct ggctcccaga taccaccggt      60
gatatccaga tgacccagtc tccatccgcc atgtctgcat ctgtaggaga cagagtcacc      120
atcacttgcc gggcgagtaa gagcattagc aaatatttag cctggtttca gcagaaacca      180
gggaaagttc ctaagctccg catccattct ggatctactt tgcaatcagg ggtcccatct      240
cggttcagtg gcagtggatc tgggacagaa tttactctca ccatcagcag cctgcagcct      300
gaagattttg caacttatta ctgtcaacag catattgaat acccgtggac gttcggccaa      360
```

```
gggaccaagg tggaaatcaa acgaggtggc ggagggtctg ggggtggcgg atccggaggt      420
ggtggctctg aggtccagct ggtacagtct ggggctgagg tgaagaagcc tggggctaca      480
gtgaagatct cctgcaaggc ttctggatac acattcactg actactacat gcactgggtg      540
caacaggccc ctggaaaagg gcttgagtgg atgggatatt ttaatcctta taatgattat      600
actagatacg cagagaagtt ccagggcaga gtcaccataa ccgcggacac gtctacagac      660
acagcctaca tggagctgag cagcctgaga tctgaggaca cggccgtgta ttactgtgca      720
agatcggatg gttactacga tgctatggac tactgggtc aaggaaccac agtcaccgtc      780
tcctcgagtg agcccaaatc ttctgacaaa actcacacat gcccaccgtg cccagcacct      840
gaagccgcgg gtgcaccgtc agtcttcctc ttccccccaa acccaaggac acccctcatg      900
atctcccgga cccctgaggt cacatgcgtg gtggtggacg tgagccacga agaccctgag      960
gtcaagttca actggtacgt ggacggcgtg gaggtgcata atgccaagac aaagccgcgg     1020
gaggagcagt acaacagcac gtaccgtgtg gtcagcgtcc tcaccgtcct gcaccaggac     1080
tggctgaatg gcaaggcgta cgcgtgcgcg gtctccaaca aagcccctcc cagcccccatc    1140 gagaaaacca tctccaaagc caaagggcag ccccgagaac cacaggtgta caccctgccc     1200
ccatcccggg atgagctgac caagaaccag gtcagcctga cctgcctggt caaaggcttc     1260
tatccaagcg acatcgccgt ggagtgggag agcaatgggc agccggagaa caactacaag     1320
accacgcctc ccgtgctgga ctccgacggc tccttcttcc tctacagcaa gctcaccgtg     1380
gacaagagca ggtggcagca ggggaacgtc ttctcatgct ccgtgatgca tgaggctctg     1440
cacaaccact acacgcagaa gagcctctcc ctgtctccgg gtaaatctag aactgtggct     1500
gcaccatctg tcttcatctt cccgccatct gatgagcagt tgaaatctgg aactgcctct     1560
gttgtgtgcc tgctgaatta cttctatccc agagaggcca aagtacagtg gaaggtggat     1620
aacgccctcc aatcgggtaa ctcccaggag agtgccacag agcaggacag caaggacagc     1680
acctacagcc tcagcagcga gctgacgctg agcaaagcag actacgagaa acacaaagtc     1740
tacgcctgcg aagtcaccca tcagggcctg agctcgcccg tcacaaagag cttcaacagg     1800
ggagagtga                                                             1809

<210> SEQ ID NO 55
<211> LENGTH: 1788
<212> TYPE: DNA
<213> ORGANISM: Artificial Sequence
<220> FEATURE:
<223> OTHER INFORMATION: humanized TSC195 Interceptor (huVL-VH#2 107-1A4
      scFv-Fc-CH1)

<400> SEQUENCE: 55
atggaagcac cagcgcagct tctcttcctc ctgctactct ggctcccaga taccaccggt       60
gatatccaga tgacccagtc tccatccgcc atgtctgcat ctgtaggaga cagagtcacc      120
atcacttgcc gggcgagtaa gagcattagc aaatatttag cctggtttca gcagaaacca      180
gggaaagttc ctaagctccg catccattct ggatctactt tgcaatcagg ggtcccatct      240
cggttcagtg gcagtggatc tgggacagaa tttactctca ccatcagcag cctgcagcct      300
gaagattttg caacttatta ctgtcaacag catattgaat cccgtggac gttcggccaa      360 gggaccaagg tggaaatcaa acgaggtggc ggagggtctg ggggtggcgg atccggaggt      420
ggtggctctc aggtccagct ggtacagtct ggggctgagg tgaagaagcc tggggcttca      480
gtgaaggtct cctgcaaggc ttctggatac acattcactg actactacat gcactgggtg      540
```

```
cgacaggccc ctggacaagg gcttgagtgg atgggatatt ttaatcctta taatgattat    600
actagatacg cacagaagtt ccagggcaga gtcaccatga ccaggacac gtctatcagc     660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa acccaaggga caccctcatg    900
atctcccgga cccctgaggt cacatgcgtg gtggtggacg tgagccacga gaccctgag     960
gtcaagttca actggtacgt ggacggcgtg gaggtgcata tgccaagac aaagccgcgg    1020
gaggagcagt acaacagcac gtaccgtgtg gtcagcgtcc tcaccgtcct gcaccaggac   1080
tggctgaatg gcaaggcgta cgcgtgcgcg gtctccaaca agccctccc agccccatc    1140
gagaaaacca tctccaaagc caagggcag ccccgagaac acaggtgta caccctgccc    1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtaaatctag agcctccacc   1500
aagggcccat cggtcttccc cctggcaccc tcctccaaga gcacctctgg gggcacagcg   1560
gccctgggct gcctggtcaa ggactacttc cccgagccgg tgacggtgtc gtggaactca   1620
ggcgccctga ccagcggcgt gcacaccttc ccggctgtcc tacagtcctc aggactctac   1680
tccctcagca gcgtggtgac cgtgccctcc agcagcttgg gcacccagac ctacatctgc   1740
aacgtgaatc acaagcccag caacaccaag gtggacaaga agtttga              1788
```

<210> SEQ ID NO 56
<211> LENGTH: 1788
<212> TYPE: DNA
<213> ORGANISM: Artificial Sequence
<220> FEATURE:
<223> OTHER INFORMATION: humanized TSC196 Interceptor (huVL-VH#1 107-1A4
      scFv-Fc-CH1)

<400> SEQUENCE: 56

```
atggaagcac cagcgcagct tctcttcctc ctgctactct ggctcccaga taccaccggt     60
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg cagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggtggcgg atccggaggt    420
ggtggctctg aggtccagct ggtacagtct ggggctgagg tgaagaagcc tggggctaca    480
gtgaagatct cctgcaaggc ttctggatac acattcactg actactacat gcactgggtg    540
caacaggccc ctggaaaagg gcttgagtgg atgggatatt ttaatcctta taatgattat    600
actagatacg cagagaagtt ccagggcaga gtcaccataa ccgcggacac gtctacagac    660
acagcctaca tggagctgag cagcctgaga tctgaggaca cggccgtgta ttactgtgca    720
agatcggatg gttactacga tgctatggac tactggggtc aaggaaccac agtcaccgtc    780
```

-continued

```
tcctcgagtg agcccaaatc ttctgacaaa actcacacat gcccaccgtg cccagcacct      840
gaagccgcgg gtgcaccgtc agtcttcctc ttccccccaa acccaaggac acccctcatg      900
atctcccgga cccctgaggt cacatgcgtg gtggtggacg tgagccacga agaccctgag      960
gtcaagttca actggtacgt ggacggcgtg gaggtgcata atgccaagac aaagccgcgg     1020
gaggagcagt acaacagcac gtaccgtgtg gtcagcgtcc tcaccgtcct gcaccaggac     1080
tggctgaatg gcaaggcgta cgcgtgcgcg gtctccaaca aagccctccc agcccccatc     1140
gagaaaacca tctccaaagc caaagggcag ccccgagaac acaggtgta caccctgccc     1200
ccatcccggg atgagctgac caagaaccag gtcagcctga cctgcctggt caaaggcttc     1260
tatccaagcg acatcgccgt ggagtgggag agcaatgggc agccggagaa caactacaag     1320
accacgcctc ccgtgctgga ctccgacggc tccttcttcc tctacagcaa gctcaccgtg     1380
gacaagagca ggtggcagca ggggaacgtc ttctcatgct ccgtgatgca tgaggctctg     1440
cacaaccact acacgcagaa gagcctctcc ctgtctccgg gtaaatctag agcctccacc     1500
aagggcccat cggtcttccc cctggcaccc tcctccaaga gcacctctgg gggcacagcg     1560
gccctgggct gcctggtcaa ggactacttc cccgagccgg tgacggtgtc gtggaactca     1620
ggcgccctga ccagcggcgt gcacaccttc ccggctgtcc tacagtcctc aggactctac     1680
tccctcagca gcgtggtgac cgtgccctcc agcagcttgg gcacccagac ctacatctgc     1740
aacgtgaatc acaagcccag caacaccaag gtggacaaga agttga                   1788
```

<210> SEQ ID NO 57
<211> LENGTH: 579
<212> TYPE: PRT
<213> ORGANISM: Artificial Sequence
<220> FEATURE:
<223> OTHER INFORMATION: TSC125 Interceptor (Cris7 scFv-Fc-CH1)

<400> SEQUENCE: 57

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Lys Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser Gly Gly Gly Ser Gly Gly
        115                 120                 125

Gly Gly Ser Gly Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Ser Val Ser Tyr Met Asn Trp Tyr Gln Gln Lys
                165                 170                 175

Pro Gly Lys Ala Pro Lys Arg Trp Ile Tyr Asp Ser Ser Lys Leu Ala
            180                 185                 190
```

Ser Gly Val Pro Ala Arg Phe Ser Gly Ser Gly Ser Gly Thr Asp Tyr
    195                 200                 205

Thr Leu Thr Ile Ser Ser Leu Gln Pro Glu Asp Phe Ala Thr Tyr Tyr
210                 215                 220

Cys Gln Gln Trp Ser Arg Asn Pro Pro Thr Phe Gly Gly Gly Thr Lys
225                 230                 235                 240

Leu Gln Ile Thr Arg Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Ala Tyr Ala
            340                 345                 350

Cys Ala Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
        450                 455                 460

His Asn His Tyr Thr Gln Lys Ser Leu Ser Leu Ser Pro Gly Lys Ser
465                 470                 475                 480

Arg Ala Ser Thr Lys Gly Pro Ser Val Phe Pro Leu Ala Pro Ser Ser
                485                 490                 495

Lys Ser Thr Ser Gly Gly Thr Ala Ala Leu Gly Cys Leu Val Lys Asp
            500                 505                 510

Tyr Phe Pro Glu Pro Val Thr Val Ser Trp Asn Ser Gly Ala Leu Thr
            515                 520                 525

Ser Gly Val His Thr Phe Pro Ala Val Leu Gln Ser Ser Gly Leu Tyr
        530                 535                 540

Ser Leu Ser Ser Val Val Thr Val Pro Ser Ser Ser Leu Gly Thr Gln
545                 550                 555                 560

Thr Tyr Ile Cys Asn Val Asn His Lys Pro Ser Asn Thr Lys Val Asp
                565                 570                 575

Lys Lys Val

<210> SEQ ID NO 58
<211> LENGTH: 582
<212> TYPE: PRT

<210> ORGANISM: Artificial Sequence
<220> FEATURE:
<223> OTHER INFORMATION: humanized TSC192 Interceptor (huVL-VH#2 107-1A4 scFv-Fc-CkYAE)

<400> SEQUENCE: 58

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380
```

```
Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys Ser Arg Thr Val Ala
465                 470                 475                 480

Ala Pro Ser Val Phe Ile Phe Pro Pro Ser Asp Glu Gln Leu Lys Ser
            485                 490                 495

Gly Thr Ala Ser Val Val Cys Leu Leu Asn Tyr Phe Tyr Pro Arg Glu
            500                 505                 510

Ala Lys Val Gln Trp Lys Val Asp Asn Ala Leu Gln Ser Gly Asn Ser
            515                 520                 525

Gln Glu Ser Ala Thr Glu Gln Asp Ser Lys Asp Ser Thr Tyr Ser Leu
530                 535                 540

Ser Ser Glu Leu Thr Leu Ser Lys Ala Asp Tyr Glu Lys His Lys Val
545                 550                 555                 560

Tyr Ala Cys Glu Val Thr His Gln Gly Leu Ser Ser Pro Val Thr Lys
            565                 570                 575

Ser Phe Asn Arg Gly Glu
            580

<210> SEQ ID NO 59
<211> LENGTH: 582
<212> TYPE: PRT
<213> ORGANISM: Artificial Sequence
<220> FEATURE:
<223> OTHER INFORMATION: humanized TSC193 Interceptor (huVL-VH#1 107-1A4
      scFv-Fc-CkYAE)

<400> SEQUENCE: 59

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
            35                  40                  45

His Ser Gly Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
            85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Glu Val Gln Leu Val
            115                 120                 125

Gln Ser Gly Ala Glu Val Lys Lys Pro Gly Ala Thr Val Lys Ile Ser
        130                 135                 140

Cys Lys Ala Ser Gly Tyr Thr Phe Thr Asp Tyr Tyr Met His Trp Val
145                 150                 155                 160
```

```
Gln Gln Ala Pro Gly Lys Gly Leu Glu Trp Met Gly Tyr Phe Asn Pro
                165                 170                 175

Tyr Asn Asp Tyr Thr Arg Tyr Ala Glu Lys Phe Gln Gly Arg Val Thr
            180                 185                 190

Ile Thr Ala Asp Thr Ser Thr Asp Thr Ala Tyr Met Glu Leu Ser Ser
        195                 200                 205

Leu Arg Ser Glu Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Ser Arg Thr Val Ala
465                 470                 475                 480

Ala Pro Ser Val Phe Ile Phe Pro Pro Ser Asp Glu Gln Leu Lys Ser
                485                 490                 495

Gly Thr Ala Ser Val Val Cys Leu Leu Asn Tyr Phe Tyr Pro Arg Glu
            500                 505                 510

Ala Lys Val Gln Trp Lys Val Asp Asn Ala Leu Gln Ser Gly Asn Ser
        515                 520                 525

Gln Glu Ser Ala Thr Glu Gln Asp Ser Lys Asp Ser Thr Tyr Ser Leu
    530                 535                 540

Ser Ser Glu Leu Thr Leu Ser Lys Ala Asp Tyr Glu Lys His Lys Val
545                 550                 555                 560

Tyr Ala Cys Glu Val Thr His Gln Gly Leu Ser Ser Pro Val Thr Lys
                565                 570                 575
```

```
Ser Phe Asn Arg Gly Glu
            580

<210> SEQ ID NO 60
<211> LENGTH: 575
<212> TYPE: PRT
<213> ORGANISM: Artificial Sequence
<220> FEATURE:
<223> OTHER INFORMATION: humanized TSC195 Interceptor (huVL-VH#2 107-1A4
      scFv-Fc-CH1)

<400> SEQUENCE: 60

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350
```

-continued

```
Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Ser Arg Ala Ser Thr
465                 470                 475                 480

Lys Gly Pro Ser Val Phe Pro Leu Ala Pro Ser Ser Lys Ser Thr Ser
                485                 490                 495

Gly Gly Thr Ala Ala Leu Gly Cys Leu Val Lys Asp Tyr Phe Pro Glu
            500                 505                 510

Pro Val Thr Val Ser Trp Asn Ser Gly Ala Leu Thr Ser Gly Val His
        515                 520                 525

Thr Phe Pro Ala Val Leu Gln Ser Ser Gly Leu Tyr Ser Leu Ser Ser
530                 535                 540

Val Val Thr Val Pro Ser Ser Ser Leu Gly Thr Gln Thr Tyr Ile Cys
545                 550                 555                 560

Asn Val Asn His Lys Pro Ser Asn Thr Lys Val Asp Lys Lys Val
                565                 570                 575

<210> SEQ ID NO 61
<211> LENGTH: 575
<212> TYPE: PRT
<213> ORGANISM: Artificial Sequence
<220> FEATURE:
<223> OTHER INFORMATION: humanized TSC196 Interceptor (huVL-VH#1 107-1A4
      scFv-Fc-CH1)

<400> SEQUENCE: 61

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Glu Val Gln Leu Val
        115                 120                 125

Gln Ser Gly Ala Glu Val Lys Lys Pro Gly Ala Thr Val Lys Ile Ser
```

-continued

```
            130                 135                 140
Cys Lys Ala Ser Gly Tyr Thr Phe Thr Asp Tyr Tyr Met His Trp Val
145                 150                 155                 160

Gln Gln Ala Pro Gly Lys Gly Leu Glu Trp Met Gly Tyr Phe Asn Pro
                    165                 170                 175

Tyr Asn Asp Tyr Thr Arg Tyr Ala Glu Lys Phe Gln Gly Arg Val Thr
                180                 185                 190

Ile Thr Ala Asp Thr Ser Thr Asp Thr Ala Tyr Met Glu Leu Ser Ser
            195                 200                 205

Leu Arg Ser Glu Asp Thr Ala Val Tyr Tyr Cys Ala Arg Ser Asp Gly
        210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                    245                 250                 255

Cys Pro Ala Pro Glu Ala Ala Gly Ala Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                    325                 330                 335

Leu His Gln Asp Trp Leu Asn Gly Lys Ala Tyr Ala Cys Ala Val Ser
                340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                    405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys Ser Arg Ala Ser Thr
465                 470                 475                 480

Lys Gly Pro Ser Val Phe Pro Leu Ala Pro Ser Ser Lys Ser Thr Ser
                    485                 490                 495

Gly Gly Thr Ala Ala Leu Gly Cys Leu Val Lys Asp Tyr Phe Pro Glu
                500                 505                 510

Pro Val Thr Val Ser Trp Asn Ser Gly Ala Leu Thr Ser Gly Val His
            515                 520                 525

Thr Phe Pro Ala Val Leu Gln Ser Ser Gly Leu Tyr Ser Leu Ser Ser
        530                 535                 540

Val Val Thr Val Pro Ser Ser Ser Leu Gly Thr Gln Thr Tyr Ile Cys
545                 550                 555                 560
```

```
Asn Val Asn His Lys Pro Ser Asn Thr Lys Val Asp Lys Lys Val
            565                 570                 575

<210> SEQ ID NO 62
<211> LENGTH: 8
<212> TYPE: PRT
<213> ORGANISM: Artificial Sequence
<220> FEATURE:
<223> OTHER INFORMATION: Linker H7

<400> SEQUENCE: 62

Gly Cys Pro Pro Cys Pro Asn Ser
1               5

<210> SEQ ID NO 63
<211> LENGTH: 21
<212> TYPE: PRT
<213> ORGANISM: Artificial Sequence
<220> FEATURE:
<223> OTHER INFORMATION: Linker H75

<400> SEQUENCE: 63

Gln Arg His Asn Asn Ser Ser Leu Asn Thr Gly Thr Gln Met Ala Gly
1               5                   10                  15

His Ser Pro Asn Ser
            20

<210> SEQ ID NO 64
<211> LENGTH: 14
<212> TYPE: PRT
<213> ORGANISM: Artificial Sequence
<220> FEATURE:
<223> OTHER INFORMATION: Linker H81

<400> SEQUENCE: 64

Glu Val Gln Ile Pro Leu Thr Glu Ser Tyr Ser Pro Asn Ser
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Linker H83

<400> SEQUENCE: 65

Ser Ser Leu Asn Thr Gly Thr Gln Met Ala Gly His Ser Pro Asn Ser
1               5                   10                  15

<210> SEQ ID NO 66
<211> LENGTH: 20
<212> TYPE: PRT
<213> ORGANISM: Artificial Sequence
<220> FEATURE:
<223> OTHER INFORMATION: Linker H91

<400> SEQUENCE: 66

Asn Ser Leu Ala Asn Gln Glu Val Gln Ile Pro Leu Thr Glu Ser Tyr
1               5                   10                  15

Ser Pro Asn Ser
            20

<210> SEQ ID NO 67
<211> LENGTH: 19
<212> TYPE: PRT
```

<213> ORGANISM: Artificial Sequence
<220> FEATURE:
<223> OTHER INFORMATION: Linker H94

<400> SEQUENCE: 67

Ser Gly Gly Gly Gly Ser Gly Gly Gly Ser Gly Gly Gly Ser
1               5                   10                  15

Pro Asn Ser

<210> SEQ ID NO 68
<211> LENGTH: 11
<212> TYPE: PRT
<213> ORGANISM: Artificial Sequence
<220> FEATURE:
<223> OTHER INFORMATION: Linker H98

<400> SEQUENCE: 68

Ser Ser Leu Asn Thr Gly Thr Gln Pro Asn Ser
1               5                   10

<210> SEQ ID NO 69
<211> LENGTH: 1494
<212> TYPE: DNA
<213> ORGANISM: Artificial Sequence
<220> FEATURE:
<223> OTHER INFORMATION: TSC210-humanized SMIP (human VH#2-VL scFv-Fc)

<400> SEQUENCE: 69

```
atggaagcac cagcgcagct tctcttcctc ctgctactct ggctcccaga taccaccggt      60
caggtccagc tggtacagtc tggggctgag gtgaagaagc tggggcttc agtgaaggtc     120
tcctgcaagg cttctggata cacattcact gactactaca tgcactgggt gcgacaggcc    180
cctggacaag gcttgagtg gatgggatat tttaatcctt ataatgatta ctactagatac    240
gcacagaagt tccagggcag agtcaccatg accagggaca cgtctatcag cacagcctac   300
atggagctga gcagcctgag atctgacgac acggccgtgt attactgtgc aagatcggat   360
ggttactacg atgctatgga ctactgggt caaggaacca cagtcaccgt ctcctcaggt    420
ggcggagggt ctggggggtgg cggatccgga ggtggtggct ctgatatcca gatgacccag   480
tctccatccg ccatgtctgc atctgtagga cacagtca ccatcacttg ccgggcgagt     540
aagagcatta gcaaatattt agcctggttt cagcagaaac cagggaaagt tcctaagctc   600
cgcatccatt ctggatctac tttgcaatca ggggtcccat ctcggttcag tggcagtgga   660
tctgggacag aatttactct caccatcagc agcctgcagc tgaagatttt gcaacttat    720
tactgtcaac agcatattga atacccgtgg acgttcggcc aagggaccaa ggtggaaatc   780
aaacgcgcct cgagtgagcc caaatcttct gacaaaactc acacatgccc accgtgccca   840
gcacctgaag ccgcgggtgc accgtcagtc ttcctcttcc cccccaaaacc caaggacacc   900
ctcatgatct cccggaccc tgaggtcaca tgcgtggtgg tggacgtgag ccacgaagac   960
cctgaggtca agttcaactg gtacgtggac ggcgtggagg tgcataatgc caagacaaag  1020
ccgcgggagg agcagtacaa cagcacgtac cgtgtggtca gcgtcctcac cgtcctgcac  1080
caggactggc tgaatggcaa ggcgtacgcg tgcgcggtct ccaacaaagc cctcccagcc  1140
cccatcgaga aaaccatctc caaagccaaa gggcagcccc gagaaccaca ggtgtacacc  1200
ctgcccccat cccgggatga gctgaccaag aaccaggtca gcctgacctg cctggtcaaa  1260
ggcttctatc caagcgacat cgccgtggag tgggagagca atgggcagcc ggagaacaac  1320
tacaagacca cgcctcccgt gctggactcc gacggctcct tcttcctcta cagcaagctc  1380
```
accgtggaca agagcaggtg gcagcagggg aacgtcttct catgctccgt gatgcatgag    1440
gctctgcaca accactacac gcagaagagc ctctccctgt ctccgggtaa atga          1494

<210> SEQ ID NO 70
<211> LENGTH: 477
<212> TYPE: PRT
<213> ORGANISM: Artificial Sequence
<220> FEATURE:
<223> OTHER INFORMATION: TSC210-humanized SMIP (human VH#2-VL scFv-Fc)

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Tyr Phe Asn Pro Tyr Asn Asp Tyr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ser Asp Gly Tyr Tyr Asp Ala Met Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ala
    130                 135                 140

Met Ser Ala Ser Val Gly Asp Arg Val Thr Ile Thr Cys Arg Ala Ser
145                 150                 155                 160

Lys Ser Ile Ser Lys Tyr Leu Ala Trp Phe Gln Gln Lys Pro Gly Lys
                165                 170                 175

Val Pro Lys Leu Arg Ile His Ser Gly Ser Thr Leu Gln Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

His Ile Glu Tyr Pro Trp Thr Phe Gly Gln Gly Thr Lys Val Glu Ile
225                 230                 235                 240

Lys Arg Ala Ser Ser Glu Pro Lys Ser Ser Asp Lys Thr His Thr Cys
                245                 250                 255

Pro Pro Cys Pro Ala Pro Glu Ala Ala Gly Ala Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Ala Tyr Ala Cys Ala
```

```
              340             345             350
Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
            370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                    405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
            450                 455                 460

His Tyr Thr Gln Lys Ser Leu Ser Leu Ser Pro Gly Lys
465                 470                 475
```

<210> SEQ ID NO 71
<211> LENGTH: 1494
<212> TYPE: DNA
<213> ORGANISM: Artificial Sequence
<220> FEATURE:
<223> OTHER INFORMATION: TSC211 humanized SMIP (human VH#1-VL scFv-Fc)

<400> SEQUENCE: 71

```
atggaagcac cagcgcagct tctcttcctc ctgctactct ggctcccaga taccaccggt     60
gaggtccagc tggtacagtc tggggctgag gtgaagaagc ctggggctac agtgaagatc    120
tcctgcaagg cttctggata cacattcact gactactaca tgcactgggt gcaacaggcc    180
cctggaaaag gcttgagtg gatgggatat tttaatcctt ataatgatta ctagatac    240
gcagagaagt tccagggcag agtcaccata accgcgaca cgtctacaga cacagcctac    300
atggagctga gcagcctgag atctgaggac acggccgtgt attactgtgc aagatcggat    360
ggttactacg atgctatgga ctactggggt caaggaacca cagtcaccgt ctcctcaggt    420
ggcggagggt ctgggggtgg cggatccgga ggtggtggct ctgatatcca gatgacccag    480
tctccatccg ccatgtctgc atctgtagga cacagagtca ccatcacttg ccgggcgagt    540
aagagcatta gcaaatattt agcctggttt cagcagaaac agggaaagt tcctaagctc    600
cgcatccatt ctggatctac tttgcaatca ggggtcccat ctcggttcag tggcagtgga    660
tctgggacag aatttactct caccatcagc agcctgcagc tgaagatttt gcaacttat    720
tactgtcaac agcatattga ataccgtgg acgttcggcc aagggaccaa ggtggaaatc    780
aaacgagcct cgagtgagcc caaatcttct gacaaaactc acacatgccc accgtgccca    840
gcacctgaag ccgcgggtgc accgtcagtc ttcctcttcc cccaaaaacc caaggacacc    900
ctcatgatct cccggacccc tgaggtcaca tgcgtggtgg tggacgtgag ccacgaagac    960
cctgaggtca agttcaactg gtacgtggac ggcgtggagg tgcataatgc caagacaaag   1020
ccgcgggagg agcagtacaa cagcacgtac cgtgtggtca gcgtcctcac cgtcctgcac   1080
caggactggc tgaatggcaa ggcgtacgcg tgcgcggtct ccaacaaagc cctcccagcc   1140
cccatcgaga aaaccatctc caaagccaaa gggcagcccc gagaaccaca ggtgtacacc   1200
ctgccccat cccgggatga gctgaccaag aaccaggtca gcctgacctg cctggtcaaa   1260
ggcttctatc caagcgacat cgccgtggag tgggagagca atgggcagcc ggagaacaac   1320
```

-continued

```
tacaagacca cgcctcccgt gctggactcc gacggctcct tcttcctcta cagcaagctc    1380
accgtggaca agagcaggtg gcagcagggg aacgtcttct catgctccgt gatgcatgag    1440
gctctgcaca accactacac gcagaagagc ctctccctgt ctccgggtaa atga          1494
```

<210> SEQ ID NO 72
<211> LENGTH: 477
<212> TYPE: PRT
<213> ORGANISM: Artificial Sequence
<220> FEATURE:
<223> OTHER INFORMATION: TSC211 humanized SMIP (human VH#1-VL scFv-Fc)

<400> SEQUENCE: 72

```
Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Tyr Phe Asn Pro Tyr Asn Asp Tyr Thr Arg Tyr Ala Glu Lys Phe
    50                  55                  60

Gln Gly Arg Val Thr Ile Thr Ala Asp Thr Ser Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Tyr Tyr Asp Ala Met Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ala
    130                 135                 140

Met Ser Ala Ser Val Gly Asp Arg Val Thr Ile Thr Cys Arg Ala Ser
145                 150                 155                 160

Lys Ser Ile Ser Lys Tyr Leu Ala Trp Phe Gln Gln Lys Pro Gly Lys
                165                 170                 175

Val Pro Lys Leu Arg Ile His Ser Gly Ser Thr Leu Gln Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

His Ile Glu Tyr Pro Trp Thr Phe Gly Gln Gly Thr Lys Val Glu Ile
225                 230                 235                 240

Lys Arg Ala Ser Ser Glu Pro Lys Ser Ser Asp Lys Thr His Thr Cys
                245                 250                 255

Pro Pro Cys Pro Ala Pro Glu Ala Ala Gly Ala Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335
```

```
Thr Val Leu His Gln Asp Trp Leu Asn Gly Lys Ala Tyr Ala Cys Ala
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 73
<211> LENGTH: 2289
<212> TYPE: DNA
<213> ORGANISM: Artificial Sequence
<220> FEATURE:
<223> OTHER INFORMATION: Humanized TSC212 Scorpion (hu VH#2-VL 107-1A4
      scFv-Fc Cris7 scFv)

<400> SEQUENCE: 73
atggaagcac cagcgcagct tctcttcctc ctgctactct ggctcccaga taccaccggt        60
caggtccagc tggtacagtc tggggctgag gtgaagaagc tggggcttc agtgaaggtc       120 tcctgcaagg cttctggata cacattcact gactactaca tgcactgggt gcgacaggcc       180
cctggacaag ggcttgagtg gatgggatat tttaatcctt ataatgatta tactagatac       240
gcacagaagt tccagggcag agtcaccatg accaggaca cgtctatcag cacagcctac       300
atggagctga gcagcctgag atctgacgac acggccgtgt attactgtgc aagatcggat       360
ggttactacg atgctatgga ctactggggt caaggaacca cagtcaccgt ctcctcaggt       420 ggcgagggt ctggggtgg cggatccgga ggtggtggct ctgatatcca gatgacccag        480
tctccatccg ccatgtctgc atctgtagga gacagagtca ccatcacttg ccgggcgagt       540
aagagcatta gcaaatattt agcctggttt cagcagaaac agggaaagt tcctaagctc       600 cgcatccatt ctggatctac tttgcaatca ggggtcccat ctcggttcag tggcagtgga       660
tctgggacag aatttactct caccatcagc agcctgcagc tgaagatttt gcaacttat       720 tactgtcaac agcatattga atacccgtgg acgttcggcc aagggaccaa ggtggaaatc       780
aaacgcgcct cgagtgagcc caaatcttct gacaaaactc acacatgccc accgtgccca       840
gcacctgaag ccgcgggtgc accgtcagtc ttcctcttcc ccccaaaacc caaggacacc       900
ctcatgatct cccggacccc tgaggtcaca tgcgtggtgg tggacgtgag ccacgaagac       960
cctgaggtca agttcaactg gtacgtggac ggcgtggagg tgcataatgc caagacaaag      1020
ccgcgggagg agcagtacaa cagcacgtac cgtgtggtca gcgtcctcac cgtcctgcac      1080
caggactggc tgaatggcaa ggcgtacgcg tgcgcggtct ccaacaaagc cctcccagcc      1140
cccatcgaga aaaccatctc caaagccaaa gggcagcccc gagaaccaca ggtgtacacc      1200
```

```
ctgcccccat cccgggatga gctgaccaag aaccaggtca gcctgacctg cctggtcaaa    1260
ggcttctatc caagcgacat cgccgtggag tgggagagca atgggcagcc ggagaacaac    1320
tacaagacca cgcctcccgt gctggactcc gacggctcct tcttcctcta cagcaagctc    1380
accgtggaca agagcaggtg gcagcagggg aacgtcttct catgctccgt gatgcatgag    1440
gctctgcaca accactacac gcagaagagc ctctccctgt ctccgggtca gaggcacaac    1500
aattcttccc tgaatacagg aactcagatg gcaggtcatt ctccgaattc tcaggtccag    1560
ctggtgcagt ctgggggcgg agtggtgcag cctgggcggt cactgaggct gtcctgcaag    1620
gcttctggct acacctttac tagatctacg atgcactggg taaggcaggc ccctggaaag    1680
ggtctggaat ggattggata cattaatcct agcagtgctt atactaatta caatcagaaa    1740
ttcaaggaca ggttcacaat cagcgcagac aaatccaaga gcacagcctt cctgcagatg    1800
gacagcctga ggcccgagga caccggcgtc tatttctgtg cacggcccca agtccactat    1860
gattacaacg gtttccttta ctggggccaa gggactcccg tcactgtctc tagcggtggc    1920
ggagggtctg ggggtggcgg atccggaggt ggtggctctg cacaagacat ccagatgacc    1980
cagtctccaa gcagcctgtc tgcaagcgtg ggggacaggg tcaccatgac ctgcagtgcc    2040
agctcaagtg taagttacat gaactggtac cagcagaagc ccgcaaggc ccccaaaaga    2100 tggatttatg actcatccaa actggcttct ggagtccctg ctcgcttcag tggcagtggg    2160
tctgggaccg actataccct cacaatcagc agcctgcagc cgaagatttt cgccacttat    2220
tactgccagc agtggagtcg taacccaccc acgttcggag gggggaccaa gctacaaatt    2280
acacgataa                                                           2289
```

<210> SEQ ID NO 74
<211> LENGTH: 742
<212> TYPE: PRT
<213> ORGANISM: Artificial Sequence
<220> FEATURE:
<223> OTHER INFORMATION: Humanized TSC212 Scorpion (huVH#2-VL 107-1A4
      scFv-Fc-Cris7 scFv)

<400> SEQUENCE: 74

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Tyr Phe Asn Pro Tyr Asn Asp Tyr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ser Asp Gly Tyr Tyr Asp Ala Met Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ala
    130                 135                 140

Met Ser Ala Ser Val Gly Asp Arg Val Thr Ile Thr Cys Arg Ala Ser
145                 150                 155                 160
```

```
Lys Ser Ile Ser Lys Tyr Leu Ala Trp Phe Gln Gln Lys Pro Gly Lys
            165                 170                 175

Val Pro Lys Leu Arg Ile His Ser Gly Ser Thr Leu Gln Ser Gly Val
            180                 185                 190

Pro Ser Arg Phe Ser Gly Ser Gly Ser Gly Thr Glu Phe Thr Leu Thr
            195                 200                 205

Ile Ser Ser Leu Gln Pro Glu Asp Phe Ala Thr Tyr Tyr Cys Gln Gln
            210                 215                 220

His Ile Glu Tyr Pro Trp Thr Phe Gly Gln Gly Thr Lys Val Glu Ile
225                 230                 235                 240

Lys Arg Ala Ser Ser Glu Pro Lys Ser Ser Asp Lys Thr His Thr Cys
                245                 250                 255

Pro Pro Cys Pro Ala Pro Glu Ala Ala Gly Ala Pro Ser Val Phe Leu
            260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Ala Tyr Ala Cys Ala
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
            370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
            450                 455                 460

His Tyr Thr Gln Lys Ser Leu Ser Leu Ser Pro Gly Gln Arg His Asn
465                 470                 475                 480

Asn Ser Ser Leu Asn Thr Gly Thr Gln Met Ala Gly His Ser Pro Asn
                485                 490                 495

Ser Gln Val Gln Leu Val Gln Ser Gly Gly Val Val Gln Pro Gly
            500                 505                 510

Arg Ser Leu Arg Leu Ser Cys Lys Ala Ser Gly Tyr Thr Phe Thr Arg
            515                 520                 525

Ser Thr Met His Trp Val Arg Gln Ala Pro Gly Lys Gly Leu Glu Trp
            530                 535                 540

Ile Gly Tyr Ile Asn Pro Ser Ser Ala Tyr Thr Asn Tyr Asn Gln Lys
545                 550                 555                 560

Phe Lys Asp Arg Phe Thr Ile Ser Ala Asp Lys Ser Lys Ser Thr Ala
                565                 570                 575

Phe Leu Gln Met Asp Ser Leu Arg Pro Glu Asp Thr Gly Val Tyr Phe
```

```
                580             585             590
Cys Ala Arg Pro Gln Val His Tyr Asp Tyr Asn Gly Phe Pro Tyr Trp
            595                 600             605
Gly Gln Gly Thr Pro Val Thr Val Ser Ser Gly Gly Gly Ser Gly
            610                 615             620
Gly Gly Gly Ser Gly Gly Gly Ser Ala Gln Asp Ile Gln Met Thr
625             630              635                 640
Gln Ser Pro Ser Ser Leu Ser Ala Ser Val Gly Asp Arg Val Thr Met
                645                 650             655
Thr Cys Ser Ala Ser Ser Val Ser Tyr Met Asn Trp Tyr Gln Gln
            660                 665             670
Lys Pro Gly Lys Ala Pro Lys Arg Trp Ile Tyr Asp Ser Ser Lys Leu
            675                 680             685
Ala Ser Gly Val Pro Ala Arg Phe Ser Gly Ser Gly Ser Gly Thr Asp
            690                 695             700
Tyr Thr Leu Thr Ile Ser Ser Leu Gln Pro Glu Asp Phe Ala Thr Tyr
705             710              715                 720
Tyr Cys Gln Gln Trp Ser Arg Asn Pro Pro Thr Phe Gly Gly Gly Thr
                725                 730             735
Lys Leu Gln Ile Thr Arg
            740
```

```
<210> SEQ ID NO 75
<211> LENGTH: 2289
<212> TYPE: DNA
<213> ORGANISM: Artificial Sequence
<220> FEATURE:
<223> OTHER INFORMATION: Humanized TSC213 Scorpion (huVH#1-VL 107-1A4
      scFv-FcCris7 scFv)

<400> SEQUENCE: 75
atggaagcac cagcgcagct tctcttcctc ctgctactct ggctcccaga taccaccggt     60
gaggtccagc tggtacagtc tggggctgag gtgaagaagc tggggctac agtgaagatc     120 tcctgcaagg cttctggata cacattcact gactactaca tgcactgggt gcaacaggcc    180
cctggaaaag ggcttgagtg gatgggatat tttaatcctt ataatgatta tactagatac    240
gcagagaagt tccagggcag agtcaccata accgcggaca gtctacagac acagcctac    300 atggagctga gcagcctgag atctgaggac acggccgtgt attactgtgc aagatcggat    360
ggttactacg atgctatgga ctactggggt caaggaacca cagtcaccgt ctcctcaggt    420
ggcggagggt ctgggggtgg cggatccgga ggtggtggct ctgatatcca gatgacccag    480
tctccatccg ccatgtctgc atctgtagga cacagagtca ccatcacttg ccgggcgagt    540
aagagcatta gcaaatattt agcctggttt cagcagaaac cagggaaagt cctaagctc    600 cgcatccatt ctggatctac tttgcaatca ggggtcccat ctcggttcag tggcagtgga    660
tctgggacag aatttactct caccatcagc agcctgcagc ctgaagattt tgcaacttat    720
tactgtcaac agcatattga atacccgtgg acgttcggcc aagggaccaa ggtggaaatc    780
aaacgagcct cgagtgagcc caaatcttct gacaaaactc acacatgccc accgtgccca    840
gcacctgaag ccgcgggtgc accgtcagtc ttcctcttcc ccccaaaacc caaggacacc    900
ctcatgatct cccggacccc tgaggtcaca tgcgtggtgg tggacgtgag ccacgaagac    960
cctgaggtca agttcaactg gtacgtggac ggcgtggagg tgcataatgc caagacaaag    1020
ccgcgggagg agcagtacaa cagcacgtac cgtgtggtca gcgtcctcac cgtcctgcac    1080
```

```
caggactggc tgaatggcaa ggcgtacgcg tgcgcggtct ccaacaaagc cctcccagcc    1140
cccatcgaga aaaccatctc caaagccaaa gggcagcccc gagaaccaca ggtgtacacc    1200
ctgcccccat cccgggatga gctgaccaag aaccaggtca gcctgacctg cctggtcaaa    1260
ggcttctatc caagcgacat cgccgtggag tgggagagca atgggcagcc ggagaacaac    1320
tacaagacca cgcctcccgt gctggactcc gacggctcct tcttcctcta cagcaagctc    1380
accgtggaca agagcaggtg gcagcagggg aacgtcttct catgctccgt gatgcatgag    1440
gctctgcaca accactacac gcagaagagc ctctccctgt ctccgggtca gaggcacaac    1500
aattcttccc tgaatacagg aactcagatg gcaggtcatt ctccgaattc tcaggtccag    1560
ctggtgcagt ctgggggcgg agtggtgcag cctgggcggt cactgaggct gtcctgcaag    1620
gcttctggct cacctttac tagatctacg atgcactggg taaggcaggc cctggaaag    1680
ggtctggaat ggattggata cattaatcct agcagtgctt atactaatta caatcagaaa    1740
ttcaaggaca ggttcacaat cagcgcagac aaatccaaga gcacagcctt cctgcagatg    1800
gacagcctga ggcccgagga caccggcgtc tatttctgtg cacggcccca agtccactat    1860
gattacaacg ggtttcctta ctggggccaa gggactcccg tcactgtctc tagcggtggc    1920
ggagggtctg ggggtggcgg atccggaggt ggtggctctg cacaagacat ccagatgacc    1980
cagtctccaa gcagcctgtc tgcaagcgtg ggggacaggg tcaccatgac ctgcagtgcc    2040
agctcaagtg taagttacat gaactggtac cagcagaagc ccggcaaggc ccccaaaaga    2100
tggatttatg actcatccaa actggcttct ggagtccctg ctcgcttcag tggcagtggg    2160
tctgggaccg actatacccct cacaatcagc agcctgcagc cgaagatttt cgccacttat    2220
tactgccagc agtggagtcg taacccaccc acgttcggag gggggaccaa gctacaaatt    2280
acacgataa                                                            2289

<210> SEQ ID NO 76
<211> LENGTH: 742
<212> TYPE: PRT
<213> ORGANISM: Artificial Sequence
<220> FEATURE:
<223> OTHER INFORMATION: Humanized TSC213 Scorpion (huVH#1-VL 107-1A4
      scFv-Fc-Cris7 scFv)

<400> SEQUENCE: 76

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Tyr Phe Asn Pro Tyr Asn Asp Tyr Thr Arg Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Gly Tyr Tyr Asp Ala Met Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ala
    130                 135                 140
```

```
Met Ser Ala Ser Val Gly Asp Arg Val Thr Ile Thr Cys Arg Ala Ser
145                 150                 155                 160

Lys Ser Ile Ser Lys Tyr Leu Ala Trp Phe Gln Gln Lys Pro Gly Lys
            165                 170                 175

Val Pro Lys Leu Arg Ile His Ser Gly Ser Thr Leu Gln Ser Gly Val
        180                 185                 190

Pro Ser Arg Phe Ser Gly Ser Gly Ser Gly Thr Glu Phe Thr Leu Thr
    195                 200                 205

Ile Ser Ser Leu Gln Pro Glu Asp Phe Ala Thr Tyr Tyr Cys Gln Gln
210                 215                 220

His Ile Glu Tyr Pro Trp Thr Phe Gly Gln Gly Thr Lys Val Glu Ile
225                 230                 235                 240

Lys Arg Ala Ser Ser Glu Pro Lys Ser Ser Asp Lys Thr His Thr Cys
                245                 250                 255

Pro Pro Cys Pro Ala Pro Glu Ala Ala Gly Ala Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Ala Tyr Ala Cys Ala
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Gln Arg His Asn
465                 470                 475                 480

Asn Ser Ser Leu Asn Thr Gly Thr Gln Met Ala Gly His Ser Pro Asn
                485                 490                 495

Ser Gln Val Gln Leu Val Gln Ser Gly Gly Val Val Gln Pro Gly
            500                 505                 510

Arg Ser Leu Arg Leu Ser Cys Lys Ala Ser Gly Tyr Thr Phe Thr Arg
        515                 520                 525

Ser Thr Met His Trp Val Arg Gln Ala Pro Gly Lys Gly Leu Glu Trp
    530                 535                 540

Ile Gly Tyr Ile Asn Pro Ser Ser Ala Tyr Thr Asn Tyr Asn Gln Lys
545                 550                 555                 560
```

```
Phe Lys Asp Arg Phe Thr Ile Ser Ala Asp Lys Ser Lys Ser Thr Ala
                565                 570                 575

Phe Leu Gln Met Asp Ser Leu Arg Pro Glu Asp Thr Gly Val Tyr Phe
            580                 585                 590

Cys Ala Arg Pro Gln Val His Tyr Asp Tyr Asn Gly Phe Pro Tyr Trp
        595                 600                 605

Gly Gln Gly Thr Pro Val Thr Val Ser Ser Gly Gly Gly Gly Ser Gly
    610                 615                 620

Gly Gly Gly Ser Gly Gly Gly Ser Ala Gln Asp Ile Gln Met Thr
625                 630                 635                 640

Gln Ser Pro Ser Ser Leu Ser Ala Ser Val Gly Asp Arg Val Thr Met
                645                 650                 655

Thr Cys Ser Ala Ser Ser Ser Val Ser Tyr Met Asn Trp Tyr Gln Gln
            660                 665                 670

Lys Pro Gly Lys Ala Pro Lys Arg Trp Ile Tyr Asp Ser Ser Lys Leu
        675                 680                 685

Ala Ser Gly Val Pro Ala Arg Phe Ser Gly Ser Gly Ser Gly Thr Asp
    690                 695                 700

Tyr Thr Leu Thr Ile Ser Ser Leu Gln Pro Glu Asp Phe Ala Thr Tyr
705                 710                 715                 720

Tyr Cys Gln Gln Trp Ser Arg Asn Pro Pro Thr Phe Gly Gly Gly Thr
                725                 730                 735

Lys Leu Gln Ile Thr Arg
            740
```

<210> SEQ ID NO 77
<211> LENGTH: 2289
<212> TYPE: DNA
<213> ORGANISM: Artificial Sequence
<220> FEATURE:
<223> OTHER INFORMATION: Humanized TSC249 Scorpion (huVL-VH#2 107-1A4 scFv-FC-DRA222 scFv)

<400> SEQUENCE: 77

```
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
gggaaagttc ctaagctccg catccattct ggatctactt tgcaatcagg ggtcccatct     240
cggttcagtg gcagtggatc tgggacagaa tttactctca ccatcagcag cctgcagcct     300
gaagattttg caacttatta ctgtcaacag catattgaat acccgtggac gttcggccaa     360
gggaccaagg tggaaatcaa acgaggtggc ggagggtctg gggtggcgg atccggaggt     420
ggtggctctc aggtccagct ggtacagtct ggggctgagg tgaagaagcc tggggcttca     480
gtgaaggtct cctgcaaggc ttctggatac acattcactg actactacat gcactgggtg     540
cgacaggccc ctggacaagg gcttgagtgg atgggatatt ttaatcctta taatgattat     600
actagatacg cacagaagtt ccagggcaga gtcaccatga ccagggacac gtctatcagc     660
acagcctaca tggagctgag cagcctgaga tctgacgaca cggccgtgta ttactgtgca     720
agatcggatg ttactacga tgctatggac tactggggtc aaggaaccac agtcaccgtc     780
tcctcgagtg agcccaaatc ttctgacaaa actcacacat gcccaccgtg cccagcacct     840
gaagccgcgg gtgcaccgtc agtcttcctc ttccccccaa aacccaagga cacctcatg     900
atctcccgga cccctgaggt cacatgcgtg gtggtggacg tgagccacga agaccctgag     960
```

```
gtcaagttca actggtacgt ggacggcgtg gaggtgcata atgccaagac aaagccgcgg    1020
gaggagcagt acaacagcac gtaccgtgtg gtcagcgtcc tcaccgtcct gcaccaggac    1080
tggctgaatg gcaaggcgta cgcgtgcgcg gtctccaaca aagcccctcc cagcccccatc  1140 gagaaaacca tctccaaagc caaagggcag ccccgagaac cacaggtgta caccctgccc    1200
ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtcagaggca acaattct      1500 tccctgaata caggaactca gatggcaggt cattctccga attctcaggt ccagctggtg    1560
gagtctgggg gcggagtggt gcagcctggg cggtcactga ggctgtcctg caaggcttct    1620
ggctacacct ttactagatc tacgatgcac tgggtaaggc aggcccctgg acaaggtctg    1680
gaatggattg gatacattaa tcctagcagt gcttatacta attacaatca gaaattcaag    1740
gacaggttca caatcagcgc agacaaatcc aagagcacag ccttcctgca gatggacagc    1800
ctgaggcccg aggacaccgg cgtctatttc tgtgcacggc cccaagtcca ctatgattac    1860
aacgggtttc cttactgggg ccaagggact cccgtcactg tctctagcgg tggcggaggg    1920 tctggggtg gcggatccgg aggtggtggc tctgcacaag acatccagat gacccagtct     1980
ccaagcagcc tgtctgcaag cgtggggac agggtcacca tgacctgcag tgccagctca    2040
agtgtaagtt acatgaactg gtaccagcag aagccgggca aggcccccaa agatggatt    2100 tatgactcat ccaaactggc ttctggagtc cctgctcgct tcagtggcag tgggtctggg    2160
accgactata ccctcacaat cagcagcctg cagcccgaag atttcgccac ttattactgc    2220
cagcagtgga gtcgtaaccc cccacgttc ggaggggga ccaagctaca aattacatcc    2280
tccagctaa                                                           2289
```

<210> SEQ ID NO 78
<211> LENGTH: 742
<212> TYPE: PRT
<213> ORGANISM: Artificial Sequence
<220> FEATURE:
<223> OTHER INFORMATION: Humanized TSC249 Scorpion (huVL-VH#2 107-1A4
      scFv-Fc-DRA222 scFv)

<400> SEQUENCE: 78

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
```

-continued

```
            115                 120                 125
Gln Ser Gly Ala Glu Val Lys Lys Pro Gly Ala Ser Val Lys Val Ser
130                 135                 140
Cys Lys Ala Ser Gly Tyr Thr Phe Thr Asp Tyr Tyr Met His Trp Val
145                 150                 155                 160
Arg Gln Ala Pro Gly Gln Gly Leu Glu Trp Met Gly Tyr Phe Asn Pro
                165                 170                 175
Tyr Asn Asp Tyr Thr Arg Tyr Ala Gln Lys Phe Gln Gly Arg Val Thr
            180                 185                 190
Met Thr Arg Asp Thr Ser Ile Ser Thr Ala Tyr Met Glu Leu Ser Ser
        195                 200                 205
Leu Arg Ser Asp Asp Thr Ala Val Tyr Tyr Cys Ala Arg Ser Asp Gly
    210                 215                 220
Tyr Tyr Asp Ala Met Asp Tyr Trp Gly Gln Gly Thr Thr Val Thr Val
225                 230                 235                 240
Ser Ser Ser Glu Pro Lys Ser Ser Asp Lys Thr His Thr Cys Pro Pro
                245                 250                 255
Cys Pro Ala Pro Glu Ala Ala Gly Ala Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Ala Tyr Ala Cys Ala Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
        435                 440                 445
Asn Val Phe Ser Cys Ser Val Met His Glu Ala Leu His Asn His Tyr
    450                 455                 460
Thr Gln Lys Ser Leu Ser Leu Ser Pro Gly Gln Arg His Asn Asn Ser
465                 470                 475                 480
Ser Leu Asn Thr Gly Thr Gln Met Ala Gly His Ser Pro Asn Ser Gln
                485                 490                 495
Val Gln Leu Val Glu Ser Gly Gly Val Val Gln Pro Gly Arg Ser
            500                 505                 510
Leu Arg Leu Ser Cys Lys Ala Ser Gly Tyr Thr Phe Thr Arg Ser Thr
        515                 520                 525
Met His Trp Val Arg Gln Ala Pro Gly Gln Gly Leu Glu Trp Ile Gly
    530                 535                 540
```

```
Tyr Ile Asn Pro Ser Ser Ala Tyr Thr Asn Tyr Asn Gln Lys Phe Lys
545                 550                 555                 560

Asp Arg Phe Thr Ile Ser Ala Asp Lys Ser Lys Ser Thr Ala Phe Leu
                565                 570                 575

Gln Met Asp Ser Leu Arg Pro Glu Asp Thr Gly Val Tyr Phe Cys Ala
            580                 585                 590

Arg Pro Gln Val His Tyr Asp Tyr Asn Gly Phe Pro Tyr Trp Gly Gln
        595                 600                 605

Gly Thr Pro Val Thr Val Ser Ser Gly Gly Gly Ser Gly Gly Gly
    610                 615                 620

Gly Ser Gly Gly Gly Ser Ala Gln Asp Ile Gln Met Thr Gln Ser
625                 630                 635                 640

Pro Ser Ser Leu Ser Ala Ser Val Gly Asp Arg Val Thr Met Thr Cys
                645                 650                 655

Ser Ala Ser Ser Ser Val Ser Tyr Met Asn Trp Tyr Gln Gln Lys Pro
            660                 665                 670

Gly Lys Ala Pro Lys Arg Trp Ile Tyr Asp Ser Ser Lys Leu Ala Ser
        675                 680                 685

Gly Val Pro Ala Arg Phe Ser Gly Ser Gly Ser Gly Thr Asp Tyr Thr
    690                 695                 700

Leu Thr Ile Ser Ser Leu Gln Pro Glu Asp Phe Ala Thr Tyr Tyr Cys
705                 710                 715                 720

Gln Gln Trp Ser Arg Asn Pro Pro Thr Phe Gly Gly Gly Thr Lys Leu
                725                 730                 735

Gln Ile Thr Ser Ser Ser
            740
```

<210> SEQ ID NO 79
<211> LENGTH: 2268
<212> TYPE: DNA
<213> ORGANISM: Artificial Sequence
<220> FEATURE:
<223> OTHER INFORMATION: Humanized TSC250 Scorpion (huVL-VH#2 107-1A4
      scFv-Fc-DRA222 scFv, with H81 linker)

<400> SEQUENCE: 79

```
atggaagcac cagcgcagct tctcttcctc ctgctactct ggctcccaga taccaccggt    60
gatatccaga tgacccagtc tccatccgcc atgtctgcat ctgtaggaga cagagtcacc   120
atcacttgcc gggcgagtaa gagcattagc aaatatttag cctggtttca gcagaaacca   180
gggaaagttc ctaagctccg catccattct ggatctactt tgcaatcagg ggtcccatct   240
cggttcagtg gcagtggatc tgggacagaa tttactctca ccatcagcag cctgcagcct   300
gaagattttg caacttatta ctgtcaacag catattgaat cccgtggac gttcggccaa   360 gggaccaagg tggaaatcaa acgaggtggc ggagggtctg ggggtggcgg atccggaggt   420
ggtggctctc aggtccagct ggtacagtct ggggctgagg tgaagaagcc tggggcttca   480
gtgaaggtct cctgcaaggc ttctggatac acattcactg actactacat gcactgggtg   540
cgacaggccc ctggacaagg gcttgagtgg atgggatatt ttaatcctta taatgattat   600
actagatacg cacagaagtt ccagggcaga gtcaccatga ccagggacac gtctatcagc   660
acagcctaca tggagctgag cagcctgaga tctgacgaca cggccgtgta ttactgtgca   720
agatcggatg ttactacga tgctatggac tactggggtc aaggaaccac agtcaccgtc   780
tcctcgagtg agcccaaatc ttctgacaaa actcacacat gcccaccgtg cccagcacct   840
```

```
gaagccgcgg gtgcaccgtc agtcttcctc ttccccccaa acccaagga cacctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agccccatc    1140
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtgaagttca aattcccttg   1500
accgaaagtt acagcccgaa ttctcaggtc cagctggtgg agtctggggg cggagtggtg   1560
cagcctgggc ggtcactgag gctgtcctgc aaggcttctg gctacacctt tactagatct   1620
acgatgcact gggtaaggca ggcccctgga caaggtctgg aatggattgg atacattaat   1680
cctagcagtg cttatactaa ttacaatcag aaattcaagg acaggttcac aatcagcgca   1740
gacaaatcca agagcacagc cttcctgcag atggacagcc tgaggcccga ggacaccggc   1800
gtctatttct gtgcacggcc ccaagtccac tatgattaca acgggtttcc ttactggggc   1860
caagggactc ccgtcactgt ctctagcggt ggcggagggt ctgggggtgg cggatccgga   1920
ggtggtggct ctgcacaaga catccagatg acccagtctc caagcagcct gtctgcaagc   1980
gtggggggaca gggtcaccat gacctgcagt gccagctcaa gtgtaagtta catgaactgg   2040
taccagcaga agccgggcaa ggccccaaa agatggattt atgactcatc caaactggct   2100
tctggagtcc ctgctcgctt cagtggcagt gggtctggga ccgactatac cctcacaatc   2160
agcagcctgc agcccgaaga tttcgccact tattactgcc agcagtggag tcgtaaccca   2220
cccacgttcg agggggggac caagctacaa attacatcct ccagctaa                2268
```

<210> SEQ ID NO 80
<211> LENGTH: 1335
<212> TYPE: PRT
<213> ORGANISM: Artificial Sequence
<220> FEATURE:
<223> OTHER INFORMATION: Humanized TSC250 Scorpion (huVL-VH#2 107-1A4
      scFv-Fc-DRA222 scFv, with H81 linker)

<400> SEQUENCE: 80

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

```
Ser Gly Gly Gly Gly Ser Gly Gly Gly Ser Gln Val Gln Leu Val
        115                 120                 125
Gln Ser Gly Ala Glu Val Lys Lys Pro Gly Ala Ser Val Lys Val Ser
130                 135                 140
Cys Lys Ala Ser Gly Tyr Thr Phe Thr Asp Tyr Tyr Met His Trp Val
145                 150                 155                 160
Arg Gln Ala Pro Gly Gln Gly Leu Glu Trp Met Gly Tyr Phe Asn Pro
                165                 170                 175
Tyr Asn Asp Tyr Thr Arg Tyr Ala Gln Lys Phe Gln Gly Arg Val Thr
                180                 185                 190
Met Thr Arg Asp Thr Ser Ile Ser Thr Ala Tyr Met Glu Leu Ser Ser
            195                 200                 205
Leu Arg Ser Asp Asp Thr Ala Val Tyr Tyr Cys Ala Arg Ser Asp Gly
        210                 215                 220
Tyr Tyr Asp Ala Met Asp Tyr Trp Gly Gln Gly Thr Thr Val Thr Val
225                 230                 235                 240
Ser Ser Ser Glu Pro Lys Ser Ser Asp Lys Thr His Thr Cys Pro Pro
                245                 250                 255
Cys Pro Ala Pro Glu Ala Ala Gly Ala Pro Ser Val Phe Leu Phe Pro
                260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
        290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Ala Tyr Ala Cys Ala Val Ser
                340                 345                 350
Asn Lys Ala Leu Pro Ala Pro Ile Glu Lys Thr Ile Ser Lys Ala Lys
            355                 360                 365
Gly Gln Pro Arg Glu Pro Gln Val Tyr Thr Leu Pro Pro Ser Arg Asp
        370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
                420                 425                 430
Phe Leu Tyr Ser Lys Leu Thr Val Asp Lys Ser Arg Trp Gln Gln Gly
            435                 440                 445
Asn Val Phe Ser Cys Ser Val Met His Glu Ala Leu His Asn His Tyr
        450                 455                 460
Thr Gln Lys Ser Leu Ser Leu Ser Pro Gly Glu Val Gln Ile Pro Leu
465                 470                 475                 480
Thr Glu Ser Tyr Ser Pro Asn Ser Gln Val Gln Leu Val Glu Ser Gly
                485                 490                 495
Gly Gly Val Val Gln Pro Gly Arg Ser Leu Arg Leu Ser Cys Lys Ala
                500                 505                 510
Ser Gly Tyr Thr Phe Thr Arg Ser Thr Met His Trp Val Arg Gln Ala
            515                 520                 525
```

```
Pro Gly Gln Gly Leu Glu Trp Ile Gly Tyr Ile Asn Pro Ser Ser Ala
            530                 535                 540

Tyr Thr Asn Tyr Asn Gln Lys Phe Lys Asp Arg Phe Thr Ile Ser Ala
545                 550                 555                 560

Asp Lys Ser Lys Ser Thr Ala Phe Leu Gln Met Asp Ser Leu Arg Pro
                565                 570                 575

Glu Asp Thr Gly Val Tyr Phe Cys Ala Arg Pro Gln Val His Tyr Asp
            580                 585                 590

Tyr Asn Gly Phe Pro Tyr Trp Gly Asp Ile Gln Met Thr Gln Ser Pro
            595                 600                 605

Ser Ala Met Ser Ala Ser Val Gly Asp Arg Val Thr Ile Thr Cys Arg
610                 615                 620

Ala Ser Lys Ser Ile Ser Lys Tyr Leu Ala Trp Phe Gln Gln Lys Pro
625                 630                 635                 640

Gly Lys Val Pro Lys Leu Arg Ile His Ser Gly Ser Thr Leu Gln Ser
                645                 650                 655

Gly Val Pro Ser Arg Phe Ser Gly Ser Gly Ser Gly Thr Glu Phe Thr
                660                 665                 670

Leu Thr Ile Ser Ser Leu Gln Pro Glu Asp Phe Ala Thr Tyr Tyr Cys
            675                 680                 685

Gln Gln His Ile Glu Tyr Pro Trp Thr Phe Gly Gln Gly Thr Lys Val
690                 695                 700

Glu Ile Lys Arg Gly Gly Gly Gly Ser Gly Gly Gly Gly Ser Gly Gly
705                 710                 715                 720

Gly Gly Ser Gln Val Gln Leu Val Gln Ser Gly Ala Glu Val Lys Lys
                725                 730                 735

Pro Gly Ala Ser Val Lys Val Ser Cys Lys Ala Ser Gly Tyr Thr Phe
                740                 745                 750

Thr Asp Tyr Tyr Met His Trp Val Arg Gln Ala Pro Gly Gln Gly Leu
            755                 760                 765

Glu Trp Met Gly Tyr Phe Asn Pro Tyr Asn Asp Tyr Thr Arg Tyr Ala
770                 775                 780

Gln Lys Phe Gln Gly Arg Val Thr Met Thr Arg Asp Thr Ser Ile Ser
785                 790                 795                 800

Thr Ala Tyr Met Glu Leu Ser Ser Leu Arg Ser Asp Asp Thr Ala Val
                805                 810                 815

Tyr Tyr Cys Ala Arg Ser Asp Gly Tyr Tyr Asp Ala Met Asp Tyr Trp
                820                 825                 830

Gly Gln Gly Thr Thr Val Thr Val Ser Ser Glu Pro Lys Ser Ser
            835                 840                 845

Asp Lys Thr His Thr Cys Pro Pro Cys Pro Ala Pro Glu Ala Ala Gly
850                 855                 860

Ala Pro Ser Val Phe Leu Phe Pro Pro Lys Pro Lys Asp Thr Leu Met
865                 870                 875                 880

Ile Ser Arg Thr Pro Glu Val Thr Cys Val Val Val Asp Val Ser His
                885                 890                 895

Glu Asp Pro Glu Val Lys Phe Asn Trp Tyr Val Asp Gly Val Glu Val
            900                 905                 910

His Asn Ala Lys Thr Lys Pro Arg Glu Glu Gln Tyr Asn Ser Thr Tyr
            915                 920                 925

Arg Val Val Ser Val Leu Thr Val Leu His Gln Asp Trp Leu Asn Gly
930                 935                 940

Lys Ala Tyr Ala Cys Ala Val Ser Asn Lys Ala Leu Pro Ala Pro Ile
```

-continued

```
               945                 950                 955                 960
          Glu Lys Thr Ile Ser Lys Ala Lys Gly Gln Pro Arg Glu Pro Gln Val
                            965                 970                 975
          Tyr Thr Leu Pro Pro Ser Arg Asp Glu Leu Thr Lys Asn Gln Val Ser
                            980                 985                 990
          Leu Thr Cys Leu Val Lys Gly Phe Tyr Pro Ser Asp Ile Ala Val Glu
                            995                 1000                1005
          Trp Glu Ser Asn Gly Gln Pro Glu Asn Asn Tyr Lys Thr Thr Pro
                  1010                1015                1020
          Pro Val Leu Asp Ser Asp Gly Ser Phe Phe Leu Tyr Ser Lys Leu
                  1025                1030                1035
          Thr Val Asp Lys Ser Arg Trp Gln Gln Gly Asn Val Phe Ser Cys
                  1040                1045                1050
          Ser Val Met His Glu Ala Leu His Asn His Tyr Thr Gln Lys Ser
                  1055                1060                1065
          Leu Ser Leu Ser Pro Gly Glu Val Gln Ile Pro Leu Thr Glu Ser
                  1070                1075                1080
          Tyr Ser Pro Asn Ser Gln Val Gln Leu Val Glu Ser Gly Gly Gly
                  1085                1090                1095
          Val Val Gln Pro Gly Arg Ser Leu Arg Leu Ser Cys Lys Ala Ser
                  1100                1105                1110
          Gly Tyr Thr Phe Thr Arg Ser Thr Met His Trp Val Arg Gln Ala
                  1115                1120                1125
          Pro Gly Gln Gly Leu Glu Trp Ile Gly Tyr Ile Asn Pro Ser Ser
                  1130                1135                1140
          Ala Tyr Thr Asn Tyr Asn Gln Lys Phe Lys Asp Arg Phe Thr Ile
                  1145                1150                1155
          Ser Ala Asp Lys Ser Lys Ser Thr Ala Phe Leu Gln Met Asp Ser
                  1160                1165                1170
          Leu Arg Pro Glu Asp Thr Gly Val Tyr Phe Cys Ala Arg Pro Gln
                  1175                1180                1185
          Val His Tyr Asp Tyr Asn Gly Phe Pro Tyr Trp Gly Gln Gly Thr
                  1190                1195                1200
          Pro Val Thr Val Ser Ser Gly Gly Gly Ser Gly Gly Gly Gly
                  1205                1210                1215
          Ser Gly Gly Gly Gly Ser Ala Gln Asp Ile Gln Met Thr Gln Ser
                  1220                1225                1230
          Pro Ser Ser Leu Ser Ala Ser Val Gly Asp Arg Val Thr Met Thr
                  1235                1240                1245
          Cys Ser Ala Ser Ser Val Ser Tyr Met Asn Trp Tyr Gln Gln
                  1250                1255                1260
          Lys Pro Gly Lys Ala Pro Lys Arg Trp Ile Tyr Asp Ser Ser Lys
                  1265                1270                1275
          Leu Ala Ser Gly Val Pro Ala Arg Phe Ser Gly Ser Gly Ser Gly
                  1280                1285                1290
          Thr Asp Tyr Thr Leu Thr Ile Ser Ser Leu Gln Pro Glu Asp Phe
                  1295                1300                1305
          Ala Thr Tyr Tyr Cys Gln Gln Trp Ser Arg Asn Pro Pro Thr Phe
                  1310                1315                1320
          Gly Gly Gly Thr Lys Leu Gln Ile Thr Ser Ser Ser
                  1325                1330                1335
```

<210> SEQ ID NO 81

<211> LENGTH: 2274
<212> TYPE: DNA
<213> ORGANISM: Artificial Sequence
<220> FEATURE:
<223> OTHER INFORMATION: Humanized TSC251 Scorpion (huVL-VH#2 107-1A4
scFv-Fc-DRA222 scFv, with H83 linker)

<400> SEQUENCE: 81

| | | |
|---|---|---|
| atggaagcac cagcgcagct tctcttcctc ctgctactct ggctcccaga taccaccggt | 60 |
| gatatccaga tgacccagtc tccatccgcc atgtctgcat ctgtaggaga cagagtcacc | 120 |
| atcacttgcc gggcgagtaa gagcattagc aaatatttag cctggtttca gcagaaacca | 180 |
| gggaaagttc ctaagctccg catccattct ggatctactt tgcaatcagg ggtcccatct | 240 |
| cggttcagtg gcagtggatc tgggacagaa tttactctca ccatcagcag cctgcagcct | 300 |
| gaagattttg caacttatta ctgtcaacag catattgaat acccgtggac gttcggccaa | 360 |
| gggaccaagg tggaaatcaa acgaggtggc ggagggtctg ggggtggcgg atccggaggt | 420 |
| ggtggctctc aggtccagct ggtacagtct ggggctgagg tgaagaagcc tggggcttca | 480 |
| gtgaaggtct cctgcaaggc ttctggatac acattcactg actactacat gcactgggtg | 540 |
| cgacaggccc ctggacaagg gcttgagtgg atgggatatt ttaatcctta taatgattat | 600 |
| actagatacg cacagaagtt ccagggcaga gtcaccatga ccagggacac gtctatcagc | 660 |
| acagcctaca tggagctgag cagcctgaga tctgacgaca cggccgtgta ttactgtgca | 720 |
| agatcggatg gttactacga tgctatggac tactggggtc aaggaaccac agtcaccgtc | 780 |
| tcctcgagtg agcccaaatc ttctgacaaa actcacacat gcccaccgtg cccagcacct | 840 |
| gaagccgcgg gtgcaccgtc agtcttcctc ttccccccaa aacccaagga caccctcatg | 900 |
| atctcccgga cccctgaggt cacatgcgtg gtggtggacg tgagccacga agaccctgag | 960 |
| gtcaagttca actggtacgt ggacggcgtg gaggtgcata atgccaagac aaagccgcgg | 1020 |
| gaggagcagt acaacagcac gtaccgtgtg gtcagcgtcc tcaccgtcct gcaccaggac | 1080 |
| tggctgaatg gcaaggcgta cgcgtgcgcg gtctccaaca agcccctccc agccccatc | 1140 |
| gagaaaacca tctccaaagc caaagggcag ccccgagaac cacaggtgta caccctgccc | 1200 |
| ccatcccggg atgagctgac caagaaccag gtcagcctga cctgcctggt caaaggcttc | 1260 |
| tatccaagcg acatcgccgt ggagtgggag agcaatgggc agccggagaa caactacaag | 1320 |
| accacgcctc ccgtgctgga ctccgacggc tccttcttcc tctacagcaa gctcaccgtg | 1380 |
| gacaagagca ggtggcagca ggggaacgtc ttctcatgct ccgtgatgca tgaggctctg | 1440 |
| cacaaccact acacgcagaa gagcctctcc ctgtctccgg gttcttccct gaatacagga | 1500 |
| actcagatgg caggtcattc tccgaattct caggtccagc tggtggagtc tgggggcgga | 1560 |
| gtggtgcagc ctgggcggtc actgaggctg tcctgcaagg cttctggcta cacctttact | 1620 |
| agatctacga tgcactgggt aaggcaggcc cctggacaag tctggaatg gattggatac | 1680 |
| attaatccta gcagtgctta tactaattac aatcagaaat tcaaggacag gttcacaatc | 1740 |
| agcgcagaca atccaagag cacagccttc ctgcagatgg acagcctgag gcccgaggac | 1800 |
| accggcgtct atttctgtgc acggccccaa gtcactatg attacaacgg gtttccttac | 1860 |
| tggggccaag gactcccgt cactgtctct agcggtggcg agggtctgg gggtggcgga | 1920 |
| tccggaggtg gtggctctgc acaagacatc cagatgaccc agtctccaag cagcctgtct | 1980 |
| gcaagcgtgg gggacagggt caccatgacc tgcagtgcca gctcaagtgt aagttacatg | 2040 |
| aactggtacc agcagaagcc gggcaaggcc cccaaaagat ggatttatga ctcatccaaa | 2100 |

```
ctggcttctg gagtccctgc tcgcttcagt ggcagtgggt ctgggaccga ctatacccct   2160
acaatcagca gcctgcagcc cgaagatttc gccacttatt actgccagca gtggagtcgt   2220
aacccaccca cgttcggagg ggggaccaag ctacaaatta catcctccag ctaa          2274
```

<210> SEQ ID NO 82
<211> LENGTH: 737
<212> TYPE: PRT
<213> ORGANISM: Artificial Sequence
<220> FEATURE:
<223> OTHER INFORMATION: Humanized TSC251 Scorpion (huVL-VH#2 107-1A4
      scFv-Fc-DRA222 scFv, with H83 linker)

<400> SEQUENCE: 82

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335
```

```
Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Ser Ser Leu Asn Thr Gly
465                 470                 475                 480

Thr Gln Met Ala Gly His Ser Pro Asn Ser Gln Val Gln Leu Val Glu
            485                 490                 495

Ser Gly Gly Gly Val Val Gln Pro Gly Arg Ser Leu Arg Leu Ser Cys
            500                 505                 510

Lys Ala Ser Gly Tyr Thr Phe Thr Arg Ser Thr Met His Trp Val Arg
            515                 520                 525

Gln Ala Pro Gly Gln Gly Leu Glu Trp Ile Gly Tyr Ile Asn Pro Ser
            530                 535                 540

Ser Ala Tyr Thr Asn Tyr Asn Gln Lys Phe Lys Asp Arg Phe Thr Ile
545                 550                 555                 560

Ser Ala Asp Lys Ser Lys Ser Thr Ala Phe Leu Gln Met Asp Ser Leu
            565                 570                 575

Arg Pro Glu Asp Thr Gly Val Tyr Phe Cys Ala Arg Pro Gln Val His
            580                 585                 590

Tyr Asp Tyr Asn Gly Phe Pro Tyr Trp Gly Gln Gly Thr Pro Val Thr
            595                 600                 605

Val Ser Ser Gly Gly Gly Gly Ser Gly Gly Gly Gly Ser Gly Gly Gly
            610                 615                 620

Gly Ser Ala Gln Asp Ile Gln Met Thr Gln Ser Pro Ser Ser Leu Ser
625                 630                 635                 640

Ala Ser Val Gly Asp Arg Val Thr Met Thr Cys Ser Ala Ser Ser Ser
            645                 650                 655

Val Ser Tyr Met Asn Trp Tyr Gln Gln Lys Pro Gly Lys Ala Pro Lys
            660                 665                 670

Arg Trp Ile Tyr Asp Ser Ser Lys Leu Ala Ser Gly Val Pro Ala Arg
            675                 680                 685

Phe Ser Gly Ser Gly Ser Gly Thr Asp Tyr Thr Leu Thr Ile Ser Ser
            690                 695                 700

Leu Gln Pro Glu Asp Phe Ala Thr Tyr Tyr Cys Gln Gln Trp Ser Arg
705                 710                 715                 720

Asn Pro Pro Thr Phe Gly Gly Gly Thr Lys Leu Gln Ile Thr Ser Ser
            725                 730                 735

Ser
```

-continued

```
<210> SEQ ID NO 83
<211> LENGTH: 2286
<212> TYPE: DNA
<213> ORGANISM: Artificial Sequence
<220> FEATURE:
<223> OTHER INFORMATION: Humanized TSC252 Scorpion (huVL-VH#2 107-1A4
      scFv-Fc-DRA222 scFv, with H91 linker)

<400> SEQUENCE: 83
```

| | | | | | |
|---|---|---|---|---|---|
| atggaagcac | cagcgcagct | tctcttcctc | ctgctactct | ggctcccaga | taccaccggt | 60 |
| gatatccaga | tgacccagtc | tccatccgcc | atgtctgcat | ctgtaggaga | cagagtcacc | 120 |
| atcacttgcc | gggcgagtaa | gagcattagc | aaatatttag | cctggtttca | gcagaaacca | 180 |
| gggaaagttc | ctaagctccg | catccattct | ggatctactt | tgcaatcagg | ggtcccatct | 240 |
| cggttcagtg | gcagtggatc | tgggacagaa | tttactctca | ccatcagcag | cctgcagcct | 300 |
| gaagattttg | caacttatta | ctgtcaacag | catattgaat | acccgtggac | gttcggccaa | 360 |
| gggaccaagg | tggaaatcaa | acgaggtggc | ggagggtctg | ggggtggcgg | atccggaggt | 420 |
| ggtggctctc | aggtccagct | ggtacagtct | ggggctgagg | tgaagaagcc | tggggcttca | 480 |
| gtgaaggtct | cctgcaaggc | ttctggatac | acattcactg | actactacat | gcactgggtg | 540 |
| cgacaggccc | ctggacaagg | gcttgagtgg | atgggatatt | ttaatcctta | taatgattat | 600 |
| actagatacg | cacagaagtt | ccagggcaga | gtcaccatga | ccagggacac | gtctatcagc | 660 |
| acagcctaca | tggagctgag | cagcctgaga | tctgacgaca | cggccgtgta | ttactgtgca | 720 |
| agatcggatg | ttactacga | tgctatggac | tactggggtc | aaggaaccac | agtcaccgtc | 780 |
| tcctcgagtg | agcccaaatc | ttctgacaaa | actcacacat | gcccaccgtg | cccagcacct | 840 |
| gaagccgcgg | gtgcaccgtc | agtcttcctc | ttccccccaa | aacccaagga | caccctcatg | 900 |
| atctcccgga | cccctgaggt | cacatgcgtg | gtggtggacg | tgagccacga | agaccctgag | 960 |
| gtcaagttca | actggtacgt | ggacggcgtg | gaggtgcata | atgccaagac | aaagccgcgg | 1020 |
| gaggagcagt | acaacagcac | gtaccgtgtg | gtcagcgtcc | tcaccgtcct | gcaccaggac | 1080 |
| tggctgaatg | gcaaggcgta | cgcgtgcgcg | gtctccaaca | aagccctccc | agcccccatc | 1140 |
| gagaaaacca | tctccaaagc | caagggcag | ccccgagaac | cacaggtgta | caccctgccc | 1200 |
| ccatcccggg | atgagctgac | caagaaccag | gtcagcctga | cctgcctggt | caaaggcttc | 1260 |
| tatccaagcg | acatcgccgt | ggagtgggag | agcaatgggc | agccggagaa | caactacaag | 1320 |
| accacgcctc | ccgtgctgga | ctccgacggc | tccttcttcc | tctacagcaa | gctcaccgtg | 1380 |
| gacaagagca | ggtggcagca | ggggaacgtc | ttctcatgct | ccgtgatgca | tgaggctctg | 1440 |
| cacaaccact | acacgcagaa | gagcctctcc | ctgtctccgg | gtaactcatt | agcaaaccaa | 1500 |
| gaagttcaaa | ttcccttgac | cgaaagttac | agcccgaatt | ctcaggtcca | gctggtggag | 1560 |
| tctgggggcg | gagtggtgca | gcctgggcgg | tcactgaggc | tgtcctgcaa | ggcttctggc | 1620 |
| tacacctttta | ctagatctac | gatgcactgg | gtaaggcagg | ccctggaca | aggtctggaa | 1680 |
| tggattggat | acattaatcc | tagcagtgct | tatactaatt | acaatcagaa | attcaaggac | 1740 |
| aggttcacaa | tcagcgcaga | caaatccaag | agcacagcct | tcctgcagat | ggacagcctg | 1800 |
| aggcccgagg | acaccggcgt | ctatttctgt | gcacggcccc | aagtccacta | tgattacaac | 1860 |
| gggtttcctt | actggggcca | aggactcccc | gtcactgtct | ctagcggtgg | cggagggtct | 1920 |
| gggggtggcg | gatccggagg | tggtggctct | gcacaagaca | tccagatgac | ccagtctcca | 1980 |
| agcagcctgt | ctgcaagcgt | ggggacagg | gtcaccatga | cctgcagtgc | cagctcaagt | 2040 |
| gtaagttaca | tgaactggta | ccagcagaag | ccgggcaagg | cccccaaaag | atggatttat | 2100 |

-continued

```
gactcatcca aactggcttc tggagtccct gctcgcttca gtggcagtgg gtctgggacc    2160
gactataccc tcacaatcag cagcctgcag cccgaagatt tcgccactta ttactgccag    2220
cagtggagtc gtaacccacc cacgttcgga ggggggacca agctacaaat tacatcctcc    2280
agctaa                                                              2286
```

<210> SEQ ID NO 84
<211> LENGTH: 1478
<212> TYPE: PRT
<213> ORGANISM: Artificial Sequence
<220> FEATURE:
<223> OTHER INFORMATION: Humanized TSC252 Scorpion (huVL-VH#2 107-1A4
      scFv-Fc-DRA222 scFv, with H91 linker)

<400> SEQUENCE: 84

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320
```

```
Glu Glu Gln Tyr Asn Ser Thr Tyr Arg Val Ser Val Leu Thr Val
                325                 330                 335
Leu His Gln Asp Trp Leu Asn Gly Lys Ala Tyr Ala Cys Ala Val Ser
                340                 345                 350
Asn Lys Ala Leu Pro Ala Pro Ile Glu Lys Thr Ile Ser Lys Ala Lys
                355                 360                 365
Gly Gln Pro Arg Glu Pro Gln Val Tyr Thr Leu Pro Pro Ser Arg Asp
                370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
                420                 425                 430
Phe Leu Tyr Ser Lys Leu Thr Val Asp Lys Ser Arg Trp Gln Gln Gly
                435                 440                 445
Asn Val Phe Ser Cys Ser Val Met His Glu Ala Leu His Asn His Tyr
                450                 455                 460
Thr Gln Lys Ser Leu Ser Leu Ser Pro Gly Ser Ser Leu Asn Thr Gly
465                 470                 475                 480
Thr Gln Met Ala Gly His Ser Pro Asn Ser Gln Val Gln Leu Val Glu
                485                 490                 495
Ser Gly Gly Gly Val Val Gln Pro Gly Arg Ser Leu Arg Leu Ser Cys
                500                 505                 510
Lys Ala Ser Gly Tyr Thr Phe Thr Arg Ser Thr Met His Trp Val Arg
                515                 520                 525
Gln Ala Pro Gly Gln Gly Leu Glu Trp Ile Gly Tyr Ile Asn Pro Ser
                530                 535                 540
Ser Ala Tyr Thr Asn Tyr Asn Gln Lys Phe Lys Asp Arg Phe Thr Ile
545                 550                 555                 560
Ser Ala Asp Lys Ser Lys Ser Thr Ala Phe Leu Gln Met Asp Ser Leu
                565                 570                 575
Arg Pro Glu Asp Thr Gly Val Tyr Phe Cys Ala Arg Pro Gln Val His
                580                 585                 590
Tyr Asp Tyr Asn Gly Phe Pro Tyr Trp Gly Gln Gly Thr Pro Val Thr
                595                 600                 605
Val Ser Ser Gly Gly Gly Gly Ser Gly Gly Gly Ser Gly Gly Gly Gly
                610                 615                 620
Gly Ser Ala Gln Asp Ile Gln Met Thr Gln Ser Pro Ser Ser Leu Ser
625                 630                 635                 640
Ala Ser Val Gly Asp Arg Val Thr Met Thr Cys Ser Ala Ser Ser Ser
                645                 650                 655
Val Ser Tyr Met Asn Trp Tyr Gln Gln Lys Pro Gly Lys Ala Pro Lys
                660                 665                 670
Arg Trp Ile Tyr Asp Ser Ser Lys Leu Ala Ser Gly Val Pro Ala Arg
                675                 680                 685
Phe Ser Gly Ser Gly Ser Gly Thr Asp Tyr Thr Leu Thr Ile Ser Ser
                690                 695                 700
Leu Gln Pro Glu Asp Phe Ala Thr Tyr Tyr Cys Gln Gln Trp Ser Arg
705                 710                 715                 720
Asn Pro Pro Thr Phe Gly Gly Gly Thr Lys Leu Gln Ile Thr Ser Ser
                725                 730                 735
```

```
Ser Asp Ile Gln Met Thr Gln Ser Pro Ser Ala Met Ser Ala Ser Val
            740                 745                 750

Gly Asp Arg Val Thr Ile Thr Cys Arg Ala Ser Lys Ser Ile Ser Lys
            755                 760                 765

Tyr Leu Ala Trp Phe Gln Gln Lys Pro Gly Lys Val Pro Lys Leu Arg
            770                 775                 780

Ile His Ser Gly Ser Thr Leu Gln Ser Gly Val Pro Ser Arg Phe Ser
785                 790                 795                 800

Gly Ser Gly Ser Gly Thr Glu Phe Thr Leu Thr Ile Ser Ser Leu Gln
            805                 810                 815

Pro Glu Asp Phe Ala Thr Tyr Tyr Cys Gln Gln His Ile Glu Tyr Pro
            820                 825                 830

Trp Thr Phe Gly Gln Gly Thr Lys Val Glu Ile Lys Arg Gly Gly Gly
            835                 840                 845

Gly Ser Gly Gly Gly Gly Ser Gly Gly Gly Ser Gln Val Gln Leu
            850                 855                 860

Val Gln Ser Gly Ala Glu Val Lys Lys Pro Gly Ala Ser Val Lys Val
865                 870                 875                 880

Ser Cys Lys Ala Ser Gly Tyr Thr Phe Thr Asp Tyr Tyr Met His Trp
            885                 890                 895

Val Arg Gln Ala Pro Gly Gln Gly Leu Glu Trp Met Gly Tyr Phe Asn
            900                 905                 910

Pro Tyr Asn Asp Tyr Thr Arg Tyr Ala Gln Lys Phe Gln Gly Arg Val
            915                 920                 925

Thr Met Thr Arg Asp Thr Ser Ile Ser Thr Ala Tyr Met Glu Leu Ser
            930                 935                 940

Ser Leu Arg Ser Asp Asp Thr Ala Val Tyr Tyr Cys Ala Arg Ser Asp
945                 950                 955                 960

Gly Tyr Tyr Asp Ala Met Asp Tyr Trp Gly Gln Gly Thr Thr Val Thr
            965                 970                 975

Val Ser Ser Glu Pro Lys Ser Ser Asp Lys Thr His Thr Cys Pro
            980                 985                 990

Pro Cys Pro Ala Pro Glu Ala Ala  Gly Ala Pro Ser Val  Phe Leu Phe
            995                 1000                1005

Pro Pro Lys Pro Lys Asp Thr  Leu Met Ile Ser Arg  Thr Pro Glu
    1010                1015                1020

Val Thr Cys Val Val Val Asp  Val Ser His Glu Asp  Pro Glu Val
    1025                1030                1035

Lys Phe Asn Trp Tyr Val Asp  Gly Val Glu Val His  Asn Ala Lys
    1040                1045                1050

Thr Lys Pro Arg Glu Glu Gln  Tyr Asn Ser Thr Tyr  Arg Val Val
    1055                1060                1065

Ser Val Leu Thr Val Leu His  Gln Asp Trp Leu Asn  Gly Lys Ala
    1070                1075                1080

Tyr Ala Cys Ala Val Ser Asn  Lys Ala Leu Pro Ala  Pro Ile Glu
    1085                1090                1095

Lys Thr Ile Ser Lys Ala Lys  Gly Gln Pro Arg Glu  Pro Gln Val
    1100                1105                1110

Tyr Thr Leu Pro Pro Ser Arg  Asp Glu Leu Thr Lys  Asn Gln Val
    1115                1120                1125

Ser Leu Thr Cys Leu Val Lys  Gly Phe Tyr Pro Ser  Asp Ile Ala
    1130                1135                1140

Val Glu Trp Glu Ser Asn Gly  Gln Pro Glu Asn Asn  Tyr Lys Thr
```

```
            1145                1150                1155

Thr Pro Pro Val Leu Asp Ser Asp Gly Ser Phe Phe Leu Tyr Ser
        1160                1165                1170

Lys Leu Thr Val Asp Lys Ser Arg Trp Gln Gln Gly Asn Val Phe
    1175                1180                1185

Ser Cys Ser Val Met His Glu Ala Leu His Asn His Tyr Thr Gln
1190                1195                1200

Lys Ser Leu Ser Leu Ser Pro Gly Asn Ser Leu Ala Asn Gln Glu
        1205                1210                1215

Val Gln Ile Pro Leu Thr Glu Ser Tyr Ser Pro Asn Ser Gln Val
    1220                1225                1230

Gln Leu Val Glu Ser Gly Gly Val Val Gln Pro Gly Arg Ser
1235                1240                1245

Leu Arg Leu Ser Cys Lys Ala Ser Gly Tyr Thr Phe Thr Arg Ser
        1250                1255                1260

Thr Met His Trp Val Arg Gln Ala Pro Gly Gln Gly Leu Glu Trp
    1265                1270                1275

Ile Gly Tyr Ile Asn Pro Ser Ser Ala Tyr Thr Asn Tyr Asn Gln
1280                1285                1290

Lys Phe Lys Asp Arg Phe Thr Ile Ser Ala Asp Lys Ser Lys Ser
        1295                1300                1305

Thr Ala Phe Leu Gln Met Asp Ser Leu Arg Pro Glu Asp Thr Gly
    1310                1315                1320

Val Tyr Phe Cys Ala Arg Pro Gln Val His Tyr Asp Tyr Asn Gly
1325                1330                1335

Phe Pro Tyr Trp Gly Gln Gly Thr Pro Val Thr Val Ser Ser Gly
        1340                1345                1350

Gly Gly Gly Ser Gly Gly Gly Ser Gly Gly Gly Ser Ala
    1355                1360                1365

Gln Asp Ile Gln Met Thr Gln Ser Pro Ser Ser Leu Ser Ala Ser
1370                1375                1380

Val Gly Asp Arg Val Thr Met Thr Cys Ser Ala Ser Ser Ser Val
        1385                1390                1395

Ser Tyr Met Asn Trp Tyr Gln Gln Lys Pro Gly Lys Ala Pro Lys
    1400                1405                1410

Arg Trp Ile Tyr Asp Ser Ser Lys Leu Ala Ser Gly Val Pro Ala
1415                1420                1425

Arg Phe Ser Gly Ser Gly Ser Gly Thr Asp Tyr Thr Leu Thr Ile
        1430                1435                1440

Ser Ser Leu Gln Pro Glu Asp Phe Ala Thr Tyr Tyr Cys Gln Gln
    1445                1450                1455

Trp Ser Arg Asn Pro Pro Thr Phe Gly Gly Gly Thr Lys Leu Gln
1460                1465                1470

Ile Thr Ser Ser Ser
        1475

<210> SEQ ID NO 85
<211> LENGTH: 20
<212> TYPE: PRT
<213> ORGANISM: Artificial Sequence
<220> FEATURE:
<223> OTHER INFORMATION: secretory signal sequence

<400> SEQUENCE: 85

Met Glu Ala Pro Ala Gln Leu Leu Phe Leu Leu Leu Leu Trp Leu Pro
```

-continued

```
1               5                   10                  15

Asp Thr Thr Gly
            20

<210> SEQ ID NO 86
<211> LENGTH: 106
<212> TYPE: PRT
<213> ORGANISM: Artificial Sequence
<220> FEATURE:
<223> OTHER INFORMATION: HuM291 VL amino acid sequence

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 87
<211> LENGTH: 120
<212> TYPE: PRT
<213> ORGANISM: Artificial Sequence
<220> FEATURE:
<223> OTHER INFORMATION: HuM291 VH amino acid sequence

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser
        115                 120

<210> SEQ ID NO 88
<211> LENGTH: 15
<212> TYPE: PRT
<213> ORGANISM: Artificial Sequence
<220> FEATURE:
<223> OTHER INFORMATION: sss(s)-hIgG1 hinge

<400> SEQUENCE: 88
```

```
Glu Pro Lys Ser Ser Asp Lys Thr His Thr Ser Pro Ser Ser
1               5                   10                  15
```

<210> SEQ ID NO 89
<211> LENGTH: 15
<212> TYPE: PRT
<213> ORGANISM: Artificial Sequence
<220> FEATURE:
<223> OTHER INFORMATION: csc(s)-hIgG1 hinge

<400> SEQUENCE: 89

```
Glu Pro Lys Ser Cys Asp Lys Thr His Thr Ser Pro Pro Cys Ser
1               5                   10                  15
```

<210> SEQ ID NO 90
<211> LENGTH: 15
<212> TYPE: PRT
<213> ORGANISM: Artificial Sequence
<220> FEATURE:
<223> OTHER INFORMATION: ssc(s)-hIgG1 hinge

<400> SEQUENCE: 90

```
Glu Pro Lys Ser Ser Asp Lys Thr His Thr Ser Pro Pro Cys Ser
1               5                   10                  15
```

<210> SEQ ID NO 91
<211> LENGTH: 15
<212> TYPE: PRT
<213> ORGANISM: Artificial Sequence
<220> FEATURE:
<223> OTHER INFORMATION: scc(s)-hIgG1 hinge

<400> SEQUENCE: 91

```
Glu Pro Lys Ser Ser Asp Lys Thr His Thr Cys Pro Pro Cys Ser
1               5                   10                  15
```

<210> SEQ ID NO 92
<211> LENGTH: 15
<212> TYPE: PRT
<213> ORGANISM: Artificial Sequence
<220> FEATURE:
<223> OTHER INFORMATION: css(s)-hIgG1 hinge

<400> SEQUENCE: 92

```
Glu Pro Lys Ser Cys Asp Lys Thr His Thr Ser Pro Pro Ser Ser
1               5                   10                  15
```

<210> SEQ ID NO 93
<211> LENGTH: 15
<212> TYPE: PRT
<213> ORGANISM: Artificial Sequence
<220> FEATURE:
<223> OTHER INFORMATION: scs(s)-hIgG1 hinge

<400> SEQUENCE: 93

```
Glu Pro Lys Ser Ser Asp Lys Thr His Thr Cys Pro Pro Ser Ser
1               5                   10                  15
```

<210> SEQ ID NO 94
<211> LENGTH: 15
<212> TYPE: PRT
<213> ORGANISM: Artificial Sequence
<220> FEATURE:
<223> OTHER INFORMATION: ccc(s)-hIgG1 hinge

<400> SEQUENCE: 94

```
Glu Pro Lys Ser Cys Asp Lys Thr His Thr Ser Pro Pro Cys Ser
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: ccc(p)-hIgG1 hinge

<400> SEQUENCE: 95

Glu Pro Lys Ser Cys Asp Lys Thr His Thr Ser Pro Pro Cys Pro
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: sss(p)-hIgG1 hinge

<400> SEQUENCE: 96

Glu Pro Lys Ser Ser Asp Lys Thr His Thr Ser Pro Pro Ser Pro
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: csc(p)-hIgG1 hinge

<400> SEQUENCE: 97

Glu Pro Lys Ser Cys Asp Lys Thr His Thr Ser Pro Pro Cys Pro
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: ssc(p)-hIgG1 hinge

<400> SEQUENCE: 98

Glu Pro Lys Ser Ser Asp Lys Thr His Thr Ser Pro Pro Cys Pro
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: scc(p)-hIgG1 hinge

<400> SEQUENCE: 99

Glu Pro Lys Ser Ser Asp Lys Thr His Thr Cys Pro Pro Cys Pro
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: css(p)-hIgG1 hinge

<400> SEQUENCE: 100

Glu Pro Lys Ser Cys Asp Lys Thr His Thr Ser Pro Pro Ser Pro
```

-continued

<210> SEQ ID NO 101
<211> LENGTH: 15
<212> TYPE: PRT
<213> ORGANISM: Artificial Sequence
<220> FEATURE:
<223> OTHER INFORMATION: scs(p)-hIgG1 hinge

<400> SEQUENCE: 101

Glu Pro Lys Ser Ser Asp Lys Thr His Thr Cys Pro Pro Ser Pro
1               5                   10                  15

<210> SEQ ID NO 102
<211> LENGTH: 6
<212> TYPE: PRT
<213> ORGANISM: Artificial Sequence
<220> FEATURE:
<223> OTHER INFORMATION: Scppcp

<400> SEQUENCE: 102

Ser Cys Pro Pro Cys Pro
1               5

<210> SEQ ID NO 103
<211> LENGTH: 20
<212> TYPE: PRT
<213> ORGANISM: Artificial Sequence
<220> FEATURE:
<223> OTHER INFORMATION: STD1

<400> SEQUENCE: 103

Asn Tyr Gly Gly Gly Gly Ser Gly Gly Gly Gly Ser Gly Gly Gly
1               5                   10                  15

Ser Gly Asn Ser
            20

<210> SEQ ID NO 104
<211> LENGTH: 38
<212> TYPE: PRT
<213> ORGANISM: Artificial Sequence
<220> FEATURE:
<223> OTHER INFORMATION: STD2

<400> SEQUENCE: 104

Asn Tyr Gly Gly Gly Gly Ser Gly Gly Gly Gly Ser Gly Gly Gly
1               5                   10                  15

Ser Gly Asn Tyr Gly Gly Gly Gly Ser Gly Gly Gly Gly Ser Gly Gly
            20                  25                  30

Gly Gly Ser Gly Asn Ser
        35

<210> SEQ ID NO 105
<211> LENGTH: 2
<212> TYPE: PRT
<213> ORGANISM: Artificial Sequence
<220> FEATURE:
<223> OTHER INFORMATION: H1

<400> SEQUENCE: 105

Asn Ser
1

<210> SEQ ID NO 106
<211> LENGTH: 8

```
<212> TYPE: PRT
<213> ORGANISM: Artificial Sequence
<220> FEATURE:
<223> OTHER INFORMATION: H2

<400> SEQUENCE: 106

Gly Gly Gly Gly Ser Gly Asn Ser
1               5

<210> SEQ ID NO 107
<211> LENGTH: 10
<212> TYPE: PRT
<213> ORGANISM: Artificial Sequence
<220> FEATURE:
<223> OTHER INFORMATION: H3

<400> SEQUENCE: 107

Asn Tyr Gly Gly Gly Gly Ser Gly Asn Ser
1               5                   10

<210> SEQ ID NO 108
<211> LENGTH: 13
<212> TYPE: PRT
<213> ORGANISM: Artificial Sequence
<220> FEATURE:
<223> OTHER INFORMATION: H4

<400> SEQUENCE: 108

Gly Gly Gly Gly Ser Gly Gly Gly Ser Gly Asn Ser
1               5                   10

<210> SEQ ID NO 109
<211> LENGTH: 15
<212> TYPE: PRT
<213> ORGANISM: Artificial Sequence
<220> FEATURE:
<223> OTHER INFORMATION: H5

<400> SEQUENCE: 109

Asn Tyr Gly Gly Gly Gly Ser Gly Gly Gly Gly Ser Gly Asn Ser
1               5                   10                  15

<210> SEQ ID NO 110
<211> LENGTH: 18
<212> TYPE: PRT
<213> ORGANISM: Artificial Sequence
<220> FEATURE:
<223> OTHER INFORMATION: H6

<400> SEQUENCE: 110

Gly Gly Gly Gly Ser Gly Gly Gly Ser Gly Gly Gly Gly Ser Gly
1               5                   10                  15

Asn Ser

<210> SEQ ID NO 111
<211> LENGTH: 12
<212> TYPE: PRT
<213> ORGANISM: Artificial Sequence
<220> FEATURE:
<223> OTHER INFORMATION: (G4S)3

<400> SEQUENCE: 111

Gly Gly Gly Ser Gly Gly Gly Ser Gly Gly Gly Ser
1               5                   10

<210> SEQ ID NO 112
```

```
<211> LENGTH: 17
<212> TYPE: PRT
<213> ORGANISM: Artificial Sequence
<220> FEATURE:
<223> OTHER INFORMATION: (GAS)4

<400> SEQUENCE: 112

Gly Gly Gly Ser Gly Gly Gly Ser Gly Gly Gly Ser Gly Gly Gly Gly
1               5                   10                  15

Ser

<210> SEQ ID NO 113
<211> LENGTH: 15
<212> TYPE: PRT
<213> ORGANISM: Artificial Sequence
<220> FEATURE:
<223> OTHER INFORMATION: H16

<400> SEQUENCE: 113

Leu Ser Val Lys Ala Asp Phe Leu Thr Pro Ser Ile Gly Asn Ser
1               5                   10                  15

<210> SEQ ID NO 114
<211> LENGTH: 20
<212> TYPE: PRT
<213> ORGANISM: Artificial Sequence
<220> FEATURE:
<223> OTHER INFORMATION: H17

<400> SEQUENCE: 114

Leu Ser Val Lys Ala Asp Phe Leu Thr Pro Ser Ile Ser Cys Pro Pro
1               5                   10                  15

Cys Pro Asn Ser
            20

<210> SEQ ID NO 115
<211> LENGTH: 15
<212> TYPE: PRT
<213> ORGANISM: Artificial Sequence
<220> FEATURE:
<223> OTHER INFORMATION: H18

<400> SEQUENCE: 115

Leu Ser Val Leu Ala Asn Phe Ser Gln Pro Glu Ile Gly Asn Ser
1               5                   10                  15

<210> SEQ ID NO 116
<211> LENGTH: 20
<212> TYPE: PRT
<213> ORGANISM: Artificial Sequence
<220> FEATURE:
<223> OTHER INFORMATION: H19

<400> SEQUENCE: 116

Leu Ser Val Leu Ala Asn Phe Ser Gln Pro Glu Ile Ser Cys Pro Pro
1               5                   10                  15

Cys Pro Asn Ser
            20

<210> SEQ ID NO 117
<211> LENGTH: 15
<212> TYPE: PRT
<213> ORGANISM: Artificial Sequence
<220> FEATURE:
<223> OTHER INFORMATION: H20
```

```
<400> SEQUENCE: 117

Leu Lys Ile Gln Glu Arg Val Ser Lys Pro Lys Ile Ser Asn Ser
1               5                   10                  15

<210> SEQ ID NO 118
<211> LENGTH: 20
<212> TYPE: PRT
<213> ORGANISM: Artificial Sequence
<220> FEATURE:
<223> OTHER INFORMATION: H21

<400> SEQUENCE: 118

Leu Lys Ile Gln Glu Arg Val Ser Lys Pro Lys Ile Ser Cys Pro Pro
1               5                   10                  15

Cys Pro Asn Ser
            20

<210> SEQ ID NO 119
<211> LENGTH: 15
<212> TYPE: PRT
<213> ORGANISM: Artificial Sequence
<220> FEATURE:
<223> OTHER INFORMATION: H22

<400> SEQUENCE: 119

Leu Asn Val Ser Glu Arg Pro Phe Pro Pro His Ile Gln Asn Ser
1               5                   10                  15

<210> SEQ ID NO 120
<211> LENGTH: 21
<212> TYPE: PRT
<213> ORGANISM: Artificial Sequence
<220> FEATURE:
<223> OTHER INFORMATION: H23

<400> SEQUENCE: 120

Leu Asp Val Ser Glu Arg Pro Phe Pro Pro His Ile Gln Ser Cys Pro
1               5                   10                  15

Pro Cys Pro Asn Ser
            20

<210> SEQ ID NO 121
<211> LENGTH: 15
<212> TYPE: PRT
<213> ORGANISM: Artificial Sequence
<220> FEATURE:
<223> OTHER INFORMATION: H24

<400> SEQUENCE: 121

Arg Glu Gln Leu Ala Glu Val Thr Leu Ser Leu Lys Ala Asn Ser
1               5                   10                  15

<210> SEQ ID NO 122
<211> LENGTH: 20
<212> TYPE: PRT
<213> ORGANISM: Artificial Sequence
<220> FEATURE:
<223> OTHER INFORMATION: H25

<400> SEQUENCE: 122

Arg Glu Gln Leu Ala Glu Val Thr Leu Ser Leu Lys Ala Cys Pro Pro
1               5                   10                  15

Cys Pro Asn Ser
            20
```

<210> SEQ ID NO 123
<211> LENGTH: 15
<212> TYPE: PRT
<213> ORGANISM: Artificial Sequence
<220> FEATURE:
<223> OTHER INFORMATION: H26

<400> SEQUENCE: 123

Arg Ile His Gln Met Asn Ser Glu Leu Ser Val Leu Ala Asn Ser
1               5                   10                  15

<210> SEQ ID NO 124
<211> LENGTH: 20
<212> TYPE: PRT
<213> ORGANISM: Artificial Sequence
<220> FEATURE:
<223> OTHER INFORMATION: H27

<400> SEQUENCE: 124

Arg Ile His Gln Met Asn Ser Glu Leu Ser Val Leu Ala Cys Pro Pro
1               5                   10                  15

Cys Pro Asn Ser
            20

<210> SEQ ID NO 125
<211> LENGTH: 15
<212> TYPE: PRT
<213> ORGANISM: Artificial Sequence
<220> FEATURE:
<223> OTHER INFORMATION: H28

<400> SEQUENCE: 125

Asp Thr Lys Gly Lys Asn Val Leu Glu Lys Ile Phe Ser Asn Ser
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: H30

<400> SEQUENCE: 126

Leu Pro Pro Glu Thr Gln Glu Ser Gln Glu Val Thr Leu Asn Ser
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: H32

<400> SEQUENCE: 127

Arg Ile His Leu Asn Val Ser Glu Arg Pro Phe Pro Pro Asn Ser
1               5                   10                  15

<210> SEQ ID NO 128
<211> LENGTH: 20
<212> TYPE: PRT
<213> ORGANISM: Artificial Sequence
<220> FEATURE:
<223> OTHER INFORMATION: H33

<400> SEQUENCE: 128

Arg Ile His Leu Asn Val Ser Glu Arg Pro Phe Pro Pro Cys Pro Pro

Cys Pro Asn Ser
            20

<210> SEQ ID NO 129
<211> LENGTH: 13
<212> TYPE: PRT
<213> ORGANISM: Artificial Sequence
<220> FEATURE:
<223> OTHER INFORMATION: H36

<400> SEQUENCE: 129

Gly Cys Pro Pro Cys Pro Gly Gly Gly Ser Asn Ser
1               5                   10

<210> SEQ ID NO 130
<211> LENGTH: 9
<212> TYPE: PRT
<213> ORGANISM: Artificial Sequence
<220> FEATURE:
<223> OTHER INFORMATION: H40

<400> SEQUENCE: 130

Gly Cys Pro Pro Cys Pro Ala Asn Ser
1               5

<210> SEQ ID NO 131
<211> LENGTH: 9
<212> TYPE: PRT
<213> ORGANISM: Artificial Sequence
<220> FEATURE:
<223> OTHER INFORMATION: H41

<400> SEQUENCE: 131

Gly Cys Pro Pro Cys Pro Ala Asn Ser
1               5

<210> SEQ ID NO 132
<211> LENGTH: 8
<212> TYPE: PRT
<213> ORGANISM: Artificial Sequence
<220> FEATURE:
<223> OTHER INFORMATION: H42

<400> SEQUENCE: 132

Gly Cys Pro Pro Cys Pro Asn Ser
1               5

<210> SEQ ID NO 133
<211> LENGTH: 13
<212> TYPE: PRT
<213> ORGANISM: Artificial Sequence
<220> FEATURE:
<223> OTHER INFORMATION: H44

<400> SEQUENCE: 133

Gly Gly Gly Ala Ser Cys Pro Pro Cys Pro Gly Asn Ser
1               5                   10

<210> SEQ ID NO 134
<211> LENGTH: 13
<212> TYPE: PRT
<213> ORGANISM: Artificial Sequence
<220> FEATURE:
<223> OTHER INFORMATION: H45

<400> SEQUENCE: 134

Gly Gly Gly Ala Ser Cys Pro Pro Cys Ala Gly Asn Ser
1               5                   10

<210> SEQ ID NO 135
<211> LENGTH: 12
<212> TYPE: PRT
<213> ORGANISM: Artificial Sequence
<220> FEATURE:
<223> OTHER INFORMATION: H46

<400> SEQUENCE: 135

Gly Gly Gly Ala Ser Cys Pro Pro Cys Ala Asn Ser
1               5                   10

<210> SEQ ID NO 136
<211> LENGTH: 15
<212> TYPE: PRT
<213> ORGANISM: Artificial Sequence
<220> FEATURE:
<223> OTHER INFORMATION: H47

<400> SEQUENCE: 136

Leu Ser Val Lys Ala Asp Phe Leu Thr Pro Ser Ile Gly Asn Ser
1               5                   10                  15

<210> SEQ ID NO 137
<211> LENGTH: 11
<212> TYPE: PRT
<213> ORGANISM: Artificial Sequence
<220> FEATURE:
<223> OTHER INFORMATION: H48

<400> SEQUENCE: 137

Ala Asp Phe Leu Thr Pro Ser Ile Gly Asn Ser
1               5                   10

<210> SEQ ID NO 138
<211> LENGTH: 15
<212> TYPE: PRT
<213> ORGANISM: Artificial Sequence
<220> FEATURE:
<223> OTHER INFORMATION: H50

<400> SEQUENCE: 138

Leu Ser Val Leu Ala Asn Phe Ser Gln Pro Glu Ile Gly Asn Ser
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: H51

<400> SEQUENCE: 139

Leu Ser Val Leu Ala Asn Phe Ser Gln Pro Glu Ile Gly Asn Ser
1               5                   10                  15

<210> SEQ ID NO 140
<211> LENGTH: 11
<212> TYPE: PRT
<213> ORGANISM: Artificial Sequence
<220> FEATURE:
<223> OTHER INFORMATION: H52

<400> SEQUENCE: 140

Ser Gln Pro Glu Ile Val Pro Ile Ser Asn Ser
1               5                   10

<210> SEQ ID NO 141
<211> LENGTH: 16
<212> TYPE: PRT
<213> ORGANISM: Artificial Sequence
<220> FEATURE:
<223> OTHER INFORMATION: H53

<400> SEQUENCE: 141

Ser Gln Pro Glu Ile Val Pro Ile Ser Cys Pro Pro Cys Pro Asn Ser
1               5                   10                  15

<210> SEQ ID NO 142
<211> LENGTH: 19
<212> TYPE: PRT
<213> ORGANISM: Artificial Sequence
<220> FEATURE:
<223> OTHER INFORMATION: H54

<400> SEQUENCE: 142

Ser Val Leu Ala Asn Phe Ser Gln Pro Glu Ile Ser Cys Pro Pro Cys
1               5                   10                  15

Pro Asn Ser

<210> SEQ ID NO 143
<211> LENGTH: 15
<212> TYPE: PRT
<213> ORGANISM: Artificial Sequence
<220> FEATURE:
<223> OTHER INFORMATION: H55

<400> SEQUENCE: 143

Arg Ile His Gln Met Asn Ser Glu Leu Ser Val Leu Ala Asn Ser
1               5                   10                  15

<210> SEQ ID NO 144
<211> LENGTH: 12
<212> TYPE: PRT
<213> ORGANISM: Artificial Sequence
<220> FEATURE:
<223> OTHER INFORMATION: H56

<400> SEQUENCE: 144

Gln Met Asn Ser Glu Leu Ser Val Leu Ala Asn Ser
1               5                   10

<210> SEQ ID NO 145
<211> LENGTH: 10
<212> TYPE: PRT
<213> ORGANISM: Artificial Sequence
<220> FEATURE:
<223> OTHER INFORMATION: H57

<400> SEQUENCE: 145

Val Ser Glu Arg Pro Phe Pro Pro Asn Ser
1               5                   10

<210> SEQ ID NO 146
<211> LENGTH: 15
<212> TYPE: PRT
<213> ORGANISM: Artificial Sequence
<220> FEATURE:
<223> OTHER INFORMATION: H58

<400> SEQUENCE: 146

```
Lys Pro Phe Phe Thr Cys Gly Ser Ala Asp Thr Cys Pro Asn Ser
1               5                   10                  15
```

<210> SEQ ID NO 147
<211> LENGTH: 15
<212> TYPE: PRT
<213> ORGANISM: Artificial Sequence
<220> FEATURE:
<223> OTHER INFORMATION: H59

<400> SEQUENCE: 147

```
Lys Pro Phe Phe Thr Cys Gly Ser Ala Asp Thr Cys Pro Asn Ser
1               5                   10                  15
```

<210> SEQ ID NO 148
<211> LENGTH: 15
<212> TYPE: PRT
<213> ORGANISM: Artificial Sequence
<220> FEATURE:
<223> OTHER INFORMATION: H60

<400> SEQUENCE: 148

```
Gln Tyr Asn Cys Pro Gly Gln Tyr Thr Phe Ser Met Pro Asn Ser
1               5                   10                  15
```

<210> SEQ ID NO 149
<211> LENGTH: 21
<212> TYPE: PRT
<213> ORGANISM: Artificial Sequence
<220> FEATURE:
<223> OTHER INFORMATION: H61

<400> SEQUENCE: 149

```
Glu Pro Ala Phe Thr Pro Gly Pro Asn Ile Glu Leu Gln Lys Asp Ser
1               5                   10                  15

Asp Cys Pro Asn Ser
            20
```

<210> SEQ ID NO 150
<211> LENGTH: 21
<212> TYPE: PRT
<213> ORGANISM: Artificial Sequence
<220> FEATURE:
<223> OTHER INFORMATION: H62

<400> SEQUENCE: 150

```
Gln Arg His Asn Asn Ser Ser Leu Asn Thr Arg Thr Gln Lys Ala Arg
1               5                   10                  15

His Cys Pro Asn Ser
            20
```

<210> SEQ ID NO 151
<211> LENGTH: 20
<212> TYPE: PRT
<213> ORGANISM: Artificial Sequence
<220> FEATURE:
<223> OTHER INFORMATION: H63

<400> SEQUENCE: 151

```
Asn Ser Leu Phe Asn Gln Glu Val Gln Ile Pro Leu Thr Glu Ser Tyr
1               5                   10                  15

Cys Pro Asn Ser
            20
```

```
<210> SEQ ID NO 152
<211> LENGTH: 15
<212> TYPE: PRT
<213> ORGANISM: Artificial Sequence
<220> FEATURE:
<223> OTHER INFORMATION: peptide linker

<400> SEQUENCE: 152
```

Gly Gly Gly Gly Ser Gly Gly Gly Ser Gly Gly Gly Gly Ser
1               5                   10                  15

```
<210> SEQ ID NO 153
<211> LENGTH: 107
<212> TYPE: PRT
<213> ORGANISM: Artificial Sequence
<220> FEATURE:
<223> OTHER INFORMATION: VL amino acid

<400> SEQUENCE: 153
```

Gln Val Val Leu Thr Gln Ser Pro Ala Ile Met Ser Ala Phe Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Ser Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Arg Asn Pro Pro Thr
                85                  90                  95

Phe Gly Gly Gly Thr Lys Leu Gln Ile Thr Arg
            100                 105

```
<210> SEQ ID NO 154
<211> LENGTH: 121
<212> TYPE: PRT
<213> ORGANISM: Artificial Sequence
<220> FEATURE:
<223> OTHER INFORMATION: VH amino acid

<400> SEQUENCE: 154
```

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
                20                  25                  30

Thr Met His Trp Val Lys Gln Arg Pro Gly Gln Gly Leu Glu Trp Ile
            35                  40                  45

Gly Tyr Ile Asn Pro Ser Ser Ala Tyr Thr Asn Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ala
            115                 120

```
<210> SEQ ID NO 155
```

```
<211> LENGTH: 16
<212> TYPE: PRT
<213> ORGANISM: Artificial Sequence
<220> FEATURE:
<223> OTHER INFORMATION: Hinge region H-105

<400> SEQUENCE: 155

Ser Gly Gly Gly Gly Ser Gly Gly Gly Gly Ser Gly Gly Gly Gly Ser
1               5                   10                  15

<210> SEQ ID NO 156
<211> LENGTH: 18
<212> TYPE: PRT
<213> ORGANISM: Artificial Sequence
<220> FEATURE:
<223> OTHER INFORMATION: Hinge Region H106 (NKG2A derived)

<400> SEQUENCE: 156

Gln Arg His Asn Asn Ser Ser Leu Asn Thr Gly Thr Gln Met Ala Gly
1               5                   10                  15

His Ser

<210> SEQ ID NO 157
<211> LENGTH: 2250
<212> TYPE: DNA
<213> ORGANISM: Artificial Sequence
<220> FEATURE:
<223> OTHER INFORMATION: Humanized TSC95 Scorpion (hu VL-VH#2 107-1A4
      scFv-Fc-DRA222 scFv, with H9 linker)

<400> SEQUENCE: 157
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
gggaaagttc ctaagctccg catccattct ggatctactt tgcaatcagg gtcccatct     240 cggttcagtg gcagtggatc tgggacagaa tttactctca ccatcagcag cctgcagcct     300
gaagattttg caacttatta ctgtcaacag catattgaat accgtggac gttcggccaa     360 gggaccaagg tggaaatcaa acgaggtggc ggagggtctg gggtggcgg atccggaggt     420 ggtggctctc aggtccagct ggtacagtct ggggctgagg tgaagaagcc tggggcttca     480
gtgaaggtct cctgcaaggc ttctggatac acattcactg actactacat gcactgggtg     540
cgacaggccc ctggacaagg gcttgagtgg atgggatatt taatcctta taatgattat     600 actagatacg cacagaagtt ccagggcaga gtcaccatga ccaggacac gtctatcagc     660 acagcctaca tggagctgag cagcctgaga tctgacgaca cggccgtgta ttactgtgca     720
agatcggatg ttactacga tgctatggac tactggggtc aaggaaccac agtcaccgtc     780
tcctcgagtg agcccaaatc ttctgacaaa actcacacat gcccaccgtg cccagcacct     840
gaagccgcgg gtgcaccgtc agtcttcctc ttccccccaa aacccaagga caccctcatg     900
atctcccgga cccctgaggt cacatgcgtg gtggtggacg tgagccacga agaccctgag     960
gtcaagttca actggtacgt ggacggcgtg gaggtgcata atgccaagac aaagccgcgg    1020
gaggagcagt acaacagcac gtaccgtgtg gtcagcgtcc tcaccgtcct gcaccaggac    1080
tggctgaatg gcaaggcgta cgcgtgcgcg gtctccaaca aagccctccc agccccatc    1140 gagaaaacca tctccaaagc caaagggcag ccccgagaac cacaggtgta caccctgccc    1200
ccatcccggg atgagctgac caagaaccag gtcagcctga cctgcctggt caaaggcttc    1260
```

-continued

```
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtgggagccc accttcaccg   1500
aattctcagg tccagctggt ggagtctggg ggcggagtgg tgcagcctgg cgggtcactg   1560
aggctgtcct gcaaggcttc tggctacacc tttactagat ctacgatgca ctgggtaagg   1620
caggcccctg acaaggtctg gaatggattg gatacatta atcctagcag tgcttatact   1680
aattacaatc agaaattcaa ggacaggttc acaatcagcg cagacaaatc caagagcaca   1740
gccttcctgc agatggacag cctgaggccc gaggacaccg cgtctatttt ctgtgcacgg   1800
ccccaagtcc actatgatta acgggtttt ccttactggg gccaagggac tcccgtcact   1860
gtctctagcg gtggcggagg gtctgggggt ggcggatccg gaggtggtgg ctctgcacaa   1920
gacatccaga tgacccagtc tccaagcagc ctgtctgcaa gcgtggggga cagggtcacc   1980
atgacctgca gtgccagctc aagtgtaagt tacatgaact ggtaccagca gaagccgggc   2040
aaggccccca aagatggat ttatgactca tccaaactgg cttctggagt ccctgctcgc   2100
ttcagtggca gtgggtctgg gaccgactat accctcacaa tcagcagcct gcagcccgaa   2160
gatttcgcca cttattactg ccagcagtgg agtcgtaacc cacccacgtt cggagggggg   2220
accaagctac aaattacatc ctccagctaa                                    2250
```

<210> SEQ ID NO 158
<211> LENGTH: 729
<212> TYPE: PRT
<213> ORGANISM: Artificial Sequence
<220> FEATURE:
<223> OTHER INFORMATION: Humanized TSC295 Scorpion (huVL-VH#2 107-1A4
      scFv-Fc-DRA222 scFv, with H9 linker)

<400> SEQUENCE: 158

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr

```
                180                 185                 190
Met Thr Arg Asp Thr Ser Ile Ser Thr Ala Tyr Met Glu Leu Ser Ser
            195                 200                 205
Leu Arg Ser Asp Asp Thr Ala Val Tyr Tyr Cys Ala Arg Ser Asp Gly
            210                 215                 220
Tyr Tyr Asp Ala Met Asp Tyr Trp Gly Gln Gly Thr Thr Val Thr Val
225                 230                 235                 240
Ser Ser Ser Glu Pro Lys Ser Ser Asp Lys Thr His Thr Cys Pro Pro
            245                 250                 255
Cys Pro Ala Pro Glu Ala Ala Gly Ala Pro Ser Val Phe Leu Phe Pro
            260                 265                 270
Pro Lys Pro Lys Asp Thr Leu Met Ile Ser Arg Thr Pro Glu Val Thr
            275                 280                 285
Cys Val Val Val Asp Val Ser His Glu Asp Pro Glu Val Lys Phe Asn
            290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
            325                 330                 335
Leu His Gln Asp Trp Leu Asn Gly Lys Ala Tyr Ala Cys Ala Val Ser
            340                 345                 350
Asn Lys Ala Leu Pro Ala Pro Ile Glu Lys Thr Ile Ser Lys Ala Lys
            355                 360                 365
Gly Gln Pro Arg Glu Pro Gln Val Tyr Thr Leu Pro Pro Ser Arg Asp
            370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
            405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
            435                 440                 445
Asn Val Phe Ser Cys Ser Val Met His Glu Ala Leu His Asn His Tyr
            450                 455                 460
Thr Gln Lys Ser Leu Ser Leu Ser Pro Gly Gly Ser Pro Ser Pro Ser
465                 470                 475                 480
Asn Ser Gln Val Gln Leu Val Glu Ser Gly Gly Gly Val Val Gln Pro
            485                 490                 495
Gly Arg Ser Leu Arg Leu Ser Cys Lys Ala Ser Gly Tyr Thr Phe Thr
            500                 505                 510
Arg Ser Thr Met His Trp Val Arg Gln Ala Pro Gly Gln Gly Leu Glu
            515                 520                 525
Trp Ile Gly Tyr Ile Asn Pro Ser Ser Ala Tyr Thr Asn Tyr Asn Gln
            530                 535                 540
Lys Phe Lys Asp Arg Phe Thr Ile Ser Ala Asp Lys Ser Lys Ser Thr
545                 550                 555                 560
Ala Phe Leu Gln Met Asp Ser Leu Arg Pro Glu Asp Thr Gly Val Tyr
            565                 570                 575
Phe Cys Ala Arg Pro Gln Val His Tyr Asp Tyr Asn Gly Phe Pro Tyr
            580                 585                 590
Trp Gly Gln Gly Thr Pro Val Thr Val Ser Ser Gly Gly Gly Gly Ser
            595                 600                 605
```

```
Gly Gly Gly Gly Ser Gly Gly Gly Ser Ala Gln Asp Ile Gln Met
            610             615                 620

Thr Gln Ser Pro Ser Ser Leu Ser Ala Ser Val Gly Asp Arg Val Thr
625             630                 635                 640

Met Thr Cys Ser Ala Ser Ser Val Ser Tyr Met Asn Trp Tyr Gln
            645                 650                 655

Gln Lys Pro Gly Lys Ala Pro Lys Arg Trp Ile Tyr Asp Ser Ser Lys
            660                 665                 670

Leu Ala Ser Gly Val Pro Ala Arg Phe Ser Gly Ser Gly Ser Gly Thr
            675                 680                 685

Asp Tyr Thr Leu Thr Ile Ser Ser Leu Gln Pro Glu Asp Phe Ala Thr
            690                 695                 700

Tyr Tyr Cys Gln Gln Trp Ser Arg Asn Pro Pro Thr Phe Gly Gly Gly
705                 710                 715                 720

Thr Lys Leu Gln Ile Thr Ser Ser Ser
                725
```

<210> SEQ ID NO 159
<211> LENGTH: 2283
<212> TYPE: DNA
<213> ORGANISM: Artificial Sequence
<220> FEATURE:
<223> OTHER INFORMATION: Humanized TSC296 Scorpion (huVL-VH#2 107-1A4
    scFv-Fc-DRA222 scFv, with H94 linker)

<400> SEQUENCE: 159

```
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
gggaaagttc ctaagctccg catccattct ggatctactt tgcaatcagg ggtcccatct     240
cggttcagtg gcagtggatc tgggacagaa tttactctca ccatcagcag cctgcagcct     300
gaagattttg caacttatta ctgtcaacag catattgaat acccgtggac gttcggccaa     360
gggaccaagg tggaaatcaa acgaggtggc ggagggtctg ggggtggcgg atccggaggt     420
ggtggctctc aggtccagct ggtacagtct ggggctgagg tgaagaagcc tggggcttca     480
gtgaaggtct cctgcaaggc ttctggatac acattcactg actactacat gcactgggtg     540
cgacaggccc ctggacaagg gcttgagtgg atgggatatt ttaatcctta taatgattat     600
actagatacg cacagaagtt ccagggcaga gtcaccatga ccagggacac gtctatcagc     660
acagcctaca tggagctgag cagcctgaga tctgacgaca cggccgtgta ttactgtgca     720
agatcggatg gttactacga tgctatggac tactggggtc aaggaaccac agtcaccgtc     780
tcctcgagtg agcccaaatc ttctgacaaa actcacacat gcccaccgtg cccagcacct     840
gaagccgcgg gtgcaccgtc agtcttcctc ttcccccca aacccaagga caccctcatg     900
atctcccgga cccctgaggt cacatgcgtg gtggtggacg tgagccacga agaccctgag     960
gtcaagttca actggtacgt ggacggcgtg gaggtgcata atgccaagac aaagccgcgg    1020
gaggagcagt acaacagcac gtaccgtgtg gtcagcgtcc tcaccgtcct gcaccaggac    1080
tggctgaatg gcaaggcgta cgcgtgcgcg gtctccaaca aagccctccc agccccatc     1140
gagaaaacca tctccaaagc caaagggcag ccccgagaac cacaggtgta caccctgccc    1200
ccatcccggg atgagctgac caagaaccag gtcagcctga cctgcctggt caaaggcttc    1260
tatccaagcg acatcgccgt ggagtgggag agcaatgggc agccggagaa caactacaag    1320
```

```
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg ttctggtgg aggcggttca     1500 ggcggaggtg gctccggcgg tggcggatcg ccgaattctc aggtccagct ggtggagtct    1560
gggggcggag tggtgcagcc tgggcggtca ctgaggctgt cctgcaaggc ttctggctac    1620
acctttacta gatctacgat gcactgggta aggcaggccc ctggacaagg tctggaatgg    1680
attggataca ttaatcctag cagtgcttat actaattaca atcagaaatt caaggacagg    1740
ttcacaatca gcgcagacaa atccaagagc acagccttcc tgcagatgga cagcctgagg    1800
cccgaggaca ccggcgtcta tttctgtgca cggccccaag tccactatga ttacaacggg    1860
tttccttact ggggccaagg gactcccgtc actgtctcta gcggtggcgg agggtctggg    1920
ggtggcggat ccggaggtgg tggctctgca caagacatcc agatgaccca gtctccaagc    1980
agcctgtctg caagcgtggg ggacagggtc accatgacct gcagtgccag ctcaagtgta    2040
agttacatga actggtacca gcagaagccg ggcaaggccc ccaaaagatg gatttatgac    2100
tcatccaaac tggcttctgg agtccctgct cgcttcagtg gcagtgggtc tgggaccgac    2160
tataccctca caatcagcag cctgcagccc gaagatttcg ccacttatta ctgccagcag    2220
tggagtcgta acccacccac gttcggaggg gggaccaagc tacaaattac atcctccagc    2280
taa                                                                  2283
```

<210> SEQ ID NO 160
<211> LENGTH: 740
<212> TYPE: PRT
<213> ORGANISM: Artificial Sequence
<220> FEATURE:
<223> OTHER INFORMATION: Humanized TSC296 Scorpion (huVL-VH#2 107-1A4
      scFv-Fc-DRA222 scFv, with H94 linker)

<400> SEQUENCE: 160

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175
```

```
Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Ser Gly Gly Gly Gly Ser
465                 470                 475                 480

Gly Gly Gly Gly Ser Gly Gly Gly Ser Pro Asn Ser Gln Val Gln
                485                 490                 495

Leu Val Glu Ser Gly Gly Gly Val Val Gln Pro Gly Arg Ser Leu Arg
            500                 505                 510

Leu Ser Cys Lys Ala Ser Gly Tyr Thr Phe Thr Arg Ser Thr Met His
        515                 520                 525

Trp Val Arg Gln Ala Pro Gly Gln Gly Leu Glu Trp Ile Gly Tyr Ile
    530                 535                 540

Asn Pro Ser Ser Ala Tyr Thr Asn Tyr Asn Gln Lys Phe Lys Asp Arg
545                 550                 555                 560

Phe Thr Ile Ser Ala Asp Lys Ser Lys Ser Thr Ala Phe Leu Gln Met
                565                 570                 575

Asp Ser Leu Arg Pro Glu Asp Thr Gly Val Tyr Phe Cys Ala Arg Pro
            580                 585                 590

Gln Val His Tyr Asp Tyr Asn Gly Phe Pro Tyr Trp Gly Gln Gly Thr
```

```
                        595                 600                 605
Pro Val Thr Val Ser Gly Gly Gly Ser Gly Gly Gly Gly Ser
        610                 615                 620
Gly Gly Gly Gly Ser Ala Gln Asp Ile Gln Met Thr Gln Ser Pro Ser
625                 630                 635                 640
Ser Leu Ser Ala Ser Val Gly Asp Arg Val Thr Met Thr Cys Ser Ala
                645                 650                 655
Ser Ser Ser Val Ser Tyr Met Asn Trp Tyr Gln Gln Lys Pro Gly Lys
            660                 665                 670
Ala Pro Lys Arg Trp Ile Tyr Asp Ser Ser Lys Leu Ala Ser Gly Val
        675                 680                 685
Pro Ala Arg Phe Ser Gly Ser Gly Ser Gly Thr Asp Tyr Thr Leu Thr
690                 695                 700
Ile Ser Ser Leu Gln Pro Glu Asp Phe Ala Thr Tyr Tyr Cys Gln Gln
705                 710                 715                 720
Trp Ser Arg Asn Pro Pro Thr Phe Gly Gly Gly Thr Lys Leu Gln Ile
                725                 730                 735
Thr Ser Ser Ser
            740

<210> SEQ ID NO 161
<211> LENGTH: 2274
<212> TYPE: DNA
<213> ORGANISM: Artificial Sequence
<220> FEATURE:
<223> OTHER INFORMATION: Humanized TSC301 Scorpion (huVL-VH#2 107-1A4
      scFv-Fc-DRA222 scFv, with H105 linker)

<400> SEQUENCE: 161
atggaagcac cagcgcagct tctcttcctc ctgctactct ggctcccaga taccaccggt     60
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa cgaggtggc ggagggtctg ggggtggcgg atccggaggt    420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccaggacac gtctatcagc    660 acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa acccaaggac accctcatg    900 atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca aagccctccc agcccccatc   1140
gagaaaacca tctccaaagc caaagggcag ccccgagaac acaggtgta caccctgccc   1200
```

```
ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gttctggtgg aggcggttca    1500
ggcggaggtg gctccggcgg tggcggatcg caggtccagc tggtggagtc tggggggga    1560 gtggtgcagc ctgggcggtc actgaggctg tcctgcaagg cttctggcta cacctttact    1620
agatctacga tgcactgggt aaggcaggcc cctggacaag tctggaatg gattggatac    1680 attaatccta gcagtgctta tactaattac aatcagaaat tcaaggacag gttcacaatc    1740
agcgcagaca aatccaagag cacagccttc ctgcagatgg acagcctgag gcccgaggac    1800
accggcgtct atttctgtgc acggccccaa gtccactatg attacaacgg gtttccttac    1860 tgggccaag ggactccgt cactgtctct agcggtggcg gagggtctgg gggtggcgga    1920
tccggaggtg gtggctctgc acaagacatc cagatgaccc agtctccaag cagcctgtct    1980
gcaagcgtgg gggacagggt caccatgacc tgcagtgcca gctcaagtgt aagttacatg    2040
aactggtacc agcagaagcc gggcaaggcc cccaaaagat ggatttatga ctcatccaaa    2100
ctggcttctg gagtccctgc tcgcttcagt ggcagtgggt ctgggaccga ctataccctc    2160
acaatcagca gcctgcagcc cgaagatttc gccacttatt actgccagca gtggagtcgt    2220
aacccaccca cgttcggagg ggggaccaag ctacaaatta catcctccag ctaa           2274
```

<210> SEQ ID NO 162
<211> LENGTH: 737
<212> TYPE: PRT
<213> ORGANISM: Artificial Sequence
<220> FEATURE:
<223> OTHER INFORMATION: Humanized TSC301 Scorpion (huVL-VH#2 107-1A4
      scFv-Fc-DRA222 scFv, with H105 linker)

<400> SEQUENCE: 162

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
```

-continued

```
                165                 170                 175
Tyr Asn Asp Tyr Thr Arg Tyr Ala Gln Lys Phe Gln Gly Arg Val Thr
                    180                 185                 190
Met Thr Arg Asp Thr Ser Ile Ser Thr Ala Tyr Met Glu Leu Ser Ser
                    195                 200                 205
Leu Arg Ser Asp Asp Thr Ala Val Tyr Tyr Cys Ala Arg Ser Asp Gly
                    210                 215                 220
Tyr Tyr Asp Ala Met Asp Tyr Trp Gly Gln Gly Thr Thr Val Thr Val
225                 230                 235                 240
Ser Ser Ser Glu Pro Lys Ser Ser Asp Lys Thr His Thr Cys Pro Pro
                    245                 250                 255
Cys Pro Ala Pro Glu Ala Ala Gly Ala Pro Ser Val Phe Leu Phe Pro
                    260                 265                 270
Pro Lys Pro Lys Asp Thr Leu Met Ile Ser Arg Thr Pro Glu Val Thr
                    275                 280                 285
Cys Val Val Val Asp Val Ser His Glu Asp Pro Glu Val Lys Phe Asn
                    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                    325                 330                 335
Leu His Gln Asp Trp Leu Asn Gly Lys Ala Tyr Ala Cys Ala Val Ser
                    340                 345                 350
Asn Lys Ala Leu Pro Ala Pro Ile Glu Lys Thr Ile Ser Lys Ala Lys
                    355                 360                 365
Gly Gln Pro Arg Glu Pro Gln Val Tyr Thr Leu Pro Pro Ser Arg Asp
                    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                    405                 410                 415
Asn Asn Tyr Lys Thr Thr Pro Pro Val Leu Asp Ser Asp Gly Ser Phe
                    420                 425                 430
Phe Leu Tyr Ser Lys Leu Thr Val Asp Lys Ser Arg Trp Gln Gln Gly
                    435                 440                 445
Asn Val Phe Ser Cys Ser Val Met His Glu Ala Leu His Asn His Tyr
                    450                 455                 460
Thr Gln Lys Ser Leu Ser Leu Ser Pro Gly Ser Gly Gly Gly Gly Ser
465                 470                 475                 480
Gly Gly Gly Gly Ser Gly Gly Gly Ser Gln Val Gln Leu Val Glu
                    485                 490                 495
Ser Gly Gly Gly Val Val Gln Pro Gly Arg Ser Leu Arg Leu Ser Cys
                    500                 505                 510
Lys Ala Ser Gly Tyr Thr Phe Thr Arg Ser Thr Met His Trp Val Arg
                    515                 520                 525
Gln Ala Pro Gly Gln Gly Leu Glu Trp Ile Gly Tyr Ile Asn Pro Ser
                    530                 535                 540
Ser Ala Tyr Thr Asn Tyr Asn Gln Lys Phe Lys Asp Arg Phe Thr Ile
545                 550                 555                 560
Ser Ala Asp Lys Ser Lys Ser Thr Ala Phe Leu Gln Met Asp Ser Leu
                    565                 570                 575
Arg Pro Glu Asp Thr Gly Val Tyr Phe Cys Ala Arg Pro Gln Val His
                    580                 585                 590
```

```
Tyr Asp Tyr Asn Gly Phe Pro Tyr Trp Gly Gln Gly Thr Pro Val Thr
            595                 600                 605

Val Ser Ser Gly Gly Gly Ser Gly Gly Gly Ser Gly Gly Gly
    610                 615                 620

Gly Ser Ala Gln Asp Ile Gln Met Thr Gln Ser Pro Ser Ser Leu Ser
625                 630                 635                 640

Ala Ser Val Gly Asp Arg Val Thr Met Thr Cys Ser Ala Ser Ser Ser
                645                 650                 655

Val Ser Tyr Met Asn Trp Tyr Gln Gln Lys Pro Gly Lys Ala Pro Lys
            660                 665                 670

Arg Trp Ile Tyr Asp Ser Ser Lys Leu Ala Ser Gly Val Pro Ala Arg
        675                 680                 685

Phe Ser Gly Ser Gly Ser Gly Thr Asp Tyr Thr Leu Thr Ile Ser Ser
    690                 695                 700

Leu Gln Pro Glu Asp Phe Ala Thr Tyr Tyr Cys Gln Gln Trp Ser Arg
705                 710                 715                 720

Asn Pro Pro Thr Phe Gly Gly Gly Thr Lys Leu Gln Ile Thr Ser Ser
                725                 730                 735

Ser

<210> SEQ ID NO 163
<211> LENGTH: 2280
<212> TYPE: DNA
<213> ORGANISM: Artificial Sequence
<220> FEATURE:
<223> OTHER INFORMATION: Humanized TSC302 Scorpion (huVL-VH#2 107-1A4
      scFv-Fc-DRA222 scFv, with H106 linker)

<400> SEQUENCE: 163
atggaagcac cagcgcagct tctcttcctc ctgctactct ggctcccaga taccaccggt    60
gatatccaga tgacccagtc tccatccgcc atgtctgcat ctgtaggaga cagagtcacc   120
atcacttgcc gggcgagtaa gagcattagc aaatatttag cctggtttca gcagaaacca   180
gggaaagttc ctaagctccg catccattct ggatctactt tgcaatcagg ggtcccatct   240
cggttcagtg gcagtggatc tgggacagaa tttactctca ccatcagcag cctgcagcct   300
gaagattttg caacttatta ctgtcaacag catattgaat cccgtggac gttcggccaa   360 gggaccaagg tggaaatcaa acgaggtggc ggagggtctg ggggtggcgg atccggaggt   420
ggtggctctc aggtccagct ggtacagtct ggggctgagg tgaagaagcc tggggcttca   480
gtgaaggtct cctgcaaggc ttctggatac acattcactg actactacat gcactgggtg   540
cgacaggccc ctggacaagg gcttgagtgg atgggatatt ttaatcctta taatgattat   600
actagatacg cacagaagtt ccagggcaga gtcaccatga ccaggacac gtctatcagc   660 acagcctaca tggagctgag cagcctgaga tctgacgaca cggccgtgta ttactgtgca   720
agatcggatg ttactacga tgctatggac tactggggtc aaggaaccac agtcaccgtc   780
tcctcgagtg agcccaaatc ttctgacaaa actcacacat gcccaccgtg cccagcacct   840
gaagccgcgg gtgcaccgtc agtcttcctc ttccccccaa aacccaagga caccctcatg   900
atctcccgga cccctgaggt cacatgcgtg gtggtggacg tgagccacga agaccctgag   960
gtcaagttca actggtacgt ggacggcgtg gaggtgcata atgccaagac aaagccgcgg  1020
gaggagcagt acaacagcac gtaccgtgtg gtcagcgtcc tcaccgtcct gcaccaggac  1080
tggctgaatg gcaaggcgta cgcgtgcgcg gtctccaaca aagccctccc agcccccatc  1140
```

```
gagaaaacca tctccaaagc caaagggcag ccccgagaac cacaggtgta caccctgccc    1200
ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtcagaggca caacaattct    1500
tccctgaata caggaactca gatggcaggt cattctcagg tccagctggt ggagtctggg    1560
ggcggagtgg tgcagcctgg gcggtcactg aggctgtcct gcaaggcttc tggctacacc    1620
tttactagat ctacgatgca ctgggtaagg caggcccctg acaaggtct ggaatggatt    1680
ggatacatta atcctagcag tgcttatact aattacaatc agaaattcaa ggacaggttc    1740
acaatcagcg cagacaaatc caagagcaca gccttcctgc agatggacag cctgaggccc    1800
gaggacaccg cgtctatttt ctgtgcacgg ccccaagtcc actatgatta caacgggttt    1860
ccttactggg gccaagggac tcccgtcact gtctctagcg gtggcggagg gtctgggggt    1920
ggcggatccg gaggtggtgg ctctgcacaa gacatccaga tgacccagtc tccaagcagc    1980
ctgtctgcaa gcgtggggga cagggtcacc atgacctgca gtgccagctc aagtgtaagt    2040
tacatgaact ggtaccagca gaagccgggc aaggccccca aaagatggat ttatgactca    2100
tccaaactgg cttctggagt ccctgctcgc ttcagtggca gtgggtctgg gaccgactat    2160
accctcacaa tcagcagcct gcagcccgaa gatttcgcca cttattactg ccagcagtgg    2220
agtcgtaacc cacccacgtt cggaggggg accaagctac aaattacatc ctccagctaa   2280
```

<210> SEQ ID NO 164
<211> LENGTH: 739
<212> TYPE: PRT
<213> ORGANISM: Artificial Sequence
<220> FEATURE:
<223> OTHER INFORMATION: Humanized TSC302 Scorpion (huVL-VH#2 107-1A4
      scFv-Fc-DRA222 scFv, with H106 linker)

<400> SEQUENCE: 164

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

```
Arg Gln Ala Pro Gly Gln Gly Leu Glu Trp Met Gly Tyr Phe Asn Pro
                165                 170                 175
Tyr Asn Asp Tyr Thr Arg Tyr Ala Gln Lys Phe Gln Gly Arg Val Thr
            180                 185                 190
Met Thr Arg Asp Thr Ser Ile Ser Thr Ala Tyr Met Glu Leu Ser Ser
        195                 200                 205
Leu Arg Ser Asp Asp Thr Ala Val Tyr Tyr Cys Ala Arg Ser Asp Gly
    210                 215                 220
Tyr Tyr Asp Ala Met Asp Tyr Trp Gly Gln Gly Thr Thr Val Thr Val
225                 230                 235                 240
Ser Ser Ser Glu Pro Lys Ser Ser Asp Lys Thr His Thr Cys Pro Pro
                245                 250                 255
Cys Pro Ala Pro Glu Ala Ala Gly Ala Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Ala Cys Ala Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
        435                 440                 445
Asn Val Phe Ser Cys Ser Val Met His Glu Ala Leu His Asn His Tyr
    450                 455                 460
Thr Gln Lys Ser Leu Ser Leu Ser Pro Gly Gln Arg His Asn Asn Ser
465                 470                 475                 480
Ser Leu Asn Thr Gly Thr Gln Met Ala Gly His Ser Gln Val Gln Leu
                485                 490                 495
Val Glu Ser Gly Gly Gly Val Val Gln Pro Gly Arg Ser Leu Arg Leu
            500                 505                 510
Ser Cys Lys Ala Ser Gly Tyr Thr Phe Thr Arg Ser Thr Met His Trp
        515                 520                 525
Val Arg Gln Ala Pro Gly Gln Gly Leu Glu Trp Ile Gly Tyr Ile Asn
    530                 535                 540
Pro Ser Ser Ala Tyr Thr Asn Tyr Asn Gln Lys Phe Lys Asp Arg Phe
545                 550                 555                 560
Thr Ile Ser Ala Asp Lys Ser Lys Ser Thr Ala Phe Leu Gln Met Asp
                565                 570                 575
Ser Leu Arg Pro Glu Asp Thr Gly Val Tyr Phe Cys Ala Arg Pro Gln
```

```
                    580                 585                 590
Val His Tyr Asp Tyr Asn Gly Phe Pro Tyr Trp Gly Gln Gly Thr Pro
            595                 600                 605

Val Thr Val Ser Ser Gly Gly Gly Ser Gly Gly Gly Ser Gly
        610                 615                 620

Gly Gly Gly Ser Ala Gln Asp Ile Gln Met Thr Gln Ser Pro Ser Ser
625                 630                 635                 640

Leu Ser Ala Ser Val Gly Asp Arg Val Thr Met Thr Cys Ser Ala Ser
                645                 650                 655

Ser Ser Val Ser Tyr Met Asn Trp Tyr Gln Gln Lys Pro Gly Lys Ala
            660                 665                 670

Pro Lys Arg Trp Ile Tyr Asp Ser Ser Lys Leu Ala Ser Gly Val Pro
        675                 680                 685

Ala Arg Phe Ser Gly Ser Gly Ser Gly Thr Asp Tyr Thr Leu Thr Ile
    690                 695                 700

Ser Ser Leu Gln Pro Glu Asp Phe Ala Thr Tyr Tyr Cys Gln Gln Trp
705                 710                 715                 720

Ser Arg Asn Pro Pro Thr Phe Gly Gly Gly Thr Lys Leu Gln Ile Thr
                725                 730                 735

Ser Ser Ser

<210> SEQ ID NO 165
<211> LENGTH: 25
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: n=5

<400> SEQUENCE: 165

Gly Gly Gly Gly Ser Gly Gly Gly Gly Ser Gly Gly Gly Gly Ser Gly
1               5                   10                  15

Gly Gly Ser Gly Gly Gly Gly Ser
            20                  25
```

PROSTATE-SPECIFIC MEMBRANE ANTIGEN BINDING PROTEINS AND RELATED COMPOSITIONS AND METHODS

CROSS REFERENCE TO RELATED APPLICATIONS

This application is a continuation of U.S. patent application Ser. No. 14/113,353, filed Feb. 12, 2014, now abandoned, which is the National Stage of International Application No. PCT/US2012/034575, filed Apr. 20, 2012, which claims priority to U.S. Provisional Patent Application No. 61/478,449, filed Apr. 22, 2011, each of which is incorporated herein by reference in its entirety.

FIELD OF THE INVENTION

The present invention relates to mono-specific and multi-specific protein therapeutics that specifically target cells expressing prostate-specific membrane antigen (PSMA) and are useful for the treatment of disorders characterized by overexpression of PSMA, such as, for example, prostate cancer (e.g., castrate-resistant prostate cancer), tumor-related angiogenesis, or benign prostatic hyperplasia (BPH). In one embodiment, the multi-specific protein therapeutic binds both PSMA-expressing cells and the T-cell receptor complex on T cells to induce target-dependent T-cell cytotoxicity, activation and proliferation.

ACCOMPANYING SEQUENCE LISTING

The contents of the text file (Name: "APVO_028_02US_SeqList.txt"; Size: 269,000 bytes; Date of Creation: May 3, 2017) submitted electronically herewith are incorporated herein by reference in their entirety.

BACKGROUND

Prostate-specific Membrane Antigen (PSMA), also known as glutamate carboxypeptidase II and N-acetylated alpha-linked acidic dipeptidase 1, is a dimeric type II transmembrane glycoprotein belonging to the M28 peptidase family encoded by the gene FOLH1 (folate hydrolase 1). The protein acts as a glutamate carboxypeptidase on different alternative substrates, including the nutrient folate and the neuropeptide N-acetyl-l-aspartyl-l-glutamate and is expressed in a number of tissues such as the prostate, and to a lesser extent, the small intestine, central and peripheral nervous system and kidney. The gene encoding PSMA is alternatively spliced to produce at least three variants. A mutation in this gene may be associated with impaired intestinal absorption of dietary folates, resulting in low blood folate levels and consequent hyperhomocysteinemia. Expression of this protein in the brain may be involved in a number of pathological conditions associated with glutamate excitotoxicity.

PSMA is a well-established, highly restricted prostate-cancer-related cell membrane antigen. In prostate cancer cells, PSMA is expressed 1000-fold higher than on normal prostate epithelium (Su et al., *Cancer Res.* 1995 44:1441-1443). Expression of PSMA increases with prostate cancer progression and is highest in metastatic disease, hormone refractory cases, and higher-grade lesions (Israeli et al., *Cancer Res.* 1994, 54:1807-1811; Wright et al., *Urologic Oncology: Seminars and Original Investigations* 1995 1:18-28; Wright et al., *Urology* 1996 48:326-332; Sweat et al., *Urology* 1998 52:637-640). Additionally, PSMA is abundantly expressed on the neovasculature of a variety of other solid tumors, including bladder, pancreas, melanoma, lung and kidney cancers, but not on normal neovasculature (Chang et al., *Urology* 2001 57:801-805; Divgi et al., *Clin. Cancer Res.* 1998 4:2729-3279).

PSMA has been shown to be an important target for immunological approaches such as vaccines or directed therapy with monoclonal antibodies. Unlike other prostate-restricted molecules that are secretory proteins (PSA, prostatic acid phosphatase), PSMA is an integral cell—surface membrane protein that is not secreted, which makes it an ideal target for antibody therapy. PROSTASCINT® (capromab pendetide) is an $^{111}$In-labelled anti-PSMA murine monoclonal antibody approved by the FDA for imaging and staging of newly diagnosed and recurrent prostate cancer patients (Hinkle et al., *Cancer* 1998, 83:739-747). However, capromab binds to an intracellular epitope of PSMA, requiring internalization or exposure of the internal domain of PSMA, therefore preferentially binding apoptotic or necrosing cells (Troyer et al., *Urologic Oncology: Seminars and Original Investigations* 1995 1:29-37; Troyer et al., *Prostate* 1997 30:232-242). As a result, capromab may not be of therapeutic benefit (Liu et al., *Cancer Res.* 1997 57:3629-3634).

Other monoclonal antibodies which target the external domain of PSMA have been developed (e.g., J591, J415, J533, and E99) (Liu et al., *Cancer Res.* 1997 57:3629-3634). Radiolabelled J591 is currently in clinical trials (Tagawa et al., Cancer 2010 116(S4):1075). However, evidence suggests that PSMA may act as a receptor mediating the internalization of a putative ligand. PSMA undergoes internalization constitutively, and PSMA-specific antibodies can induce and/or increase the rate of internalization, which then causes the antibodies to accumulate in the endosomes (Liu et al., *Cancer Res.* 1998 58:4055-4060). While PSMA-specific internalizing antibodies may aid in the development of therapeutics to target the delivery of toxins, drugs, or radioisotopes to the interior of prostate cancer cells (Tagawa et al., Cancer 2010 116(S4):1075), PSMA-specific antibodies utilizing native or engineered effector mechanisms (e.g., antibody-dependent cell-mediated cytotoxicity (ADCC), complement-dependent cytotoxicity (CDC), antibody-dependent cell-mediated phagocytosis (ADCP), or re-directed T-cell cytotoxicity (RTCC)) are problematic since the PSMA-specific antibody may be internalized before it is recognized by effector cells.

SUMMARY OF THE INVENTION

In one embodiment, the present disclosure provides a prostate-specific membrane antigen (PSMA)-binding polypeptide comprising, in order from amino-terminus to carboxyl-terminus, (a) a PSMA-binding domain that specifically binds human PSMA, (b) a hinge region, and (c) an immunoglobulin constant region. In certain embodiments, suitable PSMA-binding domains include binding domains that compete for binding to human PSMA with a single chain Fv (scFv) having the amino acid sequence set forth in SEQ ID NO:21. In certain embodiments, the PSMA-binding polypeptide is capable of forming a dimer with a second, identical polypeptide chain through association between the respective immunoglobulin constant regions and/or hinge regions.

In certain embodiments, the PSMA-binding domain comprises (i) an immunoglobulin light chain variable region comprising CDRs LCDR1, LCDR2, and LCDR3, and/or (ii) an immunoglobulin heavy chain variable region comprising CDRs HCDR1, HCDR2, and HCDR3. In certain variations, LCDR3 has the amino acid sequence set forth in SEQ ID NO:17 and/or HCDR3 has the amino acid sequence set forth in SEQ ID NO:11; in some such embodiments, LCDR1 and LCDR2 have the amino acid sequences as set forth in SEQ ID NO:15 and SEQ ID NO:16, respectively, and/or HCDR1 and HCDR2 have the amino acid sequences as set forth in SEQ ID NO:9 and SEQ ID NO:10, respectively. In another variation, (i) the light chain variable region comprises an amino acid sequence that is at least 90%, at least 95%, at least 99%, or 100% identical to the amino acid sequence set forth in SEQ ID NO:5 or SEQ ID NO:23; and/or (ii) the heavy chain variable region comprises an amino acid sequence that is at least 90%, at least 95%, at least 99%, or 100% identical to the amino acid sequence set forth in SEQ ID NO:2, SEQ ID NO:25, or SEQ ID NO:27. One or both of the light and heavy chain variable regions can be humanized.

In certain variations, the PSMA-binding domain is a single chain Fv (scFv) comprising the immunoglobulin light and heavy chain variable regions disclosed herein. In certain embodiments, PSMA-binding scFvs include, for example, scFvs comprising an amino acid sequence that is at least 90%, at least 95%, at least 99%, or 100% identical to the amino acid sequence set forth in SEQ ID NO:19, SEQ ID NO:21, SEQ ID NO:30, SEQ ID NO:31, SEQ ID NO:34, or SEQ ID NO:35. In certain embodiments, the heavy chain variable region of the scFv is carboxyl-terminal to the light chain variable region (also referred to herein as a "VL-VH orientation"). In some embodiments of an scFv having a VL-VH orientation, the scFv comprises an amino acid sequence that is at least 90%, at least 95%, at least 99%, or 100% identical to the amino acid sequence set forth in SEQ ID NO:21, SEQ ID NO:30, or SEQ ID NO:31. The light chain variable region and heavy chain variable region of the scFv can be joined by a peptide linker such as, for example, a peptide linker comprising an amino acid sequence $(Gly_4Ser)_n$, wherein n=1-5 (SEQ ID NO:165).

In some embodiments of a PSMA-binding polypeptide disclosed herein, the hinge region is derived from an immunoglobulin hinge region, such as, for example, an immunoglobulin hinge region of IgG1, IgG2, IgG3, IgG4, IgA1, IgA2, or IgD. Such an immunoglobulin hinge region can be either a wild-type or an altered immunoglobulin hinge region.

In further embodiments of a PSMA-binding polypeptide disclosed herein, the immunoglobulin constant region comprises immunoglobulin CH2 and CH3 domains, such as, for example, immunoglobulin CH2 and CH3 domains of IgG1, IgG2, IgG3, IgG4, IgA1, IgA2, or IgD. In another embodiment, the immunoglobulin constant region comprises immunoglobulin CH2 and CH3 domains and the constant region does not comprise an immunoglobulin CH1 domain.

In certain variations, a PSMA-binding polypeptide disclosed herein includes at least one effector function selected from antibody-dependent cell-mediated cytotoxicity (ADCC) and complement-dependent cytotoxicity (CDC). In some embodiments, the hinge region is derived from an immunoglobulin hinge region and the immunoglobulin constant region comprises immunoglobulin CH2 and CH3 domains of IgG1, IgG2, IgG3, or IgG4. In another embodiment, the immunoglobulin hinge region is derived from the hinge region of IgG1 and the immunoglobulin constant region comprises immunoglobulin CH2 and CH3 domains of IgG1.

In some embodiments, a PSMA-binding polypeptide disclosed herein comprises an amino acid sequence that is at least 90%, at least 95%, at least 99%, or 100% identical to the amino acid sequence set forth in SEQ ID NO:38, SEQ ID NO:39, SEQ ID NO:42, SEQ ID NO:43, SEQ ID NO:70, or SEQ ID NO:72.

In still further embodiments, a PSMA-binding polypeptide disclosed herein further includes (d) a second hinge region carboxyl-terminal to the immunoglobulin constant region, and (e) a second binding domain carboxyl-terminal to the second hinge region. In some embodiments, second hinge regions include those derived from a stalk region of a type II C lectin or an immunoglobulin hinge region. In certain variations, the second hinge region has an amino acid sequence as set forth in SEQ ID NO:63, SEQ ID NO:64, SEQ ID NO:65, or SEQ ID NO:66.

In another embodiment, the present disclosure provides a prostate-specific membrane antigen (PSMA)-binding polypeptide that specifically binds human PSMA and comprises a first binding domain comprising (i) an immunoglobulin light chain variable region comprising CDRs LCDR1, LCDR2, and LCDR3, and (ii) an immunoglobulin heavy chain variable region comprising CDRs HCDR1, HCDR2, and HCDR3; wherein LCDR3 has the amino acid sequence set forth in SEQ ID NO:17 and/or HCDR3 has the amino acid sequence set forth in SEQ ID NO:11. In some embodiments, LCDR1 and LCDR2 have the amino acid sequences as set forth in SEQ ID NO:15 and SEQ ID NO:16, respectively, and/or HCDR1 and HCDR2 have the amino acid sequences as set forth in SEQ ID NO:9 and SEQ ID NO:10, respectively. In some variations, LCDR1, LCDR2, and LCDR3 have the amino acid sequences as set forth in SEQ ID NO:15, SEQ ID NO:16, and SEQ ID NO:17, respectively; and HCDR1, HCDR2, and HCDR3 have the amino acid sequences as set forth in SEQ ID NO:9, SEQ ID NO:10 and SEQ ID NO:11, respectively. In some variations, (i) the light chain variable region comprises an amino acid sequence that is at least 90%, at least 95%, at least 99%, or 100% identical to the amino acid sequence set forth in SEQ ID NO:5 or SEQ ID NO:23; and/or (ii) the heavy chain variable region comprises an amino acid sequence that is at least 90%, at least 95%, at least 99%, or 100% identical to the amino acid sequence set forth in SEQ ID NO:2, SEQ ID NO:25, or SEQ ID NO:27. In certain embodiments, the light chain variable region is encoded by a nucleic acid sequence that is at least 90%, at least 95%, at least 99%, or 100% identical to the nucleic acid sequence set forth in SEQ ID NO:3, SEQ ID NO:4, or SEQ ID NO:22; and/or the heavy chain variable region is encoded by a nucleic acid sequence that is at least 90%, at least 95%, at least 99%, or 100% identical to the nucleic acid sequence set forth in SEQ ID NO:1, SEQ ID NO:24, or SEQ ID NO:26. One or both of the light and heavy chain variable regions can be humanized. In some embodiments, the PSMA-binding polypeptide is capable of forming a dimer with a second, identical polypeptide chain.

In certain embodiments disclosed herein, the first binding domain is a single chain Fv (scFv) comprising the immunoglobulin light and heavy chain variable regions. In some embodiments, PSMA-binding scFvs include, for example, scFvs comprising an amino acid sequence that is at least 90%, at least 95% at least 99%, or 100% identical to the amino acid set forth in SEQ ID NO:19, SEQ ID NO:21, SEQ ID NO:30, SEQ ID NO:31, SEQ ID NO:34, or SEQ ID NO:35. In certain embodiments, the heavy chain variable region of the scFv is carboxyl-terminal to the light chain variable region (a "VL-VH orientation"). In some embodiments of an scFv having a VL-VH orientation, the scFv comprises an amino acid sequence that is at least 90%, at least 95%, at least 99%, or 100% identical to the amino acid sequence set forth in SEQ ID NO:21, SEQ ID NO:30, or SEQ ID NO:31. The light chain variable region and heavy chain variable region of the scFv can be joined by a peptide linker such as, for example, a peptide linker comprising an amino acid sequence (Gly$_4$Ser)$_n$, wherein n=1-5 (SEQ ID NO:165).

In certain embodiments, the PSMA-binding polypeptide further includes an immunoglobulin constant region. For example, in some variations, the immunoglobulin constant region comprises immunoglobulin CH2 and CH3 domains of IgG1, IgG2, IgG3, IgG4, IgA1, IgA2, or IgD. In some variations, the PSMA-binding polypeptide further includes one or more hinge regions. In certain embodiments, the hinge region can be derived, for instance, from a stalk region of a type II C lectin or from an immunoglobulin hinge region.

In another embodiment, the PSMA binding polypeptide comprises, in order from amino to carboxyl-terminus, a first binding domain, a hinge region, and an immunoglobulin constant region. A PSMA-binding polypeptide in this format can also be referred to as a PSMA-specific SMIP molecule. General SMIP configurations are provided, for example, in US Patent Application Publication Nos. 2003/0133939, 2003/0118592, and 2005/0136049, which are incorporated herein in their entirety by reference.

In another embodiment, the orientation of the polypeptide is reversed such that the polypeptide comprises, in order from amino to carboxyl-terminus, an immunoglobulin constant region, a hinge region and a first binding domain. In this orientation, the polypeptide can also be referred to as a PSMA-specific PIMS molecule. General PIMS configurations are provided, for example, in US Patent Application Publication No. 2009/0148447, which is incorporated herein in its entirety by reference. In some embodiments, a PSMA-binding polypeptide having an immunoglobulin constant region and, optionally, a hinge region as disclosed herein is capable of forming a dimer with a second, identical polypeptide chain through association between the respective immunoglobulin constant regions and/or hinge regions.

In another embodiment, the PSMA-binding polypeptide includes a second binding domain, such as, e.g., a single-chain Fv (scFv). For example, in some variations, the PSMA-binding polypeptide comprises, in order from amino-terminus to carboxyl-terminus or in order from carboxyl-terminus to amino-terminus, (a) a first binding domain, (b) a first hinge region, (c) an immunoglobulin constant region, (d) a second hinge region, and (e) a second binding domain.

In yet another embodiment, the present disclosure provides a PSMA-binding polypeptide as in other embodiments disclosed herein and comprising an additional binding domain, e.g., a second binding domain, wherein the second binding domain specifically binds a T cell. In certain embodiments, the second binding domain specifically binds a T cell receptor (TCR) complex or a component thereof. In some embodiments, the second binding domain includes those that specifically bind CD3, e.g., CD3ε. In certain variations, the second binding domain competes for binding to CD3 with the CRIS-7 or HuM291 monoclonal antibody. In some such variations, the second binding domain comprises an immunoglobulin light chain variable region and an immunoglobulin heavy chain variable region derived from the CRIS-7 or HuM291 monoclonal antibody. For example, in certain embodiments, the light and heavy chain variable regions of the second binding domain are humanized variable regions comprising, respectively, the light and heavy chain CDRs of the CRIS-7 or HuM291 monoclonal antibody. In another embodiment, the light and heavy chain variable regions of the second binding domain are selected from (a) a light chain variable region comprising an amino acid sequence that is at least 90%, at least 95%, at least 99%, or 100% identical to the amino acid sequence set forth in residues 139-245 of SEQ ID NO:47 and a heavy chain variable region comprising an amino acid sequence that is at least 90%, at least 95%, at least 99%, or 100% identical to the amino acid sequence set forth in residues 1-121 of SEQ ID NO:47; and (b) a light chain variable region comprising an amino acid sequence that is at least 90%, at least 95%, at least 99%, or 100% identical to the amino acid sequence set forth in residues 634-740 of SEQ ID NO:78 and a heavy chain variable region comprising an amino acid sequence that is at least 90%, at least 95%, at least 99%, or 100% identical to the amino acid sequence set forth in residues 496-616 of SEQ ID NO:78.

In certain embodiments of a PSMA-binding polypeptide comprising a second binding domain, the second binding domain is a single-chain Fv (scFv). For example, in some embodiments of a second binding domain comprising light and heavy chain variable regions derived from the CRIS-7 monoclonal antibody, the second binding domain is a scFv comprising an amino acid sequence that is at least 90%, at least 95%, at least 99%, or 100% identical to an amino acid sequence selected from (i) the amino acid sequence set forth in residues 1-245 of SEQ ID NO:47, and (ii) the amino acid sequence set forth in residues 496-742 of SEQ ID NO:78. In some such embodiments, the PSMA-binding polypeptide comprises an amino acid sequence that is at least 90%, at least 95%, at least 99%, or 100% identical to the amino acid sequence set forth in SEQ ID NO:49, SEQ ID NO:51, SEQ ID NO:74, SEQ ID NO:76, SEQ ID NO:78, SEQ ID NO:80, SEQ ID NO:82, SEQ ID NO:84, SEQ ID NO:158, SEQ ID NO:160, SEQ ID NO:162, or SEQ ID NO:164.

In another embodiment, the present disclosure provides a dimeric PSMA-binding protein comprising first and second polypeptide chains, wherein each of said polypeptide chains is a PSMA-binding polypeptide as in any of the embodiments disclosed herein.

In another embodiment, the present disclosure provides a PSMA-binding polypeptide comprising, in order from amino-terminus to carboxyl-terminus, (a) a binding domain that specifically binds human PSMA, (b) a hinge region, (c) an immunoglobulin constant region, and (d) an immunoglobulin heterodimerization domain. The heterodimerization domain can comprise, for example, an immunoglobulin CH1 domain or an immunoglobulin CL domain. In certain embodiments, the PSMA-binding domain competes for binding to human PSMA with a single chain Fv (scFv) having the amino acid sequence set forth in SEQ ID NO:21. In certain embodiments, the PSMA-binding domains include, e.g., the PSMA-binding domains disclosed above.

In some embodiments, the hinge region is derived from an immunoglobulin hinge region, such as, for example, an immunoglobulin hinge region of IgG1, IgG2, IgG3, IgG4, IgA1, IgA2, or IgD. Such an immunoglobulin hinge region can be either a wild-type or an altered immunoglobulin hinge region. In further embodiments, the immunoglobulin constant region comprises immunoglobulin CH2 and CH3 domains, such as, for example, immunoglobulin CH2 and CH3 domains of IgG1, IgG2, IgG3, IgG4, IgA1, IgA2, IgD, or any combination thereof; an immunoglobulin CH3 domain of IgG1, IgG2, IgG3, IgG4, IgA1, IgA2, IgD, IgE, IgM or any combination thereof; or immunoglobulin CH3 and CH4 domains of IgE, IgM or a combination thereof.

In certain embodiments, a PSMA-binding polypeptide includes at least one effector function selected from antibody-dependent cell-mediated cytotoxicity (ADCC) and complement-dependent cytotoxicity (CDC). In some such embodiments, the hinge region is derived from an immunoglobulin hinge region and the immunoglobulin constant region comprises immunoglobulin CH2 and CH3 domains of IgG1, IgG2, IgG3, or IgG4. In more specific variations, the immunoglobulin hinge region is derived from the hinge region of IgG1 and the immunoglobulin constant region comprises immunoglobulin CH2 and CH3 domains of IgG1.

In certain embodiments, a PSMA-binding polypeptide comprises an amino acid sequence that is at least 90%, at least 95%, at least 99%, or 100%% identical to the amino acid sequence set forth in SEQ ID NO:46, SEQ ID NO:58, SEQ ID NO:59, SEQ ID NO:60, or SEQ ID NO:61.

In another embodiment, the present disclosure provides a PSMA-binding protein comprising two, non-identical polypeptide chains that associate by way of heterodimerization domains (e.g., immunoglobulin heterodimerization domains) to form a heterodimer. In some embodiments, the heterodimeric PSMA binding protein comprises a first polypeptide chain comprising, in order from amino-terminus to carboxyl-terminus, (a) a first binding domain that specifically binds PSMA, (b) a first hinge region, (c) a first immunoglobulin constant region, and (d) a first immunoglobulin heterodimerization domain; and a second single chain polypeptide comprising, in order from amino-terminus to carboxyl-terminus, (a') a second hinge region, (b') a second immunoglobulin sub-region, and (c') a second immunoglobulin heterodimerization domain that is different from the first immunoglobulin heterodimerization domain of the first polypeptide chain, wherein the first and second immunoglobulin heterodimerization domains associate with each other to form a heterodimer. In certain embodiments, the PSMA-binding domain competes for binding to human PSMA with a single chain Fv (scFv) having the amino acid sequence set forth in SEQ ID NO:21. In certain embodiments, the PSMA-binding domains include, e.g., the PSMA-binding domains disclosed above.

In certain embodiments, heterodimerization domains include domains comprising either an immunoglobulin CH1 domain or an immunoglobulin CL domain. In some such embodiments, the first immunoglobulin heterodimerization domain comprises a first immunoglobulin CH1 domain and the second immunoglobulin heterodimerization domain comprises a first immunoglobulin CL domain. Alternatively, in other embodiments, the first immunoglobulin heterodimerization domain comprises a first immunoglobulin CL domain and the second immunoglobulin heterodimerization domain comprises a first immunoglobulin CH1 domain.

In some embodiments, at least one of the first and second hinge regions is derived from an immunoglobulin hinge region, such as, for example, an immunoglobulin hinge region of IgG1, IgG2, IgG3, IgG4, IgA1, IgA2, or IgD. Such an immunoglobulin hinge region can be either a wild-type or an altered immunoglobulin hinge region. In further embodiments, at least one of the first and second immunoglobulin constant regions comprises immunoglobulin CH2 and CH3 domains, such as, for example, immunoglobulin CH2 and CH3 domains of IgG1, IgG2, IgG3, IgG4, IgA1, IgA2, IgD, or any combination thereof; an immunoglobulin CH3 domain of IgG1, IgG2, IgG3, IgG4, IgA1, IgA2, IgD, IgE, IgM or any combination thereof; or immunoglobulin CH3 and CH4 domains of IgE, IgM or a combination thereof.

In certain variations of a heterodimeric PSMA-binding protein as disclosed herein, one or both of the first and second polypeptide chains include at least one effector function selected from antibody-dependent cell-mediated cytotoxicity (ADCC) and complement-dependent cytotoxicity (CDC). In some such embodiments, each of the first and second hinge regions is derived from an immunoglobulin hinge region and each of the first and second immunoglobulin constant regions comprises immunoglobulin CH2 and CH3 domains of IgG1, IgG2, IgG3, or IgG4. In certain embodiments, each of the first and second hinge regions is derived from the hinge region of IgG1 and each of the first and second immunoglobulin constant region comprises immunoglobulin CH2 and CH3 domains of IgG1.

In some embodiments of a heterodimeric PSMA-binding protein as disclosed herein, the second polypeptide chain further includes a second binding domain. For example, the second polypeptide chain can further comprise a second binding domain amino-terminal to the second hinge region.

In certain variations, a heterodimeric PSMA-binding protein as disclosed herein can be monospecific monospecific for PSMA). Alternatively, in other embodiments, the heterodimeric PSMA-binding protein is multispecific. For instance, each polypeptide chain of the heterodimer can comprise different binding domains, e.g., the first polypeptide chain comprising the PSMA-binding domain and the second polypeptide chain comprising a second binding (e.g., amino-terminal to the second hinge region) that is specific for a second target antigen that is different from PSMA.

In some embodiments of a multispecific, heterodimeric PSMA-binding protein, the second binding domain specifically binds a T-cell. In certain embodiments, T-cell-binding domains include, e.g., the additional binding domains and second binding domains disclosed above. In certain embodiments of a heterodimeric PSMA-binding protein comprising a second binding domain that specifically binds a T-cell, for example, (a) the first polypeptide chain comprises an amino acid sequence that is at least 90%, at least 95%, at least 99%, or 100% identical to the amino acid sequence set forth in SEQ ID NO: 46 and the second polypeptide chain comprises an amino acid sequence that is at least 90%, at least 95%, at least 99%, or 100% identical to the amino acid sequence set forth in SEQ ID NO: 47; (b) the first polypeptide chain comprises an amino acid sequence that is at least 90%, at least 95%, at least 99%, or 100% identical to the amino acid sequence set forth in SEQ ID NO: 58 and the second polypeptide chain comprises an amino acid sequence that is at least 90%, at least 95%, at least 99%, or 100% identical to the amino acid sequence set forth in SEQ ID NO: 57; (c) the first polypeptide chain comprises an amino acid sequence that is at least 90%, at least 95%, at least 99%, or 100% identical to the amino acid sequence set forth in SEQ ID NO: 59 and the second polypeptide chain comprises an amino acid sequence that is at least 90%, at least 95%, at least 99%, or 100% identical to the amino acid sequence set forth in SEQ ID NO: 57; (d) the first polypeptide chain comprises an amino acid sequence that is at least 99%, at least 95%, at least 99%, or 100% identical to the amino acid sequence set forth in SEQ ID NO: 60 and the second polypeptide chain comprises an amino acid sequence that is at least 90%, at least 95%, at least 99%, or 100% identical to the amino acid sequence set forth in SEQ ID NO: 47; or (e) the first polypeptide chain comprises an amino acid sequence that is at least 90%, at least 95%, at least 99%, or 100% identical to the amino acid sequence set forth in SEQ ID NO: 61 and the second polypeptide chain comprises an amino acid sequence that is at least 90%, at least 95%, at least 99%, or 100% identical to the amino acid sequence set forth in SEQ ID NO: 47.

In certain embodiments of a dimeric or heterodimeric PSMA-binding protein as disclosed herein, the PSMA-binding protein exhibits increased serum half-life, reduced internalization by a cell expressing PSMA, and/or increased time of persistence on the surface of the cell expressing PSMA as compared to the murine monoclonal antibody 107-1A4.

In another embodiment, the present disclosure provides an isolated nucleic acid encoding a PSMA-binding polypeptide. For example, in certain variations, the nucleic acid comprises the nucleotide sequence set forth in SEQ ID NO NO:18, SEQ ID NO:20, SEQ ID NO:22, SEQ ID NO:24, SEQ ID NO:26, SEQ ID NO:28, SEQ ID NO:29, SEQ ID NO:32, SEQ ID NO:33, SEQ ID NO:36, SEQ ID NO:37, SEQ ID NO:40, SEQ ID NO:41, SEQ ID NO:44, SEQ ID NO:48, SEQ ID NO:50, SEQ ID NO:53, SEQ ID: NO:54, SEQ ID NO:55, SEQ ID NO:56, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:157, SEQ ID NO:159, SEQ ID NO:161, or SEQ ID NO:163.

In another embodiment, the present disclosure provides an expression vector for expressing a PSMA-binding polypeptide or protein as disclosed herein in a recombinant host cell. In some embodiments, the expression vector comprises a nucleic acid segment encoding the PSMA-binding polypeptide, wherein the nucleic acid segment is operably linked to regulatory sequences suitable for expression of the nucleic acid segment in a host cell. In some embodiments, the nucleic acid segment comprises the nucleotide sequence set forth in SEQ ID NO NO:18, SEQ ID NO:20, SEQ ID NO:22, SEQ ID NO:24, SEQ ID NO:26, SEQ ID NO:28, SEQ ID NO:29, SEQ ID NO:32, SEQ ID NO:33, SEQ ID NO:36, SEQ ID NO:37, SEQ ID NO:40, SEQ ID NO:41, SEQ ID NO:44, SEQ ID NO:48, SEQ ID NO:50, SEQ ID NO:53, SEQ ID: NO:54, SEQ ID NO:55, SEQ ID NO:56, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:157, SEQ ID NO:159, SEQ ID NO:161, or SEQ ID NO:163. In other embodiments, the expression vector comprises first and second expression units, wherein the first and second expression units respectively comprise first and second nucleic acid segments encoding the first and second polypeptide chains of a heterodimeric PSMA-binding protein as in certain embodiments disclosed herein, and wherein the first and second nucleic acid segments are operably linked to regulatory sequences suitable for expression of the nucleic acid segments in a host cell. In certain variations, (a) the first nucleic acid segment comprises the nucleotide sequence set forth in SEQ ID NO:44 and the second nucleic acid segment comprises the nucleotide sequence set forth in SEQ ID NO:45; (b) the first nucleic acid segment comprises the nucleotide sequence set forth in SEQ ID NO:53 and the second nucleic acid segment comprises the nucleotide sequence set forth in SEQ ID NO:52; (c) the first nucleic acid segment comprises the nucleotide sequence set forth in SEQ ID NO:54 and the second nucleic acid segment comprises the nucleotide sequence set forth in SEQ ID NO:52; (d) the first nucleic acid segment comprises the nucleotide sequence set forth in SEQ ID NO:55 and the second nucleic acid segment comprises the nucleotide sequence set forth in SEQ ID NO:45; or (e) the first nucleic acid segment comprises the nucleotide sequence set forth in SEQ ID NO:56 and the second nucleic acid segment comprises the nucleotide sequence set forth in SEQ ID NO:45.

In another embodiment, the present disclosure provides a recombinant host cell comprising an expression vector disclosed herein.

In another embodiment, the present disclosure provides a method for producing a PSMA-binding polypeptide or protein. For example, in some embodiments, the method is for producing a PSMA-binding polypeptide as disclosed herein. In certain embodiments, the method generally includes culturing a recombinant host cell comprising an expression vector, wherein the expression vector comprises a nucleic acid segment that encodes the PSMA-binding polypeptide and is operably linked to regulatory sequences suitable for expression of the nucleic acid segment in the host cell, and wherein the culturing is under conditions whereby the nucleic acid segment is expressed, thereby producing the PSMA-binding polypeptide. In certain variations, the nucleic acid segment comprises the nucleotide sequence set forth in SEQ ID NO NO:18, SEQ ID NO:20, SEQ ID NO:22, SEQ ID NO:24, SEQ ID NO:26, SEQ ID NO:28, SEQ ID NO:29, SEQ ID NO:32, SEQ ID NO:33, SEQ ID NO:36, SEQ ID NO:37, SEQ ID NO:40, SEQ ID NO:41, SEQ ID NO:44, SEQ ID NO:48, SEQ ID NO:50, SEQ ID NO:53, SEQ ID: NO:54, SEQ ID NO:55, SEQ ID NO:56, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:157, SEQ ID NO:159, SEQ ID NO:161, or SEQ ID NO:163. In certain embodiments, the method further includes recovering the PSMA-binding polypeptide.

In some embodiments, the method is for producing a dimeric PSMA-binding protein as disclosed herein. In certain variations, the nucleic acid segment of the expression vector encodes the PSMA-binding polypeptide as disclosed herein, and the culturing is under conditions whereby the nucleic acid segment is expressed and the encoded PSMA-binding polypeptide is produced as a dimeric PSMA-binding protein. The method can further include recovering the dimeric PSMA-binding protein.

In other embodiments, the method is for producing a heterodimeric PSMA-binding protein disclosed herein. In certain embodiments, the method generally includes culturing a recombinant host cell comprising first and second expression units, wherein the first and second expression units respectively comprise first and second nucleic acid segments encoding the first and second polypeptide chains of a heterodimeric PSMA-binding protein as set forth herein, wherein the first and second nucleic acid segments are operably linked to regulatory sequences suitable for expression of the nucleic acid segments in a host cell, and wherein the culturing is under conditions whereby the first and second nucleic acid segments are expressed and the encoded polypeptide chains are produced as the heterodimeric PSMA-binding protein. In some embodiments, the method further includes recovering the heterodimeric PSMA-binding protein.

In another embodiment, the present disclosure provides a composition comprising any of the PSMA-binding polypeptides or proteins as set forth herein and a pharmaceutically acceptable carrier, diluent, or excipient.

In another embodiment, the present disclosure provides a method for inducing antibody-dependent cell-mediated cytotoxicity (ADCC) or complement-dependent cytotoxicity (CDC) against a cell expressing PSMA. For example, in some embodiments, a method for inducing ADCC or CDC against the cell expressing PSMA includes contacting the PSMA-expressing cell with a dimeric PSMA-binding protein comprising first and second polypeptide chains, wherein each of the polypeptide chains is a PSMA-binding polypeptide as disclosed herein, and wherein the contacting is under conditions whereby ADCC or CDC against the PSMA-expressing cell is induced. In other embodiments, a method for inducing ADCC or CDC against the PSMA-expressing cell includes contacting the cell with a heterodimeric PSMA-binding protein, wherein the contacting is under conditions whereby ADCC or CDC against the PSMA-expressing cell is induced.

In another embodiment, the present disclosure provides a method for inducing redirected T-cell cytotoxicity (RTCC) against a cell expressing PSMA. In some variations, a method for inducing RTCC against the cell expressing PSMA includes contacting the PSMA-expressing cell with a dimeric PSMA-binding protein comprising first and second polypeptide chains, wherein each of said polypeptide chains is a PSMA-binding polypeptide disclosed herein, and wherein the contacting is under conditions whereby RTCC against the PSMA-expressing cell is induced. In other embodiments, a method for inducing RTCC against the PSMA-expressing cell includes contacting the cell with a heterodimeric PSMA-binding protein as disclosed herein, wherein the contacting is under conditions whereby RTCC against the PSMA-expressing cell is induced.

In another embodiment, the present disclosure provides a method for treating a disorder in a subject, wherein the disorder is characterized by overexpression of PSMA. In some embodiments, the method includes administering to the subject a therapeutically effective amount of a dimeric PSMA-binding protein disclosed above. In some such embodiments, the first and second polypeptide chains of the dimeric PSMA-binding protein is a PSMA-binding polypeptide, e.g., as disclosed above, and the dimeric PSMA-binding protein induces redirected T-cell cytotoxicity (RTCC) in the subject. In other variations, the method includes administering to the subject a therapeutically effective amount of a heterodimeric PSMA-binding protein, e.g., as disclosed above. In some variations, the heterodimeric PSMA-binding protein is a protein as disclosed above, and the heterodimeric PSMA-binding protein induces RTCC in the subject. In certain embodiments of the disclosed methods, the disorder is a cancer such as, for example, prostate cancer (e.g., castrate-resistant prostate cancer), colorectal cancer, gastric cancer, clear cell renal carcinoma, bladder cancer, or lung cancer. In some embodiments, the disorder is a prostate disorder such as, e.g., prostate cancer or benign prostatic hyperplasia. In other variations, the disorder is an neovascular disorder. The neovascular disorder to be treated can be, for example, a cancer characterized by solid tumor growth such as, e.g., clear cell renal carcinoma, colorectal cancer, bladder cancer, and lung cancer.

These and other embodiments and/or other aspects of the invention will become evident upon reference to the following detailed description of the invention and the attached drawings.

DESCRIPTION OF THE FIGURES

FIG. 8A shows the results of a competitive binding assay to determine if the humanized J591 antibody (Hu591) competes with the binding of 107-1A4, J591 or J415 murine antibodies to PSMA on C4-2 cells; FIG. 8B shows the results of a competitive binding assay to determine if the three murine antibodies compete with the binding of the chimeric 107-1A4 SMIP molecule (TSC085) to PSMA on C4-2 cells; and FIG. 8C shows the results of a competitive binding assay to determine if the three murine antibodies compete with the binding of the humanized 107-1A4 SMIP molecule (TSC189) to PSMA on C4-2 cells.

DETAILED DESCRIPTION OF THE INVENTION

I. General Description

Figure 1:
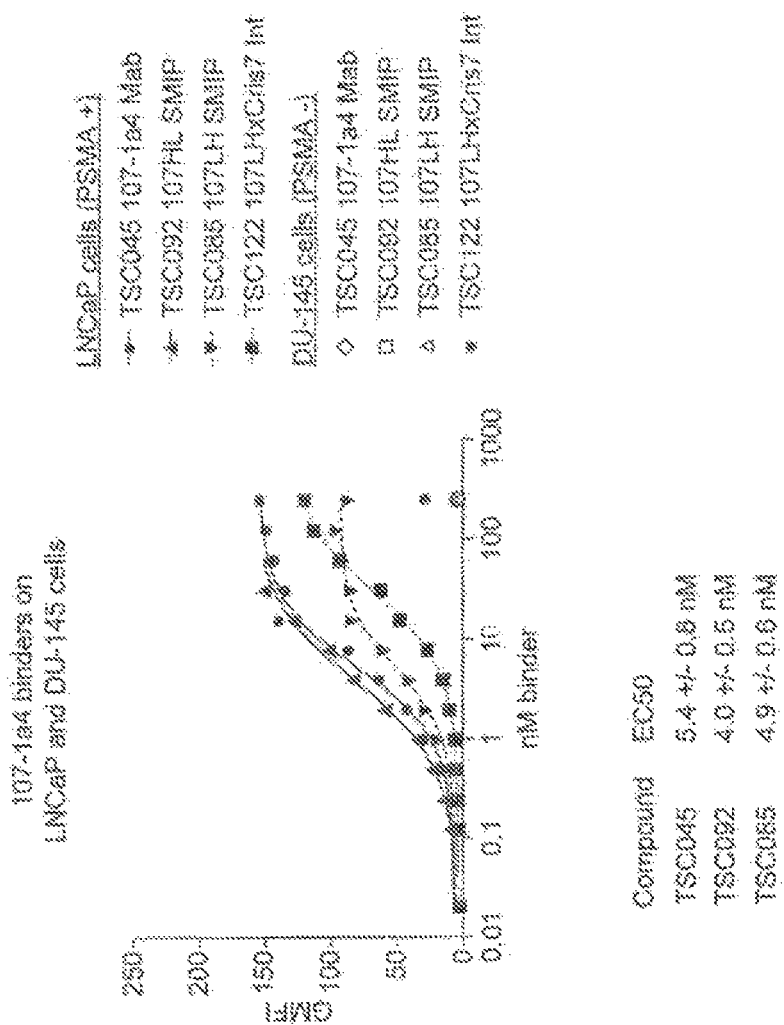
FIG. 1 is a graph illustrating the results of a binding study used to compare the parent 107-1A4 murine antibody (TSC045) with TSC085, TSC092 and TSC122 in PSMA(+) (LNCaP) and PSMA(−) (DU-145) prostate cancer cell lines.

The invention provides PSMA-binding polypeptides and proteins that specifically bind prostate-specific membrane antigen (PSMA). Administration of a therapeutically effective amount of a PSMA-binding polypeptide or protein of the invention to a patient in need thereof is useful for treatment of certain disorders associated with the overexpression of PSMA, including certain cancers and prostate disorders. In one embodiment, the PSMA-binding polypeptide or protein simultaneously bind a target cell overexpressing PSMA and a T-cell, thereby "cross-linking" the target cell over-expressing PSMA and the T-cell. The binding of both domains to their targets elicits potent target-dependent redirected T-cell cytotoxicity (RTCC) (e.g., induces target-dependent T-cell cytotoxicity, T-cell activation and T-cell proliferation).

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±20% of the indicated range, value, or structure, unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. In addition, it should be understood that the polypeptides comprising the various combinations of the components (e.g., domains or regions) and substituents described herein, are disclosed by the present application to the same extent as if each polypeptide was set forth individually. Thus, selection of particular components of individual polypeptides is within the scope of the present disclosure.

II. Definitions

As used herein, the term "binding domain" or "binding region" refers to the domain, region, portion, or site of a protein, polypeptide, oligopeptide, or peptide that possesses the ability to specifically recognize and bind to a target molecule, such as an antigen, ligand, receptor, substrate, or inhibitor (e.g., CD3, PSMA). Exemplary binding domains include single-chain antibody variable regions (e.g., domain antibodies, sFv, scFv, scFab), receptor ectodomains, and ligands (e.g., cytokines, chemokines). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions). A variety of assays are known for identifying binding domains of the present disclosure that specifically bind a particular target, including Western blot, ELISA, phage display library screening, and BIACORE® interaction analysis. As used herein, a PSMA-binding polypeptide can have a "first binding domain" and, optionally, a "second binding domain." In certain embodiments, the "first binding domain" is a PSMA-binding domain and, depending on the particular polypeptide format (e.g., SMIP or PIMS), can be located at either the amino- or carboxyl-terminus. In certain embodiments comprising both the first and second binding domains, the second binding domain is a T cell binding domain such as a scFv derived from a mouse monoclonal antibody (e.g., CRIS-7) that binds to a T cell surface antigen (e.g., CD3). In other embodiments, the second binding domain is a second PSMA-binding domain. In yet other embodiments, the second binding domain is a binding domain other than a PSMA-binding domain or a T cell binding domain.

A binding domain "specifically binds" a target if it binds the target with an affinity or $K_a$ (i.e., an equilibrium association constant of a particular binding interaction with units of 1/M) equal to or greater than $10^5$ $M^{-1}$, while not significantly binding other components present in a test sample. Binding domains can be classified as "high affinity" binding domains and "low affinity" binding domains. "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity can be defined as an equilibrium dissociation constant ($K_d$) of a particular binding interaction with units of M (e.g., $10^{-5}$ M to $10^{-13}$ M). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

"CD3" is known in the art as a multi-protein complex of six chains (see, e.g., Abbas and Lichtman, 2003; Janeway et al., p. 172 and 178, 1999), which are subunits of the T cell receptor complex. In mammals, the CD3 subunits of the T cell receptor complex are a CD3γ chain, a CD3δ chain, two CD3ε chains, and a homodimer of CD3ζ chains. The CD3γ CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. It is believed the ITAMs are important for the signaling capacity of a TCR complex. CD3 as used in the present disclosure can be from various animal species, including human, monkey, mouse, rat, or other mammals.

As used herein, a "conservative substitution" is recognized in the art as a substitution of one amino acid for another amino acid that has similar properties. Exemplary conservative substitutions are well-known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, Mass. (1990), p. 8). In certain embodiments, a conservative substitution includes a leucine to serine substitution.

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or amino acid sequence "derived from" a designated polypeptide or protein refers to the origin of the polypeptide. In certain embodiments, the polypeptide or amino acid sequence which is derived from a particular sequence (sometimes referred to as the "starting" or "parent" or "parental" sequence) has an amino acid sequence that is essentially identical to the starting sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the starting sequence.

Polypeptides derived from another polypeptide can have one or more mutations relative to the starting polypeptide, e.g., one or more amino acid residues which have been substituted with another amino acid residue or which has one or more amino acid residue insertions or deletions. The polypeptide can comprise an amino acid sequence which is not naturally occurring. Such variations necessarily have less than 100% sequence identity or similarity with the starting polypeptide. In one embodiment, the variant will have an amino acid sequence from about 60% to less than 100% amino acid sequence identity or similarity with the amino acid sequence of the starting polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the starting polypeptide.

As used herein, unless otherwise provided, a position of an amino acid residue in a variable region of an immunoglobulin molecule is numbered according to the Kabat numbering convention (Kabat, Sequences of Proteins of Immunological Interest, $5^{th}$ ed. Bethesda, Md.: Public Health Service, National Institutes of Health (1991)), and a position of an amino acid residue in a constant region of an immunoglobulin molecule is numbered according to EU nomenclature (Ward et al., 1995 Therap. Immunol. 2:77-94).

As used herein, the term "dimer" refers to a biological entity that consists of two subunits associated with each other via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis). A "heterodimer" or "heterodimeric protein," as used herein, refers to a dimer formed from two different polypeptides. A heterodimer does not include an antibody formed from four polypeptides (i.e., two light chains and two heavy chains). A "homodimer" or "homodimeric protein," as used herein, refers to a dimer formed from two identical polypeptides.

As used herein, a "hinge region" or a "hinge" refers to a polypeptide derived from (a) an interdomain region of a transmembrane protein (e.g., a type I transmembrane protein); or (b) a stalk region of a type II C-lectin. For example, a hinge region can be derived from an interdomain region of an immunoglobulin superfamily member; suitable hinge regions within this particular class include (i) immunoglobulin hinge regions (made up of, for example, upper and/or core region(s)) or functional variants thereof, including wild-type and altered immunoglobulin hinges, and (ii) regions (or functional variants thereof) that connect immunoglobulin V-like or immunoglobulin C-like domains.

A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and can comprise a human IgG hinge region.

An "altered wild-type immunoglobulin hinge region" or "altered immunoglobulin hinge region" refers to (a) a wild type immunoglobulin hinge region with up to 30% amino acid changes (e.g., up to 25%, 20%, 15%, 10%, or 5% amino acid substitutions or deletions), or (b) a portion of a wild type immunoglobulin hinge region that has a length of about 5 amino acids (e.g., about 5, 6, 7, 8, 9, 10, 11, 12, 13, 14, 15, 16, 17, 18, 19, or 20 amino acids) up to about 120 amino acids (for instance, having a length of about 10 to about 40 amino acids or about 15 to about 30 amino acids or about 15 to about 20 amino acids or about 20 to about 25 amino acids), has up to about 30% amino acid changes (e.g., up to about 25%, 20%, 15%, 10%, 5%, 4%, 3%, 2%, or 1% amino acid substitutions or deletions or a combination thereof), and has an IgG core hinge region as disclosed in PCT/US2010/62436 and PCT/US2010/62404.

As used herein, the term "humanized" refers to a process of making an antibody or immunoglobulin binding proteins and polypeptides derived from a non-human species (e.g., mouse or rat) less immunogenic to humans, while still retaining antigen-binding properties of the original antibody, using genetic engineering techniques. In some embodiments, the binding domain(s) of an antibody or immunoglobulin binding proteins and polypeptides (e.g., light and heavy chain variable regions, Fab, scFv) are humanized. Non-human binding domains can be humanized using techniques known as CDR grafting (Jones et al., Nature 321:522 (1986)) and variants thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., "Derivation of therapeutically active humanized and veneered anti-CD18 antibodies. In: Metcalf B W, Dalton B J, eds. Cellular adhesion: molecular definition to therapeutic potential. New York: Plenum Press, 1994: 291-312). If derived from a non-human source, other regions of the antibody or immunoglobulin binding proteins and polypeptides, such as the hinge region and constant region domains, can also be humanized.

An "immunoglobulin dimerization domain" or "immunoglobulin heterodimerization domain", as used herein, refers to an immunoglobulin domain of a polypeptide chain that preferentially interacts or associates with a different immunoglobulin domain of a second polypeptide chain, wherein the interaction of the different immunoglobulin heterodimerization domains substantially contributes to or efficiently promotes heterodimerization of the first and second polypeptide chains (i.e., the formation of a dimer between two different polypeptide chains, which is also referred to as a "heterodimer"). The interactions between immunoglobulin heterodimerization domains "substantially contributes to or efficiently promotes" the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL domain (e.g., Cκ or Cλ isotypes), or derivatives thereof, including wild type immunoglobulin CH1 and CL domains and altered (or mutated) immunoglobulin CH1 and CL domains, as provided therein.

An "immunoglobulin constant region" or "constant region" is a term defined herein to refer to a peptide or polypeptide sequence that corresponds to or is derived from part or all of one or more constant region domains. In certain embodiments, the immunoglobulin constant region corresponds to or is derived from part or all of one or more constant region domains, but not all constant region domains of a source antibody. In certain embodiments, the constant region comprises IgG CH2 and CH3 domains, e.g., IgG1 CH2 and CH3 domains. In certain embodiments, the constant region does not comprise a CH1 domain. In certain embodiments, the constant region domains making up the constant region are human. In some embodiments (for example, in certain variations of a PSMA-binding polypeptide or protein comprising a second binding domain that specifically binds CD3 or another T cell surface antigen), the constant region domains of a fusion protein of this disclosure lack or have minimal effector functions of antibody-dependent cell-mediated cytotoxicity (ADCC) and complement activation and complement-dependent cytotoxicity (CDC), while retaining the ability to bind some $F_c$ receptors (such as $F_cRn$, the neonatal Fc receptor) and retaining a relatively long half life in vivo. In other variations, a fusion protein of this disclosure includes constant domains that retain such effector function of one or both of ADCC and CDC. In certain embodiments, a binding domain of this disclosure is fused to a human IgG1 constant region, wherein the IgG1 constant region has one or more of the following amino acids mutated: leucine at position 234 (L234), leucine at position 235 (L235), glycine at position 237 (G237), glutamate at position 318 (E318), lysine at position 320 (K320), lysine at position 322 (K322), or any combination thereof (numbering according to EU). For example, any one or more of these amino acids can be changed to alanine. In a further embodiment, an IgG1 Fc domain has each of L234, L235, G237, E318, K320, and K322 (according to EU numbering) mutated to an alanine L234A, L235A, G237A, E318A, K320A, and K322A, respectively), and optionally an N297A mutation as well (i.e., essentially eliminating glycosylation of the CH2 domain).

"Fc region" or "Fc domain" refers to a polypeptide sequence corresponding to or derived from the portion of a source antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. However, more recently the term has been applied to a single chain consisting of CH3, CH2, and at least a portion of the hinge sufficient to form a disulfide-linked dimer with a second such chain. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

As used here the term "SMIP" is used to refer to protein scaffold as generally disclosed in, for example, in US Patent Application Publication Nos. 2003/0133939, 2003/0118592, and 2005/0136049, which are incorporated herein by reference in their entirety. The "PSMA-specific SMIP molecules" or "SMIP molecules" described in the Examples and throughout the disclosure herein should be understood to be PSMA-binding proteins comprising SMIP scaffolding, e.g., in order from amino to carboxyl-terminus, a first binding domain, a hinge region, and an immunoglobulin constant constant region.

As used here the term "PIMS" is used to refer to protein scaffold as generally disclosed in, for example, in US Patent Application Publication No. 2009/0148447, which is incorporated herein in its entirety by reference. The "PSMA-specific PIMS molecules" or "PIMS molecules" described in the Examples and throughout the disclosure herein should be understood to be PSMA-binding proteins comprising PIMS scaffolding, e.g., in order from amino to carboxyl-terminus, an immunoglobulin constant region, a hinge region and a first binding domain.

As used herein, the term "Interceptor" is used to refer to a monospecific or multispecific heterodimeric protein scaffold as generally disclosed in PCT applications PCT/US2010/62436 and PCT/US2010/62404, which are incorporated herein in their entirety. The "PSMA-specific Interceptor molecules" or "Interceptor molecules" described in the Examples and throughout the disclosure herein should be understood to be PSMA-binding proteins comprising Interceptor scaffolding, e.g., two non-identical polypeptide chains, each polypeptide chain comprising an immunoglobulin heterodimerization domain. The interfacing immunoglobulin heterodimerization domains are different. In one embodiment, the immunoglobulin heterodimerization domain comprises a CH1 domain or a derivative thereof. In another embodiment, the immunoglobulin heterodimerization domain comprises a CL domain or a derivative thereof. In one embodiment, the CL domain is a Cκ or Cλ isotype or a derivative thereof.

As used herein, "SCORPION", is a term used to refer to a multi-specific binding protein scaffold. SCORPION™ is a trademark of Emergent Product Development Seattle, LLC. Multi-specific binding proteins and polypeptides are disclosed, for instance, in PCT Application Publication No. WO 2007/146968, U.S. Patent Application Publication No. 2006/0051844, PCT Application Publication No. WO 2010/040105, PCT Application Publication No. WO 2010/003108, and U.S. Pat. No. 7,166,707, which are incorporated herein by reference in their entirety. A SCORPION polypeptide comprises two binding domains (the domains can be designed to specifically bind the same or different targets), two hinge regions, and an immunoglobulin constant region. SCORPION proteins are homodimeric proteins comprising two identical, disulfide-bonded SCORPION polypeptides. The "PSMA-specific SCORPION molecules" or "SCORPION molecules" described in the Examples and throughout the disclosure herein should be understood to be PSMA-binding proteins comprising SCORPION scaffolding, e.g., two binding domains (the domains can be designed to specifically bind the same or different targets), two hinge regions, and an immunoglobulin constant region.

As used herein, the "stalk region" of a type II C-lectin refers to the portion of the extracellular domain of the type II C-lectin that is located between the C-type lectin-like domain (CTLD; e.g., similar to CTLD of natural killer cell receptors) and the transmembrane domain. For example, in the human CD94 molecule (GenBank™ Accession No. AAC50291.1, PRI Nov. 30, 1995), the extracellular domain corresponds to amino acid residues 34-179, whereas the CTLD corresponds to amino acid residues 61-176. Accordingly, the stalk region of the human CD94 molecule includes amino acid residues 34-60, which is found between the membrane and the CTLD (see Boyington et al., *Immunity* 10:75, 1999; for descriptions of other stalk regions, see also Beavil et al., *Proc. Nat'l. Acad. Sci. USA* 89:753, 1992; and Figdor et al., *Nature Rev. Immunol.* 2:77, 2002). These type II C-lectins can also have from six to 10 junction amino acids between the stalk region and the transmembrane region or the CTLD. In another example, the 233 amino acid human NKG2A protein (GenBank™ Accession No. P26715.1, PRI Jun. 15, 2010) has a transmembrane domain ranging from amino acids 71-93 and an extracellular domain ranging from amino acids 94-233. The CTLD is comprised of amino acids 119-231, and the stalk region comprises amino acids 99-116, which is flanked by junctions of five and two amino acids. Other type II C-lectins, as well as their extracellular ligand-bind domains, interdomain or stalk regions, and CTLDs are known in the art (see, e.g., GenBank™ Accession Nos. NP_001993.2; AAH07037.1, PRI Jul. 15, 2006; NP_001773.1, PRI Jun. 20, 1010; AAL65234.1, PRI Jan. 17, 2002, and CAA04925.1, PRI Nov. 14, 2006, for the sequences of human CD23, CD69, CD72, NKG2A and NKG2D and their descriptions, respectively).

As used herein, the "interdomain region" of a transmembrane protein (e.g., a type I transmembrane protein) refers to a portion of the extracellular domain of the transmembrane protein that is located between two adjacent domains. Examples of interdomain regions include regions linking adjacent Ig domains of immunoglobulin superfamily members (e.g., an immunoglobulin hinge region from IgG, IgA, IgD, or IgE; the region linking the IgV and IgC2 domains of CD2; or the region linking the IgV and IgC domains of CD80 or CD86). Another example of an interdomain region is the region linking the non-Ig and IgC2 domain of CD22, a type I sialic acid-binding Ig-like lectin.

A polypeptide region "derived from" a stalk region of a type II C-lectin, or "derived from" a transmembrane protein interdomain region (e.g., an immunoglobulin hinge region), refers to an about five to about 150 amino acid sequence, an about 5 to about 100 amino acid sequence, an about 5 to about 50 amino acid sequence, an about 5 to about 40 amino acid sequence, an about 5 to about 30 amino acid sequence, an about 5 to about 25 amino acid sequence, an about 5 to about 20 amino acid sequence, an about 10 to about 25 amino acid sequence, an about 10 to about 20 amino acid sequence, about 8 to about 20 amino acid sequence, about 9 to about 20 amino acid sequence, about 10 to about 20 amino acid sequence, about 11 to about 20 amino acid sequence, about 12 to about 20 amino acid sequence, about 13 to about 20 amino acid sequence, about 14 to about 20 amino acid sequence, about 15 to about 20 amino acid sequence, or an about 5, 6, 7, 8, 9, 10, 11, 12, 13, 14, 15, 16, 17, 18, 19, or 20 amino acid sequence, wherein all or at least a portion of which includes (i) a wild-type stalk region or interdomain region sequence; (ii) a fragment of the wild-type stalk region or interdomain region sequence; (iii) a polypeptide having at least 80%, 85%, 90%, or 95% amino acid sequence identity with either (i) or (ii); or (iv) either (i) or (ii) in which one, two, three, four, or five amino acids have a deletion, insertion, substitution, or any combination thereof, for instance, the one or more changes are substitutions or the one or more mutations include only one deletion. In some embodiments, a derivative of a stalk region is more resistant to proteolytic cleavage as compared to the wild-type stalk region sequence, such as those derived from about eight to about 20 amino acids of NKG2A, NKG2D, CD23, CD64, CD72, or CD94.

As used herein, the term "junction amino acids" or "junction amino acid residues" refers to one or more (e.g., about 2-10) amino acid residues between two adjacent regions or domains of a polypeptide, such as between a hinge and an adjacent immunoglobulin constant region or between a hinge and an adjacent binding domain or between a peptide linker that links two immunoglobulin variable domains and an adjacent immunoglobulin variable domain. Junction amino acids can result from the construct design of a polypeptide (e.g., amino acid residues resulting from the use of a restriction enzyme site during the construction of a nucleic acid molecule encoding a polypeptide).

As used herein, the phrase a "linker between CH3 and CH1 or CL" refers to one or more (e.g., about 2-12, about 2-10, about 4-10, about 5-10, about 6-10, about 7-10, about 8-10, about 9-10, about 8-12, about 9-12, or about 10-12) amino acid residues between the C-terminus of a CH3 domain (e.g., a wild type CH3 or a mutated CH3) and the N-terminus of a CH1 domain or CL domain (e.g., Ck).

As used herein, the term "patient in need" refers to a patient at risk of, or suffering from, a disease, disorder or condition that is amenable to treatment or amelioration with a PSMA-binding protein or polypeptide or a composition thereof provided herein.

As used herein, the term "peptide linker" refers to an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids.

As used herein, the term "pharmaceutically acceptable" refers to molecular entities and compositions that do not produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

As used herein, the term "promoter" refers to a region of DNA involved in binding RNA polymerase to initiate transcription.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Cassol et al. (1992); Rossolini et al. (1994) *Mol. Cell. Probes* 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression" refers to the biosynthesis of a product encoded by a nucleic acid. For example, in the case of nucleic acid segment encoding a polypeptide of interest, expression involves transcription of the nucleic acid segment into mRNA and the translation of mRNA into one or more polypeptides.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit can further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector can also include additional nucleic acid segments such as, for example, one or more origins of replication or one or more selectable markers. Expression vectors are generally derived from plasmid or viral DNA, or can contain elements of both.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. The comparison window for nucleic acid sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison windon for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993).

When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

As used herein, a "polypeptide" or "polypeptide chain" is a single, linear and contiguous arrangement of covalently linked amino acids. It does not include two polypeptide chains that link together in a non-linear fashion, such as via an interchain disulfide bond (e.g., a half immunoglobulin molecule in which a light chain links with a heavy chain via a disulfide bond). Polypeptides can have or form one or more intrachain disulfide bonds. With regard to polypeptides as described herein, reference to amino acid residues corresponding to those specified by SEQ ID NO includes post-translational modifications of such residues.

A "protein" is a macromolecule comprising one or more polypeptide chains. A protein can also comprise non-peptidic components, such as carbohydrate groups. Carbohydrates and other non-peptidic substituents can be added to a protein by the cell in which the protein is produced, and will vary with the type of cell. Proteins are defined herein in terms of their amino acid backbone structures; substituents such as carbohydrate groups are generally not specified, but may be present nonetheless.

As used herein, "small modular immunopharmaceutical proteins" or SMIP refers to a protein scaffold generally disclosed, for instance, U.S. Patent Publication Nos. 2003/0133939, 2003/0118592, and 2005/0136049. SMIP™ is a trademark of Emergent Product Development Seattle LLC. A SMIP protein can comprise a polypeptide chain having a binding domain, a hinge region and an immunoglobulin constant region.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl-terminus of the reference sequence, but is not necessarily at the carboxyl-terminus of the complete polypeptide.

"T cell receptor" (TCR) is a molecule found on the surface of T cells that, along with CD3, is generally responsible for recognizing antigens bound to major histocompatibility complex (MHC) molecules. It consists of a disulfide-linked heterodimer of the highly variable α and β chains in most T cells. In other T cells, an alternative receptor made up of variable γ and δ chains is expressed. Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Abbas and Lichtman, *Cellular and Molecular Immunology* (5th Ed.), Editor: Saunders, Philadelphia, 2003; Janeway et al., *Immunobiology: The Immune System in Health and Disease*, 4$^{th}$ Ed., Current Biology Publications, p 148, 149, and 172, 1999). TCR as used in the present disclosure can be from various animal species, including human, mouse, rat, or other mammals.

"TCR complex," as used herein, refers to a complex formed by the association of CD3 chains with other TCR chains. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

"A component of a TCR complex," as used herein, refers to a TCR chain (i.e., TCRα, TCRβ, TCRγ or TCRδ), a CD3 chain (i.e., CD3γ, CD3δ, CD3ε or CD3ζ, or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Antibody-dependent cell-mediated cytotoxicity" and "ADCC," as used herein, refer to a cell-mediated process in which nonspecific cytotoxic cells that express FcγRs (e.g., monocytic cells such as Natural Killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., 1991, Annu. Rev. Immunol., 9:457-92.

The term "having ADCC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)), is capable of mediating antibody-dependent cell-mediated cytotoxicity (ADCC) through binding of a cytolytic Fc receptor (e.g., FcγRIII) on a cytolytic immune effector cell expressing the Fc receptor (e.g., an NK cell).

"Complement-dependent cytotoxicity" and "CDC," as used herein, refer to a process in which components in normal serum ("complement"), together with an antibody or other C1q-complement-binding protein bound to a target antigen, exhibit lysis of a target cell expressing the target antigen. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "having CDC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)) is capable of mediating complement-dependent cytotoxicity (CDC) through binding of C1q complement protein and activation of the classical complement system.

"Redirected T-cell cytotoxicity" and "RTCC," as used herein, refer to a T-cell-mediated process in which a cytotoxic T-cell is recruited to a target cell using a multi-specific protein that is capable of specifically binding both the cytotoxic T-cell and the target cell, and whereby a target-dependent cytotoxic T-cell response is elicited against the target cell.

The terms "neovascularization" and "angiogenesis" are used interchangeably herein. Neovascularization and angiogenesis refer to the generation of new blood vessels into cells, tissue, or organs. The control of angiogenesis is typically altered in certain disease states and, in many case, the pathological damage associated with the disease is related to altered or unregulated angiogenesis. Persistent, unregulated angiogenesis occurs in a variety of disease states, including those characterized by the abnormal growth by endothelial cells, and supports the pathological damage seen in these conditions including leakage and permeability of blood vessels.

The term "neovascular disorder" are used herein refers to any disease or disorder having a pathology that is mediated, at least in part, by increased or unregulated angiogenesis activity. Examples of such diseases or disorders include various cancers comprising solid tumors. Such diseases or disorders comprising a vasculature characterized by PSMA overexpression (e.g., certain cancers comprising solid tumors, such as clear cell renal carcinoma, colorectal cancer, bladder cancer, and lung cancer) are particularly amenable to certain treatment methods for inhibition angiogenesis, as described further herein.

As used herein, the term "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual, or prevent onset of additional associated diseases.

As used herein, the term "therapeutically effective amount (or dose)" or "effective amount (or dose)" of a specific binding molecule or compound refers to that amount of the compound sufficient to result in amelioration of one or more symptoms of the disease being treated in a statistically significant manner. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or concurrently in separate formulations).

As used herein, the term "transformation," "transfection," and "transduction" refer to the transfer of nucleic acid (i.e., a nucleotide polymer) into a cell. As used herein, the term "genetic transformation" refers to the transfer and incorporation of DNA, especially recombinant DNA, into a cell. The transferred nucleic acid can be introduced into a cell via an expression vector.

As used herein, the term "variant" or "variants" refers to a nucleic acid or polypeptide differing from a reference nucleic acid or polypeptide, but retaining essential properties thereof. Generally, variants are overall closely similar, and, in many regions, identical to the reference nucleic acid or polypeptide. For instance, a variant may exhibit at least about 70%, at least about 80%, at least about 90%, at least about 95%, at least about 96%, at least about 97%, at least about 98% or at least about 99% sequence identity compared to the active portion or full length reference nucleic acid or polypeptide.

The terms "light chain variable region" (also referred to as "light chain variable domain" or "VL") and "heavy chain variable region" (also referred to as "heavy chain variable domain" or "VH") refer to the variable binding region from an antibody light and heavy chain, respectively. The variable binding regions are made up of discrete, well-defined subregions known as "complementarity determining regions" (CDRs) and "framework regions" (FRs). In one embodiment, the FRs are humanized. The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 domain of the heavy chain linked to the light chain via an inter-chain disulfide bond.

III. PSMA-Binding Polypeptides, Proteins, and Components Thereof

The present disclosure provides polypeptides and proteins comprising binding domains, in particular, a first binding domain that specifically binds PSMA. The polypeptides and proteins comprising binding domains of this disclosure can further comprise immunoglobulin constant regions, linker peptides, hinge regions, immunoglobulin dimerization/heterodimerization domains, junctional amino acids, tags, etc. These components of the disclosed polypeptides and proteins are described in further detail below.

Additionally, the PSMA-binding polypeptides and proteins disclosed herein can be in the form of an antibody or a fusion protein of any of a variety of different formats (e.g., the fusion protein can be in the form of a SMIP molecule, a PIMS molecule, a SCORPION molecule or an Interceptor molecule).

A PSMA-binding protein in accordance with the present invention generally includes at least one PSMA-binding polypeptide chain comprising (a) a PSMA-binding domain as set forth herein. In certain variations, the PSMA-binding polypeptide further includes (b) a hinge region carboxyl-terminal to the PSMA-binding domain, and (c) an immunoglobulin constant region (e.g., a SMIP molecule). In further variations, the PSMA-binding polypeptide further includes (d) a second hinge region carboxyl-terminal to the immunoglobulin constant region, and (e) a second binding domain carboxyl-terminal to the second hinge region (e.g., a SCORPION polypeptide).

In yet other variations, the PSMA-binding polypeptide comprises (b) a hinge region amino-terminal to the PSMA-binding domain, and (c) an immunoglobulin sub-region amino-terminal to the hinge region (e.g., a PIMS polypeptide).

Typically, PSMA-binding polypeptides of the above formats (SMIP, SCORPION, or PIMS) are capable of homodimerization, typically through disulfide bonding, via the immunoglobulin constant region and/or hinge region (e.g., via an immunoglobulin constant region comprising IgG CH2 and CH3 domains and an IgG hinge region). Thus, in certain embodiments of the present invention, two identical PSMA-binding polypeptides homodimerize to form a dimeric PSMA-binding protein.

In other embodiments, a PSMA-binding polypeptide further includes a heterodimerization domain that is capable of heterodimerization with a different heterodimerization domain in a second, non-identical polypeptide chain. In certain variations, the second polypeptide chain for heterodimerization includes a second binding domain. Accordingly, in certain embodiments of the present invention, two non-identical polypeptide chains, one comprising the PSMA-binding domain and the second optionally comprising a second binding domain, dimerize to form a heterodimeric PSMA-binding protein.

PSMA-binding polypeptides, proteins, and their various components are further described herein below.

A. Binding Domains

As indicated above, an immunoglobulin binding polypeptide of the present disclosure comprises a binding domain that specifically binds PSMA. In some variations, the PSMA-binding domain is capable of competing for binding to PSMA with an antibody having $V_L$ and $V_H$ regions having amino acid sequences as shown in SEQ ID NO:5 and SEQ ID NO:2, respectively (e.g., mAb 107-1A4), or with a single-chain Fv (scFv) having an amino acid sequence as shown in SEQ ID NO:21. In certain embodiments, the PSMA-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. Suitable PSMA-binding domains include those having $V_L$ and $V_H$ regions derived from mAb 107-1A4. In some such embodiments, LCDR3 has the amino acid sequence set forth in SEQ ID NO:17 and/or HCDR3 has the amino acid sequence set forth in SEQ ID NO:11; and LCDR1 and LCDR2 optionally have the amino acid sequences as set forth in SEQ ID NO:15 and SEQ ID NO:16, respectively, and HCDR1 and HCDR2 optionally have the amino acid sequences as set forth in SEQ ID NO:9 and SEQ ID NO:10, respectively. In some embodiments, for example, LCDR1, LCDR2, and LCDR3 have the amino acid sequences respectively shown in SEQ ID NOs:15, 16, and 17; and/or HCDR1, HCDR2, and HCDR3 have the amino acid sequences as respectively shown in SEQ ID NOs:9, 10, and 11.

In certain embodiments, a PSMA-binding protein can comprise one or more additional binding domains (e.g., second binding domain) that bind a target other than PSMA. These other target molecules can comprise, for example, a particular cytokine or a molecule that targets the binding domain polypeptide to a particular cell type, a toxin, an additional cell receptor, an antibody, etc.

In certain embodiments, a binding domain, for instance, as part of an Interceptor or SCORPION molecule, can comprise a TCR binding domain for recruitment of T cells to target cells expressing PSMA. In certain embodiments, a polypeptide heterodimer as described herein can comprise a binding domain that specifically binds a TCR complex or a component thereof (e.g., TCRα, TCRβ, CD3γ, CD3δ, and CD3ε) and another binding domain that specifically binds to PSMA.

Exemplary anti-CD3 antibodies from which the binding domain of this disclosure can be derived include CRIS-7 monoclonal antibody (Reinherz, E. L. et al. (eds.), *Leukocyte typing II.*, Springer Verlag, New York, (1986); $V_L$ and $V_H$ amino acid sequences respectively shown in SEQ ID NO:153 (QVVLTQSPAIMSAFPGEKVTMTCSASSSV-SYMNWYQQKSGTSPKRWIYDSS KLASGVPARF- SGSGSGTSYSLTISSMETEDAATYYCQQWSRNPPTF-GGGTKLQITR) and SEQ ID NO:154 (QVQLQQSGAELARPGASVKMSCKASGYTFTRSTM-HWVKQRPGQGLEWIGYINP SSAYTNYNQKFKD-KATLTADKSSSTAYMQLSSLTSEDSAVYYCASPQVHY-DYNGFPYWGQ GTLVTVSA)); HuM291 (Chau et al. (2001) *Transplantion* 71:941-950; $V_L$ and $V_H$ amino acid sequences respectively shown in SEQ ID NO:86 (DIQMTQSPSSLSASVGDRVTITCSASSSV SYMNWY-QQKPGKAPKRLIYDTSKLASGVPSRFSGSGSGTD-FTLTISSLQPEDFATYYCQQ WSSNPPTFGGGTKVEIK) and SEQ ID NO:87 (QVQLVQSGAEVKKPGASVK-VSCKASGYTFISY TMHWVRQAPGQGLEWMGYIN-PRSGYTHYNQKLKDKATLTADKSASTAYMELSSL-RSEDT AVYYCARSAYYDYDGFAYWGQGTLVTVSS)); BC3 monoclonal antibody (Anasetti et al. (1990) *J. Exp. Med.* 172:1691); OKT3 monoclonal antibody (Ortho multicenter Transplant Study Group (1985) *N. Engl. J. Med.* 313:337) and derivatives thereof such as OKT3 ala-ala (also referred to as OKT3 AA-FL or OKT3 FL), a humanized, Fc variant with alanine substitutions at positions 234 and 235 (Herold et al. (2003) *J. Clin. Invest.* 11:409); visilizumab (Carpenter et al. (2002) *Blood* 99:2712), G19-4 monoclonal antibody (Ledbetter et al., 1986, *J. Immunol.* 136:3945) and 145-2C11 monoclonal antibody (Hirsch et al. (1988) *J. Immunol.* 140: 3766). An exemplary anti-TCR antibody is the BMA031 monoclonal antibody (Borst et al. (1990) *Human Immunology* 29:175-188).

In some embodiments, a binding domain is a single-chain Fv fragment (scFv) that comprises $V_H$ and $V_L$ regions specific for a target of interest. In certain embodiments, the $V_H$ and $V_L$ regions are human.

In certain embodiments, a PSMA-binding domain comprises or is a scFv that is at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a scFv of SEQ ID NO: 19, 21, 30, 31, 34 or 35.

In related embodiments, a PSMA-binding domain comprises or is a sequence that is at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:23) or to a heavy chain variable region ($V_H$) (e.g., SEQ ID NO:25 or SEQ ID NO:27), or both.

In further embodiments, each CDR comprises no more than one, two, or three substitutions, insertions or deletions, as compared to that from a monoclonal antibody or fragment or derivative thereof that specifically binds to a target of interest (e.g., PSMA).

In some embodiments of a PSMA-binding protein comprising a second binding domain that specifically binds CD3ε, the second binding domain competes for binding to CD3ε with the CRIS-7 or HuM291 monoclonal antibody. In certain variations, the CD3-binding domain comprises an immunoglobulin light chain variable region ($V_L$) and an immunoglobulin heavy chain variable region ($V_H$) derived from the CRIS-7 or HuM291 monoclonal antibody (e.g., the $V_L$ and $V_H$ of the second binding domain can be humanized variable regions comprising, respectively, the light chain CDRs and the heavy chain CDRs of the monoclonal antibody). For example, the $V_L$ and $V_H$ regions derived from CRIS-7 can be selected from (a) a $V_L$ region comprising an amino acid sequence that is at least 95% identical or 100% to the amino acid sequence set forth in residues 139-245 of SEQ ID NO:47 and a $V_H$ region comprising an amino acid sequence that is at least 95% identical or 100% to the amino acid sequence set forth in residues 1-122 of SEQ ID NO:47; and (b) a $V_L$ region comprising an amino acid sequence that is at least 95% identical or 100% identical to the amino acid sequence set forth in residues 634-740 of SEQ ID NO:78 and a $V_H$ region comprising an amino acid sequence that is at least 95% or 100% identical to the amino acid sequence set forth in residues 496-616 of SEQ ID NO:78.

In certain embodiments, a binding domain $V_L$ and/or $V_H$ region of the present disclosure is derived from a $V_L$ and/or $V_H$ of a known monoclonal antibody (e.g., 107-1A4, CRIS-7, or HuM291) and contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared with the $V_L$ and/or $V_H$ of a known monoclonal antibody. The insertion(s), deletion(s) or substitution(s) can be anywhere in the $V_L$ and/or $V_H$ region, including at the amino- or carboxyl-terminus or both ends of this region, provided that each CDR comprises zero changes or at most one, two, or three changes and provided a binding domain containing the modified $V_L$ and/or $V_H$ region can still specifically bind its target with an affinity similar to the wild type binding domain.

In some variations, the binding domain is a single-chain Fv (scFv) comprising immunoglobulin $V_L$ and $V_H$ regions joined by a peptide linker. The use of peptide linkers for joining $V_L$ and $V_H$ regions is well-known in the art, and a large number of publications exist within this particular field. A widely used peptide linker is a 15mer consisting of three repeats of a Gly-Gly-Gly-Gly-Ser amino acid sequence (($Gly_4Ser)_3$) (SEQ ID NO:152). Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the $V_L$ and $V_H$ regions are joined by a peptide linker having an amino acid sequence comprising the formula ($Gly_4Ser)_n$, wherein n=1-5 (SEQ ID NO:165). Other suitable linkers can be obtained by optimizing a simple linker (e.g., ($Gly_4Ser)_n$) through random mutagenesis.

In certain embodiments, a binding domain comprises humanized immunoglobulin $V_L$ and/or $V_H$ regions. Techniques for humanizing immunoglobulin $V_L$ and $V_H$ regions are known in the art and are discussed, for example, in United States Patent Application Publication No. 2006/0153837.

"Humanization" is expected to result in an antibody that is less immunogenic, with complete retention of the antigen-binding properties of the original molecule. In order to retain all of the antigen-binding properties of the original antibody, the structure of its antigen binding site should be reproduced in the "humanized" version. This can be achieved by grafting only the nonhuman CDRs onto human variable framework domains and constant regions, with or without retention of critical framework residues (Jones et al., *Nature* 321:522 (1986); Verhoeyen et al., *Science* 239:1539 (1988)) or by recombining the entire nonhuman variable domains (to preserve ligand-binding properties), but "cloaking" them with a human-like surface through judicious replacement of exposed residues (to reduce antigenicity) (Padlan, *Molec. Immunol.* 28:489 (1991)).

Essentially, humanization by CDR grafting involves recombining only the CDRs of a non-human antibody onto a human variable region framework and a human constant region. Theoretically, this should substantially reduce or eliminate immunogenicity (except if allotypic or idiotypic differences exist). However, it has been reported that some framework residues of the original antibody also may need to be preserved (Reichmann et al., *Nature*, 332:323 (1988); Queen et al., *Proc. Natl. Acad. Sci. USA*, 86:10,029 (1989)).

The framework residues that need to be preserved are amenable to identification through computer modeling. Alternatively, critical framework residues can potentially be identified by comparing known antigen-binding site structures (Padlan, *Molec. Immunol.*, 31(3):169-217 (1994), incorporated herein by reference).

The residues that potentially affect antigen binding fall into several groups. The first group comprises residues that are contiguous with the antigen site surface, which could therefore make direct contact with antigens. These residues include the amino-terminal residues and those adjacent to the CDRs. The second group includes residues that could alter the structure or relative alignment of the CDRs, either by contacting the CDRs or another peptide chain in the antibody. The third group comprises amino acids with buried side chains that could influence the structural integrity of the variable domains. The residues in these groups are usually found in the same positions (Padlan, 1994, supra) although their positions as identified may differ depending on the numbering system (see Kabat et al., "Sequences of proteins of immunological interest, 5th ed., Pub. No. 91-3242, U.S. Dept. Health & Human Services, NIH, Bethesda, Md., 1991).

Although the embodiments described herein involve the humanization of SMIP, SCORPION, and Interceptor molecules, and not antibodies, knowledge about humanized antibodies in the art is applicable to the polypeptides according to the invention.

B. Hinge Region

In certain embodiments, a hinge is a wild-type human immunoglobulin hinge region. In certain other embodiments, one or more amino acid residues can be added at the amino- or carboxyl-terminus of a wild type immunoglobulin hinge region as part of a fusion protein construct design. For example, additional junction amino acid residues at the hinge amino-terminus can be "RT," "RSS," "TG," or "T," or at the hinge carboxyl-terminus can be "SG", or a hinge deletion can be combined with an addition, such as ΔP with "SG" added at the carboxyl-terminus.

In certain embodiments, a hinge is an altered immunoglobulin hinge in which one or more cysteine residues in a wild type immunoglobulin hinge region is substituted with one or more other amino acid residues (e.g., serine or alanine).

Exemplary altered immunoglobulin hinges include an immunoglobulin human IgG1 hinge region having one, two or three cysteine residues found in a wild type human IgG1 hinge substituted by one, two or three different amino acid residues (e.g., serine or alanine). An altered immunoglobulin hinge can additionally have a proline substituted with another amino acid (e.g., serine or alanine). For example, the above-described altered human IgG1 hinge can additionally have a proline located carboxyl-terminal to the three cysteines of wild type human IgG1 hinge region substituted by another amino acid residue (e.g., serine, alanine). In one embodiment, the prolines of the core hinge region are not substituted.

In certain embodiments, a hinge polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a wild type immunoglobulin hinge region, such as a wild type human IgG1 hinge, a wild type human IgG2 hinge, or a wild type human IgG4 hinge.

In further embodiments, a hinge present in a PSMA-binding polypeptide can be a hinge that is not based on or derived from an immunoglobulin hinge (i.e., not a wild-type immunoglobulin hinge or an altered immunoglobulin hinge). Examples for such hinges include peptides of about five to about 150 amino acids derived from an interdomain region of a transmembrane protein or stalk region of a type II C-lectin, for instance, peptides of about eight to 25 amino acids and peptides of about seven to 18 amino acids.

In certain embodiments, interdomain or stalk region hinges have seven to 18 amino acids and can form an α-helical coiled coil structure. In certain embodiments, interdomain or stalk region hinges contain 0, 1, 2, 3, or 4 cysteines. Exemplary interdomain or stalk region hinges are peptide fragments of the interdomain or stalk regions, such as ten to 150 amino acid fragments from the stalk regions of CD69, CD72, CD94, NKG2A and NKG2D.

In certain embodiments, hinge sequences have about 5 to 150 amino acids, 5 to 10 amino acids, 10 to 20 amino acids, 20 to 30 amino acids, 30 to 40 amino acids, 40 to 50 amino acids, 50 to 60 amino acids, 5 to 60 amino acids, 5 to 40 amino acids, 8 to 20 amino acids, or 10 to 15 amino acids. The hinge can be primarily flexible, but can also provide more rigid characteristics or can contain primarily α-helical structure with minimal β-sheet structure. The lengths or the sequences of the hinges can affect the binding affinities of the binding domains to which the hinges are directly or indirectly (via another region or domain, such as an heterodimerization domain) connected as well as one or more activities of the Fc region portions to which the hinges are directly or indirectly connected.

In certain embodiments, hinge sequences are stable in plasma and serum and are resistant to proteolytic cleavage. The first lysine in the IgG1 upper hinge region can be mutated to minimize proteolytic cleavage, for instance, the lysine can be substituted with methionine, threonine, alanine or glycine, or is deleted.

In some embodiments of the invention, the PSMA-binding polypeptide is capable of forming a heterodimer with a second polypeptide chain and comprises a hinge region (a) immediately amino-terminal to an immunoglobulin constant region (e.g., amino-terminal to a CH2 domain wherein the immunoglobulin constant region includes CH2 and CH3 domains, or amino-terminal to a CH3 domain wherein the immunoglobulin sub-regions includes CH3 and CH4 domains), (b) interposed between and connecting a binding domain (e.g., scFv) and a immunoglobulin heterodimerization domain, (c) interposed between and connecting a immunoglobulin heterodimerization domain and an immunoglobulin constant region (e.g., wherein the immunoglobulin constant region includes CH2 and CH3 domains or CH3 and CH4 domains), (d) interposed between and connecting an immunoglobulin constant region and a binding domain, (e) at the amino-terminus of a polypeptide chain, or (f) at the carboxyl-terminus of a polypeptide chain. A polypeptide chain comprising a hinge region as described herein will be capable of associating with a different polypeptide chain to form a heterodimeric protein provided herein, and the heterodimer formed will contain a binding domain that retains its target specificity or its specific target binding affinity.

In certain embodiments, a hinge present in a polypeptide that forms a heterodimer with another polypeptide chain can be an immunoglobulin hinge, such as a wild-type immunoglobulin hinge region or an altered immunoglobulin hinge region thereof. In certain embodiments, a hinge of one polypeptide chain of a heterodimeric protein is identical to a corresponding hinge of the other polypeptide chain of the heterodimer. In certain other embodiments, a hinge of one chain is different from that of the other chain (in their length or sequence). The different hinges in the different chains allow different manipulation of the binding affinities of the binding domains to which the hinges are connected, so that the heterodimer is able to preferentially bind to the target of one binding domain over the target of the other binding domain. For example, in certain embodiments, a heterodimeric protein has a CD3- or TCR-binding domain in one chain and a PSMA-binding domain in another chain. Having two different hinges in the two chains may allow the heterodimer to bind to the PSMA first, and then to a CD3 or other TCR component second. Thus, the heterodimer may recruit CD3+ T cells to PSMA-expressing cells (e.g., PSMA-expressing tumor cells), which in turn may damage or destroy the PSMA-expressing cells.

Exemplary hinge regions suitable for use in accordance with the present invention are shown in the Tables 1 and 2 below. Additional exemplary hinge regions are set forth in SEQ ID NOs: 241-244, 601, 78, 763-791, 228, 379-434, 618-749 of WO2011/090762 (said sequences incorporated by reference herein).

TABLE 1

Exemplary hinge regions

| Hinge Region | Amino Acid Sequence | SEQ ID NO |
| --- | --- | --- |
| sss(s)-hIgG1 hinge | EPKSSDKTHTSPPSS | SEQ ID NO: 88 |
| csc(s)-hIgG1 hinge | EPKSCDKTHTSPPCS | SEQ ID NO: 89 |
| ssc(s)-hIgG1 hinge | EPKSSDKTHTSPPCS | SEQ ID NO: 90 |
| scc(s)-hIgG1 hinge | EPKSSDKTHTCPPCS | SEQ ID NO: 91 |
| css(s)-hIgG1 hinge | EPKSCDKTHTSPPSS | SEQ ID NO: 92 |
| scs(s)-hIgG1 hinge | EPKSSDKTHTCPPSS | SEQ ID NO: 93 |
| ccc(s)-hIgG1 hinge | EPKSCDKTHTSPPCS | SEQ ID NO: 94 |
| ccc(p)-hIgG1 hinge | EPKSCDKTHTSPPCP | SEQ ID NO: 95 |
| sss(p)-hIgG1 hinge | EPKSSDKTHTSPPSP | SEQ ID NO: 96 |
| csc(p)-hIgG1 hinge | EPKSCDKTHTSPPCP | SEQ ID NO: 97 |
| ssc(p)-hIgG1 hinge | EPKSSDKTHTSPPCP | SEQ ID NO: 98 |
| scc(p)-hIgG1 hinge | EPKSSDKTHTCPPCP | SEQ ID NO: 99 |
| css(p)-hIgG1 hinge | EPKSCDKTHTSPPSP | SEQ ID NO: 100 |
| scs(p)-hIgG1 hinge | EPKSSDKTHTCPPSP | SEQ ID NO: 101 |
| Scppcp | SCPPCP | SEQ ID NO: 102 |
| STD1 | NYGGGGSGGGGSGGGGSGNS | SEQ ID NO: 103 |
| STD2 | NYGGGGSGGGGSGGGGSGNYGGGGSGGGGSGGGGSGNS | SEQ ID NO: 104 |
| H1 | NS | SEQ ID NO: 105 |
| H2 | GGGGSGNS | SEQ ID NO: 106 |
| H3 | NYGGGGSGNS | SEQ ID NO: 107 |
| H4 | GGGGSGGGGSGNS | SEQ ID NO: 108 |
| H5 | NYGGGGSGGGGSGNS | SEQ ID NO: 109 |
| H6 | GGGGSGGGGSGGGGSGNS | SEQ ID NO: 110 |
| H7 | GCPPCPNS | SEQ ID NO: 62 |
| (G4S)3 | GGGGSGGGGSGGGGS | SEQ ID NO: 111 |
| H105 | SGGGGSGGGGSGGGGS | SEQ ID NO: 155 |
| (G4S)4 | GGGGSGGGGSGGGGSGGGGS | SEQ ID NO: 112 |

TABLE 1-continued

Exemplary hinge regions

| Hinge Region | Amino Acid Sequence | SEQ ID NO |
| --- | --- | --- |
| H75 (NKG2A quadruple mutant) | QRHNNSSLNTGTQMAGHSPNS | SEQ ID NO: 63 |
| H83 (NKG2A derived) | SSLNTGTQMAGHSPNS | SEQ ID NO: 65 |
| H106 (NKG2A derived) | QRHNNSSLNTGTQMAGHS | SEQ ID NO: 156 |
| H81 (NKG2D derived) | EVQIPLTESYSPNS | SEQ ID NO: 64 |
| H91 (NKG2D derived) | NSLANQEVQIPLTESYSPNS | SEQ ID NO: 66 |
| H94 | SGGGGSGGGGSGGGGSPNS | SEQ ID NO: 67 |

TABLE 2

Exemplary hinge regions (derived from H7 hinge, stalk region of a type II C-lectin, or interdomain region of a type I transmembrane protein)

| Hinge Region | Amino Acid Sequence | Molecule and/or hinge from which derived | SEQ ID NO: |
| --- | --- | --- | --- |
| H16 | LSVKADFLTPSIGNS | CD80 | SEQ ID NO: 113 |
| H17 | LSVKADFLTPSISCPPCPNS | CD80 + H7 | SEQ ID NO: 114 |
| H18 | LSVLANFSQPEIGNS | CD86 | SEQ ID NO: 115 |
| H19 | LSVLANFSQPEISCPPCPNS | CD86 + H7 | SEQ ID NO: 116 |
| H20 | LKIQERVSKPKISNS | CD2 | SEQ ID NO: 117 |
| H21 | LKIQERVSKPKISCPPCPNS | CD2 + H7 | SEQ ID NO: 118 |
| H22 | LNVSERPFPPHIQNS | CD22 | SEQ ID NO: 119 |
| H23 | LDVSERPFPPHIQSCPPCPNS | CD22 + H7 | SEQ ID NO: 120 |
| H24 | REQLAEVTLSLKANS | CD80 | SEQ ID NO: 121 |
| H25 | REQLAEVTLSLKACPPCPNS | CD80 + H7 | SEQ ID NO: 122 |
| H26 | RIHQMNSELSVLANS | CD86 | SEQ ID NO: 123 |
| H27 | RIHQMNSELSVLACPPCPNS | CD86 + H7 | SEQ ID NO: 124 |
| H28 | DTKGKNVLEKIFSNS | CD2 | SEQ ID NO: 125 |
| H30 | LPPETQESQEVTLNS | CD22 | SEQ ID NO: 126 |
| H32 | RIHLNVSERPFPPNS | CD22 | SEQ ID NO: 127 |
| H33 | RIHLNVSERPFPPCPPCPNS | CD22 + H7 | SEQ ID NO: 128 |
| H36 | GCPPCPGGGGSNS | H7 | SEQ ID NO: 129 |
| H40 | GCPPCPANS | H7 | SEQ ID NO: 130 |
| H41 | GCPPCPANS | H7 | SEQ ID NO: 131 |
| H42 | GCPPCPNS | H7 | SEQ ID NO: 132 |
| H44 | GGGASCPPCPGNS | H7 | SEQ ID NO: 133 |
| H45 | GGGASCPPCAGNS | H7 | SEQ ID NO: 134 |
| H46 | GGGASCPPCANS | H7 | SEQ ID NO: 135 |
| H47 | LSVKADFLTPSIGNS | CD80 | SEQ ID NO: 136 |
| H48 | ADFLTPSIGNS | CD80 | SEQ ID NO: 137 |
| H50 | LSVLANFSQPEIGNS | CD86 | SEQ ID NO: 138 |
| H51 | LSVLANFSQPEIGNS | CD86 | SEQ ID NO: 139 |
| H52 | SQPEIVPISNS | CD86 | SEQ ID NO: 140 |
| H53 | SQPEIVPISCPPCPNS | CD86 + H7 | SEQ ID NO: 141 |
| H54 | SVLANFSQPEISCPPCPNS | CD86 + H7 | SEQ ID NO: 142 |
| H55 | RIHQMNSELSVLANS | CD86 | SEQ ID NO: 143 |
| H56 | QMNSELSVLANS | CD86 | SEQ ID NO: 144 |
| H57 | VSERPFPPNS | CD22 | SEQ ID NO: 145 |
| H58 | KPFFTCGSADTCPNS | CD72 | SEQ ID NO: 146 |
| H59 | KPFFTCGSADTCPNS | CD72 | SEQ ID NO: 147 |
| H60 | QYNCPGQYTFSMPNS | CD69 | SEQ ID NO: 148 |

TABLE 2-continued

Exemplary hinge regions (derived from H7 hinge, stalk region of a type II C-lectin, or interdomain region of a type I transmembrane protein)

| Hinge Region | Amino Acid Sequence | Molecule and/or hinge from which derived | SEQ ID NO: |
|---|---|---|---|
| H61 | EPAFTPGPNIELQKDSDCPNS | CD94 | SEQ ID NO: 149 |
| H62 | QRHNNSSLNTRTQKARHCPNS | NKG2A | SEQ ID NO: 150 |
| H63 | NSLFNQEVQIPLTESYCPNS | NKG2D | SEQ ID NO: 151 |

C. Immunoglobulin Heterodimerization Domains

In certain embodiments, a PSMA-binding polypeptide or protein of the invention can comprise an "immunoglobulin dimerization domain" or "immunoglobulin heterodimerization domain."

An "immunoglobulin dimerization domain" or "immunoglobulin heterodimerization domain," as used herein, refers to an immunoglobulin domain of a polypeptide chain that preferentially interacts or associates with a different immunoglobulin domain of another polypeptide chain, wherein the interaction of the different immunoglobulin heterodimerization domains substantially contributes to or efficiently promotes heterodimerization of the first and second polypeptide chains (i.e., the formation of a dimer between two different polypeptide chains, which is also referred to as a "heterodimer" or "heterodimeric protein"). The interactions between immunoglobulin heterodimerization domains "substantially contributes to or efficiently promotes" the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL1 domain (e.g., Cκ or Cλ isotypes), or derivatives thereof, including wild-type immunoglobulin CH1 and CL domains and altered (or mutated) immunoglobulin CH1 and CL domains, such as provided herein.

Dimerization/heterodimerization domains can be used where it is desired to form heterodimers from two non-identical polypeptide chains, where one or both polypeptide chains comprises a binding domain. In certain embodiments, one polypeptide chain member of certain heterodimers described herein does not contain a binding domain. As indicated above, a heterodimeric protein of the present disclosure comprises an immunoglobulin heterodimerization domain in each polypeptide chain. The immunoglobulin heterodimerization domains in the polypeptide chains of a heterodimer are different from each other and thus can be differentially modified to facilitate heterodimerization of both chains and to minimize homodimerization of either chain. As shown in the examples, immunoglobulin heterodimerization domains provided herein allow for efficient heterodimerization between different polypeptides and facilitate purification of the resulting heterodimeric protein.

As provided herein, immunoglobulin heterodimerization domains useful for promoting heterodimerization of two different single chain polypeptides (e.g., one short and one long) according to the present disclosure include immunoglobulin CH1 and CL domains, for instance, human CH1 and CL domains. In certain embodiments, an immunoglobulin heterodimerization domain is a wild-type CH1 domain, such as a wild type IgG1, IgG2, IgG3, IgG4, IgA1, IgA2, IgD, IgE, or IgM CH1 domain. In further embodiments, an immunoglobulin heterodimerization domain is a wild-type human IgG1, IgG2, IgG3, IgG4, IgA1, IgA2, IgD, IgE, or IgM CH1 domain as set forth in SEQ ID NOS:114, 186-192 and 194, respectively, of PCT Publication No. WO2011/090762 (said sequences incorporated by reference herein). In certain embodiments, an immunoglobulin heterodimerization domain is a wild-type human IgG1 CH1 domain as set forth in SEQ ID NO:114 of WO2011/090762 (said sequence incorporated by reference herein).

In further embodiments, an immunoglobulin heterodimerization domain is an altered immunoglobulin CH1 domain, such as an altered IgG1, IgG2, IgG3, IgG4, IgA1, IgA2 IgD, IgE, or IgM CH1 domain. In certain embodiments, an immunoglobulin heterodimerization domain is an altered human IgG1, IgG2, IgG3, IgG4, IgA1, IgA2, IgD, IgE, or IgM CH1 domain. In still further embodiments, a cysteine residue of a wild-type CH1 domain (e.g., a human CH1) involved in forming a disulfide bond with a wild type immunoglobulin CL domain (e.g., a human CL) is deleted or substituted in the altered immunoglobulin CH1 domain such that a disulfide bond is not formed between the altered CH1 domain and the wild-type CL domain.

In certain embodiments, an immunoglobulin heterodimerization domain is a wild-type CL domain, such as a wild type Cκ domain or a wild type Cλ domain. In certain embodiments, an immunoglobulin heterodimerization domain is a wild type human Cκ or human Cλ domain as set forth in SEQ ID NOS:112 and 113, respectively, of WO2011/090762 (said sequences incorporated by reference herein). In further embodiments, an immunoglobulin heterodimerization domain is an altered immunoglobulin CL domain, such as an altered Cκ or Cλ domain, for instance, an altered human Cκ or human Cλ domain.

In certain embodiments, a cysteine residue of a wild-type CL domain (e.g., a human CL) involved in forming a disulfide bond with a wild type immunoglobulin CH1 domain (e.g., a human CH1) is deleted or substituted in the altered immunoglobulin CL domain. Such altered CL domains can further comprise an amino acid deletion at their amino-termini. An exemplary Cκ domain is set forth in SEQ ID NO:141 of WO2011/090762 (said sequence incorporated by reference herein), in which the first arginine and the last cysteine of the wild type human Ck domain are both deleted. In certain embodiments, only the last cysteine of the wild type human Ck domain is deleted in the altered Ck domain because the first arginine deleted from the wild type human Ck domain can be provided by a linker that has an arginine at its carboxyl-terminus and links the amino-terminus of the altered Ck domain with another domain (e.g., an immunoglobulin sug-region, such as a sub-region comprising immunoglobulin CH2 and CH3 domains). An exemplary Cλ domain is set forth in SEQ ID NO:140 of WO2011/090762 (said sequence incorporated by reference herein), in which the first arginine of a wild type human Cλ domain is deleted and the cysteine involved in forming a disulfide bond with a cysteine in a CH1 domain is substituted by a serine.

In further embodiments, an immunoglobulin heterodimerization domain is an altered Cκ domain that contains one or more amino acid substitutions, as compared to a wild type Cκ domain, at positions that may be involved in forming the interchain-hydrogen bond network at a Cκ-Cκ interface. For example, in certain embodiments, an immunoglobulin heterodimerization domain is an altered human Cκ domain having one or more amino acids at positions N29, N30, Q52, V55, T56, S68 or T70 that are substituted with a different amino acid. The numbering of the amino acids is based on their positions in the altered human Cκ sequence as set forth in SEQ ID NO:141 of WO2011/090762 (said sequence incorporated by reference herein). In certain embodiments, an immunoglobulin heterodimerization domain is an altered human Cκ domain having one, two, three or four amino acid substitutions at positions N29, N30, V55, or T70. The amino acid used as a substitute at the above-noted positions can be an alanine, or an amino acid residue with a bulk side chain moiety such as arginine, tryptophan, tyrosine, glutamate, glutamine, or lysine. Additional amino acid residues that can be used to substitute amino acid residues of the wild type human Ck sequence at the above noted positions (e.g., N30) include aspartate, methionine, serine and phenylalanine. Exemplary altered human Cκ domains are set forth in SEQ ID NOS:142-178 of WO2011/090762 (said sequences incorporated by reference herein). Altered human Cκ domains are those that facilitate heterodimerization with a CH1 domain, but minimize homodimerization with another Cκ domain. Representative altered human Cκ domains are set forth in SEQ ID NOS:160 (N29W V55A T70A), 161 (N29Y V55A T70A), 202 (T70E N29A N30A V55A), 167 (N30R V55A T70A), 168 (N30K V55A T70A), 170 (N30E V55A T70A), 172 (V55R N29A N30A), 175 (N29W N30Y V55A T70E), 176 (N29Y N30Y V55A T70E), 177 (N30E V55A T70E), 178 (N30Y V55A T70E), 838 (N30D V55A T70E), 839 (N30M V55A T70E), 840 (N30S V55A T70E), and 841 (N30F V55A T70E) of WO2011/090762 (said sequences incorporated by reference herein).

In certain embodiments, in addition to or alternative to the mutations in Ck domains described herein, both the immunoglobulin heterodimerization domains (i.e., immunoglobulin CH1 and CL domains) of a polypeptide heterodimer have mutations so that the resulting immunoglobulin heterodimerization domains form salt bridges (i.e., ionic interactions) between the amino acid residues at the mutated sites. For example, the immunoglobulin heterodimerization domains of a polypeptide heterodimer can be a mutated CH1 domain in combination with a mutated Ck domain. In the mutated CH1 domain, valine at position 68 (V68) of the wild type human CH1 domain is substituted by an amino acid residue having a negative charge (e.g., aspartate or glutamate), whereas leucine at position 29 (L29) of a mutated human Ck domain in which the first arginine and the last cysteine have been deleted is substituted by an amino acid residue having a positive charge (e.g., lysine, arginine or histidine). The charge-charge interaction between the amino acid residue having a negative charge of the resulting mutated CH1 domain and the amino acid residue having a positive charge of the resulting mutated Ck domain forms a salt bridge, which stabilizes the heterodimeric interface between the mutated CH1 and Ck domains. Alternatively, V68 of the wild type CH1 can be substituted by an amino acid residue having a positive charge, whereas L29 of a mutated human Ck domain in which the first arginine and the last cysteine have been deleted can be substituted by an amino acid residue having a negative charge. Exemplary mutated CH1 sequences in which V68 is substituted by an amino acid with either a negative or positive charge are set forth in SEQ ID NOS:844 and 845 of WO2011/090762 (said sequences incorporated by reference herein). Exemplary mutated Ck sequences in which L29 is substituted by an amino acid with either a negative or positive charge are set forth in SEQ ID NOS:842 and 843 of WO2011/090762 (said sequences incorporated by reference herein).

Positions other than V68 of human CH1 domain and L29 of human Ck domain can be substituted with amino acids having opposite charges to produce ionic interactions between the amino acids in addition or alternative to the mutations in V68 of CH1 domain and L29 of Ck domain. Such positions can be identified by any suitable method, including random mutagenesis, analysis of the crystal structure of the CH1-Ck pair to identify amino acid residues at the CH1-Ck interface, and further identifying suitable positions among the amino acid residues at the CH1-Ck interface using a set of criteria (e.g., propensity to engage in ionic interactions, proximity to a potential partner residue, etc.).

In certain embodiments, polypeptide heterodimers of the present disclosure contain only one pair of immunoglobulin heterodimerization domains. For example, a first chain of a polypeptide heterodimer can comprise a CH1 domain as an immunoglobulin heterodimerization domain, while a second chain can comprise a CL domain (e.g., a Cκ or Cλ) as an immunoglobulin heterodimerization domain. Alternatively, a first chain can comprise a CL domain (e.g., a Cκ or Cλ) as an immunoglobulin heterodimerization domain, while a second chain can comprise a CH1 domain as an immunoglobulin heterodimerization domain. As set forth herein, the immunoglobulin heterodimerization domains of the first and second chains are capable of associating to form a heterodimeric protein of this disclosure.

In certain other embodiments, heterodimeric proteins of the present disclosure can have two pairs of immunoglobulin heterodimerization domains. For example, a first chain of a heterodimer can comprise two CH1 domains, while a second chain can have two CL domains that associate with the two CH1 domains in the first chain. Alternatively, a first chain can comprise two CL domains, while a second chain can have two CH1 domains that associate with the two CL domains in the first chain. In certain embodiments, a first polypeptide chain comprises a CH1 domain and a CL domain, while a second polypeptide chain comprises a CL domain and a CH1 domain that associate with the CH1 domain and the CL domain, respectively, of the first polypeptide chain.

In the embodiments where a heterodimeric protein comprises only one heterodimerization pair (i.e., one immunoglobulin heterodimerization domain in each chain), the immunoglobulin heterodimerization domain of each chain can be located amino-terminal to the immunoglobulin constant region of that chain. Alternatively, the immunoglobulin heterodimerization domain in each chain can be located carboxyl-terminal to the immunoglobulin constant region of that chain.

In the embodiments where a heterodimeric protein comprises two heterodimerization pairs (i.e., two immunoglobulin heterodimerization domains in each chain), both immunoglobulin heterodimerization domains in each chain can be located amino-terminal to the immunoglobulin constant region of that chain. Alternatively, both immunoglobulin heterodimerization domains in each chain can be located carboxyl-terminal to the immunoglobulin constant region of that chain. In further embodiments, one immunoglobulin heterodimerization domain in each chain can be located amino-terminal to the immunoglobulin constant region of that chain, while the other immunoglobulin heterodimerization domain of each chain can be located carboxyl-terminal to the immunoglobulin constant region of that chain. In other words, in those embodiments, the immunoglobulin constant region is interposed between the two immunoglobulin heterodimerization domains of each chain.

D. Immunoglobulin Constant Regions

As indicated herein, in certain embodiments, PSMA-binding polypeptides of the present disclosure (e.g., SMIP, PIMS, SCORPION, and Interceptor molecules) comprise an immunoglobulin constant region (also referred to as an constant region) in each polypeptide chain. The inclusion of an immunoglobulin constant region slows clearance of the homodimeric and heterodimeric proteins formed from two PSMA-binding polypeptide chains from circulation after administration to a subject. By mutations or other alterations, an immunoglobulin constant region further enables relatively easy modulation of dimeric polypeptide effector functions (e.g., ADCC, ADCP, CDC, complement fixation, and binding to Fc receptors), which can either be increased or decreased depending on the disease being treated, as known in the art and described herein. In certain embodiments, an immunoglobulin constant region of one or both of the polypeptide chains of the polypeptide homodimers and heterodimers of the present disclosure will be capable of mediating one or more of these effector functions In other embodiments, one or more of these effector functions are reduced or absent in an immunoglobulin constant region of one or both of the polypeptide chains of the polypeptide homodimers and heterodimers of the present disclosure, as compared to a corresponding wild-type immunoglobulin constant region. For example, for dimeric PSMA-binding polypeptides designed to elicit RTCC, such as, e.g., via the inclusion of a CD3-binding domain, an immunoglobulin constant region preferably has reduced or no effector function relative to a corresponding wild-type immunoglobulin constant region.

An immunoglobulin constant region present in PSMA binding polypeptides of the present disclosure can comprise of or is derived from part or all of: a CH2 domain, a CH3 domain, a CH4 domain, or any combination thereof. For example, an immunoglobulin constant region can comprise a CH2 domain, a CH3 domain, both CH2 and CH3 domains, both CH3 and CH4 domains, two CH3 domains, a CH4 domain, two CH4 domains, and a CH2 domain and part of a CH3 domain.

A CH2 domain that can form an immunoglobulin constant region of a PSMA-binding polypeptide of the present disclosure can be a wild type immunoglobulin CH2 domain or an altered immunoglobulin CH2 domain thereof from certain immunoglobulin classes or subclasses (e.g., IgG1, IgG2, IgG3, IgG4, IgA1, IgA2, or IgD) and from various species (including human, mouse, rat, and other mammals).

In certain embodiments, a CH2 domain is a wild type human immunoglobulin CH2 domain, such as wild type CH2 domains of human IgG1, IgG2, IgG3, IgG4, IgA1, IgA2, or IgD, as set forth in SEQ ID NOS:115, 199-201 and 195-197, respectively, of PCT Publication WO2011/090762 (said sequences incorporated by reference herein). In certain embodiments, the CH2 domain is a wild type human IgG1 CH2 domain as set forth in SEQ ID NO:115 of WO2011/090762 (said sequence incorporated by reference herein).

In certain embodiments, a CH2 domain is an altered immunoglobulin CH2 region (e.g., an altered human IgG1 CH2 domain) that comprises an amino acid substitution at the asparagine of position 297 (e.g., asparagine to alanine). Such an amino acid substitution reduces or eliminates glycosylation at this site and abrogates efficient Fc binding to FcγR and C1q. The sequence of an altered human IgG1 CH2 domain with an Asn to Ala substitution at position 297 is set forth in SEQ ID NO:324 of WO2011/090762 said (sequence incorporated by reference herein).

In certain embodiments, a CH2 domain is an altered immunoglobulin CH2 region (e.g., an altered human IgG1 CH2 domain) that comprises at least one substitution or deletion at positions 234 to 238. For example, an immunoglobulin CH2 region can comprise a substitution at position 234, 235, 236, 237 or 238, positions 234 and 235, positions 234 and 236, positions 234 and 237, positions 234 and 238, positions 234-236, positions 234, 235 and 237, positions 234, 236 and 238, positions 234, 235, 237, and 238, positions 236-238, or any other combination of two, three, four, or five amino acids at positions 234-238. In addition or alternatively, an altered CH2 region can comprise one or more (e.g., two, three, four or five) amino acid deletions at positions 234-238, for instance, at one of position 236 or position 237 while the other position is substituted. The above-noted mutation(s) decrease or eliminate the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 has been replaced with one or more alanine residues. In further embodiments, only one of the amino acid residues at positions 234-238 have been deleted while one or more of the remaining amino acids at positions 234-238 can be substituted with another amino acid (e.g., alanine or serine).

In certain other embodiments, a CH2 domain is an altered immunoglobulin CH2 region (e.g., an altered human IgG1 CH2 domain) that comprises one or more amino acid substitutions at positions 253, 310, 318, 320, 322, and 331. For example, an immunoglobulin CH2 region can comprise a substitution at position 253, 310, 318, 320, 322, or 331, positions 318 and 320, positions 318 and 322, positions 318, 320 and 322, or any other combination of two, three, four, five or six amino acids at positions 253, 310, 318, 320, 322, and 331. The above-noted mutation(s) decrease or eliminate the complement-dependent cytotoxicity (CDC) of a polypeptide heterodimer that comprises the altered CH2 domain.

In certain other embodiments, in addition to the amino acid substitution at position 297, an altered CH2 region (e.g., an altered human IgG1 CH2 domain) can further comprise one or more (e.g., two, three, four, or five) additional substitutions at positions 234-238. For example, an immunoglobulin CH2 region can comprise a substitution at positions 234 and 297, positions 234, 235, and 297, positions 234, 236 and 297, positions 234-236 and 297, positions 234, 235, 237 and 297, positions 234, 236, 238 and 297, positions 234, 235, 237, 238 and 297, positions 236-238 and 297, or any combination of two, three, four, or five amino acids at positions 234-238 in addition to position 297. In addition or alternatively, an altered CH2 region can comprise one or more (e.g., two, three, four or five) amino acid deletions at positions 234-238, such as at position 236 or position 237. The additional mutation(s) decreases or eliminates the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 have been replaced with one or more alanine residues. In further embodiments, only one of the amino acid residues at positions 234-238 has been deleted while one or more of the remaining amino acids at positions 234-238 can be substituted with another amino acid (e.g., alanine or serine).

In certain embodiments, in addition to one or more (e.g., 2, 3, 4, or 5) amino acid substitutions at positions 234-238, a mutated CH2 region (e.g., an altered human IgG1 CH2 domain) in a fusion protein of the present disclosure can contain one or more (e.g., 2, 3, 4, 5, or 6) additional amino acid substitutions (e.g., substituted with alanine) at one or more positions involved in complement fixation (e.g., at positions I253, H310, E318, K320, K322, or P331). Examples of mutated immunoglobulin CH2 regions include human IgG1, IgG2, IgG4 and mouse IgG2a CH2 regions with alanine substitutions at positions 234, 235, 237 (if present), 318, 320 and 322. An exemplary mutated immunoglobulin CH2 region is mouse IGHG2c CH2 region with alanine substitutions at L234, L235, G237, E318, K320, and K322.

In still further embodiments, in addition to the amino acid substitution at position 297 and the additional deletion(s) or substitution(s) at positions 234-238, an altered CH2 region (e.g., an altered human IgG1 CH2 domain) can further comprise one or more (e.g., two, three, four, five, or six) additional substitutions at positions 253, 310, 318, 320, 322, and 331. For example, an immunoglobulin CH2 region can comprise a (1) substitution at position 297, (2) one or more substitutions or deletions or a combination thereof at positions 234-238, and one or more (e.g., 2, 3, 4, 5, or 6) amino acid substitutions at positions I253, H310, E318, K320, K322, and P331, such as one, two, three substitutions at positions E318, K320 and K322. The amino acids at the above-noted positions can be substituted by alanine or serine.

In certain embodiments, an immunoglobulin CH2 region polypeptide comprises: (i) an amino acid substitution at the asparagines of position 297 and one amino acid substitution at position 234, 235, 236 or 237; (ii) an amino acid substitution at the asparagine of position 297 and amino acid substitutions at two of positions 234-237; (iii) an amino acid substitution at the asparagine of position 297 and amino acid substitutions at three of positions 234-237; (iv) an amino acid substitution at the asparagine of position 297, amino acid substitutions at positions 234, 235 and 237, and an amino acid deletion at position 236; (v) amino acid substitutions at three of positions 234-237 and amino acid substitutions at positions 318, 320 and 322; or (vi) amino acid substitutions at three of positions 234-237, an amino acid deletion at position 236, and amino acid substitutions at positions 318, 320 and 322.

Exemplary altered immunoglobulin CH2 regions with amino acid substitutions at the asparagine of position 297 include: human IgG1 CH2 region with alanine substitutions at L234, L235, G237 and N297 and a deletion at G236 (SEQ ID NO:325 of WO2011/090762, said sequence incorporated by reference herein), human IgG2 CH2 region with alanine substitutions at V234, G236, and N297 (SEQ ID NO:326 of WO2011/090762, said sequence incorporated by reference herein), human IgG4 CH2 region with alanine substitutions at F234, L235, G237 and N297 and a deletion of G236 (SEQ ID NO:322 of WO2011/090762, said sequence incorporated by reference herein), human IgG4 CH2 region with alanine substitutions at F234 and N297 (SEQ ID NO:343 of WO2011/090762, said sequence incorporated by reference herein), human IgG4 CH2 region with alanine substitutions at L235 and N297 (SEQ ID NO:344 of WO2011/090762, said sequence incorporated by reference herein), human IgG4 CH2 region with alanine substitutions at G236 and N297 (SEQ ID NO:345 of WO2011/090762, said sequence incorporated by reference herein), and human IgG4 CH2 region with alanine substitutions at G237 and N297 (SEQ ID NO:346 of WO2011/090762, said sequence incorporated by reference herein).

In certain embodiments, in addition to the amino acid substitutions described above, an altered CH2 region (e.g., an altered human IgG1 CH2 domain) can contain one or more additional amino acid substitutions at one or more positions other than the above-noted positions. Such amino acid substitutions can be conservative or non-conservative amino acid substitutions. For example, in certain embodiments, P233 can be changed to E233 in an altered IgG2 CH2 region (see, e.g., SEQ ID NO:326 of WO2011/090762, said sequence incorporated by reference herein). In addition or alternatively, in certain embodiments, the altered CH2 region can contain one or more amino acid insertions, deletions, or both. The insertion(s), deletion(s) or substitution(s) can be anywhere in an immunoglobulin CH2 region, such as at the N- or C-terminus of a wild type immunoglobulin CH2 region resulting from linking the CH2 region with another region (e.g., a binding domain or an immunoglobulin heterodimerization domain) via a hinge.

In certain embodiments, an altered CH2 region in a polypeptide of the present disclosure comprises or is a sequence that is at least 90%, at least 91%, at least 92%, at least 93%, at least 94%, at least 95%, at least 96%, at least 97%, at least 98%, at least 99% identical to a wild type immunoglobulin CH2 region, such as the CH2 region of wild type human IgG1, IgG2, or IgG4, or mouse IgG2a (e.g., IGHG2c).

An altered immunoglobulin CH2 region in a PSMA-binding polypeptide of the present disclosure can be derived from a CH2 region of various immunoglobulin isotypes, such as IgG1, IgG2, IgG3, IgG4, IgA1, IgA2, and IgD, from various species (including human, mouse, rat, and other mammals). In certain embodiments, an altered immunoglobulin CH2 region in a fusion protein of the present disclosure can be derived from a CH2 region of human IgG1, IgG2 or IgG4, or mouse IgG2a (e.g., IGHG2c), whose sequences are set forth in SEQ ID NOS:115, 199, 201, and 320 of WO2011/090762 (said sequences incorporated by reference herein).

In certain embodiments, an altered CH2 domain is a human IgG1 CH2 domain with alanine substitutions at positions 235, 318, 320, and 322 (i.e., a human IgG1 CH2 domain with L235A, E318A, K320A and K322A substitutions) (SEQ ID NO:595 of WO2011/090762, said sequence incorporated by reference herein), and optionally an N297 mutation (e.g., to alanine). In certain other embodiments, an altered CH2 domain is a human IgG1 CH2 domain with alanine substitutions at positions 234, 235, 237, 318, 320 and 322 (i.e., a human IgG1 CH2 domain with L234A, L235A, G237A, E318A, K320A and K322A substitutions) (SEQ ID NO:596 of WO2011/090762, said sequence incorporated by reference herein), and optionally an N297 mutation (e.g., to alanine).

In certain embodiments, an altered CH2 domain is an altered human IgG1 CH2 domain with mutations known in the art that enhance immunological activities such as ADCC, ADCP, CDC, complement fixation, Fc receptor binding, or any combination thereof.

The CH3 domain that can form an immunoglobulin constant region of a PSMA-binding polypeptide of the present disclosure can be a wild type immunoglobulin CH3 domain or an altered immunoglobulin CH3 domain thereof from certain immunoglobulin classes or subclasses (e.g., IgG1, IgG2, IgG3, IgG4, IgA1, IgA2, IgD, IgE, IgM) of various species (including human, mouse, rat, and other mammals). In certain embodiments, a CH3 domain is a wild type human immunoglobulin CH3 domain, such as wild type CH3 domains of human IgG1, IgG2, IgG3, IgG4, IgA1, IgA2, IgD, IgE, or IgM as set forth in SEQ ID NOS:116, 208-210, 204-207, and 212, respectively of WO2011/090762 (said sequences incorporated by reference herein). In certain embodiments, the CH3 domain is a wild type human IgG1 CH3 domain as set forth in SEQ ID NO:116 of WO2011/090762 (said sequence incorporated by reference herein). In certain embodiments, a CH3 domain is an altered human immunoglobulin CH3 domain, such as an altered CH3 domain based on or derived from a wild-type CH3 domain of human IgG1, IgG2, IgG3, IgG4, IgA1, IgA2, IgD, IgE, or IgM antibodies. For example, an altered CH3 domain can be a human IgG1 CH3 domain with one or two mutations at positions H433 and N434 (positions are numbered according to EU numbering). The mutations in such positions can be involved in complement fixation. In certain other embodiments, an altered CH3 domain can be a human IgG1 CH3 domain but with one or two amino acid substitutions at position F405 or Y407. The amino acids at such positions are involved in interacting with another CH3 domain. In certain embodiments, an altered CH3 domain can be an altered human IgG1 CH3 domain with its last lysine deleted. The sequence of this altered CH3 domain is set forth in SEQ ID NO:761 of WO2011/090762 (said sequence incorporated by reference herein).

In certain embodiments, PSMA-binding polypeptides forming a polypeptide heterodimer comprise a CH3 pair that comprises so called "knobs-into-holes" mutations (see, Marvin and Zhu, Acta Pharmacologica Sinica 26:649-58, 2005; Ridgway et al., Protein Engineering 9:617-21, 1966). More specifically, mutations can be introduced into each of the two CH3 domains of each polypeptide chain so that the steric complementarity required for CH3/CH3 association obligates these two CH3 domains to pair with each other. For example, a CH3 domain in one single chain polypeptide of a polypeptide heterodimer can contain a T366W mutation (a "knob" mutation, which substitutes a small amino acid with a larger one), and a CH3 domain in the other single chain polypeptide of the polypeptide heterodimer can contain a Y407A mutation (a "hole" mutation, which substitutes a large amino acid with a smaller one). Other exemplary knobs-into-holes mutations include (1) a T366Y mutation in one CH3 domain and a Y407T in the other CH3 domain, and (2) a T366W mutation in one CH3 domain and T366S, L368A and Y407V mutations in the other CH3 domain.

The CH4 domain that can form an immunoglobulin constant region of PSMA-binding polypeptides of the present disclosure can be a wild type immunoglobulin CH4 domain or an altered immunoglobulin CH4 domain thereof from IgE or IgM molecules. In certain embodiments, the CH4 domain is a wild type human immunoglobulin CH4 domain, such as wild type CH4 domains of human IgE and IgM molecules as set forth in SEQ ID NOS:213 and 214, respectively, of WO2011/090762 (said sequences incorporated by reference herein). In certain embodiments, a CH4 domain is an altered human immunoglobulin CH4 domain, such as an altered CH4 domain based on or derived from a CH4 domain of human IgE or IgM molecules, which have mutations that increase or decrease an immunological activity known to be associated with an IgE or IgM Fc region.

In certain embodiments, an immunoglobulin constant region of PSMA binding polypeptides of the present disclosure comprises a combination of CH2, CH3 or CH4 domains (i.e., more than one constant region domain selected from CH2, CH3 and CH4). For example, the immunoglobulin constant region can comprise CH2 and CH3 domains or CH3 and CH4 domains. In certain other embodiments, the immunoglobulin constant region can comprise two CH3 domains and no CH2 or CH4 domains (i.e., only two or more CH3). The multiple constant region domains that form an immunoglobulin constant region can be based on or derived from the same immunoglobulin molecule, or the same class or subclass immunoglobulin molecules. In certain embodiments, the immunoglobulin constant region is an IgG CH2CH3 (e.g., IgG1 CH2CH3, IgG2 CH2CH3, and IgG4 CH2CH3) and can be a human (e.g., human IgG1, IgG2, and IgG4) CH2CH3. For example, in certain embodiments, the immunoglobulin constant region comprises (1) wild type human IgG1 CH2 and CH3 domains, (2) human IgG1 CH2 with N297A substitution (i.e., CH2(N297A)) and wild type human IgG1 CH3, or (3) human IgG1 CH2(N297A) and an altered human IgG1 CH3 with the last lysine deleted.

Alternatively, the multiple constant region domains can be based on or derived from different immunoglobulin molecules, or different classes or subclasses immunoglobulin molecules. For example, in certain embodiments, an immunoglobulin constant region comprises both human IgM CH3 domain and human IgG1 CH3 domain. The multiple constant region domains that form an immunoglobulin constant region can be directly linked together or can be linked to each other via one or more (e.g., about 2-10) amino acids.

Exemplary immunoglobulin constant regions are set forth in SEQ ID NOS:305-309, 321, 323, 341, 342, and 762 of WO2011/090762 (said sequences incorporated by reference herein).

In certain embodiments, the immunoglobulin constant regions of both PSMA-binding polypeptides of a polypeptide homodimer or heterodimer are identical to each other. In certain other embodiments, the immunoglobulin constant region of one polypeptide chain of a heterodimeric protein is different from the immunoglobulin constant region of the other polypeptide chain of the heterodimer. For example, one immunoglobulin constant region of a heterodimeric protein can contain a CH3 domain with a "knob" mutation, whereas the other immunoglobulin constant region of the heterodimeric protein can contain a CH3 domain with a "hole" mutation.

IV. Nucleic Acids, Host Cells, and Methods for Production

The invention also includes nucleic acids (e.g., DNA or RNA) encoding a PSMA-binding polypeptide as described herein, or one or more polypeptide chains of a dimeric or heterodimeric PSMA-binding protein as described herein. Nucleic acids of the invention include nucleic acids having a region that is substantially identical to a polynucleotide as listed in Table 3, infra. In certain embodiments, a nucleic acid in accordance with the present invention has at least 80%, typically at least about 90%, and more typically at least about 95% or at least about 98% identity to a polypeptide-encoding polynucleotide as listed in Table 3. Nucleic acids of the invention also include complementary nucleic acids. In some instances, the sequences will be fully complementary (no mismatches) when aligned. In other instances, there can be up to about a 20% mismatch in the sequences. In some embodiments of the invention are provided nucleic acids encoding both first and second polypeptide chains of a heterodimeric PSMA-binding protein of the invention. The nucleic acid sequences provided herein can be exploited using codon optimization, degenerate sequence, silent mutations, and other DNA techniques to optimize expression in a particular host, and the present invention encompasses such sequence modifications.

Polynucleotide molecules comprising a desired polynucleotide sequence are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the invention is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette ("expression unit") can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low- or high copy-number. A wide variety of markers are available for selection, particularly those which protect against toxins, more particularly against antibiotics. The particular marker that is chosen is selected in accordance with the nature of the host, where in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like.

Accordingly, proteins for use within the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, N.Y., 2001), and Ausubel et al., *Short Protocols in Molecular Biology* (4th ed., John Wiley & Sons, 1999).

For example, for recombinant expression of a homodimeric PSMA-binding protein comprising two identical PSMA-binding polypeptides as described herein, an expression vector will generally include a nucleic acid segment encoding the PSMA-binding polypeptide, operably linked to a promoter. For recombinant expression of a heterodimeric PSMA-binding protein, comprising different first and second polypeptide chains, the first and second polypeptide chains can be co-expressed from separate vectors in the host cell for expression of the entire heterodimeric protein. Alternatively, for the expression of heterodimeric PSMA-binding proteins, the first and second polypeptide chains are co-expressed from separate expression units in the same vector in the host cell for expression of the entire heterodimeric protein. The expression vector(s) are transferred to a host cell by conventional techniques, and the transfected cells are then cultured by conventional techniques to produce the encoded polypeptide(s) to produce the corresponding PSMA-binding protein.

To direct a recombinant protein into the secretory pathway of a host cell, a secretory signal sequence (also known as a leader sequence) is provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830). In certain variations, a secretory signal sequence for use in accordance with the present invention has the amino acid sequence MEAPAQLLFLLLLWLPDTTG (SEQ ID NO:85).

Cultured mammalian cells are suitable hosts for production of recombinant proteins for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DX611 (Hyclone, Logan, Utah); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blasticidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, N.J., 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present invention. Yeast species of in this regard include, e.g., *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii,* and *Candida maltose* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus,* and other genera are also useful host cells within the present invention. Techniques for transforming these hosts and expressing foreign DNA sequences cloned therein are well-known in the art (see, e.g., Sambrook and Russell, supra). When expressing a recombinant protein in bacteria such as *E. coli*, the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding. Antibodies, including single-chain antibodies, can be produced in bacterial host cells according to known methods. See, e.g., Bird et al., *Science* 242:423-426, 1988; Huston et al., *Proc. Natl. Acad. Sci. USA* 85:5879-5883, 1988; and Pantoliano et al., *Biochem.* 30:10117-10125, 1991.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

PSMA-binding proteins are purified by conventional protein purification methods, typically by a combination of chromatographic techniques. See generally *Affinity Chromatography: Principles & Methods* (Pharmacia LKB Biotechnology, Uppsala, Sweden, 1988); Scopes, *Protein Purification: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

V. Methods of Treatment

In another embodiment, the present invention provides a method for treating a disorder characterized by overexpression of PSMA. Generally, such methods include administering to a subject in need of such treatment a therapeutically effective amount of a PSMA-binding protein as described herein. In some embodiments, the PSMA-binding protein comprises at least one effector function selected from antibody-dependent cell-mediated cytotoxicity (ADCC) and complement-dependent cytotoxicity (CDC), such that the PSMA-binding protein induces ADCC and/or CDC against PSMA-expressing cells in the subject. In other embodiments, where the PSMA-binding protein comprises a second binding domain that specifically binds a T cell (e.g., to a TCR complex or component thereof, such as CD3ε), the PSMA-binding protein induces redirected T-cell cytotoxicity (RTCC) against PSMA-expressing cells in the subject.

In certain variations of the method, the disorder is a cancer. Exemplary cancers amenable to treatment in accordance with the present invention include, for example, prostate cancer (e.g., castrate-resistant prostate cancer), colorectal cancer, gastric cancer, clear cell renal carcinoma, bladder cancer, and lung cancer. In other variations, the disorder is a prostate disorder such as, for example, prostate cancer or benign prostatic hyperplasia (BPH). In yet other embodiments, the disorder is an neovascular disorder such as, for example, a cancer characterized by solid tumor growth. Exemplary cancers with tumor vasculatures characterized by PSMA overexpression and amenable to treatment in accordance with the present invention include, for example, clear cell renal carcinoma (CCRCC), colorectal cancer, breast cancer, bladder cancer, lung cancer, and pancreatic cancer (see, e.g., Baccala et al., *Urology* 70:385-390, 2007 (expression of PSMA in CCRCC); Liu et al., *Cancer Res.* 57:3629-3634, 1997 (expression of PSMA in various non-prostate cancers, including renal, urothelial, lung, colon, breast, and adenocarcinaoma to the liver); and Milowsky et al., *J. Clin. Oncol.* 25:540-547, 2007 (expression in, e.g., kidney, colon, bladder, and pancreatic cancers, and demonstration of specific targeting of tumor vasculature in humans using an anti-PSMA mAb).

In each of the embodiments of the treatment methods described herein, the PSMA-binding protein is delivered in a manner consistent with conventional methodologies associated with management of the disease or disorder for which treatment is sought. In accordance with the disclosure herein, an effective amount of the PSMA-binding protein is administered to a subject in need of such treatment for a time and under conditions sufficient to prevent or treat the disease or disorder.

Subjects for administration of PSMA-binding proteins as described herein include patients at high risk for developing a particular disorder characterized by PSMA overexpression as well as patients presenting with an existing such disorder.

Typically, the subject has been diagnosed as having the disorder for which treatment is sought. Further, subjects can be monitored during the course of treatment for any change in the disorder (e.g., for an increase or decrease in clinical symptoms of the disorder). Also, in some variations, the subject does not suffer from another disorder requiring treatment that involves targeting PSMA-expressing cells.

In prophylactic applications, pharmaceutical compositions or medicants are administered to a patient susceptible to, or otherwise at risk of, a particular disorder in an amount sufficient to eliminate or reduce the risk or delay the onset of the disorder. In therapeutic applications, compositions or medicants are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

To identify subject patients for treatment according to the methods of the invention, accepted screening methods can be employed to determine risk factors associated with specific disorders or to determine the status of an existing disorder identified in a subject. Such methods can include, for example, determining whether an individual has relatives who have been diagnosed with a particular disorder. Screening methods can also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, PSMA-expressing cells can be implemented as an independent treatment program or as a follow-up, adjunct, or coordinate treatment regimen to other treatments.

For administration, the PSMA-binding protein is formulated as a pharmaceutical composition. A pharmaceutical composition comprising a PSMA-binding protein can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), *Remington's Pharmaceutical Sciences* (Mack Publishing Company, 19th ed. 1995).) Formulations can further include one or more excipients, preservatives, solubilizers, buffering agents, albumin to prevent protein loss on vial surfaces, etc.

A pharmaceutical composition comprising a PSMA-binding protein is administered to a subject in a therapeutically effective amount. According to the methods of the present invention, a PSMA-binding protein can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, an antagonist can be administered to a subject in a single bolus delivery, via continuous delivery (e.g., continuous transdermal delivery) over an extended time period, or in a repeated administration protocol (e.g., on an hourly, daily, or weekly basis).

A "therapeutically effective amount" of a composition is that amount that produces a statistically significant effect in amelioration of one or more symptoms of the disorder, such as a statistically significant reduction in disease progression or a statistically significant improvement in organ function. The exact dose will be determined by the clinician according to accepted standards, taking into account the nature and severity of the condition to be treated, patient traits, etc. Determination of dose is within the level of ordinary skill in the art.

Determination of effective dosages in this context is typically based on animal model studies followed up by human clinical trials and is guided by determining effective dosages and administration protocols that significantly reduce the occurrence or severity of the subject disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically effective amount is also one in which any undesired collateral effects are outweighed by the beneficial effects of administering a PSMA-binding protein as described herein. For administration of the PSMA-binding protein, a dosage typically ranges from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring clinical symptoms of the disorder.

Dosage of the pharmaceutical composition can be varied by the attending clinician to maintain a desired concentration at a target site. For example, if an intravenous mode of delivery is selected, local concentration of the agent in the bloodstream at the target tissue can be between about 1-50 nanomoles of the composition per liter, sometimes between about 1.0 nanomole per liter and 10, 15, or 25 nanomoles per liter depending on the subject's status and projected measured response. Higher or lower concentrations can be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

Pharmaceutical compositions as described herein can also be used in the context of combination therapy. The term "combination therapy" is used herein to denote that a subject is administered at least one therapeutically effective dose of a PSMA-binding protein and another therapeutic agent.

For example, in the context of cancer immunotherapy, a PSMA-binding protein of the present invention can be used in combination with chemotherapy or radiation. A PSMA-binding protein as described herein can work in synergy with conventional types of chemotherapy or radiation. The PSMA-binding protein can further reduce tumor burden and allow more efficient killing by a chemotherapeutic.

Compositions of the present invention can also be used in combination with immunomodulatory compounds including various cytokines and co-stimulatory/inhibitory molecules. These can include, but are not limited to, the use of cytokines that stimulate anti-cancer immune responses (e.g., IL-2, IL-12, or IL-21). In addition, PSMA-binding proteins can be combined with reagents that co-stimulate various cell surface molecules found on immune-based effector cells, such as the activation of CD137 (see Wilcox et al., *J. Clin. Invest.* 109:651-9, 2002) or inhibition of CTLA4 (see Chambers et al., *Ann. Rev. Immunol.* 19:565-94, 2001). Alternatively, PSMA-binding proteins could be used with reagents that induce tumor cell apoptosis by interacting with TNF superfamily receptors (e.g., TRAIL-related receptors, DR4, DR5, Fas, or CD37). (See, e.g., Takeda et al., *J. Exp. Med.* 195:161-9, 2002; Srivastava, *Neoplasia* 3:535-46, 2001.) Such reagents include ligands of TNF superfamily receptors, including ligand-Ig fusions, and antibodies specific for TNF superfamily receptors (e.g., TRAIL ligand, TRAIL ligand-Ig fusions, anti-TRAIL antibodies, and the like).

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measureable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, Md.)

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

EXAMPLES

Example 1: Isolation of Murine Variable Domains from 107-1A4 and Preparation of Humanized Variants Murine variable domains were cloned from hybridoma cells expressing the 107-1A4 monoclonal antibody specific for human PSMA (see Brown et al, 1998, Prostate Cancer and Prostatic Diseases. 1: 208-215). Total RNA was isolated from the hybridoma using RNeasy® Protect Mini kit (QIAGEN Inc., 74124) according to the manufacturer's instructions. SMART™ RACE cDNA amplification kit (Clontech Laboratories, Inc., 634914) was used to generate 5'RACE-ready cDNA with oligo(dT) primer according to the manufacturer's instructions. $V_H$ and $V_L$ regions of antibody were PCR-amplified from cDNA by SMART™ RACE protocol using pools of proprietary degenerate gene specific primers for different murine VK or VH gene families. PCR amplification products were confirmed by gel electrophoresis, and correct sized bands were isolated and cloned into pCR®2.1-TOPO® plasmid vector using the TOPO® TA Cloning kit according to manufacturer's instructions (Invitrogen Corporation). The resulting recombinant vector was transformed into TOP10 *E. coli*. Sequencing DNA from clones revealed multiple isolates of a heavy chain region with a murine VH1 framework with high homology (92.7%) to the murine germline framework L17134 (GenBank™), and a kappa chain region with a murine Vk16 framework with very high homology (98.6%) to the murine germline framework AJ235936 (EMBL). Two restriction sites—one HindIII and one EcoRI site—were removed by neutral mutations from the DNA coding for the parent murine kappa (light) variable domain to simplify cloning into destination mammalian expression vectors, and the native murine secretion/leader sequences were also not used in favor of the human Vk3 leader sequence. The polynucleotide sequence of PSMA-specific murine VH region (107-1A4) is given in SEQ ID NO:1, and the amino acid sequence is given in SEQ ID NO:2. The polynucleotide sequence of PSMA-specific murine VL region (107-1A4) with the restriction sites is given in SEQ ID NO:3. The polynucleotide sequence of PSMA-specific murine VL region (107-1A4) modified to remove the restriction sites is given in SEQ ID NO:4, and the amino acid sequence is given in SEQ ID NO:5.

DNA sequences coding for these murine scFv sequences and cassetted for insertion into appropriate scaffolds (e.g., SMIP, SCORPION, and mono-specific or multispecific heterodimer polypeptides) were designed. The constructs were then synthesized by Blue Heron (Bothell, Wash.) and standard, restriction-digest-based cloning techniques were used to produce the gene sequences corresponding to TSC084 (SEQ ID NO:44; amino acid sequence SEQ ID NO:46), TSC085 (SEQ ID NO:36; amino acid sequence SEQ ID NO:38), and TSC092 (SEQ ID NO:37; amino acid sequence SEQ ID NO:39).

Humanized sequences designed through CDR grafting to human frameworks were similarly synthesized by Blue Heron and cloned into similar vectors using restriction digests to produce the following gene sequences using two approaches: (A) three piece ligation using a HindIII/BamHI fragment, a BamHI/XhoI fragment, and a destination vector cut with HindIII/XhoI to produce the gene sequences corresponding to TSC188 (SEQ ID NO:40; amino acid sequence SEQ ID NO:42) and TSC189 (SEQ ID NO:41; amino acid sequence SEQ ID NO:43); and (B) two piece ligation using a HindIII/XhoI fragment and a destination vector cut with HindIII/XhoI to produce the gene sequences corresponding to TSC192 (SEQ ID NO:53; amino acid sequence SEQ ID NO:58), TSC193 (SEQ ID NO:54; amino acid sequence SEQ ID NO:59), TSC194 (SEQ ID NO:48; amino acid sequence SEQ ID NO:49), TSC195 (SEQ ID NO:55; amino acid sequence SEQ ID NO:60), TSC196 (SEQ ID NO:56; amino acid sequence SEQ ID NO:61), TSC199 (SEQ ID NO:50; amino acid sequence SEQ ID NO:51), TSC210 (SEQ ID NO:69; amino acid sequence SEQ ID NO:70), TSC211 (SEQ ID NO:71; amino acid sequence SEQ ID NO:72), TSC212 (SEQ ID NO:73; amino acid sequence SEQ ID NO:74), TSC213 (SEQ ID NO:75; amino acid sequence SEQ ID NO:76); TSC249 (SEQ ID NO:77; amino acid sequence SEQ ID NO:78), TSC250 (SEQ ID NO:79; amino acid sequence SEQ ID NO:80), TSC251 (SEQ ID NO:81; amino acid sequence SEQ ID NO:82), and TSC252 (SEQ ID NO:83; amino acid sequence SEQ ID NO:84); and (C) two piece ligation using a BsrGI/EcoRI fragment and one of two destination vectors cut with BsrGI/EcoRI to produce the gene sequences corresponding to TSC295 (SEQ ID NO:157; amino acid sequence SEQ ID NO:158), TSC296 (SEQ ID NO:159; amino acid sequence SEQ ID NO:160), TSC301 (SEQ ID NO:161; amino acid sequence SEQ ID NO:162), and TSC302 (SEQ ID NO:163; amino acid sequence SEQ ID NO:164). The humanized PSMA-specific (107-1A4) VL region polynucleotide sequence is given in SEQ ID NO:22, and the amino acid sequence is given in SEQ ID NO:23. A humanized PSMA-specific (107-1A4) VH region #1 polynucleotide sequence is given in SEQ ID NO:24, and the amino acid sequence is given in SEQ ID NO:25. A humanized PSMA-specific (107-1A4) VH region #2 polynucleotide sequence is given in SEQ ID NO:26, and the amino acid sequence is given in SEQ ID NO:27.

Sequences for the various cloned sequences and components are also presented in Table 3. Amino acid sequences given for polypeptide constructs (e.g., SMIP, SCORPION, mono- or multi-specific heterodimeric proteins) do not include the human Vk3 leader sequence.

TABLE 3

Binding Polypeptide Sequences and Components

| Name | Nucleotide Sequence | Amino Acid Sequence | SEQ ID NOs: (amino acid) |
|---|---|---|---|
| Murine 107-1A4 VH region | gagatccagctgcaacagtctggacctgagctggtgaagcctggggcttca gtgaagatgtcctgcaaggcttctggatacacattcactgactactacatgcac tgggtgaagcagaacaatggagagagccttgagtggattggatatttttaatcc ttataatgattatactagatacaaccagaatttcaatggcaaggccacattgact gtagacaagtcctccagcacagcctacatgcagctcaacagcctgacatctg aggactctgcattctattactgtgcaagatcggatggttactacgatgctatgg actactggggtcaaggaacctcagtcaccgtctcctcg | eiqlqqsgpelvkpgasvk msckasgytftdyymhw vkqnngeslewigyfnpy ndytrynqnfngkatltvdk ssstaymqlnsltsedsafy ycarsdgyydamdywgq | SEQ ID NO: 1 (SEQ ID NO: 2) |
| Murine 107-1A4 VL region w/ additional restriction sites | Gatgtccagataaacccagtctccatcttatcttgctgcatctcctggagaaacc attactattaattgcagggcaagtaagagcattagcaaatatttagcctggtatc aagagaaacctgggaaagctaataagcttcttatccattctggatccactttgc aatctggaattccatcaaggttcagtggcagtggatctggtacagatttcactct caccatcagtagcctggagcctgaagattttgcaatgtattactgtcaacagca tattgaatacccgtggacgttcggtggtggcaccaaactggaaattaaacgg gct | | SEQ ID NO: 3 |

TABLE 3-continued

Binding Polypeptide Sequences and Components

| Name | Nucleotide Sequence | Amino Acid Sequence | SEQ ID NOs: (amino acid) |
|---|---|---|---|
| Murine 107-1A4 VL region modified | gatgtccagataaacccagtctccatcttatcttgctgcatctcctggagaaacc attactattaattgcagggcaagtaagagcattagcaaatatttagcctggtatc aagagaaacctgggaaagctaataagctacttatccattctggatccactttgc aatctggaataccatcaaggttcagtggcagtggatctggtacagatttcactc tcaccatcagtgcctggagcctgaagattttgcaatgtattactgtcaacagc atattgaatacccgtggacgttcggtggtggcaccaaactggaaattaaacg ggcc | dvqitqspsylaaspgetiti ncrasksiskylawyqekp gkankllihsgstlqsgipsr fsgsgsgtdftltisslepedf amyycqqhieypwtfggg tkleikra | SEQ ID NO: 4 (SEQ ID NO: 5) |
| 107-1A4 VH CDR1 | tctggatacacattcactgactactacatgcac | sgytftdyymh | SEQ ID NO: 6 (SEQ ID NO: 9) |
| 107-1A4 VH CDR2 | tattttaatccttataatgattatactaga | Yfnpyndytr | SEQ ID NO: 7 (SEQ ID NO: 10) |
| 107-1A4 VH CDR3 | tgtgcaagatcggatggttactacgatgctatggactactgg | carsdgyydamdyw | SEQ ID NO: 8 (SEQ ID NO: 11) |
| 107-1A4 VL CDR1 | Aagagcattagcaaatat | Ksisky | SEQ ID NO: 12 (SEQ ID NO: 15) |
| 107-1A4 VL CDR2 | Tctggatcc | Sgs | SEQ ID NO: 13 (SEQ ID NO: 16) |
| 107-1A4 VL CDR3 | Caacagcatattgaatacccgtggacg | Qqhieypwt | SEQ ID NO: 14 (SEQ ID NO: 17) |
| 107-1A4 VH-VL scFv | gagatccagctgcaacagtctggacctgagctggtgaagcctggggcttca gtgaagatgtcctgcaaggcttctggatacacattcactgactactacatgcac tgggtgaagcagaacaatggagagagccttgagtggattggatattttaatcc ttataatgattatactagatacaaccagaatttcaatggcaaggccacattgac tgtagacaagtcctccagcacagcctacatgcagctcaacagcctgacatctg aggactctgcattctattactgtgcaagatcggatggttactacgatgctatgg actactggggtcaaggaacctcagtcaccgtctcctcaggcggcggcggaa gcggcggtggcggcagcagcggcggcggcagcgatgtccagataa cccagtctccatcttatcttgctgcatctcctggagaaaccattactattaattgc agggcaagtaagagcattagcaaatatttagcctggtatcaagagaaacctg ggaaagctaataagctacttatccattctggatccactttgcaatctggaatacc atcaaggttcagtggcagtggatctggtacagatttcactctcaccatcagtag cctggagcctgaagattttgcaatgtattactgtcaacagcatattgaatacccc gtggacgttcggtggtggcaccaaactggaaattaaacgggcctcg | eiqlqqsgpelvkpgasvk msckasgytftdyymhw vkqnngeslewigyfnpy ndytrynqnfngkatltvdk ssstaymqlnsltsedsafy ycarsdgyydamdywgq gtsvtvssggggsggggss ggggsdvqitqspsylaasp getitincrasksiskylawy qekpgkankllihsgstlqs gipsrfsgsgsgtdftltissle pedfamyycqqhieypwt fgggtkleikras | SEQ ID NO: 18 (SEQ ID NO: 19) |
| 107-1A4 VL-VH scFv | gatgtccagataaacccagtctccatcttatcttgctgcatctcctggagaaacc attactattaattgcagggcaagtaagagcattagcaaatatttagcctggtatc aagagaaacctgggaaagctaataagctacttatccattctggatccactttgc aatctggaataccatcaaggttcagtggcagtggatctggtacagatttcactc tcaccatcagtgcctggagcctgaagattttgcaatgtattactgtcaacagc atattgaatacccgtggacgttcggtggtggcaccaaactggaaattaaacg ggccggcggcggcggaagcggcggtggcggcagcagcggcggcg gcagcgagatccagctgcaacagtctggacctgagctggtgaagcctggg gcttcagtgaagatgtcctgcaaggcttctggatacacattcactgactactac atgcactgggtgaagcagaacaatggagagagccttgagtggattggatatt ttaatccttataatgattatactagatacaaccagaatttcaatggcaaggccac attgactgtagacaagtcctccagcacagcctacatgcagctcaacagcctg acatctgaggactctgcattctattactgtgcaagatcggatggttactacgatg ctatggactactggggtcaaggaacctcagtcaccgtctcctcg | dvqitqspsylaaspgetiti ncrasksiskylawyqekp gkankllihsgstlqsgipsr fsgsgsgtdftltisslepedf amyycqqhieypwt fgggtkleikraggggsgggsg gggseiqlqqsgpelvkpg asvkmsckasgytftdyy mhwvkqnngeslewigy fnpyndytrynqnfngkatl tvdkssstaymqlnsltsed safyycarsdgyydamdy wgqgtsvtvss | SEQ ID NO: 20 (SEQ ID NO: 21) |
| Humanized 107-1A4 VL | gatatccagatgacccagtctccatccgccatgtctgcatctgtaggagacag agtcaccatcacttgccgggcgagtaagagcattagcaaatatttagcctggt ttcagcagaaaccagggaaagttcctaagctccgcatccattctggatctctt tgcaatcaggggtcccatctcggttcagtggcagtggatctgggacagaattt actctcaccatcagcagcctgcagcctgaagattttgcaacttattactgtcaa cagcatattgaatacccgtggacgttcggccaagggaccaaggtggaaatc aaacga | diqmtqspsamsasvgdr vtitcrasksiskylawfqqk pgkvpklrihsgstlqsgvp srfsgsgsgteftltisslqpe dfatyycqqhieypwtfgq gtkveikr | SEQ ID NO: 22 (SEQ ID NO: 23) |
| Humanized 107-1A4 VH#1 | gaggtccagctggtacagtctggggctgaggtgaagaagcctggggctac agtgaagatctcctgcaaggcttctggatacacattcactgactactacatgca ctgggtgcaacaggcccctggaaagggcttgagtggatgggatattttaat ccttataatgattatactagatacgcagagaagttccgggcagagtcaccat aaccgcggacacgtctacagacacagcctacatggagctgagcagcctga gatctgaggacacggccgtgtattactgtgcaagatcggatggttactacgat gctatggactactggggtcaaggaaccacagtcaccgtctcctcg | evqlvqsgaevkkpgatvk isckasgytftdyymhwv qqapgkglewmgyfnpy ndytryaekfqgrvtitadts tdtaymelssirsedtavyy carsdgyydamdywgqg ttvtvss | SEQ ID NO: 24 (SEQ ID NO: 25) |

TABLE 3-continued

Binding Polypeptide Sequences and Components

| Name | Nucleotide Sequence | Amino Acid Sequence | SEQ ID NOs: (amino acid) |
|---|---|---|---|
| Humanized 107-1A4 VH#2 | caggtccagctggtacagtctggggctgaggtgaagaagcctggggcttca gtgaaggtctcctgcaaggcttctggatacacattcactgactactacatgcac tgggtgcgacaggcccctggacaagggcttgagtggatgggatattttaatc cttataatgattatactagatacgcacagaagttccagggcagagtcaccatg accaggacacgtctatcagcacagcctacatggagctgagcagcctgaga tctgacgacacggccgtgtattactgtgcaagatcggatggttactacgatgct atggactactggggtcaaggaaccacagtcaccgtctcctcg | qvqlvqsgaevkkpgasy kvsckasgytftdyymhw vrqapgqglewmgyfnp yndytryaqkfqgrvtmtr dtsistaymelsslrsddtav yycarsdgyydamdywg qgttvtvss | SEQ ID NO: 26 (SEQ ID NO: 27) |
| Humanized 107-1A4 VL-VH#1 scFv | gatatccagatgacccagtctccatccgccatgtctgcatctgtaggagacag agtcaccatcacttgccgggcgagtaagagcattagcaaatatttagcctggt ttcagcagaaaccagggaaagttcctaagctccgcatccattctggatctactt tgcaatcaggggtcccatctcggttcagtggcagtggatctgggacagaattt actctcaccatcagcagcctgcagcctgaagattttgcaacttattactgtcaa cagcatattgaatacccgtggacgttcggccaagggaccaaggtggaaatc aaacgaggtggcggagggtctgggggtggcggatccggaggtggtggct ctgaggtccagctggtacagtctggggctgaggtgaagaagcctggggcta cagtgaagatctcctgcaaggcttctggatacacattcactgactactacatgc actgggtgcaacaggcccctggaaaaggcttgagtggatgggatattttaa tccttataatgattatactagatacgcagagaagttccagggcagagtcaccat aaccgcggacacgtctacagacacagcctacatggagctgagcagcctga gatctgaggacacggccgtgtattactgtgcaagatcggatggttactacgat gctatggactactggggtcaaggaaccacagtcaccgtctcctcg | diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsevqlvqsgaevkkp gatvkisckasgytftdyy mhwvqqapgkglewmg yfnpyndytryaekfqgrvt itadtstdtaymelsslrsedt avyycarsdgyydamdy wgqgttvtvss | SEQ ID NO: 28 (SEQ ID NO: 30) |
| Humanized 107-1A4 VL-VH#2 scFv | gatatccagatgacccagtctccatccgccatgtctgcatctgtaggagacag agtcaccatcacttgccgggcgagtaagagcattagcaaatatttagcctggt ttcagcagaaaccagggaaagttcctaagctccgcatccattctggatctactt tgcaatcaggggtcccatctcggttcagtggcagtggatctgggacagaattt actctcaccatcagcagcctgcagcctgaagattttgcaacttattactgtcaa cagcatattgaatacccgtggacgttcggccaagggaccaaggtggaaatc aaacgaggtggcggagggtctgggggtggcggatccggaggtggtggct ctcaggtccagctggtacagtctggggctgaggtgaagaagcctggggctt cagtgaaggtctcctgcaaggcttctggatacacattcactgactactacatgc actgggtgcgacaggcccctggacaagggcttgagtggatgggatattttaa tccttataatgattatactagatacgcacaggaagttccagggcagagtcaccat gaccagggacacgtctatcagcacagcctacatggagctgagcagcctgag atctgacgacacggccgtgtattactgtgcaagatcggatggttactacgatg ctatggactactggggtcaaggaaccacagtcaccgtctcctcg | diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvsckasgytftdyy mhwvrqapgqglewmg yfnpyndytryaqkfqgrv tmtrdtsistaymelsslrsd dtavyycarsdgyydamd ywgqgttvtvss | SEQ ID NO: 29 (SEQ ID NO: 31) |
| Humanized 107-1A4 VH#1-VL scFv | gaggtccagctggtacagtctggggctgaggtgaagaagcctggggctac agtgaagatctcctgcaaggcttctggatacacattcactgactactacatgc ctgggtgcaacaggcccctggaaaaggcttgagtggatgggatattttaat ccttataatgattatactagatacgcagagaagttccagggcagagtcaccat aaccgcggacacgtctacagacacagcctacatggagctgagcagcctga gatctgaggacacggccgtgtattactgtgcaagatcggatggttactacgat gctatggactactggggtcaaggaaccacagtcaccgtctcctcaggtggcg gagggtctgggggtggcggatccggaggtggtggctctgatatccagatga cccagtctccatccgccatgtctgcatctgtaggagacagagtcaccatcact tgccgggcgagtaagagcattagcaaatatttagcctggtttcagcagaaacc agggaaagttcctaagctccgcatccattctggatctactttgcaatcaggggt cccatctcggttcagtggcagtggatctgggacagaatttactctcaccatca gcagcctgcagcctgaagattttgcaacttattactgtcaacagcatattgaata cccgtggacgttcggccaagggaccaaggtggaaatcaaacgagcctcg | evqlvqsgaevkkpgatvk isckasgytftdyymhwv qqapgkglewmgyfnpy ndytryaekfqgrvtitadts tdtaymelsslrsedtavyy carsdgyydamdywgqg ttvtvssggggsggggsgg ggsdiqmtqspsamsasv gdrvtitcrasksiskylawf qqkpgkvpklrihsgstlqs gvpsrfsgsgsgteftltissl qpedfatyycqqhieypwt fgqgtkveikras | SEQ ID NO: 32 (SEQ ID NO: 34) |
| Humanized 107-1A4 VH#2-VL scFv | caggtccagctggtacagtctggggctgaggtgaagaagcctggggcttca gtgaaggtctcctgcaaggcttctggatacacattcactgactactacatgcac tgggtgcgacaggcccctggacaagggcttgagtggatgggatattttaatc cttataatgattatactagatacgcacagaagttccagggcagagtcaccatg accaggacacgtctatcagcacagcctacatggagctgagcagcctgaga tctgacgacacggccgtgtattactgtgcaagatcggatggttactacgatgct atggactactggggtcaaggaaccacagtcaccgtctcctcaggtggcgga gggtctgggggtggcggatccggaggtggtggctctgatatccagatgacc cagtctccatccgccatgtctgcatctgtaggagacagagtcaccatcacttg ccgggcgagtaagagcattagcaaatatttagcctggtttcagcagaaacca gggaaagttcctaagctccgcatccattctggatctactttgcaatcaggggtc ccatctcggttcagtggcagtggatctgggacagaatttactctcaccatcag cagcctgcagcctgaagattttgcaacttattactgtcaacagcatattgaatac ccgtggacgttcggccaagggaccaaggtggaaatcaaacgcgcctcg | qvqlvqsgaevkkpgasv kvsckasgytftdyymhw vrqapgqglewmgyfnp yndytryaqkfqgrvtmtr dtsistaymelsslrsddtav yycarsdgyydamdywg qgttvtvssggggsggggs gggsdiqmtqspsamsa svgdrvtitcrasksiskyla wfqqkpgkvpklrihsgstl qsgvpsrfsgsgsgteftltis slqpedfatyycqqhieyp wtfgqgtkveikras | SEQ ID NO: 33 (SEQ ID NO: 35) |

TABLE 3-continued

Binding Polypeptide Sequences and Components

| Name | Nucleotide Sequence | Amino Acid Sequence | SEQ ID NOs: (amino acid) |
|---|---|---|---|
| TSC085 chimeric SMIP (murine 107-1A4 VL-VH scFv-human Fc) | atggaagcaccagcgcagcttctcttcctcctgctactctggctcccagatac caccggtgatgtccagataacccagtctccatcttatcttgctgcatcctgga gaaaccattactattaattgcagggcaagtaagagcattagcaaatatttagcc tggtatcaagagaaacctgggaaagctaataagctacttatccattctggatcc actttgcaatctggaataccatcaaggttcagtggcagtggatctggtacagat ttcactctcaccatcagtagcctggagcctgaagattttgcaatgtattactgtc aacagcatattgaatacccgtggacgttcggtggtggcaccaaactggaaatt aaacgggccggcggcggcggaagcggcggtggcggcagcagcggcgg cggcggcagcgagatccagctgcaacagtctggacctgagctggtgaagc ctggggcttcagtgaagatgtcctgcaaggcttctggatacacattcactgact actacatgcactgggtgaagcagaacaatggagagagccttgagtggattg gatattttaatccttataatgattatactagatacaaccagaatttcaatggcaag gccacattgactgtagacaagtcctccagcacagcctacatgcagctcaaca gcctgacatctgaggactctgcattctattactgtgcaagatcggatggttacta cgatgctatggactactggggtcaaggaacctcagtcaccgtctcctcgagt gagcccaaatcttctgacaaaactcacacatgcccaccgtgcccagcactg aagccgcgggtgcaccgtcagtcttcctcttccccccaaaacccaaggacac cctcatgatctcccggaccctgaggtcacatgcgtggtggtggacgtgagc cacgaagaccctgaggtcaagttcaactggtacgtggacggcgtggaggtg cataatgccaagacaaagccgcgggaggagcagtacaacagcacgtaccg tgtggtcagcgtcctcaccgtcctgcaccaggactggctgaatggcaaggc gtacgcgtgcgcggtctccaacaaagccctcccagccccatcgagaaaac catctccaaagccaaagggcagccccgagaaccacaggtgtacaccctgc cccatcccgggatgagctgaccaagaaccaggtcagcctgacctgcctgg tcaaaggcttctatcccagcgacatcgccgtggagtgggagagcaatggg cagccggagaacaactacaagaccacgcctcccgtgctggactccgacggc tccttcttcctctacagcaagctcaccgtggacaagagcaggtggcagcagg ggaacgtcttctcatgctccgtgatgcatgaggctctgcacaaccactacacg cagaagagcctctccctgtctccgggtaaatga | dvqitqspsylaaspgetiti ncrasksiskylawyqekp gkankllihsgstlqsgipsr fsgsgsgtdftltisslepedf amyycqqhieypwtfggg tkleikraggggsggggssg gggseiqlqqsgpelvkpg asvkmsckasgytftdyy mhwvkqnngeslewigy fnpyndytrynqnfngkatl tvdkssstaymqlnsltsed safyycarsdgyydamdy wgqgtsvtvsssepkssdk thtcppcpapeaagapsvfl fppkpkdtlmisrtpevtcv vvdvshedpevkfnwyv dgvevhnaktkpreeqyns tyrvvsvltvlhqdwhlngka yacavsnkalpapiektisk akgqprepqvytlppsrdel tknqvsltclvkgfypsdia vewesngqpennykttpp vldsdgsfflysklyvdksr wqqgnvfscsvmhealhn hytqkslslspgk | SEQ ID NO: 36 (SEQ ID NO: 38) |
| TSC092 chimeric SMIP (murine 107-1A4 VH-VL scFv-human Fc) | atggaagcaccagcgcagcttctcttcctcctgctactctggctcccagatac caccggtgagatccagctgcaacagtctggacctgagctggtgaagcctgg ggcttcagtgaagatgtcctgcaaggcttctggatacacattcactgactacta catgcactgggtgaagcagaacaatggagagagccttgagtggattggatat tttaatccttataatgattatactagatacaaccagaatttcaatggcaaggcca cattgactgtagacaagtcctccagcacagcctacatgcagctcaacagcct gacatctgaggactctgcattctattactgtgcaagatcggatggttactacgat gctatggactactggggtcaaggaacctcagtcaccgtctcctcaggcggcg gcggaagcggcggtggcggcagcagcggcggcggcggcagcgatgtcc agataacccagtctccatcttatcttgctgcatcctggagaaaccattactatt aattgcagggcaagtaagagcattagcaaatatttagcctggtatcaagagaa acctgggaaagctaataagctacttatccattctggatccacttttgcaatctgga ataccatcaaggttcagtggcagtggatctggtacagatttcactctcaccatc agtagcctggagcctgaagattttgcaatgtattactgtcaacagcatattgaat acccgtggacgttcggtggtggcaccaaactggaaattaaacgggcctcga gtgagcccaaatcttctgacaaaactcacacatgcccaccgtgcccagcacc tgaagccgcgggtgcaccgtcagtcttcctcttccccccaaaacccaaggac accctcatgatctcccggaccctgaggtcacatgcgtggtggtggacgtga gccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagccctcccagccccatcgagaaa accatctccaaagccaaagggcagccccgagaaccacaggtgtacaccct gccccatcccgggatgagctgaccaagaaccaggtcagcctgacctgcct ggtcaaaggcttctatcccagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtaaatga | eiqlqqsgpelvkpgasvk msckasgytftdyymhw vkqnngeslewigyfnpy ndytrynqnfngkatltvdk ssstaymqlnsltsedsafy ycarsdgyydamdywgq gtsvtvssggggsggggss gggsdvqitqspsylaasp getitincrasksiskylawy qekpgkankllihsgstlqs gipsrfsgsgsgtdftltissle pedfamyycqqhieypwt fggqtkleikrassepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennyktt ppvldsdgsfflysklyvdk srwqqgnvfscsvmheal hnhytqkslslspgk | SEQ ID NO: 37 (SEQ ID NO: 39) |
| TSC188 humanized SMIP (107-1A4 VL-VH#1 scFv-Fc) | atggaagcaccagcgcagcttctcttcctcctgctactctggctcccagatac caccggtgatatccagatgacccagtctccatcctccctgtctgcatctgtag gagacagagtcaccatcacttgccgggcgagtaagagcattagcaaatattt agcctggtttcagcagaaaccagggaaagttcctaagctcccgcatccattctg gatctactttgcaatcaggggtcccatctcggttcagtggcagtggatctggg acagaattttactctcaccatcagcagcctgcagcctgaagatttttgcaacttatt actgtcaacagcatattgaataccgtggacgttcggccaagggaccaaggt ggaaatcaaacgaggtggcggaggtctggggtggcggatccgagg ggtggctctgaggtccagctggtacagtctggggctgaggtgaagaagcct ggggcctacgtgaaggtctcctgcaaggcattcactacacattcactgacta ctacatgcactgggtgcaacaggcccctggaaaggggcttgagtggatggg atattttaatccttataatgattatactagatacgcagaagttccagggcaga gtcaccataaccgcggacacgtctacagacacagccacatggagctgagc agcctgagatctgaggacacggccgtgtattactgtgcaagatcggatggtt actacgatgctatggactactggggtcaaggaaccacagtcaccgtctcctc | diqmtqspsamsasvgdr vtitcrasksiskylawfqqk pgkvpklrihsgstlqsgvp srfsgsgsgteftltisslqpe dfatyycqqhieypwtfgq gtkveikrggggsggggssg gggsevqlvqsgaevkkp gatvkisckasgytftdyy mhwvqqapgkglewmg yfnpyndytryaekfqgrvt itadtstdtaymelsslrsedt avyycarsdgyydamdy wgqgttvtvsssepkssdkt htcppcpapeaagapsvflf ppkpkdtlmisrtpevtcvv | SEQ ID NO: 40 (SEQ ID NO: 42) |

TABLE 3-continued

Binding Polypeptide Sequences and Components

| Name | Nucleotide Sequence | Amino Acid Sequence | SEQ ID NOs: (amino acid) |
|------|---------------------|---------------------|--------------------------|
| | gagtgagcccaaatcttctgacaaaactcacacatgcccaccgtgcccagca cctgaagccgcgggtgcaccgtcagtcttcctcttccccccaaaacccaagg acaccctcatgatctcccggacccctgaggtcacatgcgtggtggtggacgt gagccacgaagaccctgaggtcaagttcaactggtacgtggacggcgtggga ggtgcataatgccaagacaaagccgcgggaggagcagtacaacagcacgt accgtgtggtcagcgtcctcaccgtcctgcaccaggactggctgaatggcaa ggcgtacgcgtgcgcggtctccaacaaagccctcccagcccccatcgaga aaaccatctccaaagccaaagggcagccccgagaaccacaggtgtacacc ctgcccccatcccgggatgagctgaccaagaaccaggtcagcctgacctgc ctggtcaaaggcttctatccaagcgacatcgccgtggagtgggagagcaat gggcagccggagaacaactacaagaccacgcctcccgtgctggactccga cggctccttcttcctctacagcaagctcaccgtggacaagagcaggtggcag caggggaacgtcttctcatgctccgtgatgcatgaggctctgcacaaccacta cacgcagaagagcctctccctgtctccgggtaaatga | vdvshedpevkfnwyvd gvevhnaktkpreeqynst yrvvsvltvlhqdwlngka yacavsnkalpapiektisk akgqprepqvytlppsrdel tknqvsltclvkgfypsdia vewesngqpennykttpp vldsdgsfflyskltvdksr wqqgnvfscsvmhealhn hytqkslslspgk | |
| TSC189 humanized SMIP (107-1A4 VL-VH#2 scFv-Fc) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctccgcatccattctg gatctactttgcaatcaggggtcccatctcggttcagtggcagtggatctggg acagaatttactctcaccatcagcagcctgcagcctgaagattttgcaacttat actgtcaacagcatattgaataccgtggacgttcggccaagggaccaaggt ggaaatcaaacgaggtggcggaggttctggggtggcggatccggaggt ggtggctccaggtccagctggtacagctctggggctgaggtgaagaagcct ggggcttcagtgaaggtctcctgcaaggcttctggatacacattcactgacta ctacatgcactgggtgcgacaggcccctggacaaggcttgagtggatggg atattttaatcctataatgattatactagatacgcacagaagttccagggcaga gtcaccatgaccagggacacgtctatcagcacagcctcatggagctgagc agcctgagatctgacgacacggccgtgtattactgtgcaagatcggatggtta ctacgatgctatggactactggggtcaaggaaccacagtcaccgtctcctcg agtgagcccaaatcttctgacaaaactcacacatgcccaccgtgcccagcac ctgaagccgcgggtgcaccgtcagtcttcctcttccccccaaaacccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagccctcccagcccccatcgagaaa accatctccaaagccaaagggcagccccgagaaccacaggtgtacaccct gcccccatcccgggatgagctgaccaagaaccaggtcagcctgacctgcct ggtcaaaggcttctatccaagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtaaatga | diqmtqspsamsasvgdr vtitcrasksiskylawfqqk pgkvpklrihsgstlqsgvp srfsgsgsgteftltisslqpe dfatyycqqhieypwtfgq gtkveikrgggsgggsg gggsqvqlvqsgaevkkp gasvkvsckasgytftdyy mhwvrqapgqglewmg yfnpyndytryaqkfqgrv tmtrdtsistaymelsslrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennyktt ppvldsdgsfflyskltvdk srwqqgnvfscsvmheal hnhytqkslslspgk | SEQ ID NO: 41 (SEQ ID NO: 43) |
| TSC084 chimeric Interceptor (murine VL-VH 107-1A4 scFv-Fc-CH1) | atggaagcaccagcgcagcttctcttcctcctgctactctggctcccagatac caccggtgatgtccagataacccagtctccatcttatcttgctgcatctcctgga gaaaccattactattaattgcagggcaagtaagagcattagcaaatatttagcc tggtatcagcagaaacctgggaaagctaataagcttatccattctggaatcc actttgcaatctggaatcaataccaaggttcagtggcagtggatctggtacagat ttcactctcaccatcagtagcctggagcctgaagattttgcaatgtattactgtc aacagcatattgaatacccgtggacgttcggtggtggcaccaaactggaaatt aaacgggcggcggcggcggaagcggcggtggcggcagcagcggcg cggtggcagcggcgagatccagttgcagcagtctggacctgaagtggtgaagc ctggggcttcagtgaagatgtcctgcaaggcttctggatacacattcactgact actacatgcactgggtgaagcagaacaatggagagagccttgagtggattg gatatttaatcctataatgattatactagatacaaccagaatttcaatggcaag gccacattgactgtagacaagtcctctagcacagcctacatgcaactcaaca gcctgacatctgaggactctgcattctattactgtgcaagatcggatggttacta cgatgctatggactactggggtcaaggaacctcagtcaccgtctcctcgagc gagcccaaatcttctgacaaaactcacacatgcccaccgtgcccagcacctg aagccgcgggtgcaccgtcagtcttcctcttccccccaaaacccaaggacac cctcatgatctcccggacccctgaggtcacatgcgtggtggtggacgtgagc cacgaagaccctgaggtcaagttcaactggtacgtggacggcgtggaggtg cataatgccaagacaaagccgcgggaggagcagtacaacagcacgtaccg tgtggtcagcgtcctcaccgtcctgcaccaggactggctgaatggcaaggc gtacgcgtgcgcggtctccaacaaagccctcccagcccccatcgagaaaac catctccaaagccaaagggcagccccgagaaccacaggtgtacaccctgc ccccatcccgggatgagctgaccaagaaccaggtcagcctgacctgcctgg tcaaaggcttctatccaagcgacatcgccgtggagtgggagagcaatgggc agccggagaacaactacaagaccacgcctcccgtgctggactccgacggc tccttcttcctctacagcaagctcaccgtggacaagagcaggtggcagcagg ggaacgtcttctcatgctccgtgatgcatgaggctctgcacaaccactacacg cagaagagcctctccctgtctccgggtaaatctagagcctccaccaagggcc catcggtcttccccctggcaccctcctccaagagcacctctgggggcacagc | dvqitqspsylaaspgetiti ncrasksiskylawyqekp gkankllihsgstlqsgipsr fsgsgsgtdftltisslepedf amyycqqhieypwtfggg tkleikraggggsggggssg gggseiqlqqsgpelvkpg asvkmsckasgytftdyy mhwvkqngeslewigy fnpyndytryqnfngkatl tvdksssstaymqlnsltsed safyycarsdgyydamdy wgqgtsvtvsssepkssdk thtcppcpapeaagapsvfl fppkpkdtlmisrtpevtcv vvdvshedpevkfnwyv dgvevhnaktkpreeqyns tyrvvsvltvlhqdwlngka yacavsnkalpapiektisk akgqprepqvytlppsrdel tknqvsltclvkgfypsdia vewesngqpennykttpp vldsdgsfflyskltvdksr wqqgnvfscsvmhealhn hytqkslslspgksrastkg psvfplapssksstsggtaalg clvkdyfpepvtvswnsga ltsgvhtfpavlqssglysls svvtvpssslgtqtyicnvnh kpsntkvdkkv | SEQ ID NO: 44 (SEQ ID NO: 46) |

TABLE 3-continued

Binding Polypeptide Sequences and Components

| Name | Nucleotide Sequence | Amino Acid Sequence | SEQ ID NOs: (amino acid) |
|------|---------------------|---------------------|--------------------------|
| | ggccctgggctgcctggtcaaggactacttccccgagccggtgacggtgtc gtggaactcaggcgccctgaccagcggcgtgcacaccttcccggctgtcct acagtcctcaggactctactccctcagcagcgtggtgaccgtgccctccagc agcttgggcacccagacctacatctgcaacgtgaatcacaagcccagcaac accaaggtggacaagaaagtttga | | |
| TSC093 Interceptor (Cris7 scFv-Fc-Cκ$_{YAE}$) | atggaagcaccagcgcagcttctcttcctcctgctactctggctcccagatac caccggtcaggtccagctggtgcagtctggggggcggagtggtgcagcctg ggcggtcactgaggctgtcctgcaaggcttctggctacacctttactagatcta cgatgcactgggtaaggcaggcccctggaaagggtctggaatggattgat acattaatcctagcagtgcttatactaattacaatcagaaattcaaggacaggtt cacaatcagcgacaaatccaagagcacagccttcctgcagatggacagt cctgaggcccgaggacaccggcgtctatttctgtgcacgccccaagtcca ctatgattacaacgggtttccttactggggccaagggactccgtcactgtctc tagcggtggcggagggtctggggggtggcggatccggaggtggtggctctg cacaagacatccagatgacccagtctccaagcacctgtctgcaagcgtgg gggacagggtcaccatgacctgcagtgccagctcaagtgtaagtacatgaa ctggtaccagcagaagcccggcaaggcccccaaaagatggatttatgactc atccaaactggcttctggagtccctgctcgcttcagtggcagtgggtctggga ccgactatactctcacaatcagcagcctgcagcctgaagatttcgccactt tactgccagcagtggagtcgtaaccccacccacgttcggaggggggaccaa gctacaaattacacgctcgagtgagcccaaatcttctgacaaaactcacacat gcccaccgtgcccagcacctgaagccgcgggtgcaccgtcagtcttcctctt ccccccaaaacccaaggacaccctcatgatctcccggaccctgaggtcac atgcgtggtggtggacgtgagccacgaagaccctgaggtcaagttcaactg gtacgtggacggcgtggaggtgcataatgccaagacaaagccgcgggag gagcagtacaacagcacgtaccgtgtggtcagcgtcctcaccgtcctgcacc aggactggctgaatggcaaggagtacgcgtgcgcggtctccaacaaagcc ctcccagccccatcgagaaaacctttcccagccccatcgagaaaaccatctccaaagccaaagggcagccccgagaaccacaggtgtacaccctgccccatcccgggatgagctgaccaagaa ccaggtcagcctgacctgcctggtcaaaggcttctatccaagcgacatcgcc gtggagtgggagagcaatgggcagccggagaacaactacaagaccacg cctcccgtgctggactccgacggctccttcttcctctacagcaagctcaccgtg gacaagagcaggtggcagcaggggaacgtcttctcatgctccgtgatgcat gaggctctgcacaaccactacacgcagaagagcctctccctgtctccgggta aatctagaactgtggctgcaccatctgtcttcatcttcccgccatctgatgagca gttgaaatctggaactgcctctgtgtgtgcctgctgaatttactctatcccaga gaggccaaagtacagtggaaggtggataacgccctccaatcggtaactcc caggagagtgccacagagcaggacagcaaggacagcacctacagcctca gcagcgagctgacgctgagcaaagcagactacgagaaacacaaagtctac gcctgcgaagtcacccatcagggcctgagctcgcccgtcacaaagagcttc aacaggggagagtga | qvqlvqsggggvvqpgrslrl sckasgyftfrstmhwvrq apgkglewigyinpssayt nynqkfkdrftisadksst aflqmdslrpedtgvyfcar pqvhydyngfpywgqgt pvtvssggggsggggsgg ggsaqdiqmtqspsslsas vgdrvtmtcsassssvsymn wyqqkpgkapkrwiydss klasgvparfsgsgsgtdytl tisslqpedfatyycqqwsr nppftfggtklqitrssepks sdkthtcppcpapeaagap svflfppkpkdtlmisrtpe vtcvvvdvshedpevkfn wyvdgvevhnaktkpree qynstyvvsvltvlhqdwl ngkayacavsnkalpapie ktiskakgqprepqvytlpp srdeltknqvsltclvkgfyp sdiavewesngqpennyk ttppvldsdgsfflysklvd ksrwqqgnvfscsvmhea lhnhytqkslslspgksrtva apsvfifppsdeqlksgtas vvcllnyfypreakvqwkv dnalqsgnsqesateqdsk dstyslsseltlskadyekhk vyacevthqglsspvtksfn rge | SEQ ID NO: 45 (SEQ ID NO: 47) |
| TSC194 Scorpion (huVL-VH#2 107-1A4 scFv-Fc-Cris7 scFv) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctcctgatccattctg gatctactttgcaatcaggggtcccatctcggttcagtggcagtggatctggg acagaatttactctcaccatcagcagcctgcagcctgaagattttgccactttatt actgtcaacagcatatgataccccgtggacgttcggccaagggaccaaggt ggaaatcaaacgaggtggcggaggttctggggtggcggatccggaggt ggtggctctcaggtccagctggtacagtctggggctgaggtgaagaagcct ggggcttcagtgaaggtctcctgcaaggcttctggatacacatttcactgacta ctatatgcactgggtgcgacaggcccctggacaaggcttgagtggatggg aatattttaatccttataatgattatactagatacgcacagaagttccagggcaga gtcaccatgaccagggacacgtctatcagcacagcctacatggagctgagc agcctgagatctgacgacacggccgtgtattactgtgcaagatcggatggtta ctacgatgctatggactactggggccaagggaccacggtcaccgtctcctcg agtgagcccaaatcttctgacaaaactcacacatgcccaccgtgcccagcac ctgaagccgcgggtgcaccgtcagtcttcctcttccccccaaaacccaagga caccctcatgatctcccggacccctgaggtcacatgcgtggtggtggacgtg agccacgaagaccctgaggtcaagttcaactggtacgtggacggcgtgga ggtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagcccctcccagccccatcgagaaa accatctccaaagccaaagggcagccccgagaaccacaggtgtacaccctc cccccatcccgggatgagctgaccaagaaccaggtcagcctgacctgcct ggtcaaaggcttctatccaagcgacatcgccgtggagtgggagagcaatgg gcagccggagaacaactacaagaccacgcctcccgtgctggactccgacg gctccttcttcctctacagcaagctcaccgtggacaagagcaggtggcagcaggggaacgtcttctcatgctccgtgatgcatgaggctctgcacaaccactaca cgcagaagagcctctccctgtctccgggtcagaggcacaacaattcttccctc gaatacaggaactcagatggcaggtcattctccgaattctcaggtccagctgg tgcagtctgggggcggagtggtgcagcctgggcggtcactgaggctgtcct gcaaggcttctggctacacctttactagatctacgatgcactgggtaaggcag | diqmtqspsamsasvgdr vtitcraskssiskylawfqqk pgkvpklrihsgstlqsgvp srfsgsgsgteftltisslqpe dfatyycqqhieypwtfgq gtkveikrggggsggggsg ggsqvqlvqsgaevkkp gasvkvsckasgytftdyy mhwvrqapgqglewmg yfnpyndytryaqkfqgrv tmtrdtsistaymelsslrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyvvsvltvlhqdwlng kayacavsnkalpapiekti skakgqprepqvytlppsr deltknqvsltclvkgfyps diavewesngqpennyktt ppvldsdgsfflysklvdk srwqqgnvfscsvmheal hnhytqkslslspgqrhnns slntgtqmaghspnsqvql vqsgggvvqpgrslsrlscka sgytftrstmhwvrqapgk glewigyinpssaytapnynq kfkdrftisadksktstaflqm dslrpedtgvyfcarpqvhy dyngfpywgqgtpvtvss | SEQ ID NO: 48 (SEQ ID NO: 49) |

TABLE 3-continued

Binding Polypeptide Sequences and Components

| Name | Nucleotide Sequence | Amino Acid Sequence | SEQ ID NOs: (amino acid) |
|------|---------------------|---------------------|--------------------------|
| | gcccctggaaagggtctggaatggattggatacattaatcctagcagtgcttat actaattacaatcagaaattcaaggacaggttcacaatcagcgcagacaaatc caagagcacagccttcctgcagatggacagcctgagggcccgaggacaccg gcgtctatttctgtgcacggccccaagtccactatgattacaacgggtttcctta ctggggccaagggactcccgtcactgtctctagcggtggcggagggtctgg gggtggcggatccggaggtggtggctctgcacaagacatccagatgaccc agtctccaagcagcctgtctgcaagcgtggggacagggtcaccatgacct gcagtgccagctcaagtgtaagttacatgaactggtaccagcagaagccg gcaaggccccaaaagatggatttatgactcatccaaactggcttctggagtc cctgctcgcttcagtggcagtgggtctgggaccgactataccctcacaatcag cagcctgcagcccgaagatttcgccacttattactgccagcagtggagtcgta acccacccacgttcggaggggggaccaagctacaaattacacgataa | ggggsggggsggggsaqd iqmtqspsslsasvgdrvt mtcsassssvsymnwyqq kpgkapkrwiydssklasg vparfsgsgsgtdytltisslq pedfatyycqqwsmpptf gggtklqitr | |
| TSC199 Scorpion (huVL-VH#1 107-1A4 scFv-Fc-Cris7 scFv) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctcccgcatccattctg gatctactttgcaatcaggggtcccatctcggttcagtggcagtggatctggg acagaatttactctcaccatcagcagcctgcagcctgaagattttgcaacttat actgtcaacagcatattgaatacccgtggacgttcggccaagggaccaaggt ggaaatcaaacgaggtggcggagggtctggggggtggcggatccggaggt ggtggctctgaggtccagctggtacagtctggggctgaggtgaagaagcct ggggctacagtgaagatctcctgcaaggcttctggatacacattcactgacta ctacatgcactgggtgcaacaggcccctggaaaggggcttgagtggatggg atattttaatccttataatgattatactagatacgcagagaagttccagggcaga gtcaccataaccgcggacacgtctacagacacagccacatggagctgagc agcctgagatctgaggacacggccgtgtattactgtgcaagatcggatggtt actacgatgctatggactactgggtcaaggaaccacagtcaccgtctcctc gagtgagcccaaatcttctgacaaaactcacacatgcccaccgtgcccaagg acacccctcatgatctcccggacccctgaggtcacatgcgtggtggtggacgt gagccacgaagaccctgaggtcaagttcaactggtacgtggacggcgtgga ggtgcataatgccaagacaaagccgcggaggagcagtacaacagcacgt accgtgtggtcagcgtcctcaccgtcctgcaccaggactggctgaatggcaa ggcgtacgcgtgcgcggtctccaacaaagccctcccagcccccatcgaga aaaccatctccaaagccaaagggcagccccgagaaccacaggtgtacacc ctgcccccatcccgggatgagctgaccaagaaccaggtcagcctgacctgc ctggtcaaaggcttctatccaagcgacatcgccgtggagtgggagagcaat gggcagccggagaacaactacaagaccacgcctcccgtgctggactccga cggctccttcttcctctacagcaagctcaccgtggacaagagcaggtggcag caggggaacgtcttctcatgctccgtgatgcatgaggctctgcacaaccacta cacgcagaagagcctctccctgtctccgggtcagaggcacaacaattcttcc ctgaatacaggaactcagatggcaggtcattctccgaattctcaggtccagct ggtgcagtctggggggcggagtggtgcagcctgggcggtcactgaggctgt cctgcaaggcttctggctacacctttactagatactgtcactgggtaagg caggccctggaaagggtctggaatggattggatacattaatcctagcagtg cttatactaattacaatcagaaattcaaggacaggttcacaatcagcgcagac aaatccaagagcacagccttcctgcagatggacagcctgagggcccgagga caccggcgtctatttctgtgcacggccccaagtccactatgattacaacgggtt tccttactggggccaagggactcccgtcactgtctctagcggtggcggagg gtctggggggtggcggatccggaggtggtggctctgcacaagacatccagat gacccagtctccaagcagcctgtctgcaagcgtggggacagggtcaccat gacctgcagtgccagctcaagtgtaagttacatgaactggtaccagcagaag ccgggcaaggccccaaaagatggatttatgactcatccaaactggcttctg gagtccctgctcgcttcagtggcagtgggtctgggaccgactataccctcac aatcagcagcctgcagcccgaagatttcgccacttattactgccagcagtgg agtcgtaacccacccacgttcggaggggggaccaagctacaaattacacga taa | diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsevqlvqsgaevkkp gatvkiscasgytftdyy mhwvqqapgkglewmg yfnpyndytryaekfqgrvt itadtstdtaymelsslrsedt avyycarsdgyydamdy wgqgttvtvsssepkssdkt htcppcpapeaagapsvflf ppkpkdtlmisrtpevtcvv vdvshedpevkfnwyvd gvevhnaktkpreeqynst yrvvsvltvlhqdwlngka yacavsnkalpapiektisk akgqprepqvytlppsrdel tknqvsltclvkgfypsdia vewesngqpennykttpp vldsdgsfflyskltvdksr wqqgnvfscsvmhealhn hytqkslslspgqrhnnssl ntgtqmaghspnsqvlv qsggggvvqpgrslrlsckas gytftrstmhwvrqapgkg lewigyinpssaytnynqk fkdrftisadkskstaflqmd slrpedtgvyfcarpqvhyd yngfpywgqgtpvtvssg gggsggggsggggsaqdi qmtqspsslsasvgdrvtm tcsassssvsymnwyqqkp gkapkrwiydssklasgvp arfsgsgsgtdytltisslqpe dfatyycqqwsrnppptfgg gtklqitr | SEQ ID NO: 50 (SEQ ID NO: 51) |
| TSC125 Interceptor (Cris7 scFv-Fc-CH1) | atggaagcaccagcgcagcttctcttcctcctgctactctggctcccagatac caccggtcaggtccagctggtgcagtctggggggcggagtggtgcagcctg ggcggtcactgaggctgtcctgcaaggcttctggctacacctttactagatcta cgatgcactgggtaaggcaggcccctggaaaggggcttgaatggatttgat acattaatcctagcagtgcttatactaattacaatcagaaattcaaggacaggtt cacaatcagcgcagacaaatccaagagcacagccttcctgcagatggacag cctgagggcccgaggacaccggcgtctatttctgtgcacggccccaagtcca ctatgattacaacgggtttccttactggggccaagggactcccgtcactgtctc tagcggtggcggagggtctggggggtggcggatccggaggtggtggctctg cacaagacatccagatgacccagtctccaagcagcctgtctgcaagcgtgg gggacagggtcaccatgacctgcagtgccagctcaagtgtaagttacatgaa ctggtaccagcagaagccgggcaaggccccaaaagatggatttatgactc atccaaactggcttctggagtccctgctcgcttcagtggcagtgggtctggga ccgactataccctcacaatcagcagcctgcagcccgaagatttcgccacttat tactgccagcagtggagtcgtaacccacccacgttcggaggggggaccaa gctacaaattacacgctcgagtgagcccaaatcttctgacaaaactcacacat | qvqlvqsggggvvqpgrslrl sckasgytftrstmhwvrq apgkglewigyinpssayt nynqkfkdrftisadkskst aflqmdslrpedtgvyfcar pqvhydyngfpywgqgt pvtvssggggsggggsggg ggsaqdiqmtqspsslsas vgdrvtmtcsassssvsymn wyqqkpgkapkrwiydss klasgvparfsgsgsgtdytl tisslqpedfatyycqqwsr npptfgggtklqitrssepks sdkthtcppcpapeaagap svflfppkpkdtlmisrtpe vtcvvvdvshedpevkfn | SEQ ID NO: 52 (SEQ ID NO: 57) |

TABLE 3-continued

Binding Polypeptide Sequences and Components

| Name | Nucleotide Sequence | Amino Acid Sequence | SEQ ID NOs: (amino acid) |
|---|---|---|---|
| | gcccaccgtgcccagcacctgaagccgcgggtgcaccgtcagtcttcctctt<br>cccccaaaacccaaggacacccctcatgatctcccggacccctgaggtcac<br>atgcgtggtggtggacgtgagccacgaagaccctgaggtcaagttcaactg<br>gtacgtggacggcgtggaggtgcataatgccaagacaaagccgcgggag<br>gagcagtacaacagcacgtaccgtgtggtcagcgtcctcaccgtcctgcacc<br>aggactggctgaatggcaaggcgtacgcgtgcgcggtctccaacaaagcc<br>ctcccagcccccatcgagaaaaccatctccaaagccaaagggcagccccg<br>agaaccacaggtgtacaccctgcccccatcccgggactgagctgaccaagaa<br>ccaggtcagcctgacctgcctggtcaaaggcttctatccaagcgacatcgcc<br>gtggagtgggagagcaatgggcagccggagaacaactacaagaccacgc<br>ctcccgtgctggactccgacggctccttcttcctctacagcaagctcaccgtg<br>gacaagagcaggtggcagcaggggaacgtcttctcatgctccgtgatgcat<br>gaggctctgcacaaccactacacgcagaagagcctctccctgtctccgggta<br>aatctagagcctccaccaagggcccatcggtcttccccctggcaccctcctc<br>caagagcacctctgggggcacagcggccctgggctgcctggtcaaggact<br>acttccccgagccggtgacggtgtcgtggaactcaggcgccctgaccagcg<br>gcgtgcacaccttcccggctgtcctacagtcctcaggactctactccctcagc<br>agcgtggtgaccgtgccctccagcagcttgggcacccagacctacatctgc<br>aacgtgaatcacaagcccagcaacaccaaggtggacaagaaagtttga | wyvdgvevhnaktkpree<br>qynstyrvvsvltvlhqdwl<br>ngkayacavsnkalpapie<br>ktiskakgqprepqvytlpp<br>srdeltknqvsltclvkgfyp<br>sdiavewesngqpennyk<br>ttppvldsdgsfflyskltvd<br>ksrwqqgnvfscsvmhea<br>lhnhytqkslslspgksrast<br>kgpsvfplapssksstsggta<br>algclvkdyfpepvtvswn<br>sgaltsgvhtfpavlqssgly<br>slssvvtvpssslgtqtyicn<br>vnhkpsntkvdkkv | |
| TSC192 Interceptor (huVL-VH#2 107-1A4 scFv-Fc-Cκ$_{YAE}$) | atggaagcaccagcgcagcttctcttcctcctgctactctggctcccagatac<br>caccggtgatatccagatgacccagtctccatccgccatgtctgcatctgtag<br>gagacagagtcaccatcacttgccgggcgagtaagagcattagcaaatattt<br>agcctggtttcagcagaaaccagggaaagttcctaagctccgcatccattctg<br>gatctactttgcaatcaggggtcccatctcggttcagtggcagtggatctggg<br>acagaattttactctcaccatcagcagcctgcagcctgaagattttgcaacttatt<br>actgtcaacagcatattgaatacccgtggacgttcggccaagggaccaaggt<br>ggaaatcaaacgaggtggcggaggtctgggggtggcggatccggaggt<br>ggttggctctcgaggtccagctggtacagtctggggctgaggtgaagaagcct<br>ggggcttcagtgaaggtctcctgcaaggcttctggatacacattcactgacta<br>ctacatgcactgggtgcgacaggcccctggacaaggcttgagtggatggg<br>ataftttaatcctataatgattatactagatacgcacagaagttccagggcaga<br>gtcaccatgaccagggacgatctatcagcacagcctacatggagctgagc<br>agcctgagatctgacgacacggccgtgtattactgtgcaagatcggatggtta<br>ctacgatgctatggactactggggtcaaggaaccacagtcaccgtctcctcg<br>agtgagcccaaatcttctgacaaaactcacacatgcccaccgtgcccagcac<br>ctgaagcgcgggtgcaccgtcagtcttcctcttccccccaaaacccaagga<br>caccctcatgatctcccggacccctgaggtcacatgcgtggtggtggacgtg<br>agccacgaagaccctgaggtcaagttcaactggtacgtggacggcgtggag<br>gtgcataatgccaagacaaagccgcgggaggagcagtacaacagcacgta<br>ccgtgtggtcagcgtcctcaccgtcctgcaccaggactggctgaatggcaag<br>gcgtacgcgtgcgcggtctccaacaaagcccttccagcccccatcgagaaa<br>accatctccaaagccaaagggcagccccgagaaccacaggtgtacaccct<br>gcccccatcccgggatgagctgaccaagaaccaggtcagcctgacctgcct<br>ggtcaaaggcttctatccaagcgacatcgccgtggagtgggagagcaatgg<br>gcagccggagaacaactacaagaccacgcctcccgtgctggactccgacg<br>gctccttcttcctctacagcaagctcaccgtggacaagagcaggtggcagca<br>ggggaacgtcttctcatgctccgtgatgcatgaggctctgcacaaccactaca<br>cgcagaagagcctctccctgtctccgggtaaatctagagctgtggctgcacc<br>atctgtcttcatcttcccgccatctgatgagcagttgaaatctggaactgcctct<br>gttgtgtgcctgctgaattacttctatcccagagaggccaaagtacagtggaa<br>ggtggataacgcctccaatcgggtaactcccaggagagtgccacagagaa<br>gacagcaaggacagcacctacagcctcagcagcgagctgacgctgagc<br>aaagcactacgagaaacacaaagtctacgcctgcgaagtcacccatcag<br>ggcctgagctcgcccgtcacaaagagcttcaacaggggagagtga | diqmtqspsamsasvgdr<br>vtitcrasksiskylawfqqk<br>pgkvpklrihsgstlqsgvp<br>srfsgsgsgteftltisslqpe<br>dfatyycqqhieypwtfgq<br>gtkveikrggggsggggsg<br>gggsqvqlvqsgaevkkp<br>gasvkvsckasgytftdyy<br>mhwvrqapgqglewmg<br>yfnpyndytryaqkfqgrv<br>tmtrdtsistaymelsslrsd<br>dtavyycarsdgyydamd<br>ywgqgttvtvsssepkssd<br>kthtcppcpapeaagapsv<br>flfppkpkdtlmisrtpevtc<br>vvvdvshedpevkfnwy<br>vdgvevhnaktkpreeqy<br>nstyrvvsvltvlhqdwlng<br>kayacavsnkalpapiekti<br>skakgqprepqvytlppsr<br>deltknqvsltclvkgfyps<br>diavewesngqpennyktt<br>ppvldsdgsfflyskltvdk<br>srwqqgnvfscsvmheal<br>hnhytqkslslspgksrtva<br>apsvfifppsdeqlksgtas<br>vvcllnnyfypreakvqwkv<br>dnalqsgnsqesateqdsk<br>dstyslsseltlskadyekhk<br>vyacevthqglsspvtksfn<br>rge | SEQ ID NO: 53<br>(SEQ ID NO: 58) |
| TSC193 Interceptor (huVL-VH#1 107-1A4 scFv-Fc-Cκ$_{YAE}$) | atggaagcaccagcgcagcttctcttcctcctgctactctggctcccagatac<br>caccggtgatatccagatgacccagtctccatccgccatgtctgcatctgtag<br>gagacagagtcaccatcacttgccgggcgagtaagagcattagcaaatattt<br>agcctggtttcagcagaaaccagggaaagttcctaagctccgcatccattctg<br>gatctactttgcaatcaggggtcccatctcggttcagtggcagtggatctggg<br>acagaattttactctcaccatcagcagcctgcagcctgaagattttgcaacttatt<br>actgtcaacagcatattgaatacccgtggacgttcggccaagggaccaaggt<br>ggaaatcaaacgaggtggcggaggtctgggggtggcggatccggaggt<br>ggttggctctgaggtccagctggtacagtctggggctgaggtgaagaagcct<br>ggggcctacgtgaaggtctcctgcaaggcttctggatacacattcactgacta<br>ctacatgcactgggtgcaacaggcccctggaaaaggcttgagtggatggg<br>ataftttaatcctataatgattatactagatacgcacagaagttccagggcaga<br>gtcaccataaccgcggacacgtctacagacacagcctacatggagctgagc<br>agcctgagatctgaggacacggccgtgtattactgtgcaagatcggatggtta<br>ctacgatgctatggactactggggtcaaggaaccacagtcaccgtctcctc<br>gagtgagcccaaatcttctgacaaaactcacacatgcccaccgtgcccagca<br>cctgaagcgcgggtgcaccgtcagtcttcctcttccccccaaaacccaagg<br>acaccctcatgatctcccggacccctgaggtcacatgcgtggtggtggacgtg<br>agccacgaagaccctgaggtcaagttcaactggtacgtggacggcgtgga | diqmtqspsamsasvgdr<br>vtitcrasksiskylawfqqk<br>pgkvpklrihsgstlqsgvp<br>srfsgsgsgteftltisslqpe<br>dfatyycqqhieypwtfgq<br>gtkveikrggggsggggsg<br>gggsevqlvqsgaevkkp<br>gatvkisckasgytftdyy<br>mhwvqqapgkglewmg<br>yfnpyndytryaekfqgrvt<br>itadtstdtaymelsslrsedt<br>avyycarsdgyydamdy<br>wgqgttvtvsssepkssdkt<br>htcppcpapeaagapsvflf<br>ppkpkdtlmisrtpevtcvv<br>vdvshedpevkfnwyvd<br>gvevhnaktkpreeqynst<br>yrvvsvltvlhqdwlngka<br>yacavsnkalpapiektisk | SEQ ID NO: 54<br>(SEQ ID NO: 59) |

TABLE 3-continued

Binding Polypeptide Sequences and Components

| Name | Nucleotide Sequence | Amino Acid Sequence | SEQ ID NOs: (amino acid) |
|---|---|---|---|
| | ggtgcataatgccaagacaaagccgcgggaggagcagtacaacagcacgt accgtgtggtcagcgtcctcaccgtcctgcaccaggactggctgaatggcaa ggcgtacgcgtgcgcggtctccaacaaagccctcccagcccccatcgaga aaaccatctccaaagccaaagggcagccccgagaaccacaggtgtacacc ctgcccccatcccgggatgagctgaccaagaaccaggtcagcctgacctgc ctggtcaaaggcttctatcccagcgacatcgccgtggagtgggagagcaat gggcagccggagaacaactacaagaccacgcctcccgtgctggactccga cggctccttcttcctctacagcaagctcaccgtggacaagagcaggtggcag caggggaacgtcttctcatgctccgtgatgcatgaggctctgcacaaccacta cacgcagaagagcctctccctgtctccgggtaaatctagaactgtggctgca ccatctgtcttcatcttcccgccatctgatgagcagttgaaatctggaactgcct ctgttgtgtgcctgctgaattacttctatcccagagaggccaaagtacagtgga aggtggataacgcccctccaatcgggtaactcccaggagagtgccacagagc aggacagcaaggacagcacctacagcctcagcagcgagctgacgctgag caaagcagactacgagaaacacaaagtctacgcctgcgaagtcacccatca gggcctgagctcgcccgtcacaaagagcttcaacaggggagagtga | akgqprepqvytlppsrdel tknqvsltclvkgfypsdia vewesngqpennykttpp vldsdgsfflyskltvdksr wqqgnvfscsvmhealhn hytqkslslspgksrtvaaps vfifppsdeqlksgtasvvcl lnyfypreakvqwkvdnal qsgnsqesateqdskdstys lsseltlskadyekhkvyac evthqglsspvtksfnrge | |
| TSC195 Interceptor (huVL-VH#2 107-1A4 scFv-Fc-CH1) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctccgcatccattctg gatctactttgcaatcaggggtcccatctcggttcagtggcagtggatctggg acagaatttactctcaccatcagcagcctgcagcctgaagattttgcaacttat actgtcaacagcatattgaataccccgtggacgttcggccaagggaccaagt ggaaatcaaacgaggtggcggaggttctggggggtggcggatccggaggt ggtggctctcaggtccagctggtacagtctggggctgaggtgaagaagcct gggggcttcagtgaaggttcctgcaaggcttctggatacacattcactgacta ctacatgcactgggtgcgacaggcccctggacaagggcttgagtggatggg atattttaatccttataatgattatactagatacgcagagaagttccagggcaga gtcaccatgaccagggacacgtctatcagcacagcctacatggagctgagc agcctgagatctgacgacacggccgtgtattactgtgcaagatcggatggtta ctacgatgctatggactactggggtcaaggaaccacagtcaccgtctcctcg agtgagcccaaatcttctgacaaaactcacacatgcccaccgtgcccagca ctgaagccgcgggtgcaccgtcagtcttcctcttccccccaaaaccccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgt accgtgtggtcagcgtcctcaccgtcctgcaccaggactggctgaatggcaag gcgtacgcgtgcgcggtctccaacaaagccctcccagcccccatcgagaaa accatctccaaagccaaagggcagccccgagaaccacaggtgtacaccct gcccccatcccgggatgagctgaccaagaaccaggtcagcctgacctgcct ggtcaaaggcttctatcccagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtaaatctagaactccaccaaggg cccatcggtcttccccctggcaccctcctccaagagcacctctgggggcaca gcggccctgggctgcctggtcaaggactacttccccgagccggtgacggtg tcgtggaactcaggcgccctgaccagcggcgtgcacaccttcccggctgtc ctacagtcctcaggactctactccctcagcagcgtggtgaccgtgccctcca gcagcttgggcacccagacctacatctgcaacgtgaatcacaagcccagca acaccaaggtggacaagaaagtttga | diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvsckasgytftdyy mhwvrqapgqglewmg yfnpyndytryaqkfqgrv tmtrdtsistaymelsslrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennyktt ppvldsdgsfflyskltvdk srwqqgnvfscsvmheal hnhytqkslslspgksrast kgpsvflplapsskstsggta algclvkdyfpepvtvswn sgaltsgvhtfpavlqssgly slsssvvtvpssslgtqtyicn vnhkpsntkvdkkv | SEQ ID NO: 55 (SEQ ID NO: 60) |
| TSC196 Interceptor (huVL-VH#1 107-1A4 scFv-Fc-CH1) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctccgcatccattctg gatctactttgcaatcaggggtcccatctcggttcagtggcagtggatctggg acagaatttactctcaccatcagcagcctgcagcctgaagattttgcaacttat actgtcaacagcatattgaataccccgtggacgttcggccaagggaccaagt ggaaatcaaacgaggtggcggagggtctggggggtggcggatccggaggt ggtggctctgaggtccagctggtacagtctggggctgaggtgaagaagcct ggggctacagtgaagatcctctgcaaggcttctggatacacattcactgacta ctacatgcactgggtgcaacaggcccctggaaaaggcttgagtggatggg atattttaatccttataatgattatactagatacgcagagaagttccagggcaga gtcaccataaccgcggacacgtctacagacacagcctacatggagctgagc agcctgagatctgaggacacggccgtgtattactgtgcaagatcggatggtt actacgatgctatggactactggggtcaaggaaccacagtcaccgtctcctc gagtgagcccaaatcttctgacaaaactcacacatgcccaccgtgcccagca cctgaagccgcgggtgcaccgtcagtcttcctcttccccccaaaaccccaagg acaccctcatgatctcccggacccctgaggtcacatgcgtggtggtggacgtg agccacgaagaccctgaggtcaagttcaactggtacgtggacggcgtgga ggtgcataatgccaagacaaagccgcgggaggagcagtacaacagcacgt accgtgtggtcagcgtcctcaccgtcctgcaccaggactggctgaatggcaa ggcgtacgcgtgcgcggtctccaacaaagccctcccagcccccatcgaga | diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsevqlvqsgaevkkp gatvkisckasgytftdyy mhwvqqapgkglewmg yfnpyndytryaekfqgrvt itadtstdtaymelsslrsedt avyycarsdgyydamdy wgqgttvtvsssepkssdkt htcppcpapeaagapsvflf ppkpkdtlmisrtpevtcvv vdvshedpevkfnwyvd gvevhnaktkpreeqynst yrvvsvltvlhqdwlngka yacavsnkalpapiektisk akgqprepqvytlppsrdel tknqvsltclvkgfypsdia vewesngqpennykttpp | SEQ ID NO: 56 (SEQ ID NO: 61) |

TABLE 3-continued

Binding Polypeptide Sequences and Components

| Name | Nucleotide Sequence | Amino Acid Sequence | SEQ ID NOs: (amino acid) |
|---|---|---|---|
| | aaaccatctccaaagccaaagggcagccccgagaaccacaggtgtacacc ctgcccccatcccgggatgagctgaccaagaaccaggtcagcctgacctgc ctggtcaaaggcttctatccaagcgacatcgccgtggagtgggagagcaat gggcagccggagaacaactacaagaccacgcctcccgtgctggactcc ggctccttcttcctctacagcaagctcaccgtggacaagagcaggtggcag caggggaacgtcttctcatgctccgtgatgcatgaggctctgcacaaccacta cacgcagaagagcctctccctgtctccgggtaaatctagagcctccaccaag ggcccatcggtcttccccctggcaccctcctccaagagcacctctgggggca gcggccctgggctgcctggtcaaggactacttccccgagccggtgacgg tgtcgtggaactcaggcgccctgaccagcggcgtgcacaccttcccggctgt cctacagtcctcaggactctactccctcagcagcgtggtgaccgtgccctca gcagcttgggcacccagacctacatctgcaacgtgaatcacaagcccagca acaccaaggtggacaagaaagtttga | vldsdgsfflyskltvdksr wqqgnvfscsvmhealhn hytqkslslspgksrastkg psvfplapsskstsggtaalg clvkdyfpepvtvswnsga ltsgvhtfpavlqssglyslss vvtvpssslgtqtyicnvnh kpsntkvdkkv | |
| TSC210 human- ized SMIP (human VH#2-VL scFv- Fc) | atggaagcaccagcgcagcttctcttcctcctgctactctggctcccagatac caccggtcaggtccagctggtacagtctggggctgaggtgaagaagcctg ggcttcagtgaaggtctcctgcaaggcttctggatacacattcactgactacta catgcactgggtgcgacaggcccctggacaagggcttgagtggatgggata ttttaatcctataatgattatactagatacgcacagaagttccagggcagagtc accatgaccagggacacgtctatcagcacagcctacatggagctgagcagc ctgagatctgacgacacggccgtgtattactgtgcaagatcggatggttacta cgatgctatggactactggggtcaaggaaccacagtcaccgtctcctcaggt ggcggaggtctgggggtggcggatccgaggtggtggctctgatatcca gatgacccagtctccatccgccatgtctgcatctgtaggagacagagtcacc atcacttgccgggcgagtaagagcattagcaaatatttagcctggtttcagca gaaaccagggaaagttcctaagctccgcatccattctggatctactttgcaatc aggggtcccatctcggttcagtggcagtggatctgggacagaatttactctca ccatcagcagcctgcagcctgaagattttgcaacttattactgtcaacagcata ttgaatacccggacgttcggccaagggaccaaggtggaaatcaaacgcg cctcgagtgagcccaaatcttctgacaaaactcacacatgccaccgtgccc agcacctgaagccgcgggtgcaccgtcagtcttcctcttccccccaaaaccc aaggacaccctcatgatctcccggacccctgaggtcacatgcgtggtggtgg acgtgagccacgaagaccctgaggtcaagttcaactggtacgtggacggcg tggaggtgcataatgccaagacaaagccgcgggaggagcagtacaacagc acgtaccgtgtggtcagcgtcctcaccgtcctgcaccaggactggctgaatg gcaaggcgtacgcgtgcgcggtctccaacaaagccctcccagccccatc gagaaaccatctccaaagccaaagggcagccccgagaaccacaggtgta caccctgcccccatcccgggatgagctgaccaagaaccaggtcagcctgac ctgcctggtcaaaggcttctatccagcgacatcgccgtggagtgggagag caatgggcagccggagaacaactacaagaccacgcctcccgtgctggact ccgacggctccttcttcctctacagcaagctcaccgtggacaagagcaggtg gcagcaggggaacgtcttctcatgctccgtgatgcatgaggctctgcacaac cactacacgcagaagagcctctccctgtctccgggtaaatga | qvqlvqsgaevkkpgasv kvsckasgytftdyymhw vrqapgqglewmgyfnp yndytryaqkfqgrvtmtr dtsistaymelsslrsddtav yycarsdgyydamdywg qgttvtvssggggsggggs ggggsdiqmtqspsamsa svgdrvtitcrasksiskyla wfqqkpgkvpklrihsgstl qsgvpsrfsgsgsgteftltis slqpedfatyycqqhieyp wtfgqgtkveikrassepks sdkthtcppcpapeaagap svflfppkpkdtlmisrtpe vtcvvvdvshedpevkfn wyvdgvevhnaktkpree qynstyrvvsvltvlhqdwl ngkayacavsnkalpapie ktiskakgqprepqvytlpp srdeltknqvsltclvkgfyp sdiavewesngqpennyk ttppvldsdgsfflyskltvd ksrwqqgnvfscsvmhea lhnhytqkslslspgk | SEQ ID NO: 69 (SEQ ID NO: 70) |
| TSC211 human- ized SMIP (human VH#1-VL scFv- Fc) | atggaagcaccagcgcagcttctcttcctcctgctactctggctcccagatac caccggtgaggtccagctggtacagtctggggctgaggtgaagaagcctg ggctacagtgaagatctcctgcaaggcttctggatacacattcactgactact acatgcactgggtgcaacaggcccctggaaaagggcttgagtggatgggat attttaatcctataatgattatactagatacgcagaagttccagggcagagt caccataaccgcggacacgtctacagacacagcctacatggagctgagcag cctgagatctgaggacacggccgtgtattactgtgcaagatcggatggttact acgatgctatggactactggggtcaaggaaccacagtcaccgtctcctcagg tggcggaggtctgggggtggcggatccgaggtggtggctctgatatcca gatgacccagtctccatccgccatgtctgcatctgtaggagacagagtcacc atcacttgccgggcgagtaagagcattagcaaatatttagcctggtttcagca gaaaccagggaaagttcctaagctccgcatccattctggatctactttgcaatc aggggtcccatctcggttcagtggcagtggatctgggacagaatttactctca ccatcagcagcctgcagcctgaagattttgcaacttattactgtcaacagcata ttgaatacccggacgttcggccaagggaccaaggtggaaatcaaacgag cctcgagtgagcccaaatcttctgacaaaactcacacatgccaccgtgccc agcacctgaagccgcgggtgcaccgtcagtcttcctcttccccccaaaaccc aaggacaccctcatgatctcccggacccctgaggtcacatgcgtggtggtgg acgtgagccacgaagaccctgaggtcaagttcaactggtacgtggacggcg tggaggtgcataatgccaagacaaagccgcgggaggagcagtacaacagc acgtaccgtgtggtcagcgtcctcaccgtcctgcaccaggactggctgaatg gcaaggcgtacgcgtgcgcggtctccaacaaagccctcccagccccatc gagaaaccatctccaaagccaaagggcagccccgagaaccacaggtgta caccctgcccccatcccgggatgagctgaccaagaaccaggtcagcctgac ctgcctggtcaaaggcttctatccaagcgacatcgccgtggagtgggagag caatgggcagccggagaacaactacaagaccacgcctcccgtgctggact ccgacggctccttcttcctctacagcaagctcaccgtggacaagagcaggtg gcagcaggggaacgtcttctcatgctccgtgatgcatgaggctctgcacaac cactacacgcagaagagcctctccctgtctccgggtaaatga | evqlvqsgaevkkpgatvk isckasgytftdyymhwv qqapgkglewmgyfnpy ndytryaekfqgrvtitadts tdtaymelsslrsedtavyy carsdgyydamdywgq ttvtvssggggsggggsgg ggsdiqmtqspsamsasv gdrvtitcrasksiskylawf qqkpgkvpklrihsgstlqs gvpsrfsgsgsgteftltissl qpedfatyycqqhieypwt fgqgtkveikrassepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclykgfyps diavewesngqpennyktt ppyldsdgsfflyskltvdk srwqqgnvfscsvmheal hnhytqkslslspgk | SEQ ID NO: 71 (SEQ ID NO: 72) |

TABLE 3-continued

Binding Polypeptide Sequences and Components

| Name | Nucleotide Sequence | Amino Acid Sequence | SEQ ID NOs: (amino acid) |
|---|---|---|---|
| humanized TSC212 Scorpion (huVH#2-VL 107-1A4 scFv-Fc-Cris7 scFv) | atggaagcaccagcgcagcttctcttcctcctgctactctggctcccagatac caccggtcaggtccagctggtacagtctggggctgaggtgaagaagcctgg ggcttcagtgaaggtctcctgcaaggcttctggatacacattcactgactacta catgcactgggtgcgacaggcccctggacaagggcttgagtggatgggata ttttaatcctataatgattatactagatacgcacagaagttccagggcagagtc accatgaccagggacacgtctatcagcacagcctacatggagctgagcagc ctgagatctgacgacacggccgtgtattactgtgcaagatcggatggttacta cgatgctatggactactggggtcaaggaaccacagtcaccgtctcctcaggt ggcggagggtctgggggtggcggatccgaggtggtggctctgatatcca gatgacccagtctccatccgccatgtctgcatctgtaggagacagagtcacc atcacttgccgggcgagtaagagcattagcaaatatttagcctggtttcaga gaaaccagggaaagttcctaagctccgcatccattctggatctacttttgcatc aggggtcccatctcggttcagtggcagtggatctgggacagaatttactctca ccatcagcagcctgcagcctgaagattttgcaacttattactgtcaacagcata ttgaatacccgtggacgttcggccaagggaccaaggtggaaatcaaacgcg cctcgagtgagcccaaatcttctgacaaaactcacacatgcccaccgtgcc cagcacctgaagccgcgggtgcacctcagtcttcctcttccccccaaaaccc aaggacaccctcatgatctcccggaccctgaggtcacatgcgtggtggtgg acgtgagccacgaagaccctgaggtcaagttcaactggtacgtggacggcg tggaggtgcataatgccaagacaaagccgcgggaggagcagtacaacagc acgtaccgtgtggtcagcgtcctcaccgtcctgcaccaggactggctgaatg gcaaggcgtacgcgtgcgcggtctccaacaaagccctcccagcccccatc gagaaaaccatctccaaagccaaagggcagccccgagaaccacaggtgta caccctgcccccatcccgggatgagctgaccaagaaccaggtcagcctgac ctgcctggtcaaaggcttctatcccagcgacatcgccgtggagtgggagag caatgggcagccggagaacaactacaagaccacgcctcccgtgctggact ccgacggctccttcttcctctacagcaagctcaccgtggacaagagcaggtg gcagcaggggaacgtcttctcatgctccgtgatgcatgaggctctgcacaac cactacacgcagaagagcctctccctgtctccgggtcagaggcacaacaatt cttccctgaatacaggaactcagatggcaggtcattctccgaattctcaggtcc agctggtgcagtctggggcggagtggtgcagcctgggcggtcactgagg ctgtcctgcaaggcttctggctacaccttttactagatctacgatgcactgggta aggcaggccctggaaaggcttggattggattacattaatcctagca gtgcttatactaattacaatcagaaattcaaggacaggttcacaatcagcgca gacaaatccaagagcacagcctcctgcagatggacagcctgaggcccga ggacaccggcgtctatttctgtgcacggccccaagtccactatgattacaacg ggtttccttactggggccaagggacccccgtcactgtctcctcagcggtcgg agggtctggggtggcggatccgaggtggtggctctgcacaagacatcc agatgacccagtctccaagcagcctgtctgcaagcgtggggacagggtca ccatgacctgcagtgccagctcaagtgtaagttacatgaactggtaccagca gaagcccggcaaggccccaaaagatgatttatgactccaaactggct tctggagtccctgctcgcttcagtggcagtgggtctgggaccgactataccct cacaatcagcagcctgcagcccgaagatttcgccacttattactgccagcagt ggagtcgtaacccaccacgttcggaggggggaccaagctacaaattacac gataa | qvqlvqsgaevkkpgasv kvsckasgytftdyymhw vrqapgqglewmgyfnp yndytryaqkfqgrvtmtr dtsistaymelsslrsddtav yycarsdgyydamdywg qgttvtvssggggsggggs ggggsdiqmtqspsamsa svgdrvtitcrasksiskyla wfqqkpgkvpklrihsgstl qsgvpsrfsgsgsgteftltis slqpedfatyycqqhieyp wtfgqgtkveikrassepks sdkthtcppcpapeaagap svflfppkpkdtlmisrtpe vtcvvvdvshedpevkfn wyvdgvevhnakktkpree qynstyrvvsvltvlhqdwl ngkayacavsnkalpapie ktiskakgqprepqvytlpp srdeltknqvsltclvkgfyp sdiavewesngqpennyk ttppvldsdgsfflyskltvd ksrwqqgnvfscsvmhea lhnhytqkslslspgqrhnn sslntgtqmaghspnsqvq lvqsggvvqpgrslrlsck asgytftrstmhwvrqapg kglewigyinpssaytnyn qkfkdrftisadksksktaflq mdslrpedtgvyfcarpqv hydyngfpywgqgtpvtv ssggggsggggsgggsa qdiqmtqspsslsasvgdr vtmtcsasssvsymnwyq qkpgkapkrwiydssklas gvparfsgsgsgtdytltiss l qpedfatyycqqwsrnppt fgggtklqitr | SEQ ID NO: 73 (SEQ ID NO: 74) |
| humanized TSC213 Scorpion (huVH#1-VL 107-1A4 scFv-Fc-Cris7 scFv) | atggaagcaccagcgcagcttctcttcctcctgctactctggctcccagatac caccggtgaggtccagctggtacagtctggggctgaggtgaagaagcctg gggctacagtgaaggtcctgcaaggcttctggatacacattcactgactact acatgcactgggtgcaacaggcccctggaaagggcttgagtggatggat attttaatcctataatgattatactagatacgcagagaagttccagggcagagt caccataaccgcggacacgtctacagacacagcctacatggagctgagcag cctgagatctgaggacacggccgtgtattactgtgcaagatcggatggttact acgatgctatggactactgggggtcaaggaaccacagtcaccgtctcctcagg tggcggagggtctgggggtggcggatccgaggtggtggctctgatatcca gatgacccagtctccatccgccatgtctgcatctgtaggagacagagtcacc atcacttgccgggcgagtaagagcattagcaaatatttagcctggtttcaga gaaaccagggaaagttcctaagctccgcatccattctggatctacttttgcatc aggggtcccatctcggttcagtggcagtggatctgggacagaatttactctca ccatcagcagcctgcagcctgaagattttgcaacttattactgtcaacagcata ttgaatacccgtggacgttcggccaagggaccaaggtggaaatcaaacgag cctcgagtgagcccaaatcttctgacaaaactcacacatgcccaccgtgcc cagcacctgaagccgcgggtgcacctcagtcttcctcttccccccaaaaccc aaggacaccctcatgatctcccggaccctgaggtcacatgcgtggtggtgg acgtgagccacgaagaccctgaggtcaagttcaactggtacgtggacggcg tggaggtgcataatgccaagacaaagccgcgggaggagcagtacaacagc acgtaccgtgtggtcagcgtcctcaccgtcctgcaccaggactggctgaatg gcaaggcgtacgcgtgcgcggtctccaacaaagccctcccagcccccatc gagaaaaccatctccaaagccaaagggcagccccgagaaccacaggtgta caccctgcccccatcccgggatgagctgaccaagaaccaggtcagcctgac ctgcctggtcaaaggcttctatcccagcgacatcgccgtggagtgggagag caatgggcagccggagaacaactacaagaccacgcctcccgtgctggact ccgacggctccttcttcctctacagcaagctcaccgtggacaagagcaggtg gcagcaggggaacgtcttctcatgctccgtgatgcatgaggctctgcacaac cactacacgcagaagagcctctccctgtctccgggtcagaggcacaacaatt | Evqlvqsgaevkkpgatv kisckasgytftdyymhw vqqapgkglewmgyfnp yndytryaekfqgrvtitadt stdtaymelsslrsedtavy ycarsdgyydamdywgq gttvtvssggggsggggsg gggsdiqmtqspsamsas vgdrvtitcrasksiskylaw fqqkpgkvpklrihsgstlq sgvpsrfsgsgsgteftltiss lqpedfatyycqqhieypw tfgqgtkveikrassepkss dkthtcppcpapeaagaps vflfppkpkdtlmisrtpevt cvvvdvshedpevkfnwy vdgvevhnakktkpreeqy nstyrvvsvltvlhqdwlng kayacavsnkalpapiekti skakgqprepqvytlppsr deltknqvsltclvkgfyps diavewesngqpennyktt ppvldsdgsfflyskltvdk srwqqgnvfscsvmheal hnhytqkslslspgqrhnns slntgtqmaghspnsqvql vqsggvvqpgrslrlscka sgytftrstmhwvrqapgk glewigyinpssaytnynq | SEQ ID NO: 75 (SEQ ID NO: 76) |

TABLE 3-continued

Binding Polypeptide Sequences and Components

| Name | Nucleotide Sequence | Amino Acid Sequence | SEQ ID NOs: (amino acid) |
|---|---|---|---|
| | cttccctgaatacaggaactcagatggcaggtcattctccgaattctcaggtcc agctggtgcagtctgggggcggagtggtgcagcctgggcggtcactgagg ctgtcctgcaaggcttctggctacacctttactagatctacgatgcactgggta aggcaggcccctggaaagggtctggaatggattggatacattaatcctagca gtgcttatactaattacaatcagaaattcaaggacaggttcacaatcagcgca gacaaatccaagagcacagccttcctgcagatggacagcctgaggcccga ggacaccggcgtctatttctgtgcacggccccaagtccactatgattacaacg ggtttccttactggggccaagggacccccgtcactgtctctgcaggtggcgg aggtctgggggtggcggatccggaggtggtggctctgcacaagacatcc agatgacccagtctccaagcagcctgtctgcaagcgtggggacagggtca ccatgacctgcagtgccagctcaagtgtaagttacatgaactggtaccagca gaagccaggcaagccccccaaaagatggatttatgactgatccaaactggct tctggagtccctgctcgcttcagtggcagtgggtctgggaccgactataccct cacaatcagcagcctgcagcccgaagatttcgccacttattactgccagcagt ggagtcgtaacccaccacgttcggaggggggaccaagctacaaattacac gataa | kfkdrftisadkskstaflqm dslrpedtgvyfcarpqvhy dyngfpywgqgtpvtvss ggggsggggsggggsaqd iqmtqspsslsasvgdrvt mtcsasssvsymnwyqq kpgkapkrwiydssklasg vparfsgsgsgtdythisslq pedfatyycqqwsrnpptf gggtklqitr | |
| humanized TSC249 Scorpion (huVL-VH#2 107-1A4 scFv-Fc-DRA222 scFv) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctcccgcatccattctg gatctactttgcaatcaggggtcccatctcggttcagtggcagtggatctggg acagaatttactctcaccatcagcagcctgcagcctgaagattttgcaacttat actgcaacagcatattgaatacccgtggacgttcggccaagggaccaaggt ggaaatcaaacgaggtggcgaggtctggggtggcggatccggaggt ggtggctctcaggtccagctggtacagtctgggggctgaggtgaagaagcct ggggcttcagtgaaggtctcctgcaaggcttctggatacacattcactgacta ctacatgcactgggtgcgacaggcccctggacaagggcttgagtggatggg atattttaatccttataatgattatactagatacgcacagaagttccagggcaga gtcaccatgaccagggacacgtctatcagcacagcctacatggagctgagc agcctgagatctgacgacacggccgtgtattactgtgcaagatcggatggtta ctacgatgctatggactactggggtcaaggaaccacagtcaccgtctcctcg agtgagcccaaatcttctgacaagactcacacatgcccaccgtgcccagcac ctgaagccgcgggtgcaccgtcagtcttcctcttccccccaaaacccaagga caccctcatgatctccccgaccccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagccctcccagccccatcgagaaa accatctccaaagccaaagggcagccccgagaaccacaggtgtacaccct gcccccatcccgggatgagctgaccaagaaccaggtcagcctgacctgcct ggtcaaaggcttctatcccagcgacatcgccgtggagtgggagagcaatgg gcagccggagaacaactacaagaccacgcctcccgtgctggactccgacg gctcctttcttcctctacagcaagctcaccgtggacaagagcaggtggcagca ggggaacgtcttctcatgctccgtgatgcatgaggctctgcacaaccactaca cgcagaagagcctctccctgtctccgggtcagacacaacaattcttccct gaatacaggaactcagatggcaggtcattctccgaattctcaggtccagctgg tgagtctgggggcggagtggtgcagcctgggcggtcactgaggctgtcct gcaaggcttctggctacacctttactagatctacgatgcactgggtaaggcag gccctggacaaggtctggaatggattggatacattaatcctagcagtgcttat actaattacaatcagaaattcaaggacaggttcacaatcagcgcagacaaatc caagagcacagccttcctgcagatggacagcctgaggcccgaggacaccg gcgtctatttctgtgcacggccccaagtccactatgattacaacgggtttccttac tggggccaagggactcccgtcactgtctctgcaggtgggtctggg gggtggcggatccggaggtggtggctctgcacaagacatccagatgaccc agtctccaagcagcctgtctgcaagcgtggggacagggtcaccatgacct gcagtgccagctcaagtgtaagttacatgaactggtaccagcagaagccgg gcaagccccccaaaagatggatttatgactcatccaaactggcttctggagtc cctgctcgcttcagtggcagtgggtctgggaccgactataccctcacaatcag cagcctgcagcccgaagatttcgccacttattactgccagcagtggagtcgta acccaccacgttcggaggggggaccaagctacaaattacatcctccagct aa | Diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvscasgytftdyy mhwvrqapgqglewmg yfnpyndytryaqkfqgrv tmtrdtsistaymelsslrsd dtavyycarsdgyydamd ywgqgttvtvsssepkssd kthtcppcpapeaagapsv flfppkpkdtlmisrtpevtc vvvdvshedpevkfnwy vdgvevhnakttkpreeqy nstyrvvsvltvlhqdwlng kayacavsnkalpapiekti skakgqprepqvytlppsr deltknqvsltclvkgfyps diavewesngqpennyktt ppvldsdgsfflysktvdk srwqqgnvfscsvmheal hnhytqkslslspgqrhnns slntgtqmaghspnsqvql vesggggvqpgrslrlscka sgytftrstmhwvrqapgq glewigyinpssaytnynq kfkdrftisadkskstaflqm dslrpedtgvyfcarpqvhy dyngfpywgqgtpvtvss ggggsggggsggggsaqd iqmtqspsslsasvgdrvt mtcsasssvsymnwyqq kpgkapkrwiydssklasg vparfsgsgsgtdythisslq pedfatyycqqwsrnpptf gggtklqitsss | SEQ ID NO: 77 (SEQ ID NO: 78) |
| humanized TSC250 Scorpion (huVL-VH#2 107-1A4 scFv-Fc-DRA222 | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctcccgcatccattctg gatctactttgcaatcaggggtcccatctcggttcagtggcagtggatctggg acagaatttactctcaccatcagcagcctgcagcctgaagattttgcaacttat actgcaacagcatattgaatacccgtggacgttcggccaagggaccaaggt ggaaatcaaacgaggtggcgaggtctggggtggcggatccggaggt ggtggctctcaggtccagctggtacagtctgggggctgaggtgaagaagcct ggggcttcagtgaaggtctcctgcaaggcttctggatacacattcactgacta ctacatgcactgggtgcgacaggcccctggacaagggcttgagtggatggg atattttaatccttataatgattatactagatacgcacagaagttccagggcaga | Diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvscasgytftdyy mhwvrqapgqglewmg yfnpyndytryaqkfqgrv tmtrdtsistaymelsslrsd dtavyycarsdgyydamd | SEQ ID NO: 79 (SEQ ID NO: 80) |

TABLE 3-continued

Binding Polypeptide Sequences and Components

| Name | Nucleotide Sequence | Amino Acid Sequence | SEQ ID NOs: (amino acid) |
|---|---|---|---|
| scFv, with H81 linker) | gtcaccatgaccagggacacgtctatcagcacagcctacatggagctgagc agcctgagatctgacgacacggccgtgtattactgtgcaagatcggatggtta ctacgatgctatggactactggggtcaaggaaccacagtcaccgtctcctcg agtgagcccaaatcttctgacaaaactcacacatgcccaccgtgcccagcac ctgaagccgcgggtgcaccgtcagtcttcctcttcccccaaaacccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagcccctcccagccccatcgagaaa accatctccaaagccaaagggcagccccgagaaccacaggtgtacaccct gcccccatcccgggatgagctgaccaagaaccaggtcagcctgacctgcct ggtcaaaggcttctatccaagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtgaagttcaaattcccttgaccgaa agttacagcccgaattctcaggtccagctggtgagtctggggggcggagtg gtgcagcctgggcggtcactgaggctgtcctgcaaggcttctggctacacct tactagatctacgatgcactgggtaaggcaggcccctggacaaggtctgga atggattggatacattaatcctagcagtgcttatactaattacaatcagaaattca aggacaggttcacaatcagcgcagacaaatccaagagcacagcctcctgc agatggacagcctgaggcccgaggacaccggcgtctatttctgtgcacggc cccaagtccactatgattacaacgggtttccttactggggccaagggactccc gtcactgtctctagcggtggcggagggtctgggggtggcggatccggaggt ggtggctctgcacaagacatccagatgacccagtctccaagcagcctgtctg caagcgtgggagacagggtcaccatgacctgcagtgccagctcaagtgtaa gttacatgaactggtaccagcagaagccgggcaaggcccccaaaagatgg atttatgactcatccaaactggcttctggagtccctgctcgcttcagtggcagtg ggtctgggaccgactatacccctcacaatcagcagcctgcagcccgaagattt cgccacttattactgccagcagtggagtcgtaacccacccacgttcggaggg gggaccaagctacaaattacatcctccagctaa | ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennykt t ppvldsdgsffylysklltvdk srwqqgnvfscsvmheal hnhytqkslslspgevqiplt esyspnsqvqlvesgggvv qpgrslrlsckasgyftrst mhwvrqapgqglewigyi npssaytnynqkfkdrftis adkskstaflqmdslrpedt gvyfcarpqvhydyngfp ywgqgtpvtvssggggsg ggsggggsaqdiqmtqs psslsasvgdrvtmtcsass svsymnwyqqkpgkapk rwiydssklasgvparfsgs gsgtdytltisslqpedfaty ycqqwsrnpptfgggtklq itsss | |
| humanized TSC251 Scorpion (huVL-VH#2 107-1A4 scFv-Fc-DRA222 scFv, with H83 linker) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctccgcatccattct gatctactttgcaatcaggggtcccatctcggttcagtggcagtggatctggg acagaatttactctcaccatcagcagcctgcagcctgaagattttgcaacttat actgtcaacagcatattgaataccgtcggttcggtccgggacacaagcttgt ggaaatcaaacgaggtggcgagggtctgggggtggcggatccggaggt ggtggctctcaggtccagctggtacagtctggggctgaggtgaagaagcct ggggcttcagtgaaggtctcctgcaaggcttctggatacacattcactgacta ctacatgcactgggtgcgacaggcccctggacaaggcttgagtggatggg atattttaatcctataatgattatactagatacgcacagaagttccagggcaga gtcaccatgaccagggacacgtctatcagcacagcctacatggagctgagc agcctgagatctgacgacacggccgtgtattactgtgcaagatcggatggtta ctacgatgctatggactactggggtcaaggaaccacagtcaccgtctcctcg agtgagcccaaatcttctgacaaaactcacacatgcccaccgtgcccagcac ctgaagccgcgggtgcaccgtcagtcttcctcttcccccaaaacccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagcccctcccagccccatcgagaaa accatctccaaagccaaagggcagccccgagaaccacaggtgtacaccct gcccccatcccgggatgagctgaccaagaaccaggtcagcctgacctgcct ggtcaaaggcttctatccaagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggttcttccctgaatacaggaactcag atggcaggtcattctccgaattctcaggtccagctggtggagtctgggggcg gagtggtgcagcctgggcggtcactgaggctgtcctgcaaggcttctggcta cacctttactagatctacgatgcactgggtaaggcaggcccctggacaaggt ctgaatggattggatacattaatcctagcagtgcttatactaattacaatcaga attcaaggacaggttcacaatcagcgcagacaaatccaagagcacagcctt cctgcagatggacagcctgaggcccgaggacaccggcgtctatttctgtgca | Diqmtqspspsamsasvgdr vtitcrasksiskylawfqqk pgkvpklrihsgstlqsgvp srfsgsgsgteftltisslqpe dfatyycqqhieypwtfgq gtkveikrggggsggggs gggsgvqlvqsgaevkkp gasvkvsckasgyftfdyy mhwvrqapgqglewmg yfnpyndytryaqkfqgrv tmtrdtsistaymelssIrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennykt t ppvldsdgsffylysklltvdk srwqqgnvfscsvmheal hnhytqkslslspgssIntgt qmaghspnsqvqlvesgg gvvqpgrslrlsckasgyftf rstmhwvrqapgqglewi gyinpssaytnynqkfkdrf tisadkskstaflqmdslrpe dtgvyfcarpqvhydyngf pywgqgtpvtvssggggs ggggsggggsaqdiqmtq spsslsasvgdrvtmtcsas ssvsymnwyqqkpgkap | SEQ ID NO: 81 (SEQ ID NO: 82) |

TABLE 3-continued

Binding Polypeptide Sequences and Components

| Name | Nucleotide Sequence | Amino Acid Sequence | SEQ ID NOs: (amino acid) |
|---|---|---|---|
| | cggccccaagtccactatgattacaacgggtttccttactggggccaaggga ctcccgtcactgtctctagcggtggcggagggtctgggggtggcggatccg gaggtggtggctctgcacaagacatccagatgacccagtctccaagcagcc tgtctgcaagcgtggggacagggtcaccatgacctgcagtgccagctcaa gtgtaagttacatgaactggtaccagcagaagccgggcaaggcccccaaaa gatggatttatgactcatccaaactggcttctggagtccctgctcgcttcagtg gcagtgggtctgggaccgactataccctcacaatcagcagcctgcagcccg aagatttcgccacttattactgccagcagtggagtcgtaacccacccacgttc ggaggggggaccaagctacaaattacatcctccagctaa | krwiydssklasgvparfsg sgsgtdytltisslqpedfaty ycqqwsrnpptfgggtklq itsss | |
| humanized TSC252 Scorpion (huVL-VH#2 107-1A4 scFv-Fc-DRA222 scFv, with H91 linker) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctccgcatccattctg gatctactttgcaatcaggggtcccatctcggttcagtggcagtggatctggg acagaatttactctcaccatcagcagcctgcagcctgaagattttgcaacttat actgtcaacagcatattgaataccgtggacgttcggccaagggaccaaggt ggaaatcaaacgaggtggcggagggtctgggggtggcggatccggaggt ggtggctctcaggtccagctggtacagtctggggctgaggtgaagaagcct ggggcttcagtgaaggtctcctgcaaggcttctggatacacattcactgacta ctacatgcactgggtgcgacaggcccctggacaagggcttgagtggatggg atattttaatcctataatgattatactagatacgcacagaagttccaggcaga gtcaccatgaccagggacacgtctatcagcacagcctacatggagctgagc agcctgagatctgacgacacggccgtgtattactgtgcaagatcggatggtta ctacgatgctatggactactggggtcaagggaccacagtcaccgtctcctcg agtgagcccaaatcttctgacaaaactcacacatgcccaccgtgcccagcac ctgaagccgcgggtgcaccgtcagtcttcctcttccccccaaaacccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagcccctcccagccccatcgagaaa accatctccaaagccaaagggcagccccgagaaccacaggtgtacaccct gcccccatcccgggatgagctgaccaagaaccaggtcagcctgacctgcct ggtcaaaggcttctatccaagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtaactcattagcaaaccaagaagtt caaattcccttgaccgaaagttacagcccgaattctcaggtccagctggtgga gtctggggaggtggcggagggtctgggggcggcggcggtgtcctgcaa ggcttctggctacaccttttactagatactgcactgggtaaggcaggcc ctggacaaggtctggaatggattggatacattaatcctagcagtgcttatacta attacaatcagaaattcaaggacaggttcacaatcagcgcagacaaatccaa gagcacggcttctgcagatgggacagcttgaggacaccggcg tctatttctgtgcacggccccaagtccactatgattacaacgggtttccttactg gggccaagggactcccgtcactgtctctagcggtggcggagggtctgggg gtggcggatccggaggtggtggctctgcacaagacatccagatgacccagt ctccaagcagcagcctgtctgcaagcgtggggacagggtcaccatgacctgca gtgccagctcaagtgtaagttacatgaactggtaccagcagaagccgggca aggcccccaaaagatggatttatgactcatccaaactggcttctggagtccct gctcgcttcagtggcagtgggtctgggaccgactataccctcacaatcagca gcctgcagcccgaagatttcgccacttattactgccagcagtggagtcgtaac ccacccacgttcggaggggggaccaagctacaaattacatcctccagctaa | Diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvsckasgyltdyy mhwvrqapgqglewmg yfnpyndyttyaqkfqgry tmtrdtsistaymelsslrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennykttt ppvldsdgsfflysklt vdk srwqqgnvfscsvmheal hnhytqkslslspgnslanq evqipltesyspnsqvqlve sgggvvqpgrslrlsckasg ytftrstmhwvrqapgqgl ewigyinpssaytnynqkf kdrftisadkskstaflqmd slrpedtgvyfcarpqvhyd yngfpywgqgtpvtvssg gggsggggsggggsaqdi qmtqspsslsasvgdrvtm tcsasssvsymnwyqqkp gkapkrwiydssklasgvp arfsgsgsgtdytltisslqpe dfatyycqqwsrnpptfgg gtklqitsss | SEQ ID NO: 83 (SEQ ID NO: 84) |
| Humanized TSC295 Scorpion (huVL-VH#2 107-1A4 scFv-Fc-DRA222 scFv, with H9 linker) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggtttcagcagaaaccagggaaagttcctaagctccgcatccattctg gatctactttgcaatcaggggtcccatctcggttcagtggcagtggatctggg acagaatttactctcaccatcagcagcctgcagcctgaagattttgcaacttat actgtcaacagcatattgaataccgtggacgttcggccaagggaccaaggt ggaaatcaaacgaggtggcggagggtctgggggtggcggatccggaggt ggtggctctcaggtccagctggtacagtctggggctgaggtgaagaagcct ggggcttcagtgaaggtctcctgcaaggcttctggatacacattcactgacta ctacatgcactgggtgcgacaggcccctggacaagggcttgagtggatggg atattttaatcctataatgattatactagatacgcacagaagttccaggcaga gtcaccatgaccagggacacgtctatcagcacagcctacatggagctgagc agcctgagatctgacgacacggccgtgtattactgtgcaagatcggatggtta ctacgatgctatggactactggggtcaagggaccacagtcaccgtctcctcg agtgagcccaaatcttctgacaaaactcacacatgcccaccgtgcccagcac ctgaagccgcgggtgcaccgtcagtcttcctcttccccccaaaacccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgta | diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvsckasgytftdyy mhwvrqapgqglewmg yfnpyndytryaqkfqgrv tmtrdtsistaymelsslrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr | SEQ ID NO: 157 (SEQ ID NO: 158) |

TABLE 3-continued

Binding Polypeptide Sequences and Components

| Name | Nucleotide Sequence | Amino Acid Sequence | SEQ ID NOs: (amino acid) |
|---|---|---|---|
| | ccgtgtggtcagcgtcctcaccgtcctgcaccaggactggctgaatggcaag gcgtacgcgtgcgcggtctccaacaaagccctcccagccccatcgagaaa accatctccaaagccaaagggcagccccgagaaccacaggtgtacaccct gcccccatcccgggatgagctgaccaagaaccaggtcagcctgacctgcct ggtcaaaggcttctatccaagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtctctgcagccactactccaccgaattc tcaggtccagctggtggagtctggggcggagtggtgcagcctgggcggt cactgaggctgtcctgcaaggcttctggctacacctttactagatctacgatgc actgggtaaggcaggcccctggacaaggtctggaatggattggatacattaa tcctagcagtgcttatactaattacaatcagaaattcaaggacaggttcacaat cagcgcagacaaatccaagagcacagccttcctgcagatggacagcctga ggcccgaggacaccggcgtctatttctgtgcacggcccaagtccactatga ttacaacgggtttccttactggggccaagggactcccgtcactgtctctagcg gtggcggagggtctggggtggcggatccggaggtggtggctctgcacaa gacatccagatgacccagtctccaagcagcctgtctgcaagcgtggggac agggtcaccatgacctgcagtgccagctcaagtgtaagttacatgaactggta ccagcagaagccgggcaaggcccccaaaagatggatttatgactcatccaa actggcttctggagtccctgctcgcttcagtggcagtgggtctgggaccgact atcccctcacaatcagcagcctgcagcccgaagatttcgccacttattactgc cagcagtggagtcgtaacccacccacgttcggagggggaccaagctaca aattacatcctccagctaa | deltknqvsltclvkgfyps diavewesngqpennyktt ppvldsdgsfflysklltvdk srwqqgnvfscsvmheal hhnhytqkslslspggsppsp nsqvqlvesgggvvqpgrs lrlsckasgytftrstmhwvr qapgqglewigyinpssay tnynqkfkdrftisadkskst aflqmdslrpedtgvyfcar pqvhydyngfpywgqgt pvtvssggggsggggsgg ggsaqdiqmtqspsslsas vgdrvtmtcsassssvsymn wyqqkpgkapkrwiydss klasgvparfsgsgsgtdytl tisslqpedfatyycqqwsr nppt fgggtklqitsss | |
| Humanized TSC296 Scorpion (huVL-VH#2 107-1A4 scFv-Fc-DRA222 scFv, with H94 linker) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctgtttcagcagaaaccagggaaagcctcctaagcctccgcatccattctg gatctactttgcaatcagggatcccatctcggttcagtggcagtggatctggg acagaattttactctcaccatcagcagcctgcagcctgaagattttgcaacttat actgtcaacagcatattgaataccctgtgacgttcggccaagggaccaaggt ggaaatcaaacgaggtggcggagggtctgggggtggcggatccggaggt ggtggctctcaggtccagctggtggagtctggggggaggtgaagaagcct gggggcttcagtgaaggtctcctgcaaggtttctggatacacatttactgacta ctacatgcactgggtgcgacaggcccctggacaaggcgttgagtggatggg atattttaatcctataatgattatactagatacgcacagaagttccagggcaga gtcaccatgaccagggacacgtctatcagcacagcctacatggagctgagc agcctgagatctgacgacacggccgtgtattactgtgcaagatcggatggta ctacgatgctatgactactggggccaagtcaccgtctcctcg agtgagcccaaatcttctgacaaaactcacacatgcccaccgtgcccagcac ctgaagccgcgggtgcaccgtcagtcttcctcttccccccaaaacccaagga caccctcatgatctcccggaccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagccctcccagccccatcgagaaa accatctccaaagccaaagggcagccccgagaaccacaggtgtacaccct gcccccatcccgggatgagctgaccaagaaccaggtcagcctgacctgcct ggtcaaaggcttctatccaagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggttctggtggaggcggttcaggcg gaggtggctccggcggtggcgggatcgccgaattctcaggtccagctggtgg agtctggggcggagtggtgcagcctgggcggtcactgaggctgtcctgca aggcttctggctacacctttactagatctacgatgcactgggtaaggcaggcc cctggacaaggtctggaatggattggatacattaatcctagcagtgcttatact aattacaatcagaaattcaaggacaggttcacaatcagcgcagacaaatcca agagcacagccttcctgcagatgacagcctgaggcccgaggacaccggc gtctatttctgtgcacggcccaagtccactatgattacaacgggtttccttact ggggccaagggactcccgtcactgtctctagcggtggcggagggtctggg ggtggcggatccggaggtggtggctctgcacaagacatccagatgaccca gtctccaagcagcctgtctgcaagcgtggggacagggtcaccatgacctg cagtgccagctcaagtgtaagttacatgaactggtaccagcagaagccggg caaggcccccaaaagatggatttatgactcatccaaactggcttctggagtcc ctgctcgcttcagtggcagtgggtctgggaccgactatcccctcacaatcagc agcctgcagcccgaagatttcgccacttattactgccagcagtggagtcgtaa cccacccacgttcggagggggaccaagctacaaattacatcctccagcta a | diqmtqspsamsasvgdr vtitcrasksisky lawfqqk pgkvpklrihsgstlqsgvp srfsgsgsgteftltisslqpe dfatyycqqhieypwtfgq gtkveikrggggsggggsg gggsqvqlvqsgaevkkp gasvkvsckasgytftdyy mhwvrqapgqglewmg yfnpyndytryaqkfqgrv tmtrdtsistaymelssrsd dtavyycarsdgyydamd ywgqgttvtvsssepkssd kthtcppcpapeaagapsv flfppkpkdtlmisrtpevtc vvvdvshedpevkfnwy vdgvevhnakktkpreeqy nstyrvvsvltvlhqdwlng kayacavsnkalpapiekti skakgqprepqvytlppsr deltknqvsltclvkgfyps diavewesngqpennyktt ppvldsdgsfflysklltvdk srwqqgnvfscsvmheal hhnhytqkslslspgsggggs ggggsggggspnsqvqlv esgggvvqpgrslrlsckas gytftrstmhwvrqapgqg lewigyinpssaytnynqk fkdrftisadkskstaflqmd slrpedtgvyfcarpqvhyd yngfpywgqgtpvtvssg ggggsggggsggggsaqdi qmtqspsslsasvgdrvtm tcsassssvsymnwyqqkp gkapkrwiydssklasgvp arfsgsgsgtdytltisslqpe dfatyycqqwsrnpptfgg gtklqitsss | SEQ ID NO: 159 (SEQ ID NO: 160) |

TABLE 3-continued

Binding Polypeptide Sequences and Components

| Name | Nucleotide Sequence | Amino Acid Sequence | SEQ ID NOs: (amino acid) |
|---|---|---|---|
| Humanized TSC301 Scorpion (huVL-VH#2 107-1A4 scFv-Fc-DRA222 scFv, with H105 linker) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggttttcagcagaaacaggaaagttcctaagctccgcatccattctg gatctactttgcaatcaggggtcccatctcggttcagtggcagtggatctggg acagaatttactctcaccatcagcagcctgcagcctgaagattttgcaacttat actgtcaacagcatattgaataccgtggacgttcggccaagggaccaaggt ggaaatcaaacgaggtggcggagggtctggggtggcggatccggaggt ggtggctctcaggtccagctggtacagtctggggctgaggtgaagaagcct gggggcttcagtgaaggtcctgtcaaggcttctggatacacattcactgacta ctacatgcactgggtgcgacaggcccctggacaagggcttgagtggatggg atattttaatccttataatgattatactagatacgcacagaagttccagggcaga gtcaccatgaccagggacacgtctatcagcacagcctacatggagctgagc agcctgagatctgacgacacggccgtgtattactgtgcaagatcggatggtta ctacgatgctatggactactggggtcaaggaaccacagtcaccgtctcctcg agtgagcccaaatcttctgacaaaactcacacatgcccaccgtgcccagcac ctgaagcgcgggtgcaccgtcagtcttcctcttccccccaaaacccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagcccctcccagccccatcgagaaa accatctccaaagccaaagggcagccccgagaaccacaggtgtacaccct gccccccatcccgggatgagctgaccaagaaccaggtcagcctgacctgcct ggtcaaaggcttctatcccagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtaaaggtgggggaggcggtggcggaggt ggcggaggtggtggatcgcaggtccagctggtggagtctggg ggcggagtggtgcagcctgggcggtcactgaggctgtcctgcaaggcttct ggctacacctttactagatctacgatgcactgggtaaggcaggcccctggac aaggtggaatggattggatacattaatcctagcagtgcttatactaattacaa tcagaaatttcaaggacaggttcacaatagcagcagacaaatccaagagcac agccttcctgcagatggacagcctgaggcccgaggacaccggcgtctattc tgtgcacgggccccaagtccactatgattacaacgggtttccttactgggcca agggactctggtcactgtctctgcaggacgttctgggggaggcttc tgatccggaggtggtggctctgcacaagacatccagatgacccagtctccaa gcagcctgtctgcaagcgtggggacaggtcaccatgacctgcagtgcca gctcaagtgtaagttacatgaactggtaccagcagaagccgggcaaggccc ccaaaagatggatttatgactcatccaaactggcttctggagtccctgctcgct tcagtggcagtgggtctgggaccgactataccctcacaatcagcagcctgca gcccgaagatttcgcactttattactgccagcagtggagtcgtaacccaccca cgttcggaggggggaccaagctacaaattacatcctccagctaa | Diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvsckasgytftdyy mhwvrqapgqglewmg yfnpyndytryaqkfqgrv tmtrdtsistaymelssrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennyktt ppvldsdgsfflysklttvdk srwqqgnvfscsvmheal hnhytqkslslspgsggggs ggggsggggsqvqlvesg ggvvqpgrslrlsckasgyt ftrstmhwvrqapgqgle wigyinpssaytnynqkfk drftisadkskstaflqmdsl rpedtgvyfcarpqvhydy ngfpywgqgtpvtvssgg ggsggggsggggsaqdiq mtqspsslsasvgdrvtmt csasssvsymnwyqqkp gkapkrwiydsssklasgvp arfsgsgsgtdytltisslqpe dfatyycqqwsrnppptfgg gtklqitsss | SEQ ID NO: 161 (SEQ ID NO: 162) |
| Humanized TSC302 Scorpion (huVL-VH#2 107-1A4 scFv-Fc-DRA222 scFv, with H106 linker) | atggaagcaccagcgcagcttctcttcctcctgctactctggctcccagatac caccggtgatatccagatgacccagtctccatccgccatgtctgcatctgtag gagacagagtcaccatcacttgccgggcgagtaagagcattagcaaatattt agcctggttttcagcagaaacaggaaagttcctaagctccgcatccattctg gatctactttgcaatcaggggtcccatctcggttcagtggcagtggatctggg acagaatttactctcaccatcagcagcctgcagcctgaagattttgcaacttat actgtcaacagcatattgaataccgtggacgttcggccaagggaccaaggt ggaaatcaaacgaggtggcggagggtctggggtggcggatccggaggt ggtggctctcaggtccagctggtacagtctggggctgaggtgaagaagcct gggggcttcagtgaaggtcctgtcaaggcttctggatacacattcactgacta ctacatgcactgggtgcgacaggcccctggacaagggcttgagtggatggg atattttaatccttataatgattatactagatacgcacagaagttccagggcaga gtcaccatgaccagggacacgtctatcagcacagcctacatggagctgagc agcctgagatctgacgacacggccgtgtattactgtgcaagatcggatggtta ctacgatgctatggactactggggtcaaggaaccacagtcaccgtctcctcg agtgagcccaaatcttctgacaaaactcacacatgcccaccgtgcccagcac ctgaagcgcgggtgcaccgtcagtcttcctcttccccccaaaacccaagga caccctcatgatctcccggacccctgaggtcacatgcgtggtggtggacgtg agccacgaagaccctgaggtcaagttcaactggtacgtggacggcgtggag gtgcataatgccaagacaaagccgcgggaggagcagtacaacagcacgta ccgtgtggtcagcgtcctcaccgtcctgcaccaggactggctgaatggcaag gcgtacgcgtgcgcggtctccaacaaagcccctcccagccccatcgagaaa accatctccaaagccaaagggcagccccgagaaccacaggtgtacaccct gccccccatcccgggatgagctgaccaagaaccaggtcagcctgacctgcct ggtcaaaggcttctatcccagcgacatcgccgtggagtgggagagcaatgg gcagccggagaacaactacaagaccacgcctcccgtgctggactccgacg gctccttcttcctctacagcaagctcaccgtggacaagagcaggtggcagca ggggaacgtcttctcatgctccgtgatgcatgaggctctgcacaaccactaca cgcagaagagcctctccctgtctccgggtcagaggcacaacaattcttccct gaatacaggaactcagatggcaggtcattctcaggtccagctggtggagtct | diqmtqspsamsasvgdr vtitcrasksiskylawfqqk pgkvpklrihsgstlqsgvp srfsgsgsgteftltisslqpe dfatyycqqhieypwtfgq gtkveikrggggsggggsg gggsqvqlvqsgaevkkp gasvkvsckasgytftdyy mhwvrqapgqglewmg yfnpyndytryaqkfqgrv tmtrdtsistaymelssrsd dtavyycarsdgyydamd ywgqgttvtvsssepkssd kthtcppcpapeaagapsv flfppkpkdtlmisrtpevtc vvvdvshedpevkfnwy vdgvevhnaktkpreeqy nstyrvvsvltvlhqdwlng kayacavsnkalpapiekti skakgqprepqvytlppsr deltknqvsltclvkgfyps diavewesngqpennyktt ppvldsdgsfflysklttvdk srwqqgnvfscsvmheal hnhytqkslslspgqrhnns slntgtqmaghsqvqlves gggvvqpgrslrlsckasgy tftrstmhwvrqapgqgle wigyinpssaytnynqkfk drftisadkskstaflqmdsl | SEQ ID NO: 163 (SEQ ID NO: 164) |

TABLE 3-continued

Binding Polypeptide Sequences and Components

| Name | Nucleotide Sequence | Amino Acid Sequence | SEQ ID NOs: (amino acid) |
|---|---|---|---|
| | gggggcggagtggtgcagcctgggcggtcactgaggctgtcctgcaaggc<br>ttctggctacacctttactagatctacgatgcactgggtaaggcaggccctg<br>gacaaggtctggaatggattggatacattaatcctagcagtgcttatactaatta<br>caatcagaaattcaaggacaggttcacaatcagcgcagacaaatccaagag<br>cacagccttcctgcagatggacagcctgaggcccgaggacaccggcgtcta<br>tttctgtgcacggccccaagtccactatgattacaacgggtttccttactgggg<br>ccaagggactcccgtcactgtctctagcggtggcggagggtctgggggtgg<br>cggatccggaggtggtggctctgcacaagacatccagatgacccagtctcc<br>aagcagcctgtctgcaagcgtggggacagggtcaccatgacctgcagtgc<br>cagctcaagtgtaagttacatgaactggtaccagcagaagccgggcaaggc<br>ccccaaaagatggatttatgactcatccaaactggcttctggagtccctgctcg<br>cttcagtggcagtgggtctgggaccgactataccctcacaatcagcagcctg<br>cagcccgaagatttcgccacttattactgccagcagtggagtcgtaacccacc<br>cacgttcggaggggggaccaagctacaaattacatcctccagctaa | rpedtgvyfcarpqvhydy<br>ngfpywgqgtpvtvssgg<br>ggsgggsggggsaqdiq<br>mtqspsslsasvgdrvtmt<br>csasssvsymnwyqqkp<br>gkapkrwiydssklasgvp<br>arfsgsgsgtdytltisslqpe<br>dfatyycqqwsrnpptfgg<br>gtklqitsss | |

Example 2: Heterodimeric Molecules

PSMA-specific Interceptor molecules were made using Interceptor scaffolding as generally disclosed in International Appl. Nos. PCT/US2010/62436 and PCT/US2010/62404. Briefly, PSMA-specific polypeptide heterodimers were made by co-expressing two different polypeptides chains, one polypeptide chain comprising an immunoglobulin CH1 heterodimerization domain and the other polypeptide chain comprising an immunoglobulin CL heterodimerization domain. The day before transfection HEK293 cells were suspended at a cell concentration of $0.5 \times 10^6$ cells/ml in GIBCO® FreeStyle™ 293 expression medium (Invitrogen). 250 mls of cells were used for a large transfection, and 60 mls of cells were used for a small transfection. On transfection day, 320 ul of 293Fectin™ transfectin reagent (Invitrogen) was mixed with 8 mls of media. At the same time, 250 ug of DNA of each of the single chain polypeptide was mixed with the 8 mls of media and incubated for 5 minutes. After 15 minutes of incubation, the DNA-293fectin mixture was added to the 250 mls of 293 cells and returned to the shaker at 37° C. and shaken at a speed of 120 RPM. For the smaller transfection using 60 mls of cells, a fourth of the DNA, 293fectin, and media were used.

Protein A affinity chromatography was used to purify the proteins. 2 ml of packed protein A agarose (Repligen) was added to a Econo-Column® chromatography column, size 2.5×10 cm (Bio-Rad Laboratories), washed extensively with PBS (10× column volume), and the supernatants were loaded, washed with PBS again, and eluted with 3 column volumes of Pierce IgG elution buffer. Proteins were then dialyzed extensively against PBS. Proteins were then concentrated using Amicon® Centricon® centrifugal filter devices (Millipore Corp.) to a final volume around 0.5 ml.

Purified proteins were analyzed on a 10% SDS-PAGE gel using XCell SureLock™ Mini-Cell electrophoresis system (Invitrogen).

Bivalent polypeptide heterodimer TSC122 was made by co-expressing single chain polypeptides TSC084 and TSC093. Single chain polypeptide TSC084 comprises from its amino- to carboxyl-terminus: murine 107-1A4 (anti-PSMA) VL-VH scFv, human IgG1 SCC-P hinge, human IgG1 CH2, human IgG1 CH3, and human CH1. The nucleotide and amino acid sequences for TSC084 are set forth in SEQ ID NOs:44 and 46, respectively. Single chain polypeptide TSC093 comprises from its amino- to carboxyl-terminus: Cris7 (anti-CD3) scFv, human IgG1 SCC-P hinge, human IgG1CH2, human IgG1 CH3, and human Cκ(YAE) (i.e., human Cκ without the first Arg or last Cys, but with N30Y, V55A, and T70E substitutions). The nucleotide and amino acid sequences for TSC093 are set forth in SEQ ID NOs:45 and 47, respectively.

Bivalent polypeptide heterodimer TSC200 was made by co-expressing polypeptide chains TSC192 and TSC125. TSC192 comprises from its amino- to carboxyl-terminus: humanized 107-1A4 (anti-PSMA) VL-VH#2 scFv, human IgG1 SCC-P hinge, human IgG1 CH2, human IgG1 CH3, and human Cκ(YAE). The nucleotide and amino acid sequences for TSC192 are set forth in SEQ ID NOs:53 and 58, respectively. TSC125 comprises from its amino- to carboxyl-terminus: Cris7 (anti-CD3) scFv, human IgG1 SCC-P hinge, human IgG1 CH2, human IgG1 CH3, and human CH1. The nucleotide and amino acid sequences for TSC125 are set forth in SEQ ID NOs:52 and 57, respectively.

Bivalent polypeptide heterodimer TSC202 was made by co-expressing polypeptide chains TSC193 and TSC125. TSC193 comprises from its amino- to carboxyl-terminus: humanized 107-1A4 (anti-PSMA) VL-VH#1 scFv, human IgG1 SCC-P hinge, human IgG1 CH2, human IgG1 CH3, and human Cκ(YAE). The nucleotide and amino acid sequences for TSC193 are set forth in SEQ ID NOs: 54 and 59, respectively. TSC125 comprises from its amino- to carboxyl-terminus: Cris7 (anti-CD3) scFv, human IgG1 SCC-P hinge, human IgG1 CH2, human IgG1 CH3, and human CH1. The nucleotide and amino acid sequences for TSC125 are set forth in SEQ ID NOs:52 and 57, respectively.

Bivalent polypeptide heterodimer TSC204 was made by co-expressing polypeptide chains TSC195 and TSC093. TSC195 comprises from its amino- to carboxyl-terminus: humanized 107-1A4 (anti-PSMA) VL-VH#2 scFv, human IgG1 SCC-P hinge, human IgG1 CH2, human IgG1 CH3, and human CH1. The nucleotide and amino acid sequences for TSC195 are set forth in SEQ ID NOs:55 and 60, respectively. TSC093 comprises from its amino- to carboxyl-terminus: Cris7 (anti-CD3) scFv, human IgG1 SCC-P hinge, human IgG1 CH2, human IgG1 CH3, and human Cκ(YAE). The nucleotide and amino acid sequences for TSC093 are set forth in SEQ ID NOs: 45 and 47, respectively.

Bivalent polypeptide heterodimer TSC205 was made by co-expressing polypeptide chains TSC196 and TSC093.

TSC196 comprises from its amino- to carboxyl-terminus: humanized 107-1A4 (anti-PSMA) VL-VH#1 scFv, human IgG1 SCC-P hinge, human IgG1 CH2, human IgG1 CH3, and human CH1. The nucleotide and amino acid sequences for TSC196 are set forth in SEQ ID NOs:56 and 61, respectively. TSC093 comprises from its amino- to carboxyl-terminus: Cris7 (anti-CD3) scFv, human IgG1 SCC-P hinge, human IgG1 CH2, human IgG1 CH3, and human Cκ(YAE). The nucleotide and amino acid sequences for TSC093 are set forth in SEQ ID NOs: 45 and 47, respectively.

Example 3: SCORPION Molecule Construction

PSMA-specific SCORPION molecules (TSC194 (SEQ ID NO:48 (nucleic acid), SEQ ID NO:49 (amino acid); TSC199 (SEQ ID NO:50 (nucleic acid), SEQ ID NO:51 (amino acid)); TSC 212 (SEQ ID NO:73 (nucleic acid), SEQ ID NO:74 (amino acid)); TSC213 (SEQ ID NO:75 (nucleic acid), SEQ ID NO:76 (amino acid)); TSC249 (SEQ ID NO:77 (nucleic acid), SEQ ID NO:78 (amino acid)); TSC250 (SEQ ID NO:79 (nucleic acid), SEQ ID NO:80 (amino acid)); TSC251 (SEQ ID NO:81 (nucleic acid), SEQ ID NO:82 (amino acid)); and TSC252 (SEQ ID NO:83 (nucleic acid), SEQ ID NO:84 (amino acid))) were made using standard molecular biology techniques, starting with existing SCORPION scaffolding as templates and using the methods generally disclosed in, e.g., PCT Application Publication No. WO 2007/146968, U.S. Patent Application Publication No. 2006/0051844, PCT Application Publication No. WO 2010/040105, PCT Application Publication No. WO 2010/003108, and U.S. Pat. No. 7,166,707 (see also Table 3). Insertion of the N-terminal scFv binding domain was accomplished through digestion of the parental template and scFv insert with either the restriction enzymes HindIII and XhoI or AgeI and XhoI, desired fragments were identified and isolated by agarose gel purification, and ligation. Insertion of the C-terminal scFv binding domain was accomplished through digestion of the parental template and scFv insert with the restriction enzymes EcoRI and NotI, desired fragments were identified and isolated by agarose gel purification, and ligation.

Example 4: Binding of Chimeric and Humanized Molecules to PSMA(+) and PSMA(−) Cell Lines Monoclonal antibodies were purified from hybridoma cell culture media by standard procedures. SMIP, Interceptor, and SCORPION molecules disclosed herein were produced by transient transfection of human HEK293 cells, and purified from cell culture supernatants by Protein A affinity chromatography. If aggregates were detected after affinity chromatography, secondary size exclusion chromatography was also performed to ensure homogeneity of the protein.

Binding studies on PSMA+ (C4-2, Wu et al., 1994 Int. J. Cancer 57:406-12) and PSMA− (DU-145, Stone et al., 1978, Intl. J. Cancer 21:274-81) prostate cancer cell lines were performed by standard FACS-based staining procedures. A typical experiment would label 300,000 cells per well with a range of 200 nM to 0.1 nM binding molecule in 100 ul of FACS buffer (PBS+2% normal goat serum+2% fetal bovine serum+0.1% sodium azide) on ice, followed by washes and incubation with fluorescently-labeled secondary antibody, goat anti-human IgG (1:400 dilution of Invitrogen #11013=5 ug/ml). After washing secondary antibody off cells, cells were incubated with 7-Aminoactinomycin D (7-AAD) staining solution (BD Pharmingen™ cat #559925)(6 ul of 7AAD to 100 ul of FACS Buffer) for 20 minutes. Signal from bound molecules was detected using a FACSCalibur™ flow cytometer (BD Biosciences) and analyzed by FlowJo flow cytometry analysis software. 7-AAD+ cells were excluded from analysis. Nonlinear regression analysis to determine EC50s was performed in GraphPad Prism® graphing and statistics software.

Figure 2A:
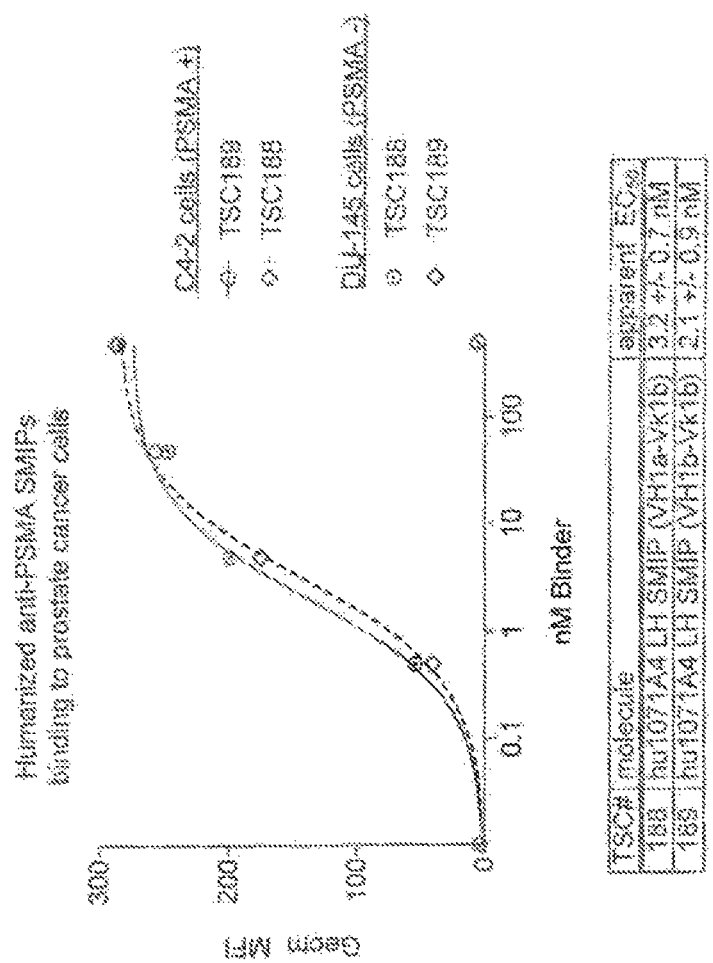
FIG. 2A is a graph illustrating the results of a binding study used to compare humanized TSC188 and TSC189 in PSMA(+) (C4-2) and PSMA(−) (DU-145) prostate cancer cell lines.
Figure 2B:
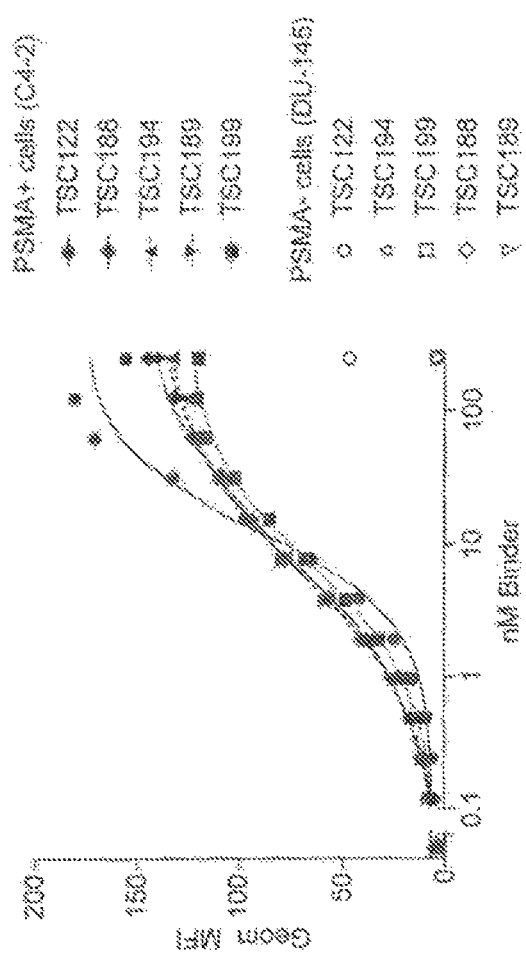
FIG. 2B is a graph illustrating the results of a binding study used to compare binding of humanized SCORPION molecules TSC194 and TSC199 to that of parent humanized SMIP molecules TSC188 and TSC189 and chimeric Interceptor molecule TSC122 in PSMA(+) (C4-2) and PSMA(−) (DU-145) prostate cancer cell lines.

Binding studies (FIG. 1) were used to compare the parent 107-1A4 murine antibody (i.e., TSC045) with the chimeric SMIP molecules (TSC085, TSC092) and the bispecific, chimeric Interceptor molecule TSC122. Both chimeric SMIP molecules showed comparable affinity to PSMA+ cells as the parent murine antibody, although one (TSC085, with a VL-VH scFv orientation) showed a lower level of saturation on the surface of the cell. The bispecific, chimeric Interceptor molecule (TSC122), which had only a single 107-1A4 binding domain, showed a lower binding affinity to the PSMA+ cells. All showed little to no binding to the PSMA− cell line DU-145. Binding studies of humanized SMIP molecules TSC188 and TSC189 (FIG. 2A) showed comparable affinities to those previously determined (data not shown) for the parent monoclonal antibody, with similarly high levels of saturation and selectivity for PSMA+ C4-2 cells over PSMA− DU-145 cells. Binding studies of humanized SCORPION molecules TSC194 and TSC199 showed comparable affinities to the parental humanized SMIP molecules TSC188 and TSC189 (FIG. 2B), with no binding to the PSMA− DU-145 cell line.

Example 5: Differential Cellular Internalization Seen Between 107-1A4 Antibody, SMIP and Interceptor Scaffolds The binding proteins for internalization studies were directly labeled with CypHer™5E Mono NHS Ester (GE Healthcare, #PA15401) according to manufacturer's instructions. CypHer5E is a pH-sensitive red excited dye that fluoresces at low pH, which is typically encountered inside of endosomes and lysosomes; CypHer5E fluorescence can be used as a proxy for cellular internalization as a result. Dye dissolved in fresh DMSO was added to purified protein in PBS/sodium carbonate buffer, pH 8.3 (9:1), at a dye:protein molar ratio of 20:1. After at least 1 hour incubation in the dark at room temperature, labeled protein was separated from unreacted dye by dialysis at 4° C. Absorbance at 280 nm and 500 nm was used to calculate protein and dye concentration for the labeled material. The resulting dye: protein ratio ranged from 6 to 14, and this value was used to normalize the imaging data. To ensure that the presence of protein aggregates did not bias the internalization data, when individual molecules had detectable levels of aggregates (>5%), secondary size exclusion chromatography was used to purify molecules to very high levels of homogeneity (>95%).

Cells were plated 2 days before experiment at 4000 cells per well in poly-D-lysine-coated 96-well plates, black with clear bottoms (BD Biocoat, 356640) in usual culture media. Media changes during experiment were conducted carefully to maintain cell adhesion to surface. Nuclei were stained with Hoechst 33342 (Invitrogen, H3570) in serum-free phenol red-free RPMI media (Invitrogen, 11835) plus 20 mM HEPES (Invitrogen, 15630) (called PRF-RPMI) for an hour. Wells were washed with PRF-RPMI plus 10% FBS, and 100 ul warm PRF-RPMI+10% FBS was added. Plates were moved to ice for 5 minutes then labeled binding proteins at various dilutions were added from 5× stock solutions for one hour binding on ice. Plates were moved to a 37° C. CO$_2$ incubator for 60 minutes to allow internalization to proceed. Before imaging, media was replaced with PRF-RPMI+1% FBS.

Wells were scanned on IN Cell Analyzer 1000 automated cellular and subcellular imaging system (GE Healthcare) to quantitate internalized protein, data was collected from 8 fields in each well. The acquisition protocol was set to collect data with suitable filter sets for Hoechst and CypHer5E, and bright field images. Data was analyzed by IN Cell Investigator software, using a protocol developed to detect fluorescent granules within a zone of cytoplasm encircling each nucleus and measuring their area. Total granule area detected was normalized to compensate for the relative level of dye substitution per labeled protein.

Figure 3:
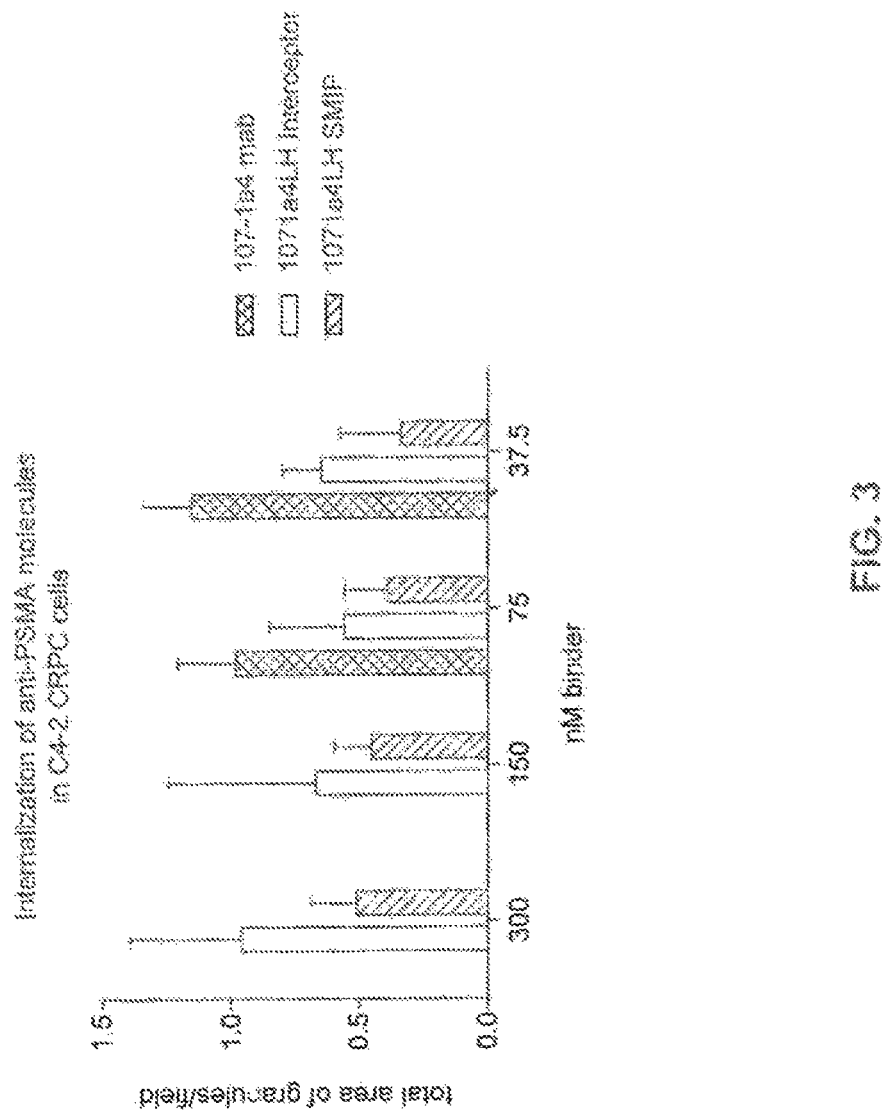
FIG. 3 is a graph illustrating the results of internalization experiments comparing the parent 107-1A4 murine antibody to PSMA-binding proteins built on Interceptor and SMIP scaffolds.

Internalization experiments using the parental 107-1A4 murine antibody, or the chimeric SMIP and Interceptor molecules, showed no internalization in the PSMA–DU-145 cell line (data not shown), but some internalization could be detected on the PSMA+ LNCaP (CRL-1740™, American Type Culture Collection) or C4-2 cell lines (FIG. 3). Internalization of the parental antibody was greater than the SMIP or Interceptor molecules at all concentrations tested. Apparent internalization from the (monovalent) Interceptor molecule was higher than from the (bivalent) SMIP molecule, which could be due to the higher potential binding stoichiometry—each Interceptor molecule can only engage one molecule of PSMA, whereas each SMIP molecule can engage two molecules of PSMA, potentially leading to twice as much Interceptor molecule accumulating on the cell surface. If both the Interceptor and SMIP molecules have similar levels of internalization, a higher apparent signal would always be seen from the Interceptor molecule.

Example 6: Redirected T-Cell Cytotoxicity Against PSMA(+) Cell Lines

Figure 4:
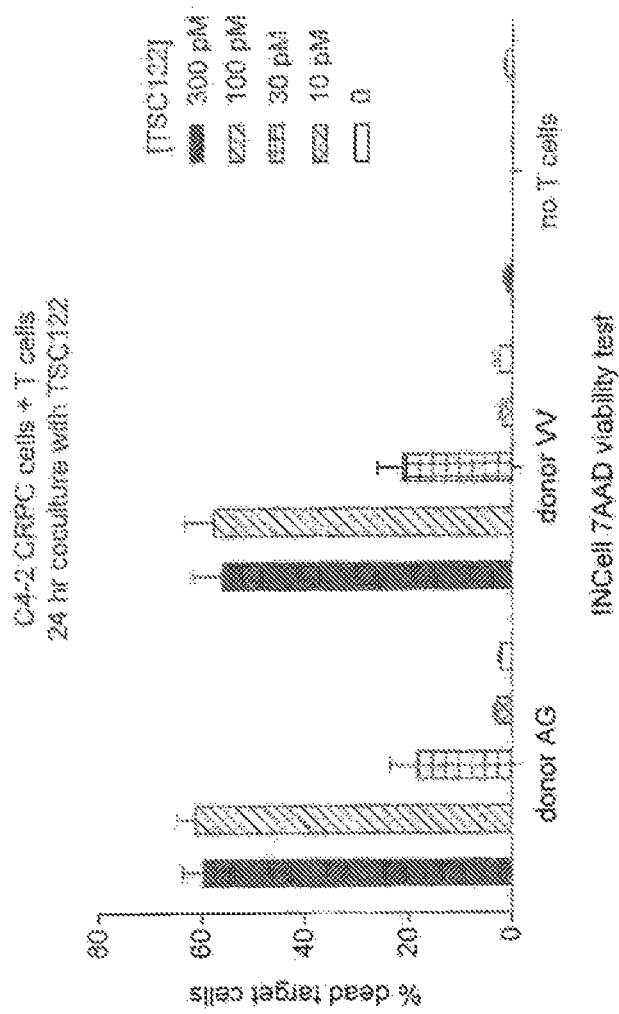
FIG. 4 is a graph illustrating potent target-dependent cytotoxic activity over 24 hours observed with the chimeric TSC122 Interceptor molecule at decreasing concentrations (300, 100, 30, 10 and 0 pM) in the presence of T cells from human blood from two different donors (labeled as AG and VV).

Peripheral blood mononuclear cells (PBMC) were isolated from human blood from two different donors (labeled as AG or VV) using standard ficoll gradients. The isolated cells were washed in saline buffer. T cells were additionally isolated using a Pan T-cell Isolation Kit II from Miltenyi Biotec (Bergisch Gladbach, Germany) using the manufacturer's protocol. T cells were used with or without stimulation, as noted in the figures (see FIGS. 4-6), and added at a 10:1 ratio (T cell:target cell) unless indicated otherwise.

C4-2 castration-resistant prostate cancer (CRPC) cells were labeled with CellTracker™ Green cytoplasmic dye (Invitrogen, C7025) following manufacturer's protocol in order to distinguish them from T cells. Labeled C4-2 cells were seeded into poly-D-lysine-coated 96-well plates, as used in Example 3, at 8000 cells per well in standard growth media, one day before addition of T cells and Interceptor molecule. Ten ul of concentrated bispecific Interceptor molecule (TSC122, TSC200, TSC202, or TSC204) was added to 100 ul of media per well, plus 50 ul of T cells (80,000 cells) in standard growth media. Cell cultures were kept in CO$_2$ incubator at 37° C. overnight. After 24 hr exposure to Interceptor molecule, cells were stained with 7-AAD and Hoechst dyes to enable quantitation of dead cells. Media was changed to 100 ul RPMI+1% FBS+10 ug/ml 7-AAD+ Hoechst at 1:1000 dilution of stock, and incubated for an additional 30 minutes.

Imaging and quantitation was performed by use of an InCell Analyzer microscope (GE), collecting data from 10 fields per well. The acquisition protocol was set to collect data with suitable filter sets for: a) nuclei detection via Hoechst stain, b) cell type discrimination via CellTracker™ Green detection, c) live/dead cell status determination via 7-AAD staining, and bright field images. Quantitation was performed by InCell Workstation software, using a decision tree application. Individual cells were detected by presence of nuclear stain by Hoechst. Threshold values of signal in the green channel (CellTracker™ Green) were used to split cells into C4-2 (positive) and T cell (negative) populations. Threshold values of signal in red channel (7-AAD) were used to split cells into dead (positive) and live (negative) populations.

Figure 5:
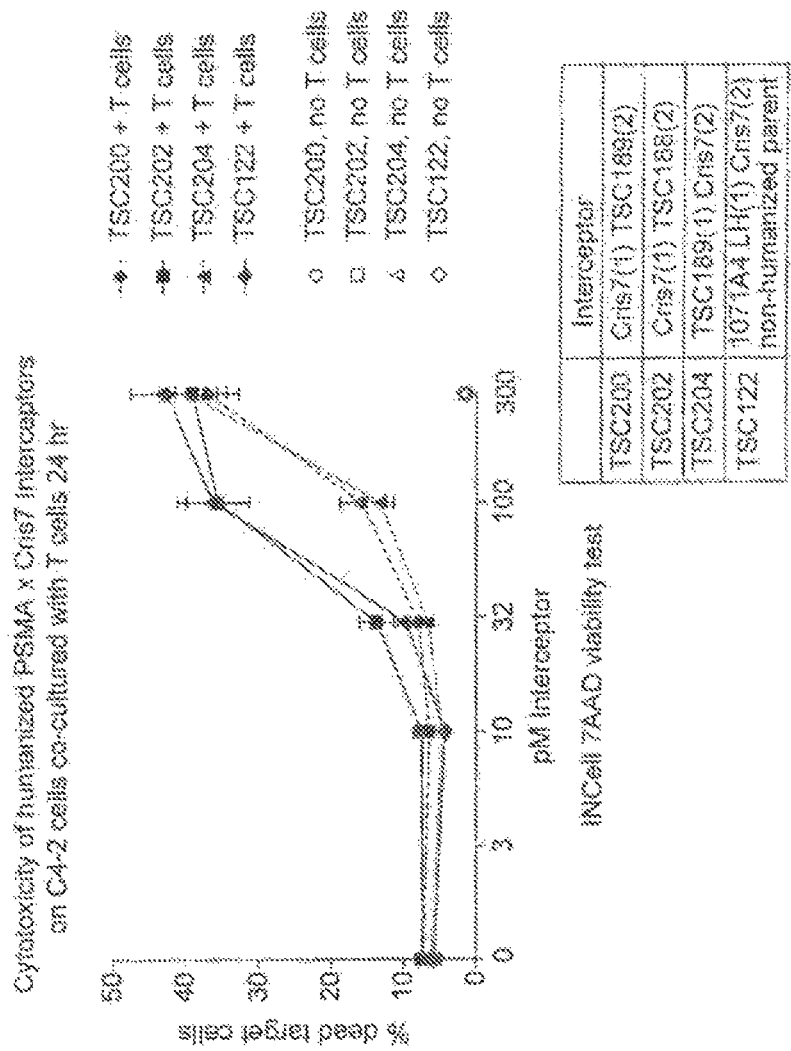
FIG. 5 is a graph illustrating cytotoxicity activity of TSC200, TSC202, TSC204 alongside the parent chimeric Interceptor molecule TSC122.

Bispecific Interceptor molecules featuring either the 107-1A4 murine scFv or humanized 107-1A4 scFv as well as an anti-CD3 scFv (Cris7) were tested for the ability to cross-link T-cells to target PSMA+ tumor cells and enable target-dependent cytotoxic T cell responses (so-called 'redirected T cell cytotoxicity', or RTCC). Potent target-dependent cytotoxic activity over 24 hours was observed with the chimeric TSC122 Interceptor molecule (FIG. 4) with T-cells from two different donors; roughly 60% of target cells were lysed by treatment with as little as 100 pM of TSC122 Interceptor molecule. No direct cytotoxicity on PSMA+ cells was observed in the absence of effector T-cells (FIG. 4); no cytotoxicity was similarly observed on PSMA– cells in the presence of effector T-cells (data not shown). The cytotoxic activity of humanized Interceptor molecules (TSC200, TSC202, and TSC204) was also tested alongside the parent chimeric Interceptor molecule (TSC122) (FIG. 5). Two of the humanized Interceptor molecules (TSC200, TSC204) showed lower RTCC activity than the parent; one humanized Interceptor molecule (TSC202) showed equal RTCC activity to the parent chimeric Interceptor molecule (TSC122) with similar, low pM potency. These results demonstrated that certain humanized Interceptor molecules had similar T cell cytotoxicity as the parental chimeric Interceptor molecule.

Figure 6:
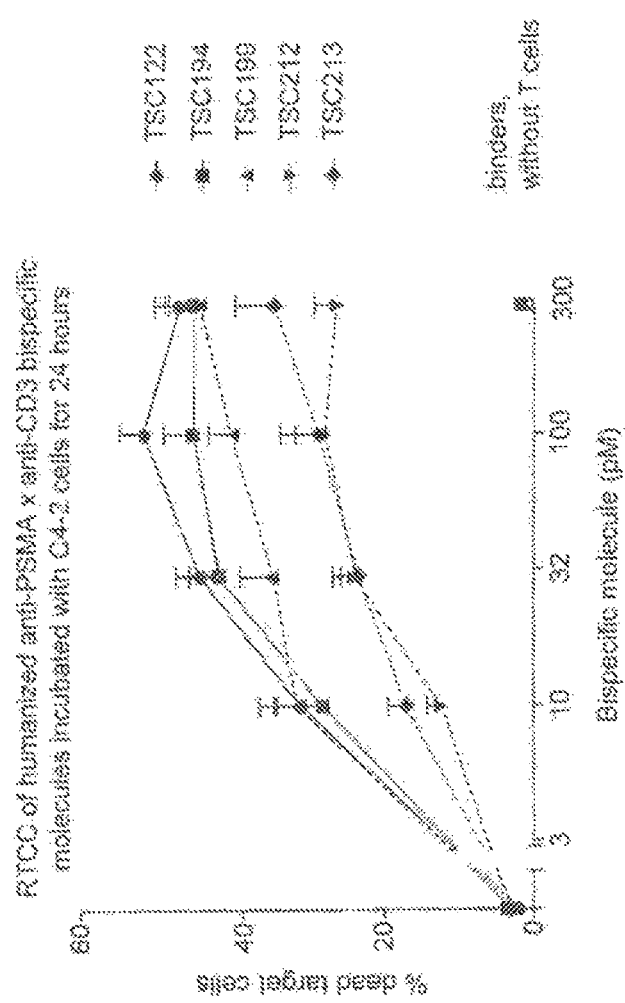
FIG. 6 is a graph illustrating T-cell cytotoxicity mediated by humanized 107-1A4 SCORPION molecules (TSC194, TSC199, TSC212, TSC213) compared to the chimeric Interceptor molecule TSC122.

The cytotoxic activity of humanized SCORPION molecules (TSC194, TSC199, TSC212, TSC213), compared to that of the chimeric Interceptor molecule TSC122, was also examined (FIG. 6). The humanized SCORPION molecules with anti-PSMA scFvs in the VL-VH orientation (TSC194, TSC199) had comparable cytotoxic activity to the bispecific chimeric Interceptor molecule (also with an scFv in the VL-VH orientation, and also including an anti-CD3 scFv (Cris7)). The humanized SCORPION molecules with anti-PSMA scFvs in the VH-VL orientation, on the other hand, had lower overall cytotoxicity.

Example 7: Target-Dependent T-Cell Activation and Proliferation Induced Against PSMA+ Cell Lines Directed by Bispecific 107-1A4-Derived Molecules To compare the effectiveness of different bispecific polypeptide molecules at inducing target-dependent T-cell activation and proliferation, four different anti-PSMA and anti-CD3 bispecific molecules including TSC122 (a chimeric Interceptor molecule), TSC202 (humanized Interceptor molecule), TSC194 (a humanized SCORPION molecule), and TSC199 (a humanized SCORPION molecule) were compared.

C4-2 prostate cancer cells (PSMA+) were obtained from MD Anderson Cancer Center (Houston, Tex.) and cultured according to the provided protocol. Peripheral blood mononuclear cells (PBMC) were isolated from human blood using standard ficoll gradients. The isolated cells were washed in saline buffer. T cells were further isolated using a Pan T-cell Isolation Kit II from Miltenyi Biotec (Bergisch Gladbach, Germany) using the manufacturer's protocol.

Proliferation was assessed by labeling isolated T cell populations with carboxyfluorescein diacetate succinimidyl ester (CFSE). CFSE-labeled T cells were plated in U-bottom 96-well plates at 100,000 cells/well, respectively, with 30,000 C4-2 tumor cells/well, to achieve T cell to tumor cell ratios of roughly 3:1. Concentrations of test molecules ranging from 10 nM to 0.1 pM were added to the cell mixtures in a total of 200 ul/well in RPMI 1640 media supplemented with 10% human or bovine serum, sodium pyruvate and non-essential amino acids. Plates were incubated at 37° C., 5% $CO_2$ in humidified incubators. After 3 days, cells were labeled with antibodies for flow cytometric analysis. Cells were labeled and washed in their original plates to minimize cell losses during transfers, and all labeling was done in saline buffer with 0.2% bovine serum albumin. First, cells were pre-incubated with 100 ug/ml human IgG at room temperature for 15 min. Subsequently, cells were incubated with a mixture (total volume 50 ul) of the following dye-labeled antibodies: CD5-PE, CD4-APC, CD8-Pacific Blue, CD25-PE-Cy7, as well as 7-Amino Actinomycin D (7AAD hereafter) for 40 min. Cells were washed twice, resuspended in 80 to 120 ul volumes, and measured immediately in a BD LSRII flow cytometer to acquire 80% of the contents of each well. The sample files were analyzed using FlowJo software to calculate the percentages and numbers of cells that had undergone at least one cell division, according to their CFSE profile, by gating sequentially on activated, live CD4+ or CD8+ T cells (7AAD−, CD5+ CD25+ CD4+ or 7AAD− CD5+ CD25+ CD8+, respectively). Mean values and standard deviations were calculated using Microsoft Excel software. Graphs were plotted using Microsoft Excel or GraphPad Prism.

Figures 7A, 7B:
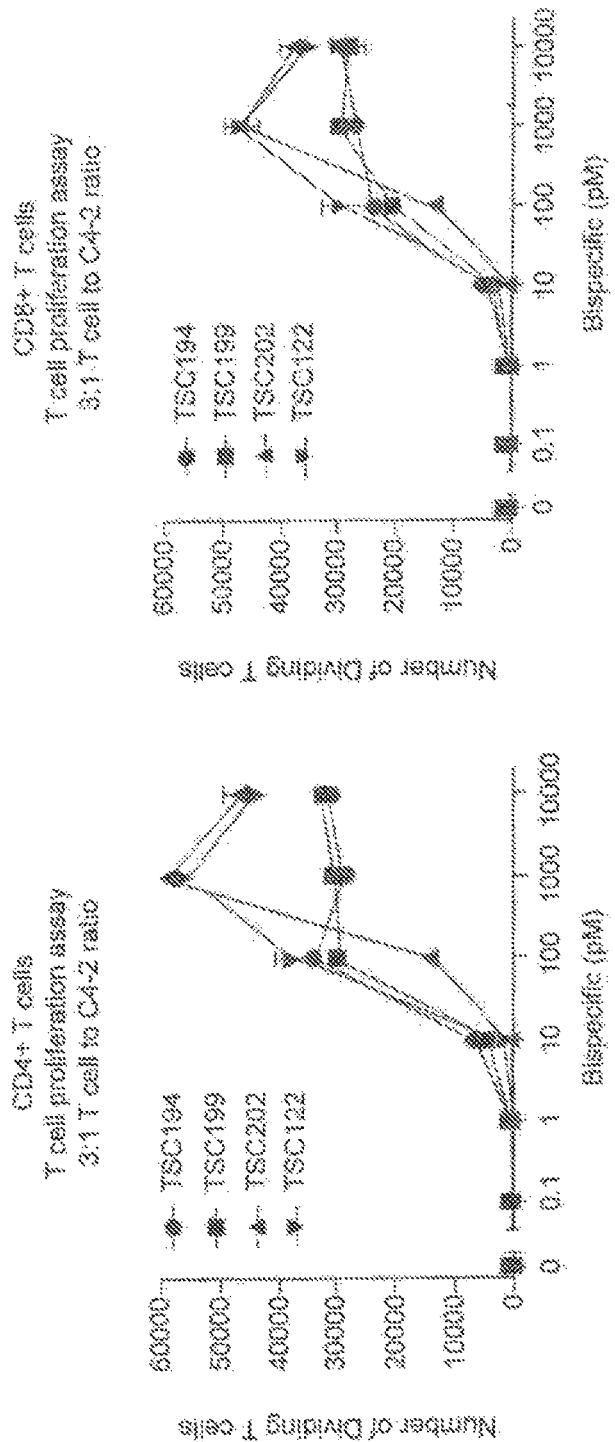
FIGS. 7A and 7B are graphs illustrating target-dependent proliferation of CD4+ T-cells (FIG. 7A) and CD8+ T-cells (FIG. 7B) induced by anti-PSMA bispecific molecules (TSC194, TSC199, TSC202 and TSC122) reacting with C4-2 cells.

Analysis of live CD4+ and CD8+ populations from wells with C4-2 cells treated with T-cells (FIG. 7A and FIG. 7B) revealed a significant increase in both the total number of cells and percent proliferating cells in the presence of C4-2 cells displaying the target PSMA antigen. Proliferation was slightly higher for CD4+ T-cells than CD8+ T-cells, and the proliferation induced by the Interceptor molecules TSC122 and TSC202 saturated at a higher level than the responses induced by the SCORPION molecules TSC194 and TSC199. All molecules showed induction of T-cell proliferation at low concentrations (100 pM). No significant differences in relative induction of CD4+ versus CD8+ cell proliferation were apparent between molecules.

Example 8: Competitive Binding Studies of Anti-PSMA Molecules Confirms 107-1A4 Binds a Unique Epitope on PSMA To show that anti-PSMA murine monoclonal antibody 107-1A4, chimeric 107-1A4 SMIP molecule (TSC085) and humanized 107-1A4 SMIP molecule (TSC189) binds a unique epitope on PSMA, which is not recognized by common literature antibodies (J415, J591), and that the conversion of murine monoclonal antibody 107-1A4 to SMIP format did not result in a shift in that binding epitope, competition binding experiments were carried out. Hybridomas producing the J591, Hu591 (a humanized version of J591) and J415 antibodies were obtained from ATCC. Monoclonal antibodies were purified from hybridoma cell culture media by standard procedures. SMIP molecules were produced by transient transfection of human 293 cells, and purified from cell culture supernatants by Protein A affinity chromatography. If aggregates were detected after affinity chromatography, secondary size exclusion chromatography was also performed to ensure homogeneity of the protein.

Competitive binding studies on the PSMA+C4-2 prostate cancer cell line were performed by standard FACS-based staining procedures. To simplify binding measurements, molecules with human Fc domains were used to compete against molecules with murine Fc domains, and either an anti-human or anti-mouse antibody was used to detect binding to the target cell line.

In a typical experiment, molecule X (binder) would be mixed with molecule Y (competitor), placed on ice, and then used to label 300,000 cells per well with 4 nM of molecule X and a range of 250 nM to 0.4 nM molecule Y in 100 ul of FACS buffer (PBS+2% normal goat serum+2% fetal bovine serum+0.1% sodium azide) on ice, followed by washes and incubation with fluorescently-labeled secondary antibody specific for molecule X, either goat anti-human IgG (1:400 dilution of Invitrogen 11013=5 ug/ml) or goat anti-mouse IgG (1:400 dilution of Invitrogen 11017). After washing secondary antibody off cells, cells were incubated with 7AAD (6 ul of BD Pharmingen 7AAD, cat #559925) to 100 ul of FACS Buffer) for 20 minutes. Signal from bound molecules was detected using a FACSCalibur flow cytometer and analyzed by FlowJo. 7AAD+ cells were excluded from analysis. Nonlinear regression analysis to determine EC50s was performed in GraphPad Prism.

Figure 8A:
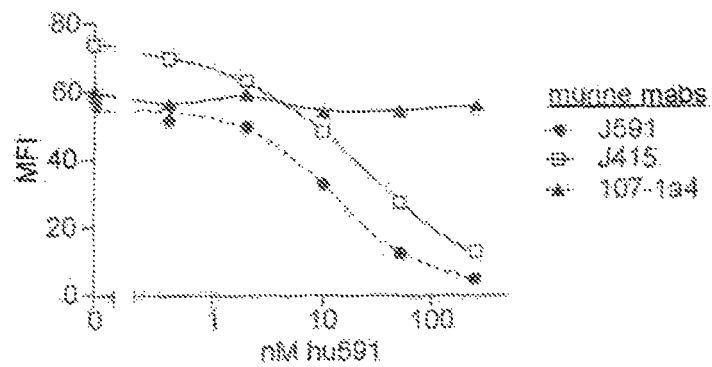
FIGS. 8A-8C are graphs illustrating competitive binding studies of mAbs J591 and J415 versus 107-1A4 mAb and chimeric and humanized 107-1A4 SMIP molecules to PSMA on C4-2 cells. Specifically.
Figure 8B:
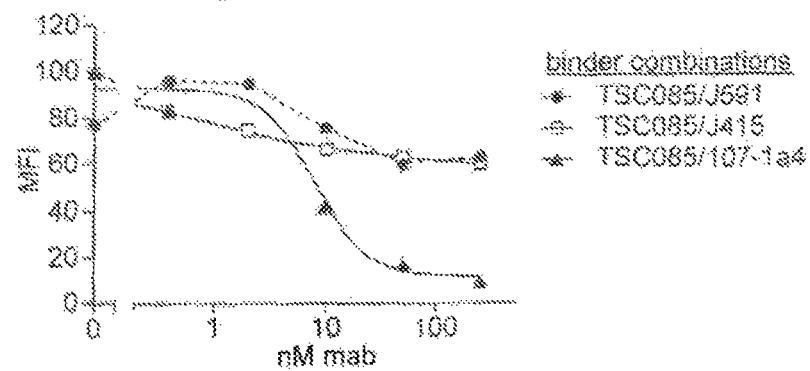
Figure 8C:
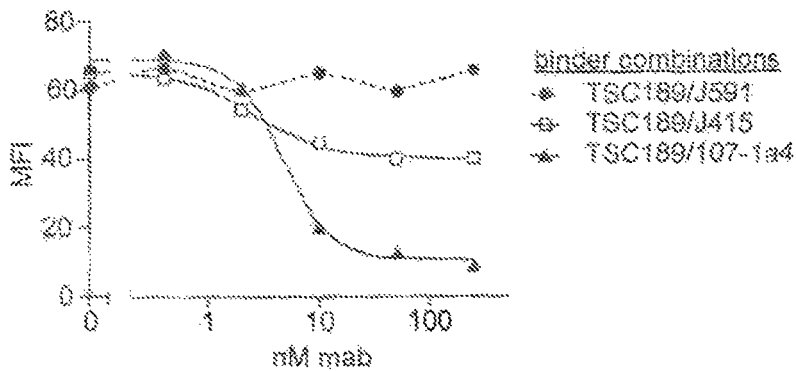

Competitive binding studies (FIG. 8A) were used to see if the humanized J591 antibody, Hu591, could compete with the binding of 107-1A4, J591 or J415 murine antibodies to cells. No competition was observed for the binding of 107-1A4, suggesting it binds a non-competitive epitope; competition was observed for the binding of both J591 and J415 antibodies, however. Next, additional binding studies were carried out to see if the three murine antibodies could compete with the binding of the chimeric 107-1A4 SMIP molecule TSC085 to cells (FIG. 8B). Strong competition was seen from binding of the parental 107-1A4 antibody, confirming that the SMIP molecule bound to the same epitope. No effective competition was seen from the J591 or J415 murine antibodies. Last, binding studies were carried out to see if the three murine antibodies could compete with the binding of the humanized 107-1A4 SMIP molecule TSC189 to cells (FIG. 8C). Again, similarly strong competition was seen from binding of the parental 107-1A4 antibody, but no effective competition was seen from the J591 or J415 murine antibodies. This confirms that 107-1A4 binds a unique epitope on PSMA. It also shows that any shift in behavior of 107-1A4-based SMIP and Interceptor molecules from that of the parental 107-1A4 antibody is not due to a shift in binding epitopes.

Example 9: Inhibition of Tumor Growth In Vivo Using an Anti-PSMA Bispecific Molecule To confirm the effectiveness of an anti-PSMA bispecific molecule of the present disclosure (e.g., anti-PSMA and anti-CD3 bispecific molecules) at inhibiting tumor growth in vivo, the anti-PSMA bispecific molecule is evaluated as follows.

Prophylactic Treatment, or Prevention of Tumor Engraftment of Subcutaneous Tumors:

Cultured, PSMA-expressing tumor cell lines (such as LNCaP, LNCaP C4-2, LNCaP C4-2B, VCaP, CWR22Rv1, LAPC4, MDA-PCa-2b, LuCaP 23.1, LuCaP 58, LuCaP 70, LuCaP 77) are mixed with human lymphocytes (either human peripheral blood mononuclear cells or purified T-cells) and injected subcutaneously into immunodeficient mice (such as SCID, NOD/SCID, etc). An anti-PSMA bispecific molecule is injected intravenously on the day of injection and on several subsequent days. Dose-dependent inhibition of tumor outgrowth, as assessed by tumor volume, indicates that the respective molecule has efficacy against PSMA-expressing tumors in vivo.

Therapeutic Treatment, or Regression of Previously Established Subcutaneous Tumors:

Cultured, PSMA-expressing tumor cell lines (such as LNCaP, LNCaP C4-2, LNCaP C4-2B, VCaP, CWR22Rv1, LAPC4, MDA-PCa-2b, LuCaP 23.1Al, LuCaP 58, LuCaP 70, LuCaP 77) are injected subcutaneously into immunodeficient mice (such as SCID, NOD/SCID, etc). Tumor growth is monitored, and the study is initiated when tumors show signs of established growth (typically a volume of ~200 mm3). Human lymphocytes (either human peripheral blood mononuclear cells or purified T-cells) are injected intravenously along with an anti-PSMA bispecific molecule on the day of injection. The anti-PSMA bispecific molecule is injected several subsequent days. Dose-dependent inhibition of tumor growth, as assessed by tumor volume, indicates that the respective molecule has efficacy against PSMA-expressing tumors in vivo.

Prophylactic Treatment, or Prevention of Tumor Engraftment of Intra-Tibial Tumors:

Cultured, PSMA-expressing tumor cell lines (such as LNCaP C4-2, LNCaP C4-2B, VCaP, CWR22Rv1, LAPC4, MDA-PCa-2b, LuCaP 23.1, LuCaP 58, LuCaP 70, LuCaP 77) are mixed with human lymphocytes (either human peripheral blood mononuclear cells or purified T-cells) and injected intra-tibially into immunodeficient mice (such as SCID, NOD/SCID, etc). An anti-PSMA bispecific molecule is injected intravenously on the day of injection and on several subsequent days. Dose-dependent inhibition of tumor growth, as assessed by serum biomarkers, radiography, fluorescent imaging, weight loss, and other proxy measurements of tumor volume, indicates that the respective molecule has efficacy against PSMA-expressing tumors in vivo.

Therapeutic Treatment, or Regression of Previously Established Intra-Tibial Tumors:

Cultured, PSMA-expressing tumor cell lines (such as LNCaP C4-2, LNCaP C4-2B, VCaP, CWR22Rv1, LAPC4, MDA-PCa-2b, LuCaP 23.1Al, LuCaP 58, LuCaP 70, LuCaP 77) are injected intra-tibially into immunodeficient mice (such as SCID, NOD/SCID, etc). Tumor growth is monitored, and the study is initiated when tumors show signs of established growth (typically a volume of ~200 mm3). Human lymphocytes (either human peripheral blood mononuclear cells or purified T-cells) are injected intravenously along with an anti-PSMA bispecific molecule on the day of injection. The anti-PSMA bispecific molecule is injected several subsequent days. Dose-dependent inhibition of tumor growth, as assessed by serum biomarkers, radiography, fluorescent imaging, weight loss, and other proxy measurements of tumor volume, indicates that the respective molecule has efficacy against PSMA expressing tumors in vivo.

The invention claimed is:

1. A prostate-specific membrane antigen (PSMA)-binding polypeptide comprising a humanized PSMA-binding domain, a first hinge region, an immunoglobulin constant region and a second binding domain, wherein the PSMA binding domain comprises:
   (i) an immunoglobulin light chain variable region comprising LCDR1, LCDR2, and LCDR3, and
   (ii) an immunoglobulin heavy chain variable region comprising HCDR1, HCDR2, and HCDR3,
   wherein the LCDR1, LCDR2 and LCDR3 have the amino acid sequences set forth in SEQ ID NOs: 15, 16 and 17, respectively, and the HCDR1, HCDR2, and HCDR3 have the amino acid sequences set forth in SEQ ID NOs: 9, 10 and 11, respectively;
   wherein the second binding domain specifically binds a T cell receptor (TCR) complex or a component thereof; and
   wherein the PSMA-binding polypeptide is capable of inducing redirected T cell cytotoxicity (RTCC) against a cell expressing PSMA.

2. The PSMA-binding polypeptide of claim 1, wherein the second binding domain specifically binds CD3.

3. The PSMA-binding polypeptide of claim 1, wherein the immunoglobulin constant region comprises immunoglobulin CH2 and CH3 domains of IgG1, IgG2, IgG3, IgG4, IgA1, IgA2 or IgD.

4. The PSMA-binding polypeptide of claim 1, wherein the PSMA-binding domain comprises an amino acid sequence that is at least 95% identical to the amino acid sequence set forth in SEQ ID NO:38, SEQ ID NO:39, SEQ ID NO:42, SEQ ID NO:43, SEQ ID NO:70, or SEQ ID NO:72.

5. The PSMA-binding polypeptide of claim 1, wherein the PSMA-binding polypeptide comprises, in order from amino-terminus to carboxyl-terminus or in order from carboxyl-terminus to amino-terminus,
   (a) the PSMA binding domain,
   (b) the first hinge region,
   (c) the immunoglobulin constant region,
   (d) a second hinge region, and
   (e) the second binding domain.

6. The PSMA-binding polypeptide of claim 5, wherein the first hinge region and/or the second hinge region is derived from (i) a stalk region of a type II C lectin or (ii) an immunoglobulin hinge region.

7. The PSMA-binding polypeptide of claim 1, wherein the light and heavy chain variable regions of the second binding domain are selected from the group consisting of:
- (a) a light chain variable region comprising an amino acid sequence that is at least 95% identical to the amino acid sequence set forth in residues 139-245 of SEQ ID NO:47 and comprising complementarity determining regions (CDRs) comprising the amino acid sequences of the corresponding CDRs set forth in residues 139-245 of SEQ ID NO:47 and a heavy chain variable region comprising an amino acid sequence that is at least 95% identical to the amino acid sequence set forth in residues 1-121 of SEQ ID NO:47 and comprising CDRs comprising the amino acid sequences of the corresponding CDRs set forth in residues 1-121 of SEQ ID NO:47;
- (b) a light chain variable region comprising an amino acid sequence that is at least 95% identical to the amino acid sequence set forth in residues 634-740 of SEQ ID NO:78 and comprising CDRs comprising the amino acid sequences of the corresponding CDRs set forth in residues 634-740 of SEQ ID NO:78 and a heavy chain variable region comprising an amino acid sequence that is at least 95% identical to the amino acid sequence set forth in residues 496-616 of SEQ ID NO:78 and comprising CDRs comprising the amino acid sequences of the corresponding CDRs set forth in residues 496-616 of SEQ ID NO:78; and
- (c) a light chain variable region comprising an amino acid sequence that is at least 95% identical to the amino acid sequence set forth in SEQ ID NO:86 and comprising CDRs comprising the amino acid sequences of the corresponding CDRs set forth in SEQ ID NO:86 and a heavy chain variable region comprising an amino acid sequence that is at least 95% identical to the amino acid sequence set forth in SEQ ID NO:87 and comprising CDRs comprising the amino acid sequences of the corresponding CDRs set forth in SEQ ID NO:87.

8. The PSMA-binding polypeptide of claim 1, wherein said PSMA-binding polypeptide comprises an amino acid sequence that is at least 95% identical to the amino acid sequence set forth in SEQ ID NO:49, SEQ ID NO:51, SEQ ID NO:74, SEQ ID NO:76, SEQ ID NO:78, SEQ ID NO:80, SEQ ID NO:82, SEQ ID NO:84, SEQ ID NO:158, SEQ ID NO:160, SEQ ID NO:162, or SEQ ID NO:164.

9. The PSMA-binding polypeptide of claim 1, wherein the PSMA-binding domain is a single chain Fv (scFv).

10. The PSMA-binding polypeptide of claim 9, wherein the light chain variable region and heavy chain variable region of the scFv are joined by an amino acid sequence comprising (Gly4Ser)n, wherein n=1-5 (SEQ ID NO:165).

11. The PSMA-binding polypeptide of claim 9, wherein the scFv comprises an amino acid sequence that is at least 95% identical to the amino acid sequence set forth in SEQ ID NO:19, SEQ ID NO:21, SEQ ID NO:30, SEQ ID NO:31, SEQ ID NO:34, or SEQ ID NO:35.

12. A dimeric PSMA-binding protein comprising first and second polypeptide chains, wherein each of said polypeptide chains is the PSMA-binding polypeptide of claim 1.

13. A composition comprising the PSMA-binding protein of claim 12 and a pharmaceutically acceptable carrier, diluent, or excipient.

14. An isolated nucleic acid encoding the PSMA-binding polypeptide of claim 1.

15. A recombinant host cell comprising the nucleic acid of claim 14.

16. A PSMA-binding polypeptide comprising a humanized PSMA-binding domain, a first hinge region, an immunoglobulin constant region and a second binding domain, wherein the PSMA binding domain comprises:
- (i) an immunoglobulin light chain variable region comprising LCDR1, LCDR2, and LCDR3, and
- (ii) an immunoglobulin heavy chain variable region comprising HCDR1, HCDR2, and HCDR3,
  wherein the LCDR1, LCDR2 and LCDR3 have the amino acid sequences set forth in SEQ ID NOs: 15, 16 and 17, respectively, and the HCDR1, HCDR2, and HCDR3 have the amino acid sequences set forth in SEQ ID NOs: 9, 10 and 11, respectively; wherein the second binding domain specifically binds a T cell receptor (TCR) complex or a component thereof;
  wherein the immunoglobulin light chain variable region comprises an amino acid sequence that is at least 95% identical to the amino acid sequence set forth in SEQ ID NO:5 or SEQ ID NO:23 and the heavy chain variable region comprises an amino acid sequence that is at least 95% identical to the amino acid sequence set forth in SEQ ID NO:2, SEQ ID NO:25, or SEQ ID NO:27; and
  wherein the PSMA-binding polypeptide is capable of inducing redirected T cell cytotoxicity (RTCC) against a cell expressing PSMA.

17. The PSMA-binding polypeptide of claim 16, wherein the light chain variable region comprises the amino acid sequence set forth in SEQ ID NO:23 and the heavy chain variable region comprises the amino acid sequence set forth in SEQ ID NO:25 or SEQ ID NO:27.

18. A method for treating a disorder in a subject, wherein the disorder is characterized by overexpression of PSMA and wherein the disorder is a cancer, a prostate disorder, or a neovascular disorder, the method comprising administering to the subject a therapeutically effective amount of the dimeric PSMA-binding protein of claim 12 under conditions whereby RTCC in the subject is induced against a cell expressing PSMA, thereby treating said disorder in the subject.

19. The method of claim 18, wherein the disorder is prostate cancer, colorectal cancer, gastric cancer, castrate-resistant prostate cancer, benign prostatic hyperplasia, solid tumor growth, clear cell renal carcinoma, colorectal cancer, bladder cancer, or lung cancer.

* * * * *